(12) United States Patent
Brunkow et al.

(10) Patent No.: US 6,495,736 B1
(45) Date of Patent: Dec. 17, 2002

(54) COMPOSITIONS AND METHODS FOR INCREASING BONE MINERALIZATION

(75) Inventors: Mary E. Brunkow, Seattle, WA (US); David J. Galas, Mercer Island, WA (US); Brian Kovacevich, Renton, WA (US); John T. Mulligan, Seattle, WA (US); Bryan W. Paeper, Seattle, WA (US); Jeffrey Van Ness, Seattle, WA (US); David G. Winkler, Seattle, WA (US)

(73) Assignee: Darwin Discovery, Ltd., Bothell, WA (US)

( * ) Notice: Subject to any disclaimer, the term of this patent is extended or adjusted under 35 U.S.C. 154(b) by 15 days.

(21) Appl. No.: 09/668,037

(22) Filed: Sep. 21, 2000

Related U.S. Application Data

(62) Division of application No. 09/449,218, filed on Nov. 24, 1999, now Pat. No. 6,395,511.
(60) Provisional application No. 60/110,283, filed on Nov. 27, 1998.

(51) Int. Cl.[7] .............................................. A01K 67/027
(52) U.S. Cl. .......................................... 800/18; 800/13
(58) Field of Search ........................................... 800/13

(56) References Cited

U.S. PATENT DOCUMENTS

| 5,453,492 A | 9/1995 | Bützow et al. ............. 530/413 |
| 5,780,263 A | 7/1998 | Hastings et al. ........... 435/69.1 |
| 5,811,238 A | 9/1998 | Stemmer et al. ................ 435/6 |
| 5,830,721 A | 11/1998 | Stemmer et al. ......... 435/172.1 |
| 5,837,458 A | 11/1998 | Minshull et al. ................ 435/6 |

FOREIGN PATENT DOCUMENTS

| WO | WO 91/13152 | 9/1991 |
| WO | WO 92/06693 | 4/1992 |

OTHER PUBLICATIONS

Wall; Trangenic Livestock: Progress and Prospects for the Future, 1996, Theriogenology 45: 57–68.*
Sigmund; Viewpoint: Are Studies in Genetically Altered Mice Out of Control?, 2000, Arterioscler Thromb Vasc Biol. 20: 1425–1429.*
Cambell et.al.; Totipotency or Multipotentiality of Cultured Cells: Applications and Progress, 1997, Theriogenology 47:69–72.*
Bradley et.al; Modifying The Mouse: Design and Desire, 1992, Bio/Technology vol. 10: 534–539.*
Mullins et.al.; Perspectives Series: Molecular Medicine in Genetically Engineered Animals, 1996, J. Clin. Invest.vol. 97, No. 7: 1557–1560.*
Serra et.al.; Expression of a Truncated, Kinase–Defective TGF–B Type 11 Receptor in Mouse Skeletal Tissue Promotes Terminal Chondrocyte Differentiation and Osteoarthritis, 1997, Journal of Cell Biology, vol. 139, No. 2: 541–552.*
Oshima et.al.; Rapid Communication . . . Sac Hematopoiesis and Vasulogenesis, 1996, Developmental Biology 179: 297–302.*
Birren et al., EMBL Sequence Database, Accession No. AC003098, Nov. 14, 1997.
Bonaldo et al., "Normalization and Subtraction: Two Approaches to Facilitate Gene Discovery," *Genome Res.* 6(9):791–1996.
Bonaldo et al., EMBL Sequence Database, Accession No. AI113131, Sep. 4, 1998.
Hillier et al., EMBL Sequence Database, Accession No. AA393939, May 19, 1997.
Hsu et al., "The Xenopus dorsalizing factor gremlin identifies a novel family of secreted proteins that antagonize BMP activities," *Molecular Cell* 1:673–683, 1998.
Iemura et al., "Direct binding of follistatin to a complex of bone–morphogenetic protein and its receptor inhibits ventral and epidermal cell fates in early Xenopus embryo," *Proc. Natl. Acad. Sci. USA* 95:9337–9342, 1998.
Khosla and Riggs, "Consice review for primary–care physicians. Treatment options for osteoporosis," *Mayo Clinic Proc* 70:978–982, 1995.
Riggs, "Overview of osteoporosis," *West J. Med.* 154:63–77, 1991.

* cited by examiner

Primary Examiner—Remy Yucel
Assistant Examiner—Sita Pappu
(74) Attorney, Agent, or Firm—Seed Intellectual Property Law Group PLLC

(57) ABSTRACT

A novel class or family of TGF-β binding proteins is disclosed. Also disclosed are assays for selecting molecules for increasing bone mineralization and methods for utilizing such molecules.

2 Claims, 6 Drawing Sheets

Common Cysteine Backbone

```
                1                                                          50
human-gremlin.pro  ---------- ---------- ---------- ---------- ----------
human-cerberus.pro MHLLLFQLLV LLPLGKTTRH QDGRQNQSSL SPVLLPRNQR ELPTGNHEEA
    human-dan.pro  ---------- ---------- ---------- ---------- ----------
   human-beer.pro  ---------- ---------- ---------- ---------- ----------

51                                                         100
human-gremlin.pro  ---------- ---------M SRTAYTVGAL LLLLGTLLPA AEGKKKGSQG
human-cerberus.pro EEKPDLFVAV PHLVAT.SPA GEGQRQREKM LSRFGRFWKK PEREMHPSRD
    human-dan.pro  ---------- ---------- ---------- ---------- ----------
   human-beer.pro  ---------- ---------- ---------- ----MQLPLA LCLVCLLVHT 101                                                        150
human-gremlin.pro  AI.PPPDKAQ HNDSEQTQSP QQPGSRNRGR GQGRGTAMPG EEVLESSQEA
human-cerberus.pro SDSEPFPPGT QSLIQPID.G MKMEKSPLRE EAKKFWHHFM FRKTPASQGV
    human-dan.pro  ---------- ---------- ---------- MLRVLVGAVL PAMLLAAPPP
   human-beer.pro  AFRVVEGQGW QAFKNDATEI IPELGEYPEP PPELENNKTM NRAENGGRPP 151        ▼          ▼          ▼   ▼                     200
human-gremlin.pro  LHVTERKYLK RDWCKTQPLK QTIHEEGCNS RTIINRF.CY GQCNSFYIPR
human-cerberus.pro ILPIKSHEVH WETCRTVPFS QTITHEGCEK VVVQNNL.CF GKCGSVHFP.
    human-dan.pro  INKLALFPDK SAWCEAKNIT QIVGHSGCEA KSIQNRA.CL GQCFSYSVPN
   human-beer.pro  HHPFETKDVS EYSCRELHFT RYVTDGPCRS AKPVTELVCS GQCGPARLLP 201          ▼         ▼                                   250
human-gremlin.pro  HIRKEEGSFQ SCSF...CKP KKFTTMMVTL NCPELQPPTK K.KRVTRVKQ
human-cerberus.pro ..GAAQHSHT SCSH...CLP AKFTTMHLPL NCTELSSVIK V...VMLVEE
    human-dan.pro  TFPQSTESLV HCDS...CMP AQSMWEIVTL ECPGHEEVPR VDKLVEKILH
   human-beer.pro  NAIGRGKWWR PSGPDFRCIP DRYRAQRVQL LCPGGEAPRA RKVRLVAS..

▼5▼                                                        300
human-gremlin.pro  CRC.ISIDLD ---------- ---------- ---------- ----------
human-cerberus.pro CQCKVKTEHE DGHILHAGSQ DSFIPGVSA~ ---------- ----------
    human-dan.pro  CSCQACGKEP SHEGLSVYVQ GEDGPGSQPG THPHPHPHPH PGGQTPEPED
   human-beer.pro  CKCKRLTRFH NQSELKDFGT EAARPQKGRK PRPRARSAKA NQAELENAY~

301        314
human-gremlin.pro  ---------- ----
human-cerberus.pro ---------- ----
    human-dan.pro  PPGAPHTEEE GAED
   human-beer.pro  ---------- ----
```

Fig. 1

RNA in Situ Hybridization of Mouse Embryo Sections

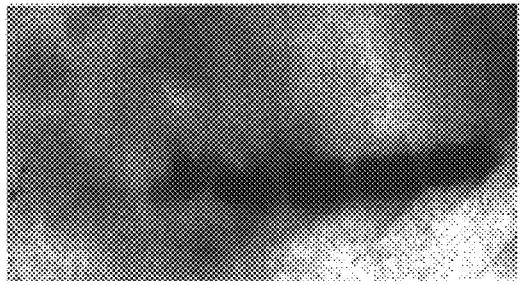
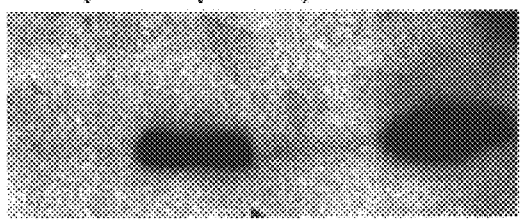
Fig. 6

COMPOSITIONS AND METHODS FOR INCREASING BONE MINERALIZATION

CROSS-REFERENCE TO RELATED APPLICATIONS

This application is a divisional of pending U.S. patent application Ser. No. 09/449,218 filed Nov. 24, 1999 (now U.S. Pat. No. 6,395,511); which application claims priority from U.S. Provisional Patent Application No. 60/110,283, filed Nov. 27, 1998.

TECHNICAL FIELD

The present invention relates generally to pharmaceutical products and methods and, more specifically, to methods and compositions suitable for increasing the mineral content of bone. Such compositions and methods may be utilized to treat a wide variety of conditions, including for example, osteopenia, osteoporosis, fractures and other disorders in which low bone mineral density are a hallmark of the disease.

BACKGROUND OF THE INVENTION

Two or three distinct phases of changes to bone mass occur over the life of an individual (see Riggs, *West J. Med.* 154:63–77, 1991). The first phase occurs in both men and women, and proceeds to attainment of a peak bone mass. This first phase is achieved through linear growth of the endochondral growth plates, and radial growth due to a rate of periosteal apposition. The second phase begins around age 30 for trabecular bone (flat bones such as the vertebrae and pelvis) and about age 40 for cortical bone (e.g., long bones found in the limbs) and continues to old age. This phase is characterized by slow bone loss, and occurs in both men and women. In women, a third phase of bone loss also occurs, most likely due to postmenopausal estrogen deficiencies. During this phase alone, women may lose an additional 10% of bone mass from the cortical bone and 25% from the trabecular compartment (see Riggs, supra). Loss of bone mineral content can be caused by a wide variety of conditions, and may result in significant medical problems. For example, osteoporosis is a debilitating disease in humans characterized by marked decreases in skeletal bone mass and mineral density, structural deterioration of bone including degradation of bone microarchitecture and corresponding increases in bone fragility and susceptibility to fracture in afflicted individuals. Osteoporosis in humans is preceded by clinical osteopenia (bone mineral density that is greater than one standard deviation but less than 2.5 standard deviations below the mean value for young adult bone), a condition found in approximately 25 million people in the United States. Another 7–8 million patients in the United States have been diagnosed with clinical osteoporosis (defined as bone mineral content greater than 2.5 standard deviations below that of mature young adult bone). Osteoporosis is one of the most expensive diseases for the health care. system, costing tens of billions of dollars annually in the United States. In addition to health care-related costs, long-term residential care and lost working days add to the financial and social costs of this disease. Worldwide approximately 75 million people are at risk for osteoporosis.

The frequency of osteoporosis in the human population increases with age, and among Caucasians is predominant in women (who comprise 80% of the osteoporosis patient pool in the United States). The increased fragility and susceptibility to fracture of skeletal bone in the aged is aggravated by the greater risk of accidental falls in this population. More than 1.5 million osteoporosis-related bone fractures are reported in the United States each year. Fractured hips, wrists, and vertebrae are among the most common injuries associated with osteoporosis. Hip fractures in particular are extremely uncomfortable and expensive for the patient, and for women correlate with high rates of mortality and morbidity.

Although osteoporosis has been defined as an increase in the risk of fracture due to decreased bone mass, none of the presently available treatments for skeletal disorders can substantially increase the bone density of adults. There is a strong perception among all physicians that drugs are needed which could increase bone density in adults, particularly in the bones of the wrist, spinal column and hip that are at risk in osteopenia and osteoporosis.

Current strategies for the prevention of osteoporosis may offer some benefit to individuals but cannot ensure resolution of the disease. These strategies include moderating physical activity (particularly in weight-bearing activities) with the onset of advanced age, including adequate calcium in the diet, and avoiding consumption of products containing alcohol or tobacco. For patients presenting with clinical osteopenia or osteoporosis, all current therapeutic drugs and strategies are directed to reducing further loss of bone mass by inhibiting the process of bone absorption, a natural component of the bone remodeling process that occurs constitutively.

For example, estrogen is now being prescribed to retard bone loss. There is, however, some controversy over whether there is any long term benefit to patients and whether there is any effect at all on patients over 75 years old. Moreover, use of estrogen is believed to increase the risk of breast and endometrial cancer.

High doses of dietary calcium with or without vitamin D has also been suggested for postmenopausal women. However, high doses of calcium can often have unpleasant gastrointestinal side effects, and serum and urinary calcium levels must be continuously monitored (see Khosla and Rigss, *Mayo Clin. Proc.* 70:978–982, 1995).

Other therapeutics which have been suggested include calcitonin, bisphosphonates, anabolic steroids and sodium fluoride. Such therapeutics however, have undesirable side effects (e.g., calcitonin and steroids may cause nausea and provoke an immune reaction, bisphosphonates and sodium fluoride may inhibit repair of fractures, even though bone density increases modestly) that may prevent their usage (see Khosla and Rigss, supra).

No currently practiced therapeutic strategy involves a drug that stimulates or enhances the growth of new bone mass. The present invention provides compositions and methods which can be utilized to increase bone mineralization, and thus may be utilized to treat a wide variety of conditions where it is desired to increase bone mass. Further, the present invention provides other, related advantages.

SUMMARY OF THE INVENTION

As noted above, the present invention provides a novel class or family of TGF-beta binding-proteins, as well as assays for selecting compounds which increase bone mineral content and bone mineral density, compounds which increase bone mineral content and bone mineral density and methods for utilizing such compounds in the treatment or prevention of a wide variety of conditions.

Within one aspect of the present invention, isolated nucleic acid molecules are provided, wherein said nucleic acid molecules are selected from the group consisting of: (a) an isolated nucleic acid molecule comprising sequence ID Nos. 1, 5, 7, 9, 11, 13, or, 15, or complementary sequence thereof; (b) an isolated nucleic acid molecule that specifically hybridizes to the nucleic acid molecule of (a) under conditions of high stringency; and (c) an isolated nucleic acid that encodes a TGF-beta binding-protein according to (a) or (b). Within related aspects of the present invention, isolated nucleic acid molecules are provided based upon hybridization to only a portion of one of the above-identified sequences (e.g., for (a) hybridization may be to a probe of at least 20, 25, 50, or 100 nucleotides selected from nucleotides 156 to 539 or 555 to 687 of Sequence ID No. 1). As should be readily evident, the necessary stringency to be utilized for hybridization may vary based upon the size of the probe. For example, for a 25-mer probe high stringency conditions could include: 60 mM Tris pH 8.0, 2 mM EDTA, 5×Denhardt's, 6×SSC. 0.1% (w/v) N-laurylsarcosine, 0.5% (w/v) NP-40 (nonidet P-40) overnight at 45 degrees C., followed by two washes with with 0.2×SSC/0.1% SDS at 45–50 degrees. For a 100-mer probe under low stringency conditions, suitable conditions might include the following: 5×SSPE, 5×Denhardt's, and 0.5% SDS overnight at 42–50 degrees, followed by two washes with 2×SSPE (or 2×SSC)/0.1% SDS at 42–50 degrees.

Within related aspects of the present invention, isolated nucleic acid molecules are provided which have homology to Sequence ID Nos. 1, 5, 7, 9, 11, 13, or 15, at a 50%, 60%, 75%, 80%, 90%, 95%, or 98% level of homology utilizing a Wilbur-Lipman algorithm. Representative examples of such isolated molecules include, for example, nucleic acid molecules which encode a protein comprising Sequence ID NOs. 2, 6, 10, 12, 14, or 16, or have homology to these sequences at a level of 50%, 60%, 75%, 80%, 90%, 95%, or 98% level of homology utilizing a Lipman-Pearson algorithm.

Isolated nucleic acid molecules are typically less than 100 kb in size, and. within certain embodiments, less than 50 kb, 25 kb, 10 kb, or even 5 kb in size. Further, isolated nucleic acid molecules, within other embodiments, do not exist in a "library" of other unrelated nucleic acid molecules (e.g., a subclone BAC such as described in GenBank Accession No. AC003098 and EMB No. AQ171546). However, isolated nucleic acid molecules can be found in libraries of related molecules (e.g., for shuffling, such as is described in U.S. Pat. Nos. 5,837,458; 5,830,721; and 5,811,238). Finally, isolated nucleic acid molecules as described herein do not include nucleic acid molecules which encode Dan, Cerberus, Gremlin, or SCGF (U.S. Pat. No. 5,780,263).

Also provided by the present invention are cloning vectors which contain the above-noted nucleic acid molecules, and expression vectors which comprise a promoter (e.g., a regulatory sequence) operably linked to one of the above-noted nucleic acid molecules. Representative examples of suitable promoters include tissue-specific promoters, and viral—based promoters (e.g., CMV-based promoters such as CMV I-E, SV40 early promoter, and MuLV LTR). Expression vectors may also be based upon, or derived from viruses (e.g., a "viral vector"). Representative examples of viral vectors include herpes simplex viral vectors, adenoviral vectors, adenovirus-associated viral vectors and retroviral vectors. Also provided are host cells containing or comprising any of above-noted vectors (including for example, host cells of human, monkey, dog, rat, or mouse origin).

Within other aspects of the present invention, methods of producing TGF-beta binding-proteins are provided, comprising the step of culturing the aforementioned host cell containing vector under conditions and for a time sufficient to produce the TGF-beta binding protein. Within further embodiments, the protein produced by this method may be further purified (eg., by column chromatography, affinity purification, and the like). Hence, isolated proteins which are encoded by the above-noted nucleic acid molecules (e.g., Sequence ID NOs. 2, 4, 6, 8, 10, 12, 14, or 16) may be readily produced given the disclosure of the subject application.

It should also be noted that the aforementioned proteins, or fragments thereof, may be produced as fusion proteins. For example, within one aspect fusion proteins are provided comprising a first polypeptide segment comprising a TGF-beta binding-protein encoded by a nucleic acid molecule as described above, or a portion thereofofat least 10, 20, 30, 50, or 100 amino acids in length, and a second polypeptide segment comprising a non-TGF-beta binding-protein. Within certain embodiments, the second polypeptide may be a tag suitable for purification or recognition (e.g., a polypeptide comprising multiple anionic amino acid residues—see U.S. Pat. No. 4,851,341), a marker (e.g., green fluorescent protein, or alkaline phosphatase), or a toxic. molecule (e.g., ricin).

Within another aspect of the present invention, antibodies are provided which are capable of specifically binding the above-described class of TGF-beta binding proteins (e.g., human BEER). Within various embodiments, the antibody may be a polyclonal antibody, or a monoclonal antibody (e.g., of human or murine origin). Within further embodiments, the antibody is a fragment of an antibody which retains the binding characteristics of a whole antibody (e.g., an F(ab')$_2$, F(ab)$_2$, Fab', Fab, or Fv fragment, or even a CDR). Also provided are hybridomas and other cells which are capable of producing or expressing the aforementioned antibodies.

Within related aspects of the invention, methods are provided detecting a TGF-beta binding protein, comprising the steps of incubating an antibody as described above under conditions and for a time sufficient to permit said antibody to bind to a TGF-beta binding protein, and detecting the binding. Within various embodiments the antibody may be bound to a solid support to facilitate washing or separation, and/or labeled. (e.g., with a marker selected from the group consisting of enzymes, fluorescent proteins, and radioisotopes).

Within other aspects of the present invention, isolated oligonucleotides are provided which hybridize to a nucleic acid molecule according to Sequence ID NOs. 1, 3, 5, 7, 9, 11, 13, 15, 17, or 18 or the complement thereto, under conditions of high stringency. Within further embodiments, the oligonucleotide may be found in the sequence which encodes Sequence ID Nos. 2, 4, 6, 8, 10, 12, 14, or 16. Within certain embodiments, the oligonucleotide is at least 15, 20, 30, 50, or 100 nucleotides in length. Within further embodiments, the oligonucleotide is labeled with another molecule (e.g. an enzyme, fluorescent molecule, or radioisotope). Also provided are primers which are capable of specifically amplifying all or a portion of the above-mentioned nucleic acid molecules which encode TGF-beta binding-proteins. As utilized herein, the term "specifically amplifying" should be understood to refer to primers which amplify the aforementioned TGF-beta binding-proteins, and not other TGF-beta binding proteins such as Dan, Cerberus, Gremlin, or SCGF (U.S. Pat. No. 5,780,263).

Within related aspects of the present invention, methods are provided for detecting a nucleic acid molecule which encodes a TGF-beta binding protein, comprising the steps of incubating an oligonucleotide as described above under conditions of high stringency, and detecting hybridization of said oligonucleotide. Within certain embodiments, the oligonucleotide may be labeled and/or bound to a solid support.

Within other aspects of the present invention, ribozymes are provided which are capable of cleaving RNA which encodes one of the above-mentioned TGF-beta binding-proteins (e.g., Sequence ID NOs. 2, 6, 8, 10, 12, 14, or 16). Such ribozymes may be composed of DNA, RNA (including 2'-O-methyl ribonucleic acids), nucleic acid analogs (e.g., nucleic acids having phosphorothioate linkages) or mixtures thereof. Also provided are nucleic acid molecules (e.g., DNA or cDNA) which encode these ribozymes, and vectors which are capable of expressing or producing the ribozymes. Representative examples of vectors include plasmids, retrotransposons. cosmids, and viral-based vectors (e.g., viral vectors generated at least in part from a retrovirus, adenovirus, or, adeno-associated virus). Also provided are host cells (e.g., human, dog, rat, or mouse cells) which contain these vectors. In certain embodiments, the host cell may be stably transformed with the vector.

Within further aspects of the invention, methods are provided for producing ribozymes either synthetically, or by in vitro or in vivo transcription. Within further embodiments, the ribozymes so produced may be further purified and/or formulated into pharmaceutical compositions (e.g., the ribozyme or nucleic acid molecule encoding the ribozyme along with a pharmaceutically acceptable carrier or diluent). Similarly, the antisense oligonucleotides and antibodies or other selected molecules described herein may be formulated into pharmaceutical compositions.

Within other aspects of the present invention, antisense oligonucleotides are provided comprising a nucleic acid molecule which hybridizes to a nucleic acid molecule according to Sequence ID NOs. 1, 3, 5, 7, 9, 11, 13, or 15, or the complement thereto, and wherein said oligonucleotide inhibits the expression of TGF-beta binding protein as described herein (e.g., human BEER). Within various embodiments, the oligonucleotide is 15, 20, 25, 30, 35, 40, or 50 nucleotides in length. Preferably, the oligonucleotide is less than 100, 75, or 60 nucleotides in length. As should be readily evident, the oligonucleotide may be comprised of one or more nucleic acid analogs, ribonucleic acids, or deoxyribonucleic acids. Further, the oligonucleotide may be modified by one or more, linkages, including for example, covalent linkage such as a phosphorothioate linkage, a phosphotriester linkage, a methyl phosphonate linkage, a methylene(methylimino) linkage, a morpholino linkage, an amide linkage, a polyamide linkage, a short chain alkyl intersugar linkage, a cycloalkyl intersugar linkage, a short chain heteroatomic intersugar linkage and a heterocyclic intersugar linkage. One representative example of a chimeric oligonucleotide is provied in U.S. Pat. No. 5,989,912.

Within yet another aspect of the present invention, methods are provided for increasing bone mineralization, comprising introducing into a warm-blooded animal an effective amount of the ribozyme as described above. Within related aspects, such methods comprise the step of introducing into a patient an effective amount of the nucleic acid molecule or vector as described herein which is capable of producing the desired ribozyme, under conditions favoring transcription of the nucleic acid molecule to produce the ribozyme.

Within other aspects of the invention transgenic, non-human animals are provided. Within one embodiment a transgenic animal is provided whose germ cells and somatic cells contain a nucleic acid molecule encoding a TGF-beta binding-protein as described above which is operably linked to a promoter effective for the expression of the gene, the gene being introduced into the animal, or an ancestor of the animal, at an embryonic stage, with the proviso that said animal is not a human. Within other embodiments, transgenic knockout animals are provided, comprising an animal whose germ cells and somatic cells comprise a disruption of at least one allele of an endogenous nucleic acid molecule which hybridizes to a nucleic acid molecule which encodes a TGF-binding protein as described herein, wherein the disruption prevents transcription of messenger RNA from said allele as compared to an animal without the disruption, with the proviso that the animal is not a human. Within various embodiments, the disruption is a nucleic acid deletion, substitution, or, insertion. Within other embodiments the transgenic animal is-a mouse, rat, sheep, pig, or dog.

Within further aspects of the invention, kits are provided for the detection of TGF-beta binding-protein gene expression, comprising a container that comprises a nucleic acid molecule, wherein the nucleic acid molecule is selected from the group consisting of (a) a nucleic acid molecule comprising the nucleotide sequence of SEQ ID NOs: 1, 3, 5, 7, 9, 11, 13, or 15; (b) a nucleic acid molecule comprising the complement of the nucleotide sequence of (a), (c) a nucleic acid molecule that is a fragment of (a) or (b) of at least 15, 20 30, 50, 75, or, 100 nucleotides in length. Also provided are kits for the detection of a TGF-beta binding-protein which comprise a container that comprise one of the TGF-beta binding protein antibodies described herein.

For example, within one aspect of the present invention methods are provided for determining whether a selected molecule is capable of increasing bone mineral content, comprising the steps of (a) mixing one or more candidate molecules with TGF-beta-binding-protein encoded by the nucleic acid molecule according to claim 1 and a selected member of the TGF-beta family of proteins (e.g., BMP 5 or 6), (b) determining whether the candidate molecule alters the signaling of the TGF-beta family member, or alters the binding of the TGF-beta binding-protein to the TGF-beta family member. Within certain embodiments, the molecule alters the ability of TGF-beta to function as a positive regulator of mesenchymal cell differentiation. Within this aspect of the present invention, the candidate molecule(s) may alter signaling or binding by, for example, either decreasing (e.g., inhibiting), or increasing (e.g., enhancing) signaling or binding.

Within yet another aspect, methods are provided for determining whether a selected molecule is capable of increasing bone mineral content, comprising the step of determining whether a selected molecule inhibits the binding of TGF-beta binding-protein to bone, or an analogue thereof. Representative examples of bone or analogues thereof include hydroxyapatite and primary human bone samples obtained via biopsy.

Within certain embodiments of the above-recited methods, the selected molecule is contained within a mixture of molecules and the methods may further comprise the step of isolating one or more molecules which are functional within the assay. Within yet other embodiments, TGF-beta family of proteins is bound to a solid support and the binding of TGF-beta binding-protein is measured or TGF-beta binding-protein are bound to a solid support and the binding of TGF-beta proteins are measured.

Utilizing methods such as those described above, a wide variety of molecules may be assayed for their ability to increase bone mineral content by inhibiting the binding of the TGF-beta binding-protein to the TGF-beta family of proteins. Representative examples of such molecules include proteins or peptides organic molecules, and nucleic acid molecules.

Within other related aspects of the invention, methods are provided for increasing bone mineral content in a warm-blooded animal, comprising the step of administering to a warm-blooded animal a therapeutically effective amount of a molecule identified from the assays recited herein. Within another aspect, methods are provided for increasing bone mineral content in a warm-blooded animal, comprising the step of administering to a warm-blooded animal a therapeutically effective amount of a molecule which inhibits the binding of the TGF-beta binding-protein to the TGF-beta super-family of proteins, including bone morphogenic proteins (BMPs). Representative examples of suitable molecules include antisense molecules, ribozymes, ribozyme genes, and antibodies (e.g., a humanized antibody) which specifically recognize and alter the activity of the TGF-beta binding-protein.

Within another aspect of the present invention, methods are provided for increasing bone mineral content in a warm-blooded animal, comprising the steps of (a) introducing into cells which home to the bone a vector which directs the expression of a molecule which inhibits the binding of the TGF-beta binding-protein to the TGF-beta family of proteins and bone morphogenic proteins (BMPs), and (b) administering the vector-containing cells to a warm-blooded animal. As utilized herein, it should be understood that cells "home to bone" if they localize within the bone matrix after peripheral administration. Within one embodiment, such methods further comprise, prior to the step of introducing, isolating cells from the marrow of bone which home to the bone. Within a further embodiment, the cells which home to bone are selected from the group consisting of CD34+ cells and osteoblasts.

Within other aspects of the present invention, molecules are provided (preferably isolated) which inhibit the binding of the TGF-beta binding-protein to the TGF-beta super-family of proteins.

Within further embodiments, the molecules may be provided as a composition, and can further comprise an inhibitor of bone resorption. Representative examples of such inhibitors include calcitonin, estrogen, a bisphosphonate, a growth factor having anti-resorptive activity and tamoxifen.

Representative examples of molecules which may be utilized in the afore-mentioned therapeutic contexts include, e.g., ribozymes, ribozyme genes. antisense molecules, and/or antibodies (e.g., humanized antibodies). Such molecules may depending upon their selection, used to alter, antagonize, or agonize the signalling or binding of a TGF-beta binding-protein family member as described herein.

Within various embodiments of the invention, the above-described molecules and methods of treatment or prevention may be utilized on conditions such as osteoporosis, osteomalasia, periodontal disease, scurvy, Cushing's Disease. bone fracture and conditions due to limb immobilization and steroid usage.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS

FIG. 1 is a schematic illustration comparing the amino acid sequence of Human Dan (SEQ ID NO:44); Human Gremlin (SEQ ID NO:42); Human Cerberus (SEQ ID NO:43) and Human Beer (SEQ ID NO:45). Arrows indicate the Cysteine backbone.

FIG. 4 illustrates, by western blot analysis, the specificity of three different polyclonal antibodies for their respective antigens (described in more detail in EXAMPLE 4).

FIG. 6 demonstrates that the ionic interaction between the TGF-beta binding-protein, Beer, and BMP-5 has a dissociation constant in the 15–30 nM range.

DETAILED DESCRIPTION OF THE INVENTION

Definitions

Figure 2:
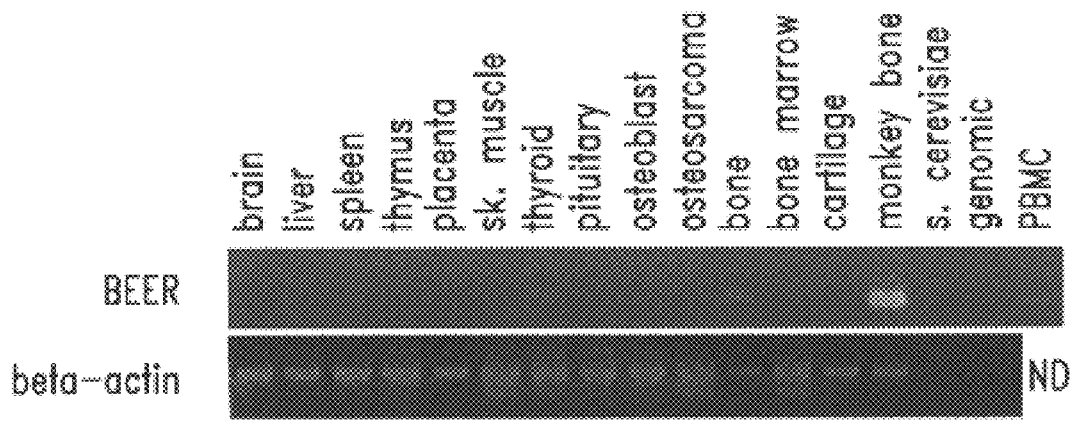
FIG. 2 summarizes the results obtained from surveying a variety of human tissues for the expression of a TGF-beta binding-protein gene, specifically, the Human Beer gene. A semi-quantitative Reverse Transcription-Polymerase Chain Reaction (RT-PCR) procedure was used to amplify a portion of the gene from first-strand cDNA synthesized from total RNA (described in more detail in EXAMPLE 2A).
Figure 3A:
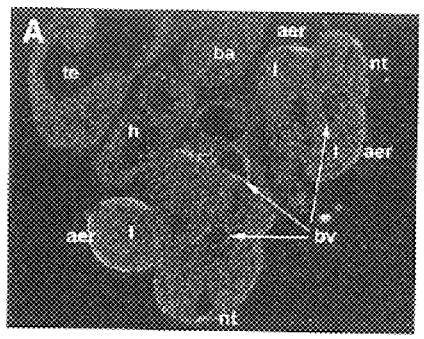
FIG. 3 summarizes the results obtained from RNA in situ hybridization of mouse embryo sections, using a cRNA probe that is complementary to the mouse Beer transcript (described in more detail in EXAMPLE 2B). Panel A is a transverse section of 10.5 dpc embryo. Panel B is a sagittal section of 12.5 dpc embryo and panels C and D are sagittal sections of 15.5 dpc embryos.
Figure 3B:
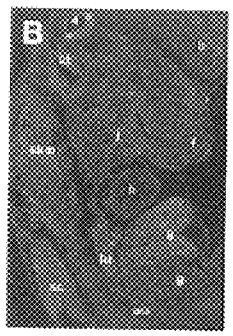
Figure 3C:
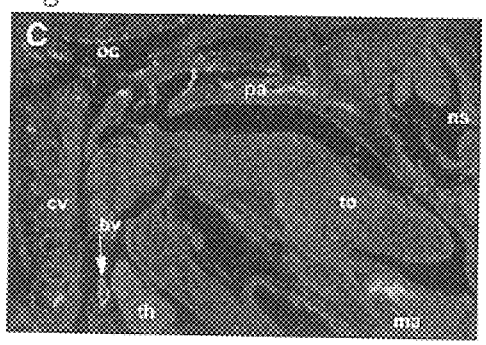
Figure 3D:
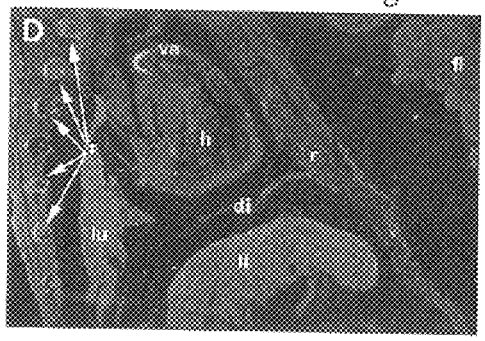
Figure 4A:
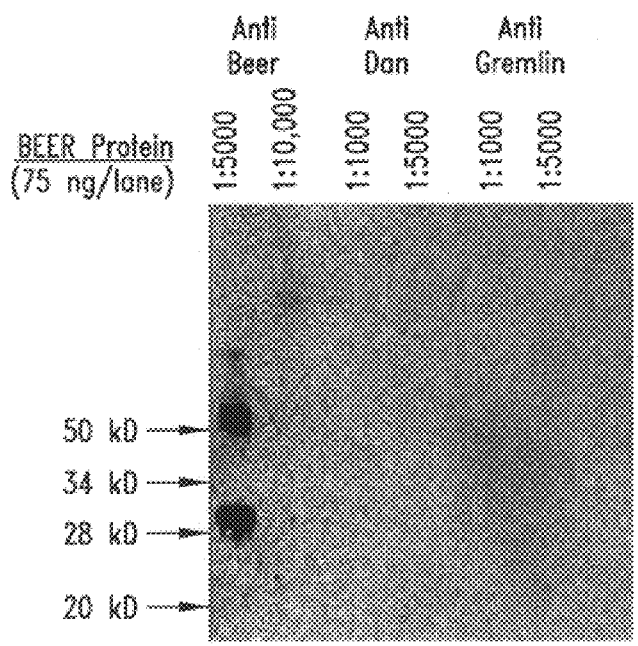
FIG. 4A shows specific reactivity of an anti-H. Beer antibody for H. Beer antigen, but not H. Dan or H. Gremlin.
Figure 4B:
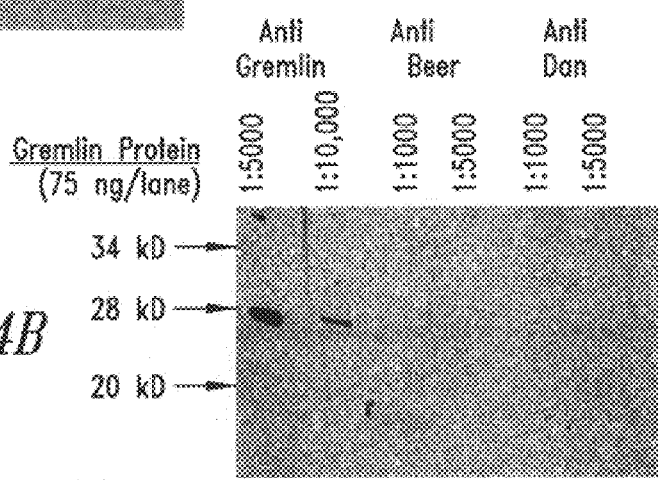
FIG. 4B shows reactivity of an anti-H. Gremlin antibody for H. Gremlin antigen, but not H. Beer or H. Dan.
Figure 4C:
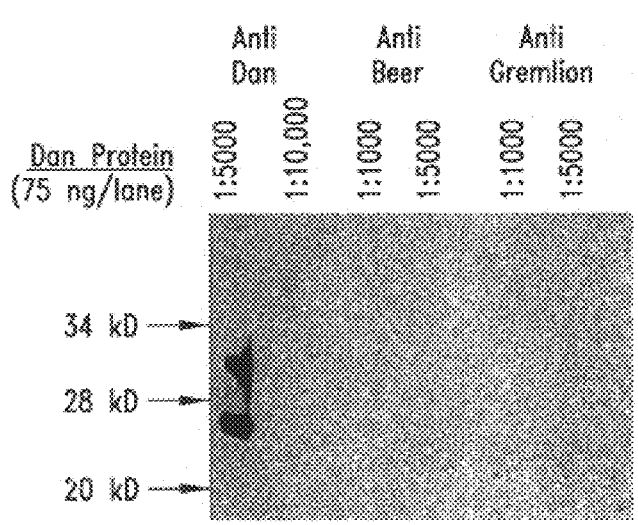
FIG. 4C shows reactivity of an anti-H. Dan antibody for H. Dan, but not H. Beer or H. Gremlin.

Prior to setting forth the invention in detail, it may be helpful to an understanding thereof to set forth definitions of certain terms and to list and to define the abbreviations that will be used hereinafter.

"Molecule" should be understood to include proteins or peptides (e.g., antibodies, recombinant binding partners, peptides with a desired binding affinity), nucleic acids (e.g., DNA, RNA, chimeric nucleic acid molecules, and nucleic acid analogues such as PNA); and organic or inorganic compounds.

"TGF-beta" should be understood to include any known or novel member of the TGF-beta super-family, which also includes bone morphogenic proteins (BMPs).

"TGF-beta receptor" should be understood to refer to the receptor specific for a particular member of the TGF-beta super-family (including bone morphogenic proteins (BMPs)).

"TGF-beta binding-protein" should be understood to refer to a protein with specific binding affinity for a particular member or subset of members of the TGF-beta super-family (including bone morphogenic proteins (BMPs)). Specific examples of TGF-beta binding-proteins include proteins encoded by Sequence ID Nos. 1, 5, 7, 9, 11, 13, and 15.

Inhibiting the "binding of the TGF-beta binding-protein to the TGF-beta family of proteins and bone morphogenic proteins (BMPs)" should be understood to refer to molecules which allow the activation of TGF-beta or bone morphogenic proteins (BMPs), or allow the binding of TGF-beta family members including bone morphogenic proteins (BMPs) to their respective receptors, by removing or preventing TGF-beta from binding to TGF-binding-protein. Such inhibition may be accomplished, for example, by molecules which inhibit the binding of the TGF-beta binding-protein to specific members of the TGF-beta superfamily.

"Vector" refers to an assembly which is capable of directing the expression of desired protein. The vector must include transcriptional promoter elements which are operably linked to the gene(s) of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

An "isolated nucleic acid molecule" is a nucleic acid molecule that is not integrated in the genomic DNA of an organism. For example, a DNA molecule that encodes a TGF-binding protein that has been separated from the genomic DNA of a eukaryotic cell is an isolated DNA molecule. Another example of an isolated nucleic acid molecule is a chemically-synthesized nucleic acid molecule that is not integrated in the genome of an organism. The isolated nucleic acid molecule may be genomic DNA, cDNA, RNA, or composed at least in part of nucleic acid analogs.

An "isolated polypeptide" is a polypeptide that is essentially free from contaminating cellular components, such as carbohydrate, iipid, or other proteinaceous impurities associated with the polypeptide in nature. Within certain embodiments, a particular protein preparation contains an isolated polypeptide if it appears nominally as a single band on SDS-PAGE gel with Coomassie Blue staining. "Isolated", when referring to organic molecules means that the compounds are greater than 90 percent pure utilizing methods which are well known in the art (e.g., NMR, melting point).

"Sclerosteosis" Sclerosteosis is a term that was applied by Hansen (1967) (Hansen, H. G., Sklerosteose. In: Opitz, H.; Schmid, F., Handbuch der Kinderheilkunde. Berlin: Springer (pub.) 6 1967. Pp. 351–355) to a disorder similar to van Buchem hyperostosis corticalis generalisata but possibly differing in radiologic appearance of the bone changes and in the presence of asymmetric cutaneous syndactyly of the index and middle fingers in many cases. The jaw has an unusually square appearance in this condition.

"Humanized antibodies" are recombinant proteins in which murine complementary determining regions of monoclonal antibodies have been transferred from heavy and light variable chains of the murine immunoglobulin into a human variable domain.

As used herein, an "antibody framrent" is a portion of an antibody such as F(ab')$_2$, F(ab)$_2$, Fab', Fab, and the like. Regardless of structure, an antibody fragment binds with the same antigen that is recognized by the intact antibody. For example, an anti-TGF-beta binding-protein monoclonal antibody fragment binds with an epitope of TGF-beta binding-protein.

The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, enzymes, and other marker moieties.

As used herein, an "immunoconjugate" is a molecule comprising an anti-TGF-beta binding-protein antibody, or an antibody fragment, and a detectable label. An immunoconjugate has roughly the same, or only slightly reduced, ability to bind TGF-beta binding-protein after conjugation as before conjugation.

Abbreviations: TGF-beta—"Transforming Growth Factor-beta"; TGF-bBP—"Transforming Growth Factor-beta binding-protein" (one representative TGF-bBP is designated "H. Beer"); BMP—"bone morphogenic protein"; PCR—"polymerase chain reaction"; RT-PCR—PCR process in which RNA is first transcribed into DNA at the first step using reverse transcriptase (RT); cDNA—any DNA made by copying an RNA sequence into DNA form.

As noted above, the present invention provides a novel class of TGF-beta binding-proteins, as well as methods and compositions for increasing bone mineral content in warm-blooded animals. Briefly, the present inventions are based upon the unexpected discovery that a mutation in the gene which encodes a novel member of the TGF-beta binding-protein family results in a rare condition (sclerosteosis) characterized by bone mineral contents which are one- to four-fold higher than in normal individuals. Thus, as discussed in more detail below this discovery has led to the development of assays which may be utilized to select molecules which inhibit the binding of the TGF-beta binding-protein to the TGF-beta family of proteins and bone morphogenic proteins (BMPs), and methods of utilizing such molecules for increasing the bone mineral content of warm-blooded animals (including for example, humans).

Discussion of the Disease Known as Sclerosteosis

Sclerosteosis is a term that was applied by Hansen (1967) (Hansen, H. G., Sklerosteose.In: Opitz, H.; Schmid, F., Handbuch der Kinderheilkunde. Berlin: Springer (pub.) 6 1967. Pp. 351–355) to a disorder similar to van Buchem hyperostosis corticalis generalisata but possibly differing in radiologic appearance of the bone changes and in the presence of asymmetric cutaneous syndactyly of the index and middle fingers in many cases.

Sclerosteosis is now known to be an autosomal semi-dominant disorder which is characterized by widely disseminated sclerotic lesions of the bone in the adult. The condition is progressive. Sclerosteosis also has a developmental aspect which is associated with syndactyly (two or more fingers are fused together). The Sclerosteosis Syndrome is associated with large stature and many affected individuals attain a height of six feet or more. The bone mineral content of homozygotes can be 1 to 6 fold over normal individuals and bone mineral density can be 1 to 4 fold above normal values (e.g., from unaffected siblings).

The Sclerosteosis Syndrome occurs primarily in Afrikaaners of Dutch descent in South Africa. Approximately 1/140 individuals in the Afrikaaner population are carriers of the mutated gene (heterozygotes). The mutation shows 100% penetrance. There are anecdotal reports of increased of bone mineral density in heterozygotes with no associated pathologies (syndactyly or skull overgrowth).

It appears at the present time that there is no abnormality of the pituitary-hypothalamus axis in Sclerosteosis. In particular, there appears to be no over-production of growth hormone and cortisone. In addition, sex hormone levels are normal in affected individuals. However, bone turnover markers (osteoblast specific alkaline phosphatase, osteocalcin, type 1 procollagen C' propeptide (PICP), and total alkaline phosphatase; (see Comier, C., Curr. Opin. in Rheu. 7:243, 1995) indicate that there is hyperosteoblastic activity associated with the disease but that there is normal to slightly decreased osteoclast activity as measured by markers of bone resorption (pyridinoline, deoxypryridinoline, N-telopeptide, urinary hydroxyproline, plasma tartrate-resistant acid phosphatases and galactosyl hydroxylysine (see Comier, supra)).

Sclerosteosis is characterized by the continual deposition of bone throughout the skeleton during the lifetime of the affected individuals. In homozygotes the continual deposition of bone mineral leads to an overgrowth of bone in areas of the skeleton where there is an absence of mechanoreceptors (skull, jaw, cranium). In homozygotes with Sclerosteosis, the overgrowth of the bones of the skull leads to cranial compression and eventually to death due to excessive hydrostatic pressure on the brain stem. In all other parts of the skeleton there is a generalized and diffuse sclerosis. Cortical areas-of the long bones are greatly thickened resulting in a substantial increase in bone strength. Trabecular connections are increased in thickness which in turn increases the strength of the trabecular bone. Sclerotic bones appear unusually opaque to x-rays.

As described in more detail in Example 1, the rare genetic mutation that is responsible for the Sclerosteosis syndrome has been localized to the region of human chromosome 17 that encodes a novel member of the TGF-beta binding-protein family (one representative example of which is designated "H. Beer"). As described in more detail below, based upon this discovery, the mechanism of bone mineralization is more fully understood, allowing the development of assays for molecules which increase bone mineralization, and use of such molecules to increase bone mineral content, and in the treatment or prevention of a wide number of diseases.

TGF-beta Super-family

The Transforming Growth Factor-beta (TGF-beta) super-family contains a variety of growth factors that share common sequence elements and structural motifs (at both the secondary and tertiary levels). This protein family is known to exert a wide spectrum of biological responses on a large variety of cell types. Many of them have important functions during the embryonic development in pattern formation and tissue specification; in adults they are involved, e.g., in wound healing and bone repair and bone remodeling, and in the modulation of the immune system. In addition to the three TGF-beta's, the super-family includes the Boric Morphogenic Proteins (BMPs), Activins, Inhibins, Growth and Differentiation Factors (GDFs), and Glial-Derived Neurotrophic Factors (GDNFs). Primary classification is established through general sequence features that bin a specific protein into a general sub-family. Additional stratification within the sub-family is possible due to stricter sequence conservation between members of the smaller group. In certain instances, such as with BMP-5, BMP-6 and BMP-7, this can be as high as 75 percent amino acid homology between members of the smaller group. This level of identity enables a single representative sequence to illustrate the key biochemical elements of the sub-group that separates it from other members of the larger family.

TGF-beta signals by inducing the formation of hetero-oligomeric complexes of type I and type II receptors. The crystal structure of TGF-beta2 has been determined. The general fold of the TGF-beta2 monomer contains a stable, compact, cysteine knotlike structure formed by three disulphide bridges. Dimerization, stabilized by one disulphide bridge, is antiparallel.

TGF-beta family members initiate their cellular action by binding to receptors with intrinsic serine/threonine kinase activity. This receptor family consists of two subfamilies, denoted type I and type II receptors. Each member of the TGF-beta family binds to a characteristic combination of type I and type II receptors, both of which are needed for signaling. In the current model for TGF-beta receptor activation, TGF-beta first binds to the type II receptor (TbR-II), which occurs in the cell membrane in an oligomeric form with activated kinase. Thereafter, the type I receptor (TbR-I), which can not bind ligand in the absence of TbR-II, is recruited into the complex. TbR-II then phosphorylates TbR-I predominantly in a domain rich in glycine and serine residues (GS domain) in the juxtamembrane region, and thereby activates TbR-I.

Thus far seven type I receptors and five type II receptors have been identified.

Bone Morphogenic Proteins (BMPS) are Key Regulatory Proteins in Determining Bone Mineral Density in Humans A major advance in the understanding of bone formation was the identification of the bone morphogenic proteins (BMPs), also known as osteogenic proteins (OPs), which regulate cartilage and bone differentiation in vivo. BMPs/OPs induce endochondral bone differentiation through a cascade of events which include formation of cartilage, hypertrophy and calcification of the cartilage, vascular invasion, differentiation of osteoblasts, and formation of bone. As described above, the BMPs/OPs (BMP 2–14, and osteogenic protein 1 and -2, OP-1 and OP-2) are members of the TGF-beta super-family. The striking evolutionary conservation between members the BMP/OP sub-family suggests that they are critical in the normal development and function of animals. Moreover, the presence of multiple forms of BMPs/OPs raises an important question about the biological relevance of this apparent redundancy. In addition to postfetal chondrogenesis and osteogenesis, the BMPs/OPs play multiple roles in skeletogenesis (including the development of craniofacial and dental tissues) and in embryonic development and organogenesis of parenchymatous organs, including the kidney. It is now understood that nature relies on common (and few) molecular mechanisms tailored to provide the emergence of specialized tissues and organs. The BMP/OP super-family is an elegant example of nature parsimony in programming multiple specialized functions deploying molecular isoforms with minor variation in amino acid motifs within highly conserved carboxy-terminal regions.

BMP Antagonism

The BMP and Activin sub-families are subject to significant post-translational regulation. An intricate extracellular control system exists, whereby a high affinity antagonist is synthesized and exported, and subsequently complexes selectively with BMPs or activins to disrupt their biological activity (W. C. Smith (1999) TIG 15(1) 3–6). A number of these natural antagonists have been identified, and based on sequence divergence appear to have evolved independently due to the lack of primary sequence conservation. There has been no structural work to date on this class of proteins. Studies of these antagonists has highlighted a distinct preference for interacting and neutralizing BMP-2 and BMP-4. Furthermore, the mechanism of inhibition seems to differ for the different antagonists (S. Iemura et al. (1998) Proc Natl Acad Sci USA 95 9337–9342).

Novel TGF-beta Binding-proteins

1. Background re: TGF-beta Binding-proteins

As noted above, the present invention provides a novel class of TGF-beta binding-proteins that possess a nearly identical cysteine (disulfide) scaffold when compared to Human DAN, Human Gremlin, and Human Cerberus, and SCGF (U.S. Pat. No. 5,780,263) but almost no homology at the nucleotide level (for background information, see generally Hsu, D. R., Economides, A. N., Wang, X., Eimon, P. M., Harland, R. M., "The Xenopus Dorsalizing Factor Gremlin Identifies a Novel Family of Secreted Proteins that Antagonize BMP Activities," *Molecular Cell* 1:673–683, 1998).

One representative example of the novel class of TGF-beta binding-proteins is disclosed in Sequence ID Nos. 1, 5, 9, 11, 13, and 15. Representative members of this class of binding proteins should also be understood to include variants of the TGF-beta binding-protein (e.g., Sequence ID Nos. 5 and 7). As utilized herein, a "TGF-beta binding-protein variant gene" refers to nucleic acid molecules that encode a polypeptide having an amino acid sequence that is a modification of SEQ ID Nos: 2, 10, 12, 14 or 16. Such variants include naturally-occurring polymorphisms or allelic variants of TGF-beta binding-protein genes, as well as synthetic genes that contain conservative amino acid substitutions of these amino acid sequences. Additional variant forms of a TGF-beta binding-protein gene are nucleic acid molecules that contain insertions or deletions of the nucleotide sequences described herein. TGF-beta binding-protein variant genes can be identified by determining whether the genes hybridize with a nucleic acid molecule having the nucleotide sequence of SEQ ID Nos: 1, 5, 7, 9, 11, 13, or 15 under stringent conditions. In addition, TGF-beta binding-protein variant genes should encode a protein having a cysteine backbone.

As an alternative, TGF-beta binding-protein variant genes can be. identified by sequence comparison. As used herein, two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski. *The Internet and the New Biology: Tools for Genontic and Molecular Research* (ASM Press, Inc. 1997), Wu et al. (eds.), "Information Superhighway and Computer Databases of Nucleic Acids and Proteins," in Methods in Gene Biotechnology, pages 123–151 (CRC Press, Inc. 1997), and Bishop (ed.), Guide to Human Genome Computing, 2nd Edition (Academic Press, Inc. 1998)).

A variant TGF-beta binding-protein should have at least a 50% amino acid sequence identity to SEQ ID NOs: 2, 6, 10, 12, 14 or 16 and preferably, greater than 60%, 65%, 70%, 75%, 80%, 85%, 90%, or 95% identity. Alternatively, TGF-beta binding-protein variants can be identified by having at least a 70% nucleotide sequence identity to SEQ ID NOs: 1, 5, 9, 11, 13 or 15. Moreover, the present invention contemplates TGF-beta binding-protein gene variants having greater than 75%, 80%, 85%, 90%, or 95% identity to SEQ ID NO:1. Regardless of the particular method used to identify a TGF-beta binding-protein variant gene or variant TGF-beta binding-protein, a variant TGF-beta binding-protein or a polypeptide encoded by a variant TGF-beta binding-protein gene can be functionally characterized by, for example, its ability to bind to and/or inhibit the signaling of a selected member of the TGF-beta family of proteins, or by its ability to bind specifically to an anti-TGF-beta binding-protein antibody.

The present invention includes functional fragments of TGF-beta binding-protein genes. Within the context of this invention, a "functional fragment" of a TGF-beta binding-protein gene refers to a nucleic acid molecule that encodes a portion of a TGF-beta binding-protein polypeptide which either (1) possesses the above-noted function activity, or (2) specifically binds with an anti-TGF-beta binding-protein antibody. For example, a functional fragment of a TGF-beta binding-protein gene described herein comprises a portion of the nucleotide sequence of SEQ ID Nos: 1, 5, 9, 11, 13, or 15.

2. Isolation of the TGF-beta Binding-protein Gene

DNA molecules encoding a binding-protein gene can be obtained by screening a human cDNA or genomic library using polynucleotide probes based upon, for example, SEQ ID NO: 1.

For example, the first step in the preparation of a cDNA library is to isolate RNA using methods well-known to those of skill in the art. In general, RNA isolation techniques must provide a method for breaking cells, a means of inhibiting RNase-directed degradation of RNA, and a method of separating RNA from DNA, protein, and polysaccharide contaminants. For example, total RNA can be isolated by freezing tissue in liquid nitrogen, grinding the frozen tissue with a mortar and pestle to lyse the cells, extracting the ground tissue with a solution of phenol/chloroform to remove proteins, and separating RNA from the remaining impurities by selective precipitation with lithium chloride (see, for example, Ausubel et al. (eds.), *Short Protocols in Molecular Biology, 3rd Edition*, pages 4-1 to 4-6 (John Wiley & Sons 1995) ["Ausubel (1995)"]; Wu et al., *Methods in Gene Biotechnology*, pages 33–41 (CRC Press, Inc. 1997) ["Wu (1997)"]).

Alternatively, total RNA can be isolated by extracting ground tissue with guanidinium isothiocyanate, extracting with organic solvents, and separating RNA from contaminants using differential centrifugation (see, for example, Ausubel (1995) at pages 4-1 to 4-6; Wu (1997) at pages 33–41).

In order to construct a cDNA library, poly(A)$^+$ RNA must be isolated from a total RNA preparation. Poly(A)$^+$ RNA can be isolated from total RNA by using the standard technique of oligo(dT)-cellulose chromatography (see, for example, Ausubel (1995) at pages 4-11 to 4-12).

Double-stranded cDNA molecules are synthesized from poly(A)+ RNA using techniques well-known to those in the art. (see, for example, Wu (1997) at pages 41–46). Moreover, commercially available kits can be used to synthesize double-stranded cDNA molecules. For example, such kits are available from Life Technologies, Inc. (Gaithersburg, Md.), CLONTECH Laboratories, Inc. (Palo Alto, Calif.), Promega Corporation (Madison, Wis.) and Stratagene Cloning Systems (La Jolla, Calif.).

The basic approach for obtaining TGF-beta binding-protein cDNA clones can be modified by constructing a subtracted cDNA library which is enriched in TGF-binding-protein-specific cDNA molecules. Techniques for constructing subtracted libraries are well-known to those of skill in the art (see, for example, Sargent, "Isolation of Differentially Expressed Genes," in *Meth. Enzymol.* 152:423, 1987, and Wu et al. (eds.), "Construction and Screening of Subtracted and Complete Expression cDNA Libraries," in *Methods in Gene Biotechnology*, pages 29–65 (CRC Press, Inc. 1997)).

Various cloning vectors are appropriate for the construction of a cDNA library. For example, a cDNA library can be prepared in a vector derived from bacteriophage, such as a λgt10 vector (see, for example, Huynh et al., "Constructing and Screening cDNA Libraries in λgt10 and λgt11," in *DNA Cloning: A Practical Approach Vol.* 1, Glover (ed.), page 49 (IRL Press, 1985); Wu (1997) at pages 47–52).

Alternatively, double-stranded cDNA molecules can be inserted into a plasmid vector, such as a pBluescript vector (Stratagene Cloning Systems; La Jolla, Calif.), a LambdaGEM-4 (Promega Corp.; Madison. Wis.) or other commercially available vectors. Suitable cloning vectors also can be obtained from the American Type Culture Collection (Rockville, Md.).

In order to amplify the cloned cDNA molecules, the cDNA library is inserted into a prokaryotic host, using standard techniques. For example, a cDNA library can be introduced into competent *E. coli* DH5 cells, which can be obtained from Life Technologies, Inc. (Gaithersburg, Md.).

A human genomic DNA library can be prepared by means well-known in the art (see, for example, Ausubel (1995) at pages 5-1 to 5-6; Wu (1997) at pages 307–327). Genomic DNA can be isolated by lysing tissue with the detergent Sarkosyl, digesting the lysate with proteinase K, clearing insoluble debris from the lysate by centrifugation, precipitating nucleic acid from the lysate using isopropanol, and purifying resuspended DNA on a cesium chloride density gradient.

DNA fragments that are suitable for the production of a genomic library can be obtained by the random shearing of genomic DNA or by the partial digestion of genomic DNA with restriction endonucleases. Genomic DNA fragments can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for such manipulation are well-known in the art (see, for example, Ausubel (1995) at pages 5-1 to 5-6; Wu (1997) at pages 307–327).

Nucleic acid molecules that encode a TGF-beta binding-protein gene can also be obtained using the polymerase chain reaction (PCR) with oligonucleotide primers having nucleotide sequences that are based upon the nucleotide sequences of the human TGF-beta binding-protein gene, as described herein. General methods for screening libraries with PCR are provided by, for example, Yu et al., "Use of the Polymerase Chain Reaction to Screen Phage Libraries," in *Methods in Molecular Biology, Vol.* 15: *PCR Protocols: Current Methods and Applications,* White (ed.), pages 211–215 (Humana Press. Inc. 1993). Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol.* 15: *PCR Protocols: Current Methods and Applications,* White (ed.), pages 317–337 (Humana Press, Inc. 1993).

Alternatively, human genomic libraries can be obtained from commercial sources such as Research Genetics (Huntsville, Ala.) and the American Type Culture Collection (Rockville, Md.).

A library containing cDNA or genomic clones can be screened with one or more polynucleotide probes based upon SEQ ID NO: 1, using standard methods (see, for example, Ausubel (1995) at pages 6-1 to 6-11).

Anti-TGF-beta binding-protein antibodies, produced as described below, can also be used to isolate DNA sequences that encode TGF-beta binding-protein genes from cDNA libraries. For example, the antibodies can be used to screen λgt11 expression libraries, or the antibodies can be used for immunoscreening following hybrid selection and translation (see, for example, Ausubel (1995) at pages 6-12 to 6-16; Margolis et al., "Screening λ expression libraries with antibody and protein probes," in *DNA Cloning* 2: *Expression Systems,* 2nd Edition, Glover et al. (eds.), pages 1–14 (Oxford University Press 1995)).

The sequence of a TGF-beta binding-protein cDNA or TGF-beta binding-protein genomic fragment can be determined using standard methods. Moreover, the identification of genomic fragments containing a TGF-beta binding-protein promoter or regulatory element can be achieved using well-established techniques, such as deletion analysis (see, generally, Ausubel (1995)).

As an alternative, a TGF-beta binding-protein gene can be obtained by synthesizing DNA molecules using mutually priming long oligonucleotides and the nucleotide sequences described herein (see, for example, Ausubel (1995) at pages 8-8 to 8-9). Established techniques using the polymerase chain reaction provide the ability to synthesize DNA molecules at least two kilobases in length (Adang et al., *Plant Molec. Biol.* 21:1131, 1993; Bambot et al., *PCR Methods and Applications* 2:266, 1993; Dillon et al., "Use of the Polymerase Chain Reaction for the Rapid Construction of Synthetic Genes," in *Methods in Molecular Biology, Vol* 15: *PCR Protocols: Current Methods and Applications,* White (ed.), pages 263–268, (Humana Press, Inc. 1993); Holowachuk et al., *PCR Methods Appl.* 4:299, 1995).

3. Production of TGF-beta Binding-protein Genes

Nucleic acid molecules encoding variant TGF-beta binding-protein genes can be obtained by screening various cDNA or genomic libraries with polynucleotide probes having nucleotide sequences based upon SEQ ID NO: 1, 5, 9, 11, 13, or 15, using procedures described above. TGF-beta binding-protein gene variants can also be constructed synthetically. For example, a nucleic acid molecule can be devised that encodes a polypeptide having a conservative amino acid change, compared with the amino acid sequence of SEQ ID NOs: 2, 6, 8, 10, 12, 14, or 16. That is, variants can be obtained that contain one or more amino acid substitutions of SEQ ID NOs: 2, 6, 8, 10, 12, 14 or 16, in which an alkyl amino acid is substituted for an alkyl amino acid in a TGF-beta binding-protein amino acid sequence, an aromatic amino acid is substituted for an aromatic amino acid in a TGF-beta binding-protein amino acid sequence, a sulfur-containing amino acid is substituted for a sulfur-containing amino acid in a TGF-beta binding-protein amino acid sequence, a hydroxy-containing amino acid is substituted for a hydroxy-containing amino acid in a TGF-beta binding-protein amino acid sequence, an acidic amino acid is substituted for an acidic amino acid in a TGF-beta binding-protein amino acid sequence, a basic amino acid is substituted for a basic amino acid in a TGF-beta binding-protein amino acid sequence, or a dibasic monocarboxylic amino acid is substituted for a dibasic monocarboxylic amino acid in a TGF-beta binding-protein amino acid sequence.

Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. In making such substitutions, it is important to, where possible, maintain the cysteine backbone outlined in FIG. 1.

Conservative amino acid changes in a TGF-beta binding-protein gene can be introduced by substituting nucleotides for the nucleotides recited in SEQ ID NO:1. Such "conservative amino acid" variants can be obtained, for example, by oligonucleotide-directed mutagenesis, linker-scanning mutagenesis, mutagenesis using the polymerase chain reaction, and the like (see Ausubel (1995) at pages 8-10 to 8-22; and McPherson (ed.), *Directed Mutagenesis: A Practical Approach* (IRL Press 1991)). The functional ability of such variants can be determined using a standard method, such as the assay described herein. Alternatively, a variant TGF-beta binding-protein polypeptide can be identified by the ability to specifically bind anti-TGF-beta binding-protein antibodies.

Routine deletion analyses of nucleic acid molecules can be performed to obtain "functional fragments" of a nucleic acid molecule that encodes a TGF-beta binding-protein polypeptide. As an illustration, DNA molecules having the nucleotide sequence of SEQ ID NO: 1 can be digested with Bal31 nuclease to obtain a series of nested deletions. The fragments are then inserted into expression vectors in proper reading frame, and the expressed polypeptides are isolated and tested for activity, or for the ability to bind anti-TGF-beta binding-protein antibodies. One alternative to exonuclease digestion is to use oligonucleotide-directed mutagenesis to introduce deletions or stop codons to specify production of a desired fragment. Alternatively, particular fragments of a TGF-beta binding-protein gene can be synthesized using the polymerase chain reaction.

Standard techniques for functional analysis of proteins are described by, for example, Treuter et al., *Molec. Gen. Genet.* 240:113, 1993; Content et al., "Expression and preliminary deletion analysis of the 42 kDa 2-5A synthetase induced by human interferon," in *Biological Interferon Systems, Proceedings of ISIR-TNO Meeting on Interferon Systems,* Cantell (ed.), pages 65–72 (Nijhoff 1987); Herschman, "The EGF Receptor," in *Control of Animal Cell Proliferation, Vol.* 1, Boynton et al., (eds.) pages 169–199 (Academic Press 1985); Coumailleau et al., *J. Biol. Chem.* 270:29270, 1995; Fukunaga et al., *J. Biol. Chem.* 270:25291, 1995; Yamaguchi et al., *Biochem. Pharmacol.* 50:1295, 1995; and Meisel et al., *Plant Molec. Biol.* 30:1, 1996.

The present invention also contemplates functional fragments of a TGF-beta binding-protein gene that have conservative amino acid changes.

A TGF-beta binding-protein variant gene can be identified on the basis of structure by determining the level of identity with nucleotide and amino acid sequences of SEQ ID NOs: 1, 5, 9, 11, 13, or, 15 and 2, 6, 10, 12, 14, or 16, as discussed above. An alternative approach to identifying a variant gene on the basis of structure is to determine whether a nucleic acid molecule encoding a potential variant TGF-beta binding-protein gene can hybridize under stringent conditions to a nucleic acid molecule having the nucleotide sequence of SEQ ID Nos: 1, 5, 9, 11, 13, or, 15, or a portion thereof of at least 15 or 20 nucleotides in length. As an illustration of stringent hybridization conditions, a nucleic acid molecule having a variant TGF-beta binding-protein sequence can bind with a fragment of a nucleic acid molecule having a sequence from SEQ ID NO:1 in a buffer containing, for example, 5×SSPE (1×SSPE=180 mM sodium chloride, 10 mM sodium phosphate, 1 mM EDTA (pH 7.7), 5×Denhardt's solution (100×Denhardt's=2% (w/v) bovine serum albumin, 2% (w/v) Ficoll, 2% (w/v) polyvinylpyrrolidone) and 0.5% SDS incubated overnight at 55–60° C. Post-hybridization washes at high stringency are typically performed in 0.5×SSC (1×SSC=150 mM sodium chloride, 15 mM trisodium citrate) or in 0.5×SSPE at 55–60° C.

Regardless of the particular nucleotide sequence of a variant TGF-beta binding-protein gene, the gene encodes a polypeptide that can be characterized by its functional activity, or by the ability to bind specifically to an anti-TGF-beta binding-protein antibody. More specifically, variant TGF-beta binding-protein genes encode polypeptides which exhibit at least 50%, and preferably, greater than 60, 70, 80 or 90%, of the activity of polypeptides encoded by the human TGF-beta binding-protein gene described herein.

4. Production of TGF-beta Binding-protein in Cultured Cells

To express a TGF-beta binding-protein gene, a nucleic acid molecule encoding the polypeptide must be operably linked to regulatory sequences that control transcriptional expression in an expression vector and then introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence.

TGF-beta binding-proteins of the present invention are preferably expressed in mammalian cells. Examples of mammalian host cells include African green monkey kidney cells (Vero; ATCC CRL 1587), human embryonic kidney cells (293-HEK; ATCC CRL 1573), baby hamster kidney cells (BHK-21; ATCC CRL 8544), canine kidney cells (MDCK; ATCC CCL 34), Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothioneinI gene [Hamer et al., *J. Molec. Appl. Genet.* 1:273, 1982], the TK promoter of Herpes virus [McKnight, *Cell* 31:355, 1982], the SV40 early promoter [Benoist et al., *Nature* 290:304, 1981], the Rous sarcoma virus promoter [Gorman et al., *Proc. Nat'l Acad. Sci. USA* 79:6777, 1982], the cytomegalovirus promoter [Foecking et al., *Gene* 45:101, 1980], and the mouse mammary tumor virus promoter (see, generally, Etcheverry, "Expression of Engineered Proteins in Mammalian Cell Culture," in *Protein Engineering: Principles and Practice,* Cleland et al. (eds.), pages 163–181 (John Wiley & Sons, Inc. 1996)).

Alternatively, a prokaryotic promoter, such as the bacteriophage T3 RNA polymerase promoter, can be used to control TGF-beta binding-protein gene expression in mammalian cells if the prokaryotic promoter is regulated by a eukaryotic promoter (Zhou et al., *Mol. Cell. Biol.* 10:4529, 1990; Kaufman et al., *Nucl. Acids Res.* 19:4485, 1991).

TGF-beta binding-protein genes may also be expressed in bacterial, yeast, insect, or plant cells. Suitable promoters that can be used to express TGF-beta binding-protein polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA. heat shock, lacUV5, tac, lpp-lacSpr, phoA, and lacZ promoters of *E. coli,* promoters of *B. subtilis,* the promoters of the bacteriophages of Bacillus, Streptomyces promoters, the int promoter of bacterio-phage lambda, the bla promoter of pBR322, and the CAT promoter of the chloramphenicol acetyl transferase gene. Prokaryotic promoters have been reviewed by Glick, *J. Ind. Microbiol.* 1:277, 1987, Watson et al., *Molecular Biology of the Gene,* 4th Ed. (Benjamin Cummins 1987), and by Ausubel et al. (1995).

Preferred prokaryotic hosts include *E. coli* and *Bacillus subtilus.* Suitable strains of *E. coli* include BL21(DE3), BL21(DE3)pLysS, BL21(DE3)pLysE, DH1, DH4I, DH5, DH5I, DH5IF, DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (Ed.), *Molecular Biology Labfax* (Academic Press 1991)). Suitable strains of *Bacillus subtilus* include BR151, YB886, MI119, MI120, and B170 (see, for example, Hardy, "Bacillus Cloning Methods," in *DNA Cloning: A Practical Approach,* Glover (Ed.) (IRL Press 1985)).

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems,* 2nd Edition, Glover et al. (eds.), page 15 (Oxford University Press 1995); Ward et al., "Genetic Manipulation and Expression of Antibodies," in *Monoclonal Antibodies: Principles and Applications,* page 137 (Wiley-Liss, Inc. 1995); and Georgiou, "Expression of Proteins in Bacteria," in *Protein Engineering: Principles and Practice,* Cleland et al. (eds.), page 101 (John Wiley & Sons, Inc. 1996)).

The baculovirus system provides an efficient means to introduce cloned TGF-beta binding-protein genes into insect cells. Suitable expression vectors are based upon the *Autographa californica* multiple nuclear polyhedrosis virus (AcMNPV), and contain well-known promoters such as Drosophila heat shock protein (hsp) 70 promoter, *Autographa californica* nuclear polyhedrosis virus immediate-early gene promoter (ie-1) and the delayed early 39K promoter, baculovirus p10 promoter, and the Drosophila metallothionein promoter. Suitable insect host cells include cell lines derived from IPLB-Sf-21, a *Spodoptera frugiperda* pupal ovarian cell line, such as Sf9 (ATCC CRL 1711), Sf2AE, and Sf21 (Invitrogen Corporation; San Diego, Calif.), as well as Drosophila Schneider-2 cells. Established techniques for producing recombinant proteins in baculovirus systems are provided by Bailey et al., "Manipulation of Baculovirus Vectors," in *Methods in Molecular Biology, Volume 7: Gene Transfer and Expression Protocols,* Murray (ed.), pages 147–168 (The Humana Press, Inc. 1991), by Patel et al., "The baculovirus expression system," in *DNA Cloning 2: Expression Systems,* 2nd Edition, Glover et al. (eds.), pages 205–244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice,* Cleland et al. (eds.), pages 183–218 (John Wiley & Sons, Inc. 1996).

Promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. One skilled in the art will appreciate that there are a wide variety of suitable vectors for expression in yeast cells.

Expression vectors can also be introduced into plant protoplasts, intact plant tissues, or isolated plant cells. General methods of culturing plant tissues are provided, for example, by Miki et al., "Procedures for Introducing Foreign DNA into Plants," in *Methods in Plant Molecular Biology and Biotechnology,* Glick et al. (eds.), pages 67–88 (CRC Press, 1993).

An expression vector can be introduced into host cells using a variety of standard techniques including calcium phosphate transfection, liposome-mediated transfection, microprojectile-mediated delivery, electroporation, and the like. Preferably, the transfected cells are selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.). *Gene Transfer and Expression Protocols* (Humana Press 1991). Methods for introducing expression vectors into bacterial, yeast, insect, and plant cells are also provided by Ausubel (1995).

General methods for expressing and recovering foreign protein produced by a mammalian cell system is provided by, for example, Etcheverry, "Expression of Engineered Proteins in Mammalian Cell Culture," in *Protein Engineer-* ing: *Principles and Practice,* Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition,* Glover et al. (eds.), pages 59–92 (Oxford University Press 1995). Established methods for isolating recombinant proteins from a baculovirus system are described by Richardson (ed.), *Baculovirus Expression Protocols* (The Humana Press, Inc., 1995).

More generally, TGF-beta binding-protein can be isolated by standard techniques, such as affinity chromatography, size exclusion chromatography, ion exchange chromatography, HPLC and the like. Additional variations in TGF-beta binding-protein isolation and purification can be devised by those of skill in the art. For example, anti-TGF-beta binding-protein antibodies, obtained as described below, can be used to isolate large quantities of protein by immunoaffinity purification.

5. Production of Antibodies to TGF-beta Binding-proteins

Antibodies to TGF-beta binding-protein can be obtained, for example, using the product of an expression vector as an antigen. Particularly useful anti-TGF-beta binding-protein antibodies "bind specifically" with TGF-beta binding-protein of Sequence ID Nos. 2, 6, 10, 12, 14, or 16, but not to other TGF-beta binding-proteisn such as Dan, Cerberus, SCGF, or Gremlin. Antibodies of the present invention (including fragments and derivatives thereof may be a polyclonal or, especially a monoclonal antibody. The antibody may belong to any immoglobulin class, and may be for example an IgG, for example $IgG_1$, $IgG_2$, $IgG_3$, $IgG_4$; IgE; IgM; or IgA antibody. It may be of animal, for example mammalian oligin, and may be for example a murine, rat, human or other primate antibody. Where desired the antibody may be an internalising antibody.

Polyclonal antibodies to recombinant TGF-beta binding-protein can be prepared using methods well-known to those of skill in the art (see, for example, Green et al., "Production of Polyclonal Antisera," in *Immunochemical Protocols* (Manson, ed.), pages 1–5 (Humana Press 1992); Williams et al., "Expression of foreign proteins in *E. coli* using plasmid vectors and purification of specific polyclonal antibodies." in *DNA Cloning 2: Expression Systems, 2nd Edition,* Glover et al. (eds.), page 15 (Oxford University Press 1995)). Although polyclonal antibodies are typically raised in animals such as rats, mice, rabbits, goats, or sheep, an anti-TGF-beta binding-protein antibody of the present invention may also be derived from a subhuman primate antibody. General techniques for raising diagnostically and therapeutically useful antibodies in baboons may be found, for example, in Goldenberg et al., international patent publication No. WO 91/11465 (1991), and in Losman et al., *Int. J. Cancer* 46:310, 1990.

The antibody should comprise at least a variable region domain. The variable region domain may be of any size or amino acid composition and will generally comprise at least one hypervariable amino acid sequence responsible for antigen binding embedded in a framework sequence. In general terms the variable (V) region domain may be any suitable arrangement of immunoglobulin heavy ($V_H$) and/or light ($V_L$) chain variable domains. Thus for example the V region domain may be monomeric and be a $V_H$ or $V_L$ domain where these are capable of independently binding antigen with acceptable affinity. Alternatively the V region domain may be dimeric and contain $V_H$—$V_H$, $V_H$-$V_L$, or $V_L$—$V_L$, dimers in which the $V_H$ and $V_L$ chains are non-covalently associated (abbreviated hereinafter as $F_v$). Where desired, however, the chains may be covalently coupled either directly, for example via a disulphide bond between the two variable domains, or through a linker, for example a peptide linker, to form a single chain domain (abbreviated hereinafter as $scF_v$).

The variable region domain may be any naturally occuring variable domain or an engineered version thereof. By engineered version is meant a variable region domain which has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and optionally one or more framework amino acids from one antibody and the remainder of the variable region domain from a second antibody.

The variable region domain may be covalently attached at a C-terminal amino acid to at least one other antibody domain or a fragment thereof. Thus, for example where a $V_H$ domain is present in the variable region domain this may be linked to an immunoglobulin $C_H1$ domain or a fragment thereof. Similarly a $V_L$ domain may be linked to a $C_K$ domain or a fragment thereof. In this way for example the antibody may be a Fab fragment wherein the antigen binding domain contains associated $V_H$ and $V_L$ domains covalently linked at their C-tennini to a CH1 and $C_K$ domain respectively. The CH1 domain may be extended with further amino acids, for example to provide a hinge region domain as found in a Fab' fragment, or to provide further domains, such as antibody CH2 and CH3 domains.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application,* Ritter et al. (eds.). page 166 (Cambridge University Press 1995); and Ward et al., "Genetic Manipulation and Expression of Antibodies," in *Monoclonal Antibodies: Principles and Applications,* Birch et al., (eds.), page 137 (Wiley-Liss, Inc. 1995)).

Antibodies for use in the invention may in general be monoclonal (prepared by conventional immunisation and cell fusion procedures) or in the case of fragments, derived therefrom using any suitable standard chemical e.g. reduction or enzymatic cleavage and/or digestion techniques, for example by treatment with pepsin More specifically, monoclonal anti-TGF-beta binding-protein antibodies can be generated utilizing a variety of techniques. Rodent monoclonal antibodies to specific antigens may be obtained by methods known to those skilled in the art (see, for example, Kohler et al., *Nature* 256:495, 1975; and Coligan et al. (eds.), *Current Protocols in Immunology,* 1:2.5.1–2.6.7 (John Wiley & Sons 1991) ["Coligan"]; Picksley et al., "Production of monoclonal antibodies against proteins expressed in *E. coli,*" in *DNA Cloning 2: Expression Systems, 2nd Edition,* Glover et al. (eds.), page 93 (Oxford University Press 1995)).

Briefly, monoclonal antibodies can be obtained by injecting mice with a composition comprising a TGF-beta binding-protein gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-TGF-beta binding-protein antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13, 1994; Lonberg et al., *Nature* 368:856, 1994; and Taylor et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology, Vol.* 10, pages 79–104 (The Humana Press, Inc. 1992)).

For particular uses, it may be desirable to prepare fragments of anti-TGF-beta binding-protein antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230, 1960, Porter, *Biochem. J.* 73:1.19, 1959, Edelman et al., in *Methods. in Enzymology* 1:422 (Academic Press 1967), and by Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Alternatively, the antibody may be a recombinant or engineered antibody obtained by the use of recombinant DNA techniques involving the manipulation and re-expression of DNA encoding antibody variable and/or constant regions. Such DNA is known and/or is readily available from DNA libraries including for example phage-antibody libraries (see Chiswell, D J and McCafferty, J. Tibtech. 10 80–84 (1992)) or where desired can be synthesised. Standard molecular biology and/or chemistry procedures may be used to sequence and manipulate the DNA, for example, to introduce codons to create cysteine residues, to modify, add or delete other amino acids or domains as desired.

From here, one or more replicable expression vectors containing the DNA may be prepared and used to transform an appropriate cell line, e.g. a non-producing myeloma cell line, such as a mouse NSO line or a bacterial, e.g. *E.coli* line, in which production of the antibody will occur. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al (Molecular Cloning, Cold Spring Harbor Laboratory, New York, 1989); DNA sequencing can be performed as described in Sanger et al (PNAS 74, 5463, (1977)) and the Amersham International plc sequencing handbook; and site directed mutagenesis can be carried out according to the method of Kramer et al (Nucl. Acids Res. 12, 9441, (1984)) and the Anglian-Biotechnology Ltd handbook. Additionally, there are numerous publications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews (ed. Tombs, M P, 10, Chapter 1, 1992, Intercept, Andover, UK) and in International Patent Specification No. WO 91/09967.

Where desired, the antibody according to the invention may have one or more effector or reporter molecules attached to it and the invention extends to such modified proteins. The effector or reporter molecules may be attached to the antibody through any available amino acid side-chain, terminal amino acid or, where present carbohydrate functional group located in the antibody, always provided of course that this does not adversely affect the binding properties and eventual usefulness of the molecule. Particular functional groups include, for example any free amino, imino, thiol, hydroxyl, carboxyl or aldehyde group. Attachment of the antibody and the effector and/or reporter molecule(s) may be achieved via such groups and an appropriate functional group in the effector or reporter molecules. The linkage may be direct or indirect, through spacing or bridging groups.

Effector molecules include, for example, antineoplastic agents, toxins (such as enzymatically active toxins of bacterial or plant origin and fragments thereof e.g. ricin and fragments thereof) biologically active proteins, for example enzymes, nucleic acids and fragments thereof, e.g. DNA, RNA and fragments thereof, naturally occurring and synthetic polymers e.g. polysaccharides and polyalkylene polymers such as poly(ethylene glycol) and derivatives thereof, radionuclides, particularly radioiodide, and chelated metals. Suitable reporter groups include chelated metals, fluorescent compounds or compounds which may be detected by NMR or ESR spectroscopy.

Particular antineoplastic agents include cytotoxic and cytostatic agents, for example alkylating agents, such as nitrogen mustards (e.g. chlorambucil, melphalan, mechlorethamine, cyclophosphamide, or uracil mustard) and derivatives thereof, triethylenephosphoramide, triethylenethiophosphor-amide, busulphan, or cisplatin;

antimetabolites, such as methotrexate, fluorouracil, floxuridine, cytarabine, mercaptopurine, thioguanine, fluoroacetic acid or fluorocitric acid, antibiotics, such as bleomycins (e.g. bleomycin sulphate), doxorubicin, daunorubicin, mitomycins (e.g. mitomycin C), actinomycins (e.g. dactinomycin) plicamycin, calichaemicin and derivatives thereof, or esperanicin and derivatives thereof; mitotic inhibitors, such as etoposide, vincristine or vinblastine and derivatives thereof; alkaloids, such as ellipticine; polyols such as taxicin-I or taxicin-II; hormones, such as androgens (e.g. dromostanolone or testolactone), progestins (e.g. megestrol acetate or medroxyprogesterone acetate), estrogens (e.g. dimethylstilbestrol diphosphate, polyestradiol phosphate or estramustine phosphate) or antiestrogens (e.g. tamoxifen); anthraquinones,such as mitoxantrone, ureas, such as hydroxyurea; hydrazines, such as procarbazine; or imidazoles, such as dacarbazine.

Particularly useful effector groups are calichaernicin and derivatives thereof (see for example South African Patent Specifications Nos. 85/8794. 88/8127 and 90/2839).

Chelated metals include chelates of di-or tripositive metals having a coordination number from 2 to 8 inclusive. Particular examples of such metals include technetium (Tc), rhenium (Re), cobalt (Co), copper (Cu), gold (Au), silver (Ag), lead (Pb), bismuth (Bi), indium (In), gallium (Ga), yttrium (Y), terbium (Th), gadolinium (Gd), and scandium (Sc). In general the metal is preferably a radionuclide. Particular radionuclides include $^{99m}Tc$, $^{186}Re$, $^{188}Re$, $^{58}Co$, $^{60}Co$, $^{67}Cu$, $^{195}Au$, $^{199}Au$, $^{110}Ag$, $^{203}Pb$, $^{206}Bi$, $^{207}Bi$. $^{111}In$, $^{67}Ga$, $^{68}Ga$, $^{88}Y$, $^{90}Y$, $^{160}Tb$, $^{153}Gd$ and $^{47}Sc$.

The chelated metal may be for example one of the above types of metal chelated with any suitable polydentate chelating agent, for example acyclic or cyclic polyamines, polyethers, (e.g. crown ethers and derivatives thereof); polyamides; porphyrins; and carbocyclic derivatives.

In general, the type of chelating agent will depend on the metal in use. One particularly useful group of chelating agents in conjugates according to the invention, however, are acyclic and cyclic polyamines, especially polyaminocarboxylic acids, for example diethylenetriaminepentaacetic acid and derivatives thereof, and macrocyclic amines, e.g. cyclic tri-aza and tetra-aza derivatives (for example as described in International Patent Specification No. WO 92/22583); and polyamides, especially desferrioxamine and derivatives thereof.

Thus for example when it is desired to use a thiol group in the antibody as the point of attachment this may be achieved through reaction with a thiol reactive group present in the effector or reporter molecule. Examples of such groups include an a-halocarboxylic acid or ester, e.g. iodoacetamide, an imide, e.g. maleimide, a vinyl sulphone, or a disulphide. These and other suitable linking procedures are generally and more particularly described in International Patent Specifications Nos. WO 93/06231, WO 92/22583, WO 90/091195 and WO 89/01476.

Assays for Selecting Molecular which Increase Bone Density

As discussed above the present invention provides methods for selecting and/or isolating compounds which are capable of increasing bone density. For example, within one aspect of the present invention methods are provided for determining whether a selected molecule is capable of increasing bone mineral content, comprising the steps of (a) mixing a selected molecule with TGF-beta binding protein and a selected member of the TGF-beta family of proteins, (b) determining whether the selected molecule stimulates signaling by the TGF-beta family of proteins, or inhibits the binding of the TGF-beta binding protein to the TGF-beta family of proteins. Within certain embodiments, the molecule enhances the ability of TGF-beta to function as a positive regulator of mesenchymal cell differentiation.

Within other aspects of the invention, methods are provided for determining whether a selected molecule is capable of increasing bone mineral content, comprising the steps of (a) exposing a selected molecule to cells which express TGF-beta binding-protein and (b) determining whether the expression (or activity) of TGF-beta binding-protein from said exposed cells decreases, and therefrom determining whether the compound is capable of increasing bone mineral content. Within one embodiment, the cells are selected from the group consisting of the spontaneously transformed or untransformed normal human bone from bone biopsies and rat parietal bone osteoblasts. Such methods may be accomplished in a wide variety of assay formats including, for example, Countercurrent Immuno-Electrophoresis (CIEP), Radioimmunoassays, Radioimmunoprecipitations, Enzyme-Linked Immuno-Sorbent Assays (ELISA), Dot Blot assays, Inhibition or Competition assays, and sandwich assays (see U.S. Pat. Nos. 4,376,110 and 4,486,530; see also Antibodies: A Laboratory Manual, supra).

Representative embodiments of such assays are provided below in Examples 5 and 6. Briefly, a family member of the TGF-beta super-family or a TGF-beta binding protein is first bound to a solid phase, followed by addition of a candidate molecule. The labeled family member of the TGF-beta super-family or a TGF-beta binding protein is then added to the assay, the solid phase washed, and the quantity of bound or labeled TGF-beta super-family member or TGF-beta binding protein on the solid support determined. Molecules which are suitable for use in increasing bone mineral content as described herein are those molecules which decrease the binding of TGF-beta binding protein to a member or members of the IGF-beta super-family in a statistically significant manner. Obviously, assays suitable for use within the present invention should not be limited to the embodiments described within Examples 2 and 3. In particular, numerous parameters may be altered, such as by binding TGF-beta to a solid phase, or by elimination of a solid phase entirely.

Within other aspects of the invention, methods are provided for determining whether a selected molecule is capable of increasing bone mineral content, comprising the steps of (a) exposing a selected molecule to cells which express TGF-beta and (b) determining whether the activity of TGF-beta from said exposed cells is altered, and therefrom determining whether the compound is capable of increasing bone mineral content. Similar to the above described methods, a wide variety of methods may be utilized to assess the changes of TGF-beta binding-protein expression due to a selected test compound.

For example, within one aspect of the present invention methods are provided for determining whether a selected molecule is capable of increasing bone mineral content, comprising the steps of (a) mixing a selected molecule with TGF-beta-binding-protein and a selected member of the TGF-beta family of proteins, (b) determining whether the selected molecule up-regulates the signaling of the TGF-beta family of proteins, or inhibits the binding of the TGF-beta binding-protein to the TGF-beta family of proteins. Within certain embodiments, the molecule enhances the ability of TGF-beta to function as a positive regulator of mechemchymal cell differentiation.

Similar to the above described methods, a wide variety of methods may be utilized to assess stimulation of TGF-beta due to a selected test compound. One such representative method is provided below in Example 6 (see also Durham et al., *Endo.* 136:1374–1380.

Within yet other aspects of the present invention, methods are provided for determining whether a selected molecule is capable of increasing bone mineral content, comprising the step of determining whether a selected molecule inhibits the binding of TGF-beta binding-protein to bone, or an analogue thereof. As utilized herein, it should be understood that bone or analogues thereof refers to hydroxyapatite, or a surface composed of a powdered form of bone, crushed bone or intact bone. Similar to the above described methods, a wide variety of methods may be utilized to assess the inhibition of TGF-beta binding-protein localization to bone matrix. One such representative method is provided below in Example 7.

It should be noted that while the methods recited herein may refer to the analysis of an individual test molecule, that the present invention should not be so limited. In particular, the selected molecule may be contained within a mixture of compounds. Hence, the recited methods may further comprise the step of isolating a molecule which inhibits the binding of TGF-beta binding-protein to a TGF-beta family member.

Candidate Molecules

A wide variety of molecules may be assayed for their ability to inhibit the binding of TGF-beta binding-protein to a TGF-beta family member. Representative examples which are discussed in more detail below include organic molecules, proteins or peptides, and nucleic acid molecules. Although it should be evident from the discussion below that the candidate molecules described herein may be utilized in the assays described herein, it should also be readily apparent that such molecules can also be utilized in a variety of diagnostic and therapeutic settins.

1. Organic Molecules

Numerous organic molecules may be assayed for their ability to inhibit the binding of TGF-beta binding-protein to a TGF-beta family member.

For example, within one embodiment of the invention suitable organic molecules may be selected from either a chemical library, wherein chemicals are assayed individually, or from combinatorial chemical libraries where multiple compounds are assayed at once, then deconvoluted to determine and isolate the most active compounds.

Representative examples of such combinatorial chemical libraries include those described by Agrafiotis et al., "System and method of automatically generating chemical compounds with desired properties," U.S. Pat. No. 5,463,564; Armstrong, R. W., "Synthesis of combinatorial arrays of organic compounds through the use of multiple component combinatorial array syntheses," WO 95/02566; Baldwin, J. J. et al., "Sulfonamide derivatives and their use," WO 95/24186; Baldwin, J. J. et al., "Combinatorial dihydrobenzopyran library," WO 95/30642; Brenner, S., "New kit for preparing combinatorial libraries," WO 95/16918; Chenera, B. et al., "Preparation of library of resin-bound aromatic carbocyclic compounds," WO 95/16712; Ellman, J. A., "Solid phase and combinatorial synthesis of benzodiazepine compounds on a solid support," U.S. Pat. No. 5,288,514; Felder, E. et al., "Novel combinatorial compound libraries," WO 95/16209; Lerner, R. et al., "Encoded combinatorial chemical libraries," WO 93/20242; Pavia, M. R. et al., "A method for preparing and selecting pharmaceutically useful non-peptide compounds from a structurally diverse universal library," WO 95/04277; Summerton, J. E. and D. D. Weller, "Morpholino-subunit combinatorial library and method," U.S. Pat. No. 5,506,337; Holmes, C., "Methods for the Solid Phase Synthesis of Thiazolidinones, Metathiazanones, and Derivatives thereof," WO 96/00148; Phillips, G. B. and G. P. Wei, "Solid-phase Synthesis of Benzimidazoles," *Tet. Letters* 37:4887–90, 1996; Ruhland, B. et al., "Solid-supported Combinatorial Synthesis of Structurally Diverse β-Lactams," *J. Amer. Chem. Soc.* 111:25–34, 1996; Look, G. C. et al., "The Indentification of Cyclooxygenase-1 Inhibitors from 4-Thiazolidinone Combinatorial Libraries," i Bioorg and Med. Chem. Letters 6:707–12, 1996.

2. Proteins and Peptides

A wide range of proteins and peptides may likewise be utilized as candidate molecules for inhibitors of the binding of TGF-beta binding-protein to a TGF-beta family member.

a. Combinatorial Peptide Libraries

Peptide molecules which are putative inhibitors of the binding of TGF-beta binding-protein to a TGF-beta family member may be obtained through the screening of combinatorial peptide libraries. Such libraries may either be prepared by one of skill in the art (see e.g., U.S. Pat. Nos. 4,528,266 and 4,359,535, and Patent Cooperation Treaty Publication Nos. WO 92/15679, WO 92/15677, WO 90/07862, WO 90/02809, or purchased from commercially available sources (e.g., New England Biolabs Ph.D.™ Phage Display Peptide Library Kit).

b. Antibodies

Antibodies which inhibit the binding of TGF-beta binding-protein to a TGF-beta family member may readily be prepared given the disclosure provided herein. Within the context of the present invention, antibodies are understood to include monoclonal antibodies, polyclonal antibodies, anti-idiotypic antibodies, antibody fragments (e.g., Fab, and $F(ab')_2$, $F_v$, variable regions, or complementarity determining regions). As discussed above, antibodies are understood to be specific against TGF-beta binding-protein, or against a specific TGF-beta family member, if they bind with a $K_a$ of greater than or equal to $10^7 M$, preferably greater than or equal to $10^8 M$, and do not bind to other TGF-beta binding-proteins, or, bind with a $K_a$ of less than or equal to $10^6 M$. Furthermore, antibodies of the present invention should block or inhibit the binding of TGF-beta binding-protein to a TGF-beta family member.

The affinity of a monoclonal antibody or binding partner, as well as inhibition of binding can be readily determined by one of ordinary skill in the art (see Scatchard, *Ann. N.Y. Acad. Sci.* 51:660–672, 1949).

Briefly, polyclonal antibodies may be readily generated by one of ordinary skill in the art from a variety of warm-blooded animals such as horses, cows, various fowl, rabbits, mice, or rats. Typically, the TGF-beta binding-protein or unique peptide thereof of 13–20 amino acids (preferably conjugated to keyhole limpet hemocyanin by cross-linking with glutaraldehyde) is utilized to immunize the animal through intraperitoneal, intramuscular, intraocular, or subcutaneous injections, along with an adjuvant such as Freund's complete or incomplete adjuvant. Following several booster immunizations, samples of serum are collected and tested for reactivity to the protein or peptide. Particularly preferred polyclonal antisera will give a signal on one of these assays that is at least three times greater than background. Once the titer of the animal has reached a plateau in terms of its reactivity to the protein, larger quantities of antisera may be readily obtained either by weekly bleedings, or by exsanguinating the animal.

Monoclonal antibodies may also be readily generated using conventional techniques (see U.S. Pat. Nos. RE 32,011, 4,902,614, 4,543,439, and 4,411,993 which are incorporated herein by reference; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988, which are also incorporated herein by reference).

Briefly, within one embodiment a subject animal such as a rat or mouse is immunized with TGF-beta binding-protein or portion thereof as described above. The protein may be admixed with an adjuvant such as Freund's complete or incomplete adjuvant in order to increase the resultant immune response. Between one and three weeks after the initial immunization the animal may be reimmuunized with another booster immunization, and tested for reactivity to the protein utilizing assays described above. Once the animal has reached a plateau in its reactivity to the injected protein, it is sacrificed, and organs which contain large numbers of B cells such as the spleen and lymph nodes are harvested.

Cells which are obtained from the immunized animal may be immortalized by infection with a virus such as the Epstein-Barr virus (EBV) (see Glasky and Reading, *Hybridoma* 8(4):377–389, 1989). Alternatively, within a preferred embodiment, the harvested spleen and/or lymph node cell suspensions are fused with a suitable myeloma cell in order to create a "hybridoma" which secretes monoclonal antibody. Suitable myeloma lines include, for example, NS-1 (ATCC No. TIB 18), and P3X63-Ag 8.653 (ATCC No. CRL 1580).

Following the fusion, the cells. may be placed into culture plates containing a suitable medium, such as RPMI 1640, or DMEM (Dulbecco's Modified Eagles Medium) (JRH Biosciences, Lenexa, Kans.), as well as additional ingredients, such as fetal bovine serum (FBS, i.e., from Hyclone, Logan, Utah, or JRH Biosciences). Additionally, the medium should contain a reagent which selectively allows for the growth of fused spleen and myeloma cells such as HAT (hypoxanthine, aminopterin, and thymidine) (Sigma Chemical Co., St. Louis, Mo.). After about seven days, the resulting fused cells or hybridomas may be screened in order to determine the presence of antibodies which are reactive against TGF-beta binding-protein (depending on the antigen used), and which block or inhibit the binding of TGF-beta binding-protein to a TGF-beta family member.

A wide variety of assays may be utilized to determine the presence of antibodies which are reactive against the proteins of the present invention, including for example countercurrent immuno-electrophoresis, radioimmunoassays, radioimmunoprecipitations, enzyme-linked immunosorbent assays (ELISA), dot blot assays, western blots, immunoprecipitation, inhibition or competition assays, and sandwich assays (see U.S. Pat. Nos. 4,376,110 and 4,486,530; see also *Antibodies: A Laboratory Manual*, Harlow and Lane (eds.), Cold Spring Harbor Laboratory Press, 1988). Following several clonal dilutions and reassays, a hybridoma producing antibodies reactive against the desired protein may be isolated.

Other techniques may also be utilized to construct monoclonal antibodies (see William D. Huse et al., "Generation of a Large Combinational Library of the Immunoglobulin Repertoire in Phage Lambda," *Science* 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad Sci. USA* 86:5728–5732, August 1989; see also Michelle Alting-Mees et al., "Monoclonal Antibody Expression Libraries: A Rapid Alternative to Hybridomas," *Strategies in Molecular Biology* 3:1–9, January 1990). These references describe a commercial system available from Stratagene (La Jolla, Calif.) which enables the production of antibodies through recombinant techniques. Briefly, mRNA is isolated from a B cell population, and utilized to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid which allows high level expression of monoclonal antibody fragments from *E. coli*.

Similarly, portions or fragments, such as Fab and Fv fragments, of antibodies may also be constructed utilizing conventional enzymatic digestion or recombinant DNA techniques to incorporate the variable regions of a gene which encodes a specifically binding antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. Stratagene (La Jolla, Calif.) sells primers for mouse and human variable regions including, among others, primers for $V_{Ha}$, $V_{Hb}$, $V_{Hc}$, $V_{Hd}$, $C_{H1}$, $V_L$ and $C_L$ regions. These primers may be utilized to amplify heavy or light chain variable regions, which may then be inserted into vectors such as ImmunoZAP™ H or ImmunoZAP™ L (Stratagene), respectively. These vectors may then be introduced into *E. coli*, yeast, or mammalian-based systems for expression. Utilizing these techniques, large amounts of a single-chain protein containing a fusion of the $V_H$ and $V_L$ domains may-be produced (see Bird et al., *Science* 242:423–426, 1988). In addition, such techniques may be utilized to change a "murine" antibody to a "human" antibody, without altering the binding specificity of the antibody.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

c. Mutant TGF-beta Binding-proteins

As described herein and below in the Examples (e.g., Examples 8 and 9), altered versions of TGF-beta binding-protein which compete with native TGF-beta binding-protein's ability to block the activity of a particular TGF-beta family member should lead to increased bone density. Thus, mutants of TGF-beta binding-protein which bind to the TGF-beta family member but do not inhibit the function of the TGF-beta family member would meet the criteria. The mutant versions must effectively compete with the endogenous inhibitory functions of TGF-beta binding-protein.

d. Production of Proteins

Although various genes (or portions thereof) have been provided herein, it should be understood that within the context of the present invention, reference to one or more of these genes includes derivatives of the genes that are substantially similar to the genes (and, where appropriate, the proteins (including peptides and polypeptides) that are encoded by the genes and their derivatives). As used herein, a nucleotide sequence is deemed to be "substantially similar" if: (a) the nucleotide sequence is derived from the coding region of the above-described genes and includes, for example, portions of the sequence or allelic variations of the sequences discussed above, or alternatively, encodes a molecule which inhibits the binding of TGF-beta binding-protein to a member of the TGF-beta family, (b) the nucleotide sequence is capable of hybridization to nucleotide sequences of the present invention under moderate, high or very high stringency (see Sambrook et al., *Molecular Cloning: A Laboratory Manual,* 2nd ed., Cold Spring Harbor Laboratory Press, NY, 1989); or (c) the DNA sequences are degenerate as a result of the genetic code to the DNA sequences defined in (a) or (b). Further, the nucleic acid molecule disclosed herein includes both complementary and non-complementary sequences, provided the sequences otherwise meet the criteria set forth herein. Within the context of the present invention, high stringency means standard hybridization conditions (e.g., 5×SSPE, 0.5% SDS at 65° C., or the equivalent).

The structure of the proteins encoded by the nucleic acid molecules described herein may be predicted from the primary translation products using the hydrophobicity plot function of, for example, P/C Gene or Intelligenetics Suite (Intelligenetics, Mountain View, Calif.), or according to the methods described by Kyte and Doolittle (*J. Mol. Biol.* 157:105–132. 1982).

Proteins of the present invention may be prepared in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Moreover, due to degeneracy in the genetic code, for example, there may be considerable variation in nucleotide sequences encoding the same amino acid sequence.

Other derivatives of the proteins disclosed herein include conjugates of the proteins along with other proteins or polypeptides. This may be accomplished, for example, by the synthesis of N-terminal or C-terminal fusion proteins which may be added to facilitate purification or identification of proteins (see U.S. Pat. No. 4,851,341, see also, Hopp et al., *Bio/Technology* 6:1204, 1988.) Alternatively, fusion proteins such as Flag/TGF-beta binding-protein be constructed in order to assist in the identification, expression, and analysis of the protein.

Proteins of the present invention may be constructed using a wide variety of techniques described herein. Further, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques,* January 1985, 12–19); Smith et al. (*Genetic Engineering: Principles and Methods,* Plenum Press, 1981); and Sambrook et al. (supra). Deletion or truncation derivatives of proteins (e.g., a soluble extracellular portion) may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (*Molecular Cloning: A Laboratory Manual,* 2d Ed., Cold Spring Harbor Laboratory Press, 1989).

Mutations which are made in the nucleic acid molecules of the present invention preferably preserve the reading frame of the coding sequences. Furthermore, the mutations will preferably not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Nucleic acid molecules which encode proteins of the present invention may also be constructed utilizing techniques of PCR mutagenesis, chemical mutagenesis (Drinkwater and Klinedinst, *PNAS* 83:3402–3406, 1986), by forced nucleotide misincorporation (e.g., Liao and Wise *Gene* 88:107–111, 1990), or by use of randomly mutagenized oligonucleotides (Horwitz et al., *Genome* 3:112–117, 1989).

The present invention also provides for the manipulation and expression of the above described genes by culturing host cells containing a vector capable of expressing the above-described genes. Such vectors or vector constructs include either synthetic or cDNA-derived nucleic acid molecules encoding the desired protein, which are operably linked to suitable transcriptional or translational regulatory elements. Suitable regulatory elements may be derived from a variety of sources, including bacterial, fungal, viral, mammalian, insect, or plant genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a transcriptional terminator, and a ribosomal binding sequence, including a translation initiation signal.

Nucleic acid molecules that encode any of the proteins described above may be readily expressed by a wide variety of prokaryotic and eukaryotic host cells, including bacterial, mammalian, yeast or other fungi, viral, insect, or plant cells. Methods for transforming or transfecting such cells to express foreign DNA are well known in the art (see, e.g., Itakura et al., U.S. Pat. No. 4,704,362; Hinnen et al., *Proc.*

*Natl. Acad. Sci. USA* 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. *Molecular Cloning: A Laboratory Manual,* 2nd ed., Cold Spring Harbor Laboratory Press. 1989; for plant cells see Czako and Marton, *Plant Physiol.* 104:1067–1071, 1994; and Paszkowski et al., *Biotech.* 24:387–392, 1992).

Bacterial host cells suitable for carrying out the present invention include *E. coli, B. subtilis, Salmonella typhimurium,* and various species within the genera Pseudomonas, Streptomyces, and Staphylococcus, as well as many other bacterial species well known to one of ordinary skill in the art. Representative examples of bacterial host cells include DH5α (Stratagene, LaJolla, Calif.).

Bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60–89, 1990), the lambda promoter (Elvin et al., *Gene* 87:123–126, 1990), the trp promoter (Nichols and Yanofsky, *Meth. in Enzymology* 101:155, 1983) and the tac promoter (Russell et al., *Gene* 20:231, 1982). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC118, pUC119 (see Messing, *Meth in Enzymology* 101:20–77, 1983 and Vieira and Messing, *Gene* 19:259–268, 1982), and pNH8A, pNH16a, pNH18a, and Bluescript M13 (Stratagene, La Jolla, Calif.).

Yeast and fungi host cells suitable for carrying out the present invention include, among others, *Saccharomyces pombe, Saccharomyces cerevisiae,* the genera Pichia or Kluyveromyces and various species of the genus Aspergillus (McKnight et al., U.S. Pat. No. 4,935,349). Suitable expression vectors for yeast and fungi include, among others, YCp50 (ATCC No. 37419) for yeast, and the amdS cloning vector pV3 (Turnbull, *Bio/Technology* 7:169, 1989), YRp7 (Struhl et al., *Proc. Natl. Acad. Sci. USA* 76:1035–1039, 1978), YEp13 (Broach et al., *Gene* 8:121–133, 1979), pJDB249 and pJDB219 (Beggs, *Nature* 275:104–108, 1978) and derivatives thereof.

Preferred promoters for use in yeast include promoters from yeast glycolytic genes (Hitzeman et al., *J. Biol. Chem.* 255:12073–12080, 1980; Alber and Kawasaki, *J. Mol. Appl. Genet.* 1:419–434, 1982) or alcohol dehydrogenase genes (Young et al., in *Genetic Engineering of Microorganisms for Chemicals,* Hollaender et al. (eds.), p. 355, Plenum, New York, 1982; Ammerer, *Meth. Enzymol.* 101:192–201, 1983). Examples of useful promoters for fungi vectors include those derived from *Aspergillus nidulans* glycolytic genes, such as the adh3 promoter (McKnight et al., *EMBO J.* 4:2093–2099, 1985). The expression units may also include a transcriptional terminator. An example of a suitable terminator is the adh3 terminator (McKnight et al., ibid., 1985).

As with bacterial vectors, the yeast vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include leu2 (Broach et al., ibid.), ura3 (Botstein et al., *Gene* 8:17, 1979), or his3 (Struhl et al., ibid.). Another suitable selectable marker is the cat gene, which confers chloramphenicol resistance on yeast cells.

Techniques for transforming fungi are well known in the literature, and have been described, for instance, by Beggs (ibid.). Hinnen et al. (*Proc. Natl. Acad. Sci. USA* 75:1929–1933, 1978), Yelton et al. (*Proc. Natl. Acad. Sci. USA* 81:1740–1747, 1984), and Russell (*Nature* 301:167–169, 1983). The genotype of the host cell may contain a genetic defect that is complemented by the selectable marker present on the expression vector. Choice of a particular host and selectable marker is well within the level of ordinary skill in the art.

Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (see Itoh et al., *J. Bacteriology* 153:163, 1983). Transformation of fungi may also be carried out using polyethylene glycol as described by Cullen et al. (*Bio/Technology* 5:369, 1987).

Viral vectors include those which comprise a promoter that directs the expression of an isolated nucleic acid molecule that encodes a desired protein as described above. A wide variety of promoters may be utilized within the context of the present invention, including for example, promoters such as MoMLV LTR, RSV LTR, Friend MuLV LTR, adenoviral promoter (Ohno et al., *Science* 265:781–784, 1994), neomycin phosphotransferase promoter/enhancer, late parvovirus promoter (Koering et al., *Hum. Gene Therap.* 5:457–463, 1994), Herpes TK promoter, SV40 promoter, metallothionein IIa gene enhancer/promoter, cytomegalovirus immediate early promoter, and the cytomegalovirus immediate late promoter. Within particularly preferred embodiments of the invention, the promoter is a tissue-specific promoter (see e.g., WO 91/02805; EP 0,415,731; and WO 90/07936). Representative examples of suitable tissue specific promoters include neural specific enolase promoter, platelet derived growth factor beta promoter, bone morphogenic protein promoter, human alpha1-chimaerin promoter, synapsin I promoter and synapsin II promoter. In addition to the above-noted promoters, other viral-specific promoters (e.g., retroviral promoters (including those noted above, as well as others such as HIV promoters), hepatitis, herpes (e.g., EBV), and bacterial, fungal or parasitic (e.g., malarial)-specific promoters may be utilized in order to target a specific cell or tissue which is infected with a virus, bacteria, fungus or parasite.

Mammalian cells suitable for carrying out the present invention include, among others COS, CHO, SaOS, osteosarcomas, KS483, MG-63, primary osteoblasts, and human or mammalian bone marrow stroma. Mammalian expression vectors for use in carrying out the present invention will include a promoter capable of directing the transcription of a cloned gene or cDNA. Preferred promoters include viral promoters and cellular promoters. Bone specific promoters include the bone sialo-protein and the promoter for osteocalcin. Viral promoters include the cytomegalovirus immediate early promoter (Boshart et al., *Cell* 41:521–530, 1985), cytomegalovirus immediate late promoter, SV40 promoter (Subramani et al., *Mol. Cell. Biol.* 1:854–864, 1981), MMTV LTR, RSV LTR, metallothionein-1, adenovirus E1a. Cellular promoters include the mouse metallothionein-1 promoter (Palmiter et al., U.S. Pat. No. 4,579,821), a mouse $V_K$ promoter (Bergman et al., Proc. Natl. Acad. Sci. USA 81:7041–7045, 1983; Grant et al., Nucl. Acids Res. 15:5496, 1987) and a mouse $V_H$ promoter (Loh et al., Cell 33:85–93, 1983). The choice of promoter will depend, at least in part, upon the level of expression desired or the recipient cell line to be transfected.

Such expression vectors may also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., Nuc. Acids Res. 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commercial sources (e.g., Stratagene, La Jolla, Calif.).

Vector constructs comprising cloned DNA sequences can be introduced into cultured mammalian cells by, for example, calcium phosphate-mediated transfection (Wigler et al., Cell 14:725, 1978; Corsaro and Pearson, Somatic Cell Genetics 7:603, 1981; Graham and Van der Eb, Virology 52:456, 1973), electroporation (Neumann et al., EMBO J. 1:841–845, 1982), or DEAE-dextran mediated transfection (Ausubel et al. (eds.), Current Protocols in Molecular Biology, John Wiley and Sons, Inc., NY, 1987). To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (Mammalian Cell Technology, Butterworth Publishers, Stoneham, Mass., which is incorporated herein by reference).

Mammalian cells containing a suitable vector are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Protocols for the transfection of mammalian cells are well known to those of ordinary skill in the art. Representative methods include calcium phosphate mediated transfection, electroporation, lipofection, retroviral, adenoviral and protoplast fusion-mediated transfection (see Sambrook et al., supra). Naked vector constructs can also be taken up by muscular cells or other suitable cells subsequent to injection into the muscle of a mammal (or other animals).

Numerous insect host cells known in the art can also be useful within the present invention, in light of the subject specification. For example, the use of baculoviruses as vectors for expressing heterologous DNA sequences in insect cells has been reviewed by Atkinson et al. (Pestic. Sci. 28:215–224,1990).

Numerous plant host cells known in the art can also be useful within the present invention, in light of the subject specification. For example, the use of Agrobacterium rhizogenes as vectors for expressing genes in plant cells has been reviewed by Sinkar et al. (J. Biosci. (Bangalore) 11:47–58, 1987).

Within related aspects of the present invention, proteins of the present invention may be expressed in a transgenic animal whose germ cells and somatic cells contain a gene which encodes the desired protein and which is operably linked to a promoter effective for the expression of the gene. Alternatively, in a similar manner transgenic animals may be prepared that lack the desired gene (e.g., "knock-out" mice). Such transgenics may be prepared in a variety of non-human animals, including mice, rats, rabbits, sheep, dogs, goats and pigs (see Hammer et al., Nature 315:680–683, 1985, Palmiter et al., Science 222:809–814, 1983, Brinster et al., Proc. Nat. Acad. Sci. USA 82:4438–4442, 1985, Palmiter and Brinster, Cell 41:343–345, 1985, and U.S. Pat. Nos. 5,175,383, 5,087,571, 4,736,866, 5,387,742, 5,347,075, 5,221,778, and 5,175,384). Briefly, an expression vector, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al. 1983, ibid), which allows regulated expression of the transgene.

Proteins can be isolated by, among other methods, culturing suitable host and vector systems to produce the recombinant translation products of the present invention. Supernatants from such cell lines, or protein inclusions or whole cells where the protein is not excreted into the supernatant can then be treated by a variety of purification procedures in order to isolate the desired proteins. For example, the supernatant may be first concentrated using commercially available protein concentration filters, such as an Amicon or Millipore Pellicon ultrafiltration unit. Following concentration, the concentrate may be applied to a suitable purification matrix such as, for example, an anti-protein antibody bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the skill of the art.

A protein is deemed to be "isolated" within the context of the present invention if no other (undesired) protein is detected pursuant to SDS-PAGE analysis followed by Coomassie blue staining. Within other embodiments, the desired protein can be isolated such that no other (undesired) protein is detected pursuant to SDS-PAGE analysis followed by silver staining.

3. Nucleic Acid Molecules

Within other aspects of the invention, nucleic acid molecules are provided which are capable of inhibiting TGF-beta binding-protein binding to a member of the TGF-beta family. For example, within one embodiment antisense oligonucleotide molecules are provided which specifically inhibit expression of TGF-beta binding-protein nucleic acid sequences (see generally, Hirashima et al. in *Molecular Biology of RNA: New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004–1012, 1993; WO 95/10607; U.S. Pat. No. 5,359,051; WO 92/06693; and EP-A2–612844). Briefly, such molecules are constructed such that they are complementary to, and able to form Watson-Crick base pairs with, a region of transcribed TGF-beta binding-protein mRNA sequence. The resultant double-stranded nucleic acid interferes with subsequent processing of the mRNA, thereby preventing protein synthesis (see Example 10).

Within other aspects of the invention, ribozymes are provided which are capable of inhibiting the TGF-beta binding-protein binding to a member of the TGF-beta family. As used herein, "ribozymes" are intended to include RNA molecules that contain anti-sense sequences for specific recognition, and an RNA-cleaving enzymatic activity. The catalytic strand cleaves a specific site in a target RNA at greater than stoichiometric concentration. A wide variety of ribozymes may be utilized within the context of the present invention, including for example, the hammerhead ribozyme (for example, as described by Forster and Symons, *Cell* 48:211–220, 1987; Haseloff and Gerlach, *Nature* 328:596–600, 1988; Walbot and Bruening, *Nature* 334:196, 1988; Haseloff and Gerlach, *Nature* 334:585, 1988); the hairpin ribozyme (for example, as described by Haseloff et al., U.S. Pat. No. 5,254,678, issued Oct. 19, 1993 and Hempel et al., European Patent Publication No. 0 360 257, published Mar. 26, 1990); and Tetrahymena ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

4. Labels

The gene product or any of the candidate molecules described above and below, may be labeled with a variety of compounds, including for example, fluorescent molecules, toxins, and radionuclides. Representative examples of fluorescent molecules include fluorescein, Phycobili proteins, such as phycoerythrin, rhodamine, Texas red and luciferase. Representative examples of toxins include ricin, abrin diphtheria toxin, cholera toxin, gelonin, pokeweed antiviral protein, tritin, Shigella toxin, and Pseudomonas exotoxin A. Representative examples of radionuclides include Cu-64, Ga-67, Ga-68, Zr-89, Ru-97, Tc-99m, Rh-105, Pd-109, In111, I-123, I-125, I-131, Re-186, Re-188, Au-198, Au-199, Pb-203, At-211, Pb-212 and Bi-212. In addition, the antibodies described above may also be labeled or conjugated to one partner of a ligand binding pair. Representative examples include avidin-biotin, and riboflavin-riboflavin binding protein.

Methods for conjugating or labeling the molecules described herein with the representative labels set forth above may be readily accomplished by one of ordinary skill in the art (see Trichothecene Antibody Conjugate, U.S. Pat. No. 4,744,981; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods In Enymology*, Vol. 34, *Affinity Techniques, Enzyme Purification: Part B*, Jakoby and Wilchek (eds.), Academic Press, New York, p. 30, 1974; see also Wilchek and Bayer, "The Avidin-Biotin Complex in Bioanalytical Applications," *Anal. Biochem.* 171:1–32, 1988).

Pharmaceutical Compositions

As noted above, the present invention also provides a variety of pharmaceutical compositions, comprising one of the above-described molecules which inhibits the TGF-beta binding-protein binding to a member of the TGF-beta family along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

Methods of Treatment

The present invention also provides methods for increasing the mineral content and mineral density of bone. Briefly, numerous conditions result in the loss of bone mineral content, including for example, disease, genetic predisposition, accidents which result in the lack of use of bone (e.g., due to fracture), therapeutics which effect bone resorption, or which kill bone forming cells and normal aging. Through use of the molecules described herein which inhibit the TGF-beta binding-protein binding to a TGF-beta family member such conditions may be treated or prevented. As utilized herein, it should be understood that bone mineral content has been increased, if bone mineral content has been increased in a statistically significant manner (e.g., greater than one-half standard deviation), at a selected site.

A wide variety of conditions which result in loss of bone mineral content may be treated with the molecules described herein. Patients with such conditions may be identified through clinical diagnosis utilizing well known techniques (see, e.g., Harrison's Principles of Internal Medicine, McGraw-Hill, Inc.). Representative examples of diseases that may be treated included dysplasias, wherein there is abnormal growth or development of bone. Representative examples of such conditions include achondroplasia, cleidocranial dysostosis, enchondromatosis, fibrous dysplasia, Gaucher's, hypophosphatemic rickets, Marfan's, multiple hereditary exotoses, neurofibromatosis, osteogenesis imperfecta, osteopetrosis, osteopoikilosis, sclerotic lesions, fractures, periodontal disease, pseudoarthrosis and pyogenic osteomyelitis.

Other conditions which may be treated or prevented include a wide variety of causes of osteopenia (i.e., a condition that causes greater than one standard deviation of bone mineral content or density below peak skeletal mineral content at youth). Representative examples of such conditions include anemic states, conditions caused steroids, conditions caused by heparin, bone marrow disorders, scurvy, malnutrition, calcium deficiency, idiopathic osteoporosis, congenital osteopenia or osteoporosis, alcoholism, chronic liver disease, senility, postmenopausal state, oligomenorrhea, amenorrhea, pregnancy, diabetes mellitus, hyperthyroidism, Cushing's disease, acromegaly, hypogonadism, immobilization or disuse, reflex sympathetic dystrophy syndrome, transient regional osteoporosis and osteomalacia.

Within one aspect of the present invention, bone mineral content or density may be increased by administering to a warm-blooded animal a therapeutically effective amount of a molecule which inhibits the TGF-beta binding-protein binding to a TGF-beta family member. Examples of warm-blooded animals that may be treated include both vertebrates and mammals, including for example horses, cows, pigs, sheep, dogs, cats, rats and mice. Representative examples of therapeutic molecules include ribozymes, ribozyme genes, antisense oligonticleotides and antibodies (e.g, humanized antibodies).

Within other aspects of the present invention, methods are provided for increasing bone density, comprising the step of introducing into cells which home to bone a vector which directs the expression of a molecule which inhibits the TGF-beta binding-protein binding to a member of the TGF-beta family, and administering the vector containing cells to a warm-blooded animal. Briefly, cells which home to bone may be obtained directly from the bone of patients (e.g., cells obtained from the bone marrow such as CD34+, osteoblasts, osteocytes, and the like). from peripheral blood, or from cultures.

A vector which directs the expression of a molecule that inhibits the TGF-beta binding-protein binding to a member of the TGF-beta family is introduced into the cells. Representative examples of suitable vectors include viral vectors such as herpes viral vectors (e.g., U.S. Pat. No. 5.288,641), adenoviral vectors (e.g., WO 94/26914, WO 93/9191; Kolls et al. *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207. 1993; Zabner et al., *Cell* 75(2):207–216, 1993; Li et al., *Hum Gene Ther.* 4(4):403–409, 1993; Caillaud et al., *Eur. J. Neurosci.* 5(10:1287–1291, 1993; Vincent et al., *Nat. Genet.* 5(2):130–134, 1993; Jaffe et al., *Nat. Genet.* 1(5):372–378. 1992; and Levrero et al., *Gene* 101(2):195–202, 1991), adeno-associated viral vectors (WO 95/13365; Flotte et al., *PNAS* 90(22):10613–10617, 1993), baculovirus vectors, parvovirus vectors (Koering et al., *Hum. Gene Therap.* 5:457–463, 1994), pox virus vectors (Panicali and Paoletti, *PNAS* 79:4927–4931, 1982; and Ozaki et al., *Biochem. Biophys. Res. Comm.* 193(2):653–660, 1993), and retroviruses (e.g., EP 0,415,731; WO 90/07936; WO 91/0285, WO 94/03622; WO 91/25698; WO 93/25234; U.S. Pat. No. 5,219,740; WO 93/11230; WO 93/10218). Viral vectors may likewise be constructed which contain a mixture of different elements (e.g., promoters, envelope sequences and the like) from different viruses, or non-viral sources. Within various embodiments, either the viral vector itself, or a viral particle which contains the viral vector may be utilized in the methods and compositions described below.

Within other embodiments of the invention, nucleic acid molecules which encode a molecule which inhibits the TGF-beta binding-protein binding to a member of the TGF-beta family themselyes may be administered by a variety of techniques, including, for example, administration of asialoosomucoid (ASOR) conjugated with poly-L-lysine DNA complexes (Cristano et al., *PNAS* 92122–92126, 1993), DNA linked to killed adenovirus (Curiel et al., *Hum. Gene Ther.* 3(2):147–154, 1992), cytofectin-mediated introduction (DMRIE-DOPE, Vical, Calif.), direct DNA injection (Acsadi et al., *Nature* 352:815–818, 1991); DNA ligand (Wu et al., *J. of Biol. Chem.* 264:16985–16987, 1989); lipofection (Felgner et al., *Proc. Natl. Acad. Sci. USA* 84:7413–7417, 1989); liposomes (Pickering et al., *Circ.* 89(1):13–21, 1994; and Wang et al., *PNAS* 84:7851–7855, 1987); microprojectile bombardment (Williams et al., *PNAS* 88:2726–2730, 1991); and direct delivery of nucleic acids which encode the protein itself either alone (Vile and Hart, *Cancer Res.* 53: 3860–3864, 1993), or utilizing PEG-nucleic acid complexes.

Representative examples of molecules which may be expressed by the vectors of present invention include ribozymes and antisense molecules, each of which are discussed in more detail above.

Determination of increased bone mineral content may be determined directly through the use of X-rays (e.g., Dual Energy X-ray Absorptometry or "DEXA"), or by inference through bone turnover markers (osteoblast specific alkaline phosphatase, osteocalcin, type 1 procollagen C' propeptide (PICP), and total alkaline phosphatase; see Comier, C., *Curr. Opin. in Rheu.* 7:243, 1995), or markers of bone resorption (pyridinoline, deoxypryridinoline, N-telopeptide, urinary hydroxyproline, plasma tartrate-resistant acid phosphatases and galactosyl hydroxylysine; see Comier, supra). The amount of bone mass may also be calculated from body weights, or utilizing other methods (see Guinness-Hey, *Metab. Bone Dis. and Rel. Res.* 5:177–181, 1984).

As will be evident to one of skill in the art, the amount and frequency of administration will depend, of course, on such factors as the nature and severity of the indication being treated, the desired response, the condition of the patient, and so forth. Typically, the compositions maybe administered by a variety of techniques, as noted above.

The following examples are offered by way of illustration, and not by way of limitation.

EXAMPLES

Example 1

Sclerosteosis Maps to the Long Arm of Human Chromosome 17

Genetic mapping of the defect responsible for sclerosteosis in humans localized the gene responsible for this disorder to the region of human chromosome 17 that encodes a novel TGF-beta binding-protein family member. In sclerosteosis, skeletal bone displays a substantial increase in mineral density relative to that of unafflicted individuals. Bone in the head displays overgrowth as well. Sclerosteosis patients are generally healthy although they may exhibit variable degrees of syndactyly at birth and variable degrees of cranial compression and nerve compression in the skull.

Linkage analysis of the gene defect associated with sclerosteosis was conducted by applying the homozygosity mapping method to DNA samples collected from 24 South African Afrikaaner families in which the disease occurred. (Sheffield. et al., 1994, *Human Molecular Genetics* 3:1331–1335. "Identification of a Bardet-Biedl syndrome locus on chromosome 3 and evaluation of an efficient approach to homozygosity mapping"). The Afrikaaner population of South Africa is genetically homogeneous; the population is descended from a small number of founders who colonized the area several centuries ago, and it has been isolated by geographic and social barriers since the founding. Sclerosteosis is rare everywhere in the world outside the Afrikaaner community, which suggests that a mutation in the gene was present in the founding population and has since increased in numbers along with the increase in the population. The use of homozygosity mapping is based on the assumption that DNA mapping markers adjacent to a recessive mutation are likely to be homozygous in affected individuals from consanguineous families and isolated populations.

A set of 371 microsatellite markers (Research Genetics, Set 6) from the autosomal chromosomes was selected to type pools of DNA from sclerosteosis patient samples. The DNA samples for this analysis came from 29 sclerosteosis patients in 24 families, 59 unaffected family members and a set of unrelated control individuals from the same population. The pools consisted of 4–6 individuals, either affected individuals, affected individuals from consanguineous families, parents and unaffected siblings, or unrelated controls. In the pools of unrelated individuals and in most of the pools with affected individuals or family members analysis of the markers showed several allele sizes for each marker. One marker, D17S1299, showed an indication of homozygosity: one band in several of the pools of affected individuals.

All 24 sclerosteosis families were typed with a total of 19 markers in the region of D17S1299 (at 17q12-q21). Affected individuals from every family were shown to be homozygous in this region, and 25 of the 29 individuals were homozygous for a core haplotype; they each had the same alleles between D17S1787 and D17S930. The other four individuals had one chromosome which matched this haplotype and a second which did not. In sum, the data compellingly suggested that this 3 megabase region contained the sclerosteosis mutation. Sequence analysis of most of the exons in this 3 megabase region identified a nonsense mutation in the novel TGF-beta binding-protein coding sequence (C>T mutation at position 117 of Sequence ID No. 1 results in a stop codon). This mutation was shown to be unique to sclerosteosis patients and carriers of Afrikaaner descent. The identity of the gene was further confirmed by identifying a mutation in its intron (A>T mutation at position +3 of the intron) which results in improper mRNA processing in a single, unrelated patient with diagnosed sclerosteosis.

Example 2

Tissue-Specialty of TGF-beta Binding-Protein Gene Expression

A. Human Beer Gene Expression by RT-PCR

First-strand cDNA was prepared from the following total RNA samples using a commercially available kit ("Superscript Preamplification System for First-Strand cDNA Synthesis", Life Technologies, Rockville, Md.): human brain, human liver, human spleen, human thymus, human placenta, human skeletal muscle, human thyroid, human pituitary, human osteoblast (NHOst from Clonetics Corp., San Diego, Calif.), human osteosarcoma cell line (Saos-2, ATCC# HTB-85), human bone, human bone marrow, human cartilage, vervet monkey bone, *saccharomyces cerevisiae*, and human peripheral blood monocytes. All RNA samples were purchased from a commercial source (Clontech, Palo Alto, Calif.), except the following which were prepared in-house: human osteoblast, human osteosarcoma cell line, human bone, human cartilage and vervet monkey bone. These in-house RNA samples were prepared using a commercially available kit ("TRI Reagent", Molecular Research Center, Inc., Cincinnati, Ohio).

PCR was performed on these samples, and additionally on a human genomic sample as a control. The sense Beer oligonucleotide primer had the sequence 5'-CCGGA-GCTGGAGAACAACAAG-3' (SEQ ID NO:19). The antisense Beer oligonucleotide primer had the sequence 5'-GCACTGGCCGGAGCACACC-3' (SEQ ID NO:20). In addition, PCR was performed using primers for the human beta-actin gene, as a control. The sense beta-actin oligonucleotide primer had the sequence 5'-AGGCCAACCGC-GAGAAGATGA CC-3' (SEQ ID NO:21). The antisense beta-actin oligonucleotide primer had the sequence 5'-GAAGT CCAGGGCGACGTAGCA-3' (SEQ ID NO:22). PCR was performed using standard conditions in 25 ul reactions, with an annealing temperature of 61 degrees Celsius. Thirty-two cycles of PCR were performed with the Beer primers and twenty-four cycles were performed with the beta-actin primers.

Following amplification, 12 ul from each reaction were analyzed by agarose gel electrophoresis and ethidium bromide staining. See FIG. 2A.

B. RNA In-situ Hybridization of Mouse Embryo Sections

The full length mouse Beer cDNA (Sequence ID No. 11) was cloned into the pCR2.1 vector (Invitrogen, Carlsbad, Calif.) in the antisense and sense direction using the manufacturer's protocol. $^{35}$S-alpha-GTP-labeled cRNA sense and antisense transcripts were synthesized using in-vitro transcription reagents supplied by Ambion, Inc (Austin, Tex.). In-situ hybridization was performed according to the protocols of Lyons et al. (*J. Cell Biol.* 111:2427–2436, 1990).

The mouse Beer cRNA probe detected a specific message expressed in the neural tube, limb buds, blood vessels and ossifying cartilages of developing mouse embryos. Panel A in FIG. 3 shows expression in the apical ectodermal ridge (aer) of the limb (1) bud, blood vessels (bv) and the neural tube (nt). Panel B shows expression in the $4^{th}$ ventricle of the brain (4). Panel C shows expression in the mandible (ma) cervical vertebrae (cv), occipital bone (oc), palate (pa) and a blood vessel (bv). Panel D shows expression in the ribs (r) and a heart valye (va). Panel A is a transverse section of 10.5 dpc embryo. Panel B is a sagittal section of 12.5 dpc embryo and panels C and D are sagittal sections of 15.5 dpc embryos.

ba=branchial arch, h=heart, te=telencephalon (forebrain), b=brain, f=frontonasal mass, g=gut, h=heart, j=jaw, li=liver, lu=lung, ot=tic vesicle, ao=, sc=spinal cord, skm=skeletal muscle, ns=nasal sinus, th=thymus, to=tongue, fl=forelimb, di=diaphragm Example 3

Expression and Purification of Recombinant Beer Protein

A. Expression in COS-1 Cells

The DNA sequence encoding the full length human Beer protein was amplified using the following PCR oligonucleotide primers: The 5' oligonucleotide primer had the sequence 5'-AAGCTTGGTACCATGCAGCTCCCAC-3'

(SEQ ID NO:23) and contained a HindIII restriction enzyme site (in bold) followed by 19 nucleotides of the Beer gene starting 6 base pairs prior to the presumed amino terminal start codon (ATG). The 3' oligonucleotide primer had the sequence 5'-AAGCTTCTA CTTGTCATCGTCGTCCT TGTAGTC GTAGGCGTTCT- CCAGCT-3' (SEQ ID NO:24) and contained a HindIII restriction enzyme site (in bold) followed by a reverse complement stop codon (CTA) followed by the reverse complement of the FLAG epitope (underlined, Sigma- Aldrich Co., St. Louis, Mo.) flanked by the reverse complement of nucleotides coding for the carboxy terminal 5 amino acids of the Beer. The PCR product was TA cloned ("Original TA Cloning Kit", Invitrogen, Carlsbad, Calif.) and individual clones were screened by DNA sequencing. A sequence-verified clone was then digested by HindIII and purified on a 1.5% agarose gel using a commercially available reagents ("QIAquick Gel Extraction Kit", Qiagen Inc., Valencia, Calif.). This fragment was then ligated to HindIII digested, phosphatase-treated pcDNA3.1 (Invitrogen, Carlsbad, Calif.) plasmid with T4 DNA ligase. DH10B *E. coli* were transformed and plated on LB, 100 μg/ml ampicillin plates. Colonies bearing the desired recombinant in the proper orientation were identified by a PCR-based screen, using a 5' primer corresponding to the T7 promoter/priming site in pcDNA3.1 and a 3' primer with the sequence 5'-GCACTGGCCGGAGCACACC-3' (SEQ ID NO:25) that corresponds to the reverse complement of internal BEER sequence. The sequence of the cloned fragment was confirmed by DNA sequencing.

COS-1 cells (ATCC# CRL-1650) were used for transfection. 50 μg of the expression plasmid pcDNA-Beer-Flag was transfected using a commercially available kit following protocols supplied by the manufacturer ("DEAE-Dextran Transfection Kit", Sigma Chemical Co., St. Louis, Mo.). The final media following transfection was DMEM (Life Technologies, Rockville, Md.) containing 0.1% Fetal Bovine Serum. After 4 days in culture, the media was removed. Expression of recombinant BEER was analyzed by SDS-PAGE and Western Blot using anti-FLAG M2 monoclonal antibody (Sigma-Aldrich Co., St. Louis, Mo.). Purification of recombinant BEER protein was performed using an anti-FLAG M2 affinity column ("Mammalian Transient Expression System", Sigma-Aldrich Co., St. Louis, Mo.). The column profile was analyzed via SDS-PAGE and Western Blot using anti-FLAG M2 monoclonal antibody.

B. Expression in SF9 Insect Cells

The human Beer gene sequence was amplified using PCR with standard conditions and the following primers:
Sense primer: 5'-GTCGTCGGATCCATGGGGTGG- CAGGCGTTCAAGAATGAT-3' (SEQ ID NO:26)
Antisense primer: 5'-GTCGTCAAGCTTCTACTTGTCAT- CGTCCTTGTAGTCGTA GGCGTTCTCCAG- CTCGGC-3' (SEQ ID NO:27)

The resulting cDNA contained the coding region of Beer with two modifications. The N-terminal secretion signal was removed and a FLAG epitope tag (Sigma) was fused in frame to the C-terminal end of the insert. BamH1 and HindIII cloning sites were added and the gene was subcloned into pMelBac vector (1nvitrogen) for transfer into a baculoviral expression vector using standard methods.

Recombinant baculoviruses expressing Beer protein were made using the Bac-N-Blue transfection kit (Invitrogen) and purified according to the manufacturers instructions.

SF9 cells (Invitrogen) were maintained in TNM_FH media (Invitrogen) containing 10% fetal calf serum. For protein expression, SF9 cultures in spinner flasks were infected at an MOI of greater than 10. Samples of the media and cells were taken daily for five days, and Beer expression monitored by western blot using an anti-FLAG M2 monoclonal antibody (Sigma) or an anti-Beer rabbit polyclonal antiserum.

After five days the baculovirus-infected SF9 cells were harvested by centrifugation and cell associated protein was extracted from the cell pellet using a high salt extraction buffer (1.5 M NaCl, 50 mM Tris pH 7.5). The extract (20 ml per 300 ml culture) was clarified by centrifugation, dialyzed three times against four liters of Tris buffered saline (150 mM NaCl, 50 mM Tris pH 7.5), and clarified by centrifugation again. This high salt fraction was applied to Hitrap Heparin (Pharmacia; 5 ml bed volume), washed extensively with HEPES buffered saline (25 mM HEPES 7.5, 150 mM Nacl) and bound proteins were eluted with a gradient from 150 mM NaCl to 1200 mM NaCl. Beer elution was observed at aproximately 800 mM NaCl. Beer containing fractions were supplemented to 10% glycerol and 1 mM DTT and frozen at −80 degrees C.

Example 4

Preparation and Testing of Polyclonal Antibodies to Beer Gremlin, and Dan

A. Preparation of Antigen

The DNA sequences of Human Beer, Human Gremlin, and Human Dan were amplified using standard PCR methods with the following oligonucleotide primers:
H. Beer
Sense: 5'-GACTTGGATCCCAGGGGTGGCAGGCGTTC- 3' (SEQ ID NO:28)
Antisense 5'-AGCATAAGCTTCTAGTAGGCGTTCT- CCAG-3' (SEQ ID NO:29)
H. Gremlin
Sense: 5'-GACTTGGATCCGAAGGGAAAAAGAAA- GGG-3' (SEQ ID NO:30)
Antisense: 5'-AGCATAAGCTTTTAATCCAAATC- GATGGA-3' (SEQ ID NO:31)
H. Dan
Sense: 5'-ACTACGAGCTCGGCCCCACACCACCC- ATCAACAAG-3' (SEQ ID NO:32)
Antisense: 5'-ACTTAGAAGCTTTCAGTCCTCAGCCCCCTCTT- CC-3' (SEQ ID NO:33)

In each case the listed primers amplified the entire coding region minus the secretion signal sequence. These include restriction sites for subcloning into the bacterial expression vector pQE-30 (Qiagen Inc., Valencia, Calif.) at sites BamHI/HindIII for Beer and Gremlin, and sites SacI/HindIII for Dan pQE30 contains a coding sequence for a 6×His tag at the 5' end of the cloning region. The completed constructs were transformed into *E. coli* strain M-15/pRep (Qiagen Inc) and individual clones verified by sequencing. Protein expression in M-15/pRep and purification (6×His affinity tag binding to Ni-NTA coupled to Sepharose) were performed as described by the manufacturer (Qiagen, The QiAexpressionist).

The *E. coli*-derived Beer protein was recovered in significant quantity using solubilization in 6M guanidine and dialyzed to 2–4M to prevent precipitation during storage. Gremlin and Dan protein were recovered in higher quantity with solubilization in 6M guanidine and a post purification guanidine concentration of 0.5M.

B. Production and Testing of Polyclonal Antibodies

Polyclonal antibodies to each of the three antigens were produced in rabbit and in chicken hosts using standard protocols (R & R Antibody, Stanwood, Wash.; standard protocol for rabbit immunization and antisera recovery; Short Protocols in Molecular Biology. 2nd edition. 1992. 11.37–11.41. Contributors Helen M. Cooper and Yvonne Paterson; chicken antisera was generated with Strategic Biosolutions, Ramona, Calif.).

Rabbit antisera and chicken egg Igy fraction were screened for activity via Western blot. Each of the three antigens was separated by PAGE and transferred to 0.45 um nitrocellulose (Novex, San Diego, Calif.). The membrane was cut into strips with each strip containing approximately 75 ng of antigen. The strips were blocked in 3% Blotting Grade Block (Bio-Rad Laboratories, Hercules, Calif.) and washed 3 times in 1×Tris buffer saline (TBS)/0.02% TWEEN buffer. The primary antibody (preimrnmunization bleeds, rabbit antisera or chicken egg IgY in dilutions ranging from 1:100 to 1:10,000 in blocking buffer) was incubated with the strips for one hour with gentle rocking. A second series of three washes 1×TBS/0.02%TWEEN was followed by an one hour incubation with the secondary antibody (peroxidase conjugated donkey anti-rabbit, Amersharn Life Science, Piscataway, N.J.; or peroxidase conjugated donkey anti-chicken, Jackson ImmunoResearch, West Grove, Pa.). A final cycle of 3×washes of 1×TBS/0.02%TWEEN was performed and the strips were developed with Lumi-Light Western Blotting Substrate (Roche Molecular Biochemicals, Mannheim, Germany).

C. Antibody Cross-reactivity Test

Following the protocol described in the previous section, nitrocellulose strips of Beer, Gremlin or Dan were incubated with dilutions (1:5000 and 1:10,000) of their respective rabbit antisera or chicken egg IgY as well as to antisera or chicken egg Igy (dilutions 1:1000 and 1:5000) made to the remaining two antigens. The increased levels of nonmatching antibodies was performed to detect low affinity binding by those antibodies that may be seen only at increased concentration. The protocol and duration of development is the same for all three binding events using the protocol described above. There was no antigen cross-reactivity observed for any of the antigens tested.

Example 5

Interaction of Beer with TGF-beta Super-family Proteins

Figure 5:
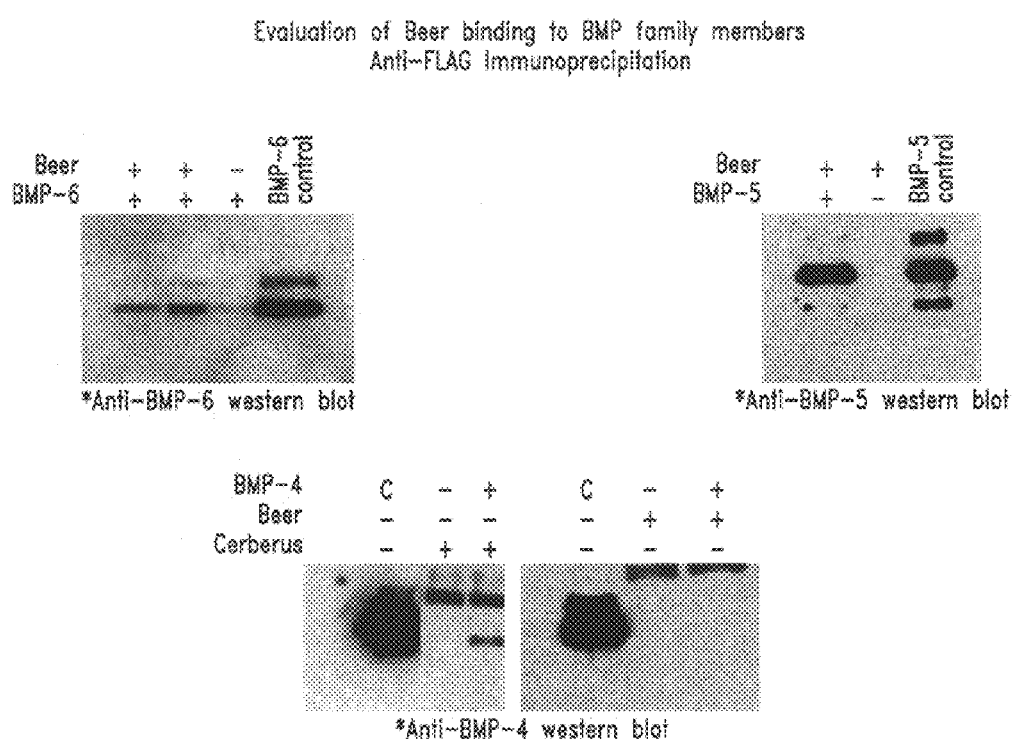
FIG. 5 illustrates, by western blot analysis, the selectivity of the TGF-beta binding-protein, Beer, for BMP-5 and BMP-6, but not BMP-4 (described in more detail in EXAMPLE 5).

The interaction of Beer with proteins from different phylogenetic arms of the TGF-β superfamily were studied using immunoprecipitation methods. Purified TGFβ-1, TGFβ-2, TGFβ-3, BMP-4, BMP-5, BMP-6 and GDNF were obtained from commerical sources (R&D systems; Minneapolis, Minn.). A representative protocol is as follows. Partially purified Beer was dialyzed into HEPES buffered saline (25 mM HEPES 7.5, 150 mM NaCl). Immunoprecipitations were done in 300 ul of IP buffer (150 mM NaCl, 25 mM Tris pH 7.5, 1 mM EDTA, 1.4 mM β-mercaptoethanol, 0.5% triton×100, and 10% glycerol). 30 ng recombinant human BMP-5 protein (R&D systems) was applied to 15 ul of FLAG affinity matrix (Sigma; St Louis Mo.)) in the presence and absence of 500 ng FLAG epitope-tagged Beer. The proteins were incubated for 4 hours @ 4° C. and then the affinity matrix-associated proteins were washed 5 times in IP buffer (1 ml per wash). The bound proteins were eluted from the affinity matrix in 60 microliters of 1×SDS PAGE sample buffer. The proteins were resolved by SDS PAGE and Beer associated BMP-5 was detected by western blot using anti-BMP-5 antiserum (Research Diagnostics, Inc) (see FIG. 5).

BEER Ligand Binding Assay

FLAG-Beer protein (20 ng) is added to 100 ul PBS/0.2% BSA and adsorbed into each well of 96 well microtiter plate previously coated with anti-FLAG monoclonal antibody (Sigma; St Louis Mo.) and blocked with 10% BSA in PBS. This is conducted at room temperature for 60 minutes. This protein solution is removed and the wells are washed to remove unbound protein. BMP-5 is added to each well in concentrations ranging from 10 pM to 500 nM in PBS/0.2% BSA and incubated for 2 hours at room temperature. The binding solution is removed and the plate washed with three times with 200 ul volumes of PBS/0.2% BSA. BMP-5 levels are then detected using BMP-5 anti-serum via ELISA (F. M. Ausubel et al (1998) Current Protocols in Mol Biol. Vol 2 11.2.1–11.2.22). Specific binding is calculated by subtracting non-specific binding from total binding and analyzed by the LIGAND program (Munson and Podbard, Anal. Biochem., 107, p220–239, (1980).

In a variation of this method, Beer is engineered and expressed as a human Fc fusion protein. Likewise the ligand BMP is engineered and expressed as mouse Fc fusion. These proteins are incubated together and the assay conducted as described by Mellor et al using homogeneous time resolved fluorescence detection (G. W. Mellor et al., *J of Biomol Screening*, 3(2) 91–99, 1998).

Example 6

Screening Assay for Inhibition of TGF-beta binding-protein Binding to TGF-beta Family Members The assay described above is replicated with two exceptions. First, BMP concentration is held fixed at the Kd determined previously. Second, a collection of antagonist candidates is added at a fixed concentration (20 uM in the case of the small organic molecule collections and 1 uM in antibody studies). These candidate molecules (antagonists) of TGF-beta binding-protein binding include organic compounds derived from commercial or internal collections representing diverse chemical structures. These compounds are prepared as stock solutions in DMSO and are added to assay wells at ≦1% of final volume under the standard assay conditions. These are incubated for 2 hours at room temperature with the BMP and Beer, the solution removed and the bound BMP is quantitated as described. Agents that inhibit 40% of the BMP binding observed in the absence of compound or antibody are considered antagonists of this interaction. These are further evaluated as potential inhibitors based on titration studies to determine their inhibition constants and their influence on TGF-beta binding-protein binding affinity. Comparable specificity control assays may also be conducted to establish the selectivity profile for the identified antagonist through studies using assays dependent on the BMP ligand action (e.g. BMP/BMP receptor competition study).

Example 7

Inhibition of TGF-beta Binding-protein Localization to Bone Matrix

Evaluation of inhibition of localization to bone matrix (hydroxyapatite) is conducted using modifications to the method of Nicolas (Nicolas, V. *Calcif Tissue Int* 57:206, 1995). Briefly, $^{125}$I-labelled TGF-beta binding-protein is prepared as described by Nicolas (supra). Hydroxyapatite is added to each well of a 96 well microtiter plate equipped with a polypropylene filtration membrane (Polyfiltroninc, Weymouth Mass.). TGF-beta binding-protein is added to 0.2% albumin in PBS buffer. The wells containing matrix are washed 3 times with this buffer. Adsorbed TGF-beta binding-protein is eluted using 0.3M NaOH and quantitated.

Inhibitor identification is conducted via incubation of TGF-beta binding-protein with test molecules and applying the mixture to the matrix as described above. The matrix is washed 3 times with 0.2% albunin in PBS buffer. Adsorbed TGF-beta binding-protein is eluted using 0.3 M NaOH and quantitated. Agents that inhibit 40% of the TGF-beta binding-protein binding observed in the absence of compound or antibody are considered bone localization inhibitors. These inhibitors are further characterized through dose response studies to determine their inhibition constants and their influence on TGF-beta binding-protein binding affinity.

Example 8

Construction of TGF-beta Binding-protein Mutant

A. Mutagenesis

A full-length TGF-beta binding-protein cDNA in pBluescript SK serves as a template for mutagenesis. Briefly, appropriate primers (see the discussion provided above) are utilized to generate the DNA fragment by polymerase chain reaction using Vent DNA polymerase (New England Biolabs, Beverly, Mass.). The polymerase chain reaction is run for 23 cycles in buffers provided by the manufacturer using a 57° C. annealing temperature. The product is then exposed to two restriction enzymes and after isolation using agarose gel electrophoresis, ligated back into pRBP4-503 from which the matching sequence has been removed by enzymatic digestion. Integrity of the mutant is verified by DNA sequencing.

B. Mammalian Cell Expression and Isolation of Mutant TGF-beta Binding-protein

The mutant TGF-beta binding-protein cDNAs are transferred into the pcDNA3.1 mammalian expression vector described in EXAMPLE 3. After verifying the sequence, the resultant constructs are transfected into COS-1 cells, and secreted protein is purified as described in EXAMPLE 3.

Example 9

Animal Models-I

Generation of Transgenic Mice Overexpressing the Beer Gene

The ~200 kilobase (kb) BAC clone 15G5, isolated from the CITB mouse genomic DNA library (distributed by Research Genetics, Huntsville, Ala.) was used to determine the complete sequence of the mouse Beer gene and its 5' and 3' flanking regions. A 41 kb SalI fragment, containing the entire gene body, plus ~17 kb of 5' flanking and ~20 kb of 3' flanking sequence was sub-cloned into the BamHI site of the SuperCosI cosmid vector (Stratagene, La Jolla, Calif.) and propagated in the *E. coli* strain DH10B. From this cosmid construct, a 35 kb MluI-AvilI restriction fragment (Sequence No. 6), including the entire mouse Beer gene, as well as 17 kb and 14 kb of 5' and 3' flanking sequence, respectively, was then gel purified, using conventional means, and used for microinjection of mouse zygotes (DNX Transgenics; U.S. Pat. No. 4,873,191). Founder animals in which the cloned DNA fragment was integrated randomly into the genome were obtained at a frequency of 5–30% of live-born pups. The presence of the transgene was ascertained by performing Southern blot analysis of genomic DNA extracted from a small amount of mouse tissue, such as the tip of a tail. DNA was extracted using the following protocol: tissue was digested overnight at 55° C. in a lysis buffer containing 200 mM NaCl, 100 mM Tris pH8.5, 5 mM EDTA, 0.2% SDS and 0.5 mg/ml Proteinase K. The following day, the DNA was extracted once with phenol/chloroform (50:50), once with chloroform/isoamylalcohol (24:1) and precipitated with ethanol. Upon resuspension in TE (10 mM Tris pH7.5, 1 mM EDTA) 8–10 ug of each DNA sample were digested with a restriction endonuclease, such as EcoRI, subjected to gel electrophoresis and transferred to a charged nylon membrane, such as HyBondN+ (Amersham, Arlington Heights, Ill.). The resulting filter was then hybridized with a radioactively labelled fragment of DNA deriving from the mouse Beer gene locus, and able to recognize both a fragment from the endogenous gene locus and a fragment of a different size deriving from the transgene. Founder animals were bred to normal non-transgenic mice to generate sufficient numbers of transgenic and non-transgenic progeny in which to determine the effects of Beer gene overexpression. For these studies, animals at various ages (for example, 1 day, 3 weeks, 6 weeks, 4 months) are subjected to a number of different assays designed to ascertain gross skeletal formation, bone mineral density, bone mineral content, osteoclast and osteoblast activity, extent of endochondral ossification, cartilage formation, etc. The transcriptional activity from the transgene may be determined by extracting RNA from various tissues, and using an RT-PCR assay which takes advantage of single nucleotide polymorphisms between the mouse strain from which the transgene is derived (129Sv/J) and the strain of mice used for DNA microinjection [(C57BL5/J×SJL/J)F2].

Animal Models-II

Disruption of the Mouse Beer Gene by Homologous Recombination

Homologous recombination in embryonic stem (ES) cells can be used to inactivate the endogenous mouse Beer gene and subsequently generate animals carrying the loss-of-function mutation. A reporter gene, such as the *E. coli* β-galactosidase gene, was engineered into the targeting vector so that its expression is controlled by the endogenous Beer gene's promoter and translational initiation signal. In this way, the spatial and temporal patterns of Beer gene expression can be determined in animals carrying a targeted allele.

The targeting vector was constructed by first cloning the drug-selectable phosphoglycerate kinase (PGK) promoter driven neomycin-resistance gene (neo) cassette from pGT-N29 (New England Biolabs, Beverly, Mass.) into the cloning vector pSP72 (Promega, Madson, Wis.). PCR was used to flank the PGKneo cassette with bacteriophage P1 loxP sites, which are recognition sites for the P1 Cre recombinase (Hoess et al., PNAS USA, 79:3398, 1982). This allows subsequent removal of the neo-resistance marker in targeted ES cells or ES cell-derived animals (U.S. Pat. No. 4,959, 317). The PCR primers were comprised of the 34 nucleotide (ntd) loxP sequence, 15–25 ntd complementary to the 5' and 3' ends of the PGKneo cassette, as well as restriction enzyme recognition sites (BamHI in the sense primer and EcoRI in the anti-sense primer) for cloning into pSP72. The sequence of the sense primer was 5'-AATCTGGATCCATAACTTCG-TATAG CATAC ATTATAC G AAG TTAF CTG CAG GATTCGAGGGCCCCT-3' (SEQ ID NO:34); sequence of the anti-sense primer was 5'-AATCTGAATTCCACCG-GTGTTAATTAAATAACTTCGT ATAATGTATGC-TATACGAAGTTATAGATCTAGAG TCAGCTTCTGA-3' (SEQ ID NO:35).

The next step was to clone a 3.6 kb XhoI-HindIII fragment, containing the E. coli β-galactosidase gene and SV40 polyadenylation signal from pSVβ (Clontech, Palo Alto, Calif.) into the pSP72-PGKneo plasmid. The "short arm" of homology from the mouse Beer gene locus was generated by amplifying a 2.4 kb fragment from the BAC clone 15G5. The 3' end of the fragment coincided with the translational initiation site of the Beer gene, and the anti-sense primer used in the PCR also included 30 ntd complementary to the 5' end of the β-galactosidase gene so that its coding region could be fused to the Beer initiation site in-frame. The approach taken for introducing the "short arm" into the pSP72-βgal-PGKneo plasmid was to linearize the plasmid at a site upstream of the β-gal gene and then to co-transform this fragment with the "short arm" PCR product and to select for plasmids in which the PCR product was integrated by homologous recombination. The sense primer for the "short arm" amplification included 30 ntd complementary to the pSP72 vector to allow for this recombination event. The sequence of the sense primer was 5'-ATTTAGGTGACACTATAGAACTCGAGCAGCTGA-AGCTTAACCACATGGTGGCTCACAACCAT-3' (SEQ ID NO:36) and the sequence of the anti-sense primer was 5'AACGACGGCCAGTGAATCCGTA ATCATGGTC-ATGCTGCCAGGTGGAGGAGGGCA-3' (SEQ ID NO:37).

The "long arm" from the Beer gene locus was generated by amplifying a 6.1 kb fragment from BAC clone 15G5 with primers which also introduce the rare-cutting restriction enzyme sites SgrAI, FseI, AscI and PacI. Specifically, the sequence of the sense primer was 5'-ATTACC-ACCGGTGACACCCGCTTCCTGACAG-3' (SEQ ID NO:38); the sequence of the anti-sense primer was 5'-ATTACTTAATTAAACATGGCGCGCCAT ATGGCCGGCCCCTAATTGCGGCGCATCGTTAATT-3' (SEQ ID NO:39). The resulting PCR product was cloned into the TA vector (Invitrogen, Carlsbad, Calif.) as an intermediate step.

The mouse Beer gene targeting construct also included a second selectable marker, the herpes simplex virus I thymidine kinase gene (HSVTK) under the control of rous sarcoma virus long terminal repeat element (RSV LTR). Expression of this gene renders mammalian cells sensitive (and inviable) to gancyclovir; it is therefore a convenient way to select against neomycin-resistant cells in which the construct has integrated by a non-homologous event (U.S. Pat. No. 5,464,764). The RSVLTR-HSVTK cassette was amplified from pPS1337 using primers that allow subsequent cloning into the FseI and AscI sites of the "long arm"-TA vector plasmid. For this PCR, the sequence of the sense primer was 5'-ATTACGGCCGCCGCAAAGG-AATTCAAGATCTGA-3' (SEQ ID NO:40); the sequence of the anti-sense primer was 5'-ATTACGGCGCGCCCCTC ACAGGCCGCACCCAGCT-3' (SEQ ID NO:41).

The final step in the construction of the targeting vector involved cloning the 8.8 kb SgrAI-AscI fragment containing the "long arm" and RSVLTR-HSVTK gene into the SgrAI and AscI sites of the pSP72-"short arm"-βgal-PGKneo plasmid. This targeting vector was linearized by digestion with either AscI or PacI before electroporation into ES cells.

Example 10

Antisense-mediated Beer Inactivation 17-nucleotide antisense oligonucleotides are prepared in an overlapping format, in such a way that the 5' end of the first oligonucleotide overlaps the translation initiating AUG of the Beer transcript, and the 5' ends of successive oligonucleotides occur in 5 nucleotide increments moving in the 5' direction (up to 50 nucleotides away), relative to the Beer AUG. Corresponding control oligonucleotides are designed and prepared using equivalent base composition but redistributed in sequence to inhibit any significant hybridization to the coding mRNA. Reagent delivery to the test cellular system is conducted through cationic lipid delivery (P. L. Felgner, Proc. Natl. Acad. Sci. USA 84:7413, 1987). 2 ug of antisense oligonucleotide is added to 100 ul of reduced serum media (Opti-MEM I reduced serum media; Life Technologies, Gaithersburg Md.) and this is mixed with Lipofectin reagent (6 ul) (Life Technologies, Gaithersburg Md.) in the 100 ul of reduced serum media. These are mixed, allowed to complex for 30 minutes at room temperature and the mixture is added to previously seeded MC3T3E21 or KS483 cells. These cells are cultured and the mRNA recovered. Beer mRNA is monitored using RT-PCR in conjunction with Beer specific primers. In addition, separate experimental wells are collected and protein levels characterized through western blot methods described in Example 4. The cells are harvested, resuspended in lysis buffer (50 mM Tris pH 7.5, 20 mM NaCl, 1 mM EDTA, 1% SDS) and the soluble protein collected. This material is applied to 10–20% gradient denaturing SDS PAGE. The separated proteins are transferred to nitrocellulose and the western blot conducted as above using the antibody reagents described. In parallel, the control oligonucleotides are added to identical cultures and experimental operations are repeated. Decrease in Beer mRNA or protein levels are considered significant if the treatment with the antisense oligonucleotide results in a 50% change in either instance compared to the control scrambled oligonucleotide. This methodology. enables selective gene inactivation and subsequent phenotype characterization of the mineralized nodules in the tissue culture model.

SEQUENCE LISTING

<160> NUMBER OF SEQ ID NOS: 45

<210> SEQ ID NO 1
<211> LENGTH: 2301
<212> TYPE: DNA
<213> ORGANISM: Homo sapien

<400> SEQUENCE: 1
agagcctgtg ctactggaag gtggcgtgcc ctcctctggc tggtaccatg cagctcccac    60

-continued

```
tggccctgtg tctcgtctgc ctgctggtac acacagcctt ccgtgtagtg gagggccagg      120
ggtggcaggc gttcaagaat gatgccacgg aaatcatccc cgagctcgga gagtaccccg      180
agcctccacc ggagctggag aacaacaaga ccatgaaccg ggcggagaac ggagggcggc      240
ctccccacca cccctttgag accaaagacg tgtccgagta cagctgccgc gagctgcact      300
tcacccgcta cgtgaccgat gggccgtgcc gcagcgccaa gccggtcacc gagctggtgt      360
gctccggcca gtgcggcccg gcgcgcctgc tgcccaacgc catcggccgc ggcaagtggt      420
ggcgacctag tgggcccgac ttccgctgca tccccgaccg ctaccgcgcg cagcgcgtgc      480
agctgctgtg tccggtggt gaggcgccgc gcgcgcgcaa ggtgcgcctg gtggcctcgt       540
gcaagtgcaa cgcctcacc cgcttccaca ccagtcgga gctcaaggac ttcgggaccg        600
aggccgctcg gccgcagaag ggccggaagc cgcggccccg cgcccggagc gccaaagcca      660
accaggccga gctggagaac gcctactaga gcccgcccgc gccctcccc accggcgggc       720 gccccggccc tgaacccgcg ccccacattt ctgtcctctg cgcgtggttt gattgtttat      780
atttcattgt aaatgcctgc aacccagggc aggggggctga ccttccag gccctgagga      840 atcccgggcg ccggcaaggc cccctcagc ccgccagctg agggtccca cggggcaggg        900 gagggaattg agagtcacag acactgagcc acgcagcccc gcctctgggg ccgcctacct      960
ttgctggtcc cacttcagag gaggcagaaa tggaagcatt tcaccgccc tggggttttta     1020 agggagcggt gtgggagtgg gaaagtccag ggactggtta agaaagttgg ataagattcc      1080
cccttgcacc tcgctgccca tcagaaagcc tgaggcgtgc ccagagcaca agactgggg      1140 caactgtaga tgtggtttct agtcctggct ctgccactaa cttgctgtgt aaccttgaac      1200
tacacaattc tccttcggga cctcaatttc cactttgtaa aatgagggtg gaggtgggaa      1260
taggatctcg aggagactat tggcatatga ttccaaggac tccagtgcct tttgaatggg      1320
cagaggtgag agagagagag agaaagagag agaatgaatg cagttgcatt gattcagtgc      1380
caaggtcact tccagaattc agagttgtga tgctctcttc tgacagccaa agatgaaaaa      1440
caaacagaaa aaaaaaagta aagagtctat ttatggctga catatttacg gctgacaaac      1500
tcctggaaga agctatgctg cttcccagcc tggcttcccc ggatgtttgg ctacctccac      1560
ccctccatct caaagaaata acatcatcca ttggggtaga aaaggagagg gtccgagggt      1620
ggtgggaggg atagaaatca catccgcccc aacttcccaa agagcagcat ccctcccccg      1680
acccatagcc atgtttttaaa gtcaccttcc gaagagaagt gaaaggttca aggacactgg      1740
ccttgcaggc ccgagggagc agccatcaca aactcacaga ccagcacatc ccttttgaga      1800
caccgccttc tgcccaccac tcacggacac atttctgcct agaaaacagc ttcttactgc      1860
tcttacatgt gatggcatat cttacactaa agaatatta ttgggggaaa aactacaagt       1920
gctgtacata tgctgagaaa ctgcagagca taatagctgc cacccaaaaa tcttttttgaa    1980 aatcatttcc agacaacctc ttactttctg tgtagttttt aattgttaaa aaaaaaaagt     2040
tttaaacaga agcacatgac atatgaaagc ctgcaggact ggtcgttttt ttggcaattc     2100
ttccacgtgg gacttgtcca caagaatgaa agtagtggtt tttaaagagt taagttacat    2160
atttattttc tcacttaagt tatttatgca aaagttttc ttgtagagaa tgacaatgtt      2220
aatattgctt tatgaattaa cagtctgttc ttccagagtc cagagacatt gttaataaag     2280
acaatgaatc atgaccgaaa g                                                2301
```

<210> SEQ ID NO 2
<211> LENGTH: 213

```
<212> TYPE: PRT
<213> ORGANISM: Homo sapien

<400> SEQUENCE: 2

Met Gln Leu Pro Leu Ala Leu Cys Leu Val Cys Leu Leu Val His Thr
 1               5                  10                  15

Ala Phe Arg Val Val Glu Gly Gln Gly Trp Gln Ala Phe Lys Asn Asp
                20                  25                  30

Ala Thr Glu Ile Ile Pro Glu Leu Gly Glu Tyr Pro Glu Pro Pro
         35                  40                  45

Glu Leu Glu Asn Asn Lys Thr Met Asn Arg Ala Glu Asn Gly Gly Arg
     50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
                100                 105                 110

Arg Leu Leu Pro Asn Ala Ile Gly Arg Gly Lys Trp Trp Arg Pro Ser
            115                 120                 125

Gly Pro Asp Phe Arg Cys Ile Pro Asp Arg Tyr Arg Ala Gln Arg Val
        130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210

<210> SEQ ID NO 3
<211> LENGTH: 2301
<212> TYPE: DNA
<213> ORGANISM: Homo sapien

<400> SEQUENCE: 3
agagcctgtg ctactggaag gtggcgtgcc ctcctctggc tggtaccatg cagctcccac      60
tggccctgtg tctcgtctgc ctgctggtac acacagcctt ccgtgtagtg gagggctagg    120
ggtggcaggc gttcaagaat gatgccacgg aaatcatccc cgagctcgga gagtaccccg    180
agcctccacc ggagctggag aacaacaaga ccatgaaccg ggcggagaac ggagggcggc    240
ctccccacca cccctttgag accaaagacg tgtccgagta cagctgccgc gagctgcact    300
tcacccgcta cgtgaccgat gggccgtgcc gcagcgccaa gccggtcacc gagctggtgt    360
gctccggcca gtgcgggccg gcgcgcctgc tgcccaacgc catcggccgc ggcaagtggt    420
ggcgacctag tgggcccgac ttccgctgca tccccgaccg ctaccgcgcg cagcgcgtgc    480
agctgctgtg tccggtggt gaggcgccgc gcgcgcaa ggtgcgcctg gtggcctcgt       540
gcaagtgcaa gcgcctcacc cgcttccaca accagtcgga gctcaaggac ttcgggaccg    600
aggccgctcg gccgcagaag ggccggaagc cgcggcccg cgcccggagc gccaaagcca    660
accaggccga gctggagaac gcctactaga gcccgcccgc gcccctcccc accggcgggc    720
```

-continued

| | |
|---|---|
| gccccggccc tgaacccgcg ccccacattt ctgtcctctg cgcgtggttt gattgtttat | 780 |
| atttcattgt aaatgcctgc aacccagggc agggggctga gaccttccag gccctgagga | 840 |
| atcccgggcg ccggcaaggc cccctcagc ccgccagctg aggggtccca cggggcaggg | 900 |
| gagggaattg agagtcacag acactgagcc acgcagcccc gcctctgggg ccgcctacct | 960 |
| ttgctggtcc cacttcagag gaggcagaaa tggaagcatt ttcaccgccc tggggttttta | 1020 |
| agggagcggt gtgggagtgg gaaagtccag ggactggtta agaaagttgg ataagattcc | 1080 |
| cccttgcacc tcgctgccca tcagaaagcc tgaggcgtgc ccagagcaca agactggggg | 1140 |
| caactgtaga tgtggtttct agtcctggct ctgccactaa cttgctgtgt aaccttgaac | 1200 |
| tacacaattc tccttcggga cctcaatttc cactttgtaa aatgagggtg gaggtgggaa | 1260 |
| taggatctcg aggagactat tggcatatga ttccaaggac tccagtgcct tttgaatggg | 1320 |
| cagaggtgag agagagagag agaaagagag agaatgaatg cagttgcatt gattcagtgc | 1380 |
| caaggtcact tccagaattc agagttgtga tgctctcttc tgacagccaa agatgaaaaa | 1440 |
| caaacagaaa aaaaaagta aagagtctat ttatggctga catatttacg gctgacaaac | 1500 |
| tcctggaaga agctatgctg cttcccagcc tggcttcccc ggatgtttgg ctacctccac | 1560 |
| ccctccatct caaagaaata acatcatcca ttggggtaga aaaggagagg gtccgagggt | 1620 |
| ggtgggaggg atagaaatca catccgcccc aacttcccaa agagcagcat ccctcccccg | 1680 |
| acccatagcc atgttttaaa gtcaccttcc gaagagaagt gaaaggttca aggacactgg | 1740 |
| ccttgcaggc ccgagggagc agccatcaca aactcacaga ccagcacatc ccttttgaga | 1800 |
| caccgccttc tgcccaccac tcacggacac atttctgcct agaaaacagc ttcttactgc | 1860 |
| tcttacatgt gatggcatat cttacactaa agaatatta ttgggggaaa aactacaagt | 1920 |
| gctgtacata tgctgagaaa ctgcagagca taatagctgc cacccaaaaa tcttttttgaa | 1980 |
| aatcatttcc agcaacctc ttactttctg tgtagttttt aattgttaaa aaaaaaaagt | 2040 |
| tttaaacaga agcacatgac atatgaaagc ctgcaggact ggtcgttttt ttggcaattc | 2100 |
| ttccacgtgg gacttgtcca caagaatgaa agtagtggtt tttaaagagt taagttacat | 2160 |
| atttattttc tcacttaagt tatttatgca aaagttttc ttgtagagaa tgacaatgtt | 2220 |
| aatattgctt tatgaattaa cagtctgttc ttccagagtc cagagacatt gttaataaag | 2280 |
| acaatgaatc atgaccgaaa g | 2301 |

<210> SEQ ID NO 4
<211> LENGTH: 23
<212> TYPE: PRT
<213> ORGANISM: Homo sapien

<400> SEQUENCE: 4

Met Gln Leu Pro Leu Ala Leu Cys Leu Val Cys Leu Leu Val His Thr
1               5                   10                  15

Ala Phe Arg Val Val Glu Gly
            20

<210> SEQ ID NO 5
<211> LENGTH: 2301
<212> TYPE: DNA
<213> ORGANISM: Homo sapien

<400> SEQUENCE: 5

| | |
|---|---|
| agagcctgtg ctactggaag gtggcgtgcc ctcctctggc tggtaccatg cagctcccac | 60 |
| tggccctgtg tctcatctgc ctgctggtac acacagcctt ccgtgtagtg gagggccagg | 120 |

```
ggtggcaggc gttcaagaat gatgccacgg aaatcatccg cgagctcgga gagtaccccg      180
agcctccacc ggagctggag aacaacaaga ccatgaaccg gcggagaac ggagggcggc       240 ctccccacca cccctttgag accaaagacg tgtccgagta cagctgccgc gagctgcact      300
tcacccgcta cgtgaccgat gggccgtgcc gcagcgccaa gccggtcacc gagctggtgt     360
gctccggcca gtgcggcccg cgcgcgcctgc tgcccaacgc catcggccgc ggcaagtggt    420
ggcgacctag tgggcccgac ttccgctgca tccccgaccg ctaccgcgcg cagcgcgtgc     480
agctgctgtg tcccggtggt gaggcgccgc gcgcgcgcaa ggtgcgcctg gtggcctcgt    540
gcaagtgcaa gcgcctcacc cgcttccaca accagtcgga gctcaaggac ttcgggaccg    600
aggccgctcg gccgcagaag ggccggaagc gcgcggcccccg cgcccggagc gccaaagcca   660
accaggccga gctggagaac gcctactaga gcccgcccgc gcccctcccc accggcgggc    720
gccccggccc tgaacccgcg ccccacattt ctgtcctctg cgcgtggttt gattgtttat    780
atttcattgt aaatgcctgc aacccagggc aggggctga gaccttccag gccctgagga      840
atcccgggcg ccgcaaggc cccctcagc ccgccagctg aggggtccca cgggcaggg      900 gagggaattg agagtcacag acactgagcc acgcagcccc gcctctgggg ccgcctacct    960 tgctggtcc cacttcagag gaggcagaaa tggaagcatt ttcaccgccc tggggttta      1020 agggagcggt gtgggagtgg gaaagtccag ggactggtta agaaagttgg ataagattcc    1080
cccttgcacc tcgctgccca tcagaaagcc tgaggcgtgc ccagagcaca agactggggg   1140
caactgtaga tgtggtttct agtcctggct ctgccactaa cttgctgtgt aaccttgaac   1200
tacacaattc tccttcggga cctcaatttc cactttgtaa aatgagggtg gaggtgggaa    1260
taggatctcg aggagactat tggcatatga ttccaaggac tccagtgcct tttgaatggg    1320
cagaggtgag agagagagag agaaagagag agaatgaatg cagttgcatt gattcagtgc    1380
caaggtcact tccagaattc agagttgtga tgctctcttc tgacagccaa agatgaaaaa    1440
caaacagaaa aaaaaagta aagagtctat ttatggctga catatttacg gctgacaaac    1500
tcctggaaga agctatgctg cttcccagcc tggcttcccc ggatgtttgg ctacctccac    1560
ccctccatct caaagaaata acatcatcca ttggggtaga aaaggagagg gtccgagggt    1620
ggtgggaggg ataggaaatca catccgcccc aacttcccaa agagcagcat ccctcccccg   1680
acccatagcc atgttttaaa gtcaccttcc gaagagaagt gaaaggttca aggacactgg   1740
ccttgcaggc ccgagggagc agccatcaca aactcacaga ccagcacatc ccttttgaga   1800
caccgccttc tgcccaccac tcacggacac atttctgcct agaaaacagc ttcttactgc    1860
tcttacatgt gatggcatat cttacactaa aagaatatta ttgggggaaa aactacaagt     1920
gctgtacata tgctgagaaa ctgcagagca taatagctgc cacccaaaaa tcttttttgaa   1980 aatcatttcc agacaacctc ttactttctg tgtagttttt aattgttaaa aaaaaaagt     2040 tttaaacaga agcacatgac atatgaaagc ctgcaggact ggtcgttttt ttggcaattc     2100
ttccacgtgg gacttgtcca caagaatgaa agtagtggtt tttaaagagt taagttacat    2160
atttattttc tcacttaagt tatttatgca aaagttttc ttgtagagaa tgacaatgtt     2220
aatattgctt tatgaattaa cagtctgttc ttccagagtc cagagacatt gttaataaag    2280
acaatgaatc atgaccgaaa g                                              2301
```

<210> SEQ ID NO 6
<211> LENGTH: 213
<212> TYPE: PRT

<213> ORGANISM: Homo sapien

<400> SEQUENCE: 6

| | | | | | | | | | | | | | | |
|---|---|---|---|---|---|---|---|---|---|---|---|---|---|---|
| Met | Gln | Leu | Pro | Leu | Ala | Leu | Cys | Leu | Ile | Cys | Leu | Leu | Val | His | Thr |
| 1 | | | | 5 | | | | | 10 | | | | | 15 | |

Ala Phe Arg Val Val Glu Gly Gln Gly Trp Gln Ala Phe Lys Asn Asp
              20               25              30

Ala Thr Glu Ile Ile Arg Glu Leu Gly Glu Tyr Pro Glu Pro Pro Pro
        35               40              45

Glu Leu Glu Asn Asn Lys Thr Met Asn Arg Ala Glu Asn Gly Gly Arg
   50              55              60

Pro Pro His His Pro Phe Glu Thr Lys Asp Val Ser Glu Tyr Ser Cys
65             70              75              80

Arg Glu Leu His Phe Thr Arg Tyr Val Thr Asp Gly Pro Cys Arg Ser
              85               90              95

Ala Lys Pro Val Thr Glu Leu Val Cys Ser Gly Gln Cys Gly Pro Ala
        100             105             110

Arg Leu Leu Pro Asn Ala Ile Gly Arg Gly Lys Trp Trp Arg Pro Ser
           115            120             125

Gly Pro Asp Phe Arg Cys Ile Pro Asp Arg Tyr Arg Ala Gln Arg Val
   130              135              140

Gln Leu Leu Cys Pro Gly Gly Glu Ala Pro Arg Ala Arg Lys Val Arg
145             150              155              160

Leu Val Ala Ser Cys Lys Cys Lys Arg Leu Thr Arg Phe His Asn Gln
           165            170             175

Ser Glu Leu Lys Asp Phe Gly Thr Glu Ala Ala Arg Pro Gln Lys Gly
        180             185             190

Arg Lys Pro Arg Pro Arg Ala Arg Ser Ala Lys Ala Asn Gln Ala Glu
           195            200             205

Leu Glu Asn Ala Tyr
   210

<210> SEQ ID NO 7
<211> LENGTH: 2301
<212> TYPE: DNA
<213> ORGANISM: Homo sapien

<400> SEQUENCE: 7

| | | | | |
|---|---|---|---|---|
| agagcctgtg | ctactggaag | gtggcgtgcc | ctcctctggc | tggtaccatg | cagctcccac | 60 |
| tggccctgtg | tctcgtctgc | ctgctggtac | acacagcctt | ccgtgtagtg | gagggccagg | 120 |
| ggtggcaggc | gttcaagaat | gatgccacgg | aaatcatccg | cgagctcgga | gagtaccccg | 180 |
| agcctccacc | ggagctggag | aacaacaaga | ccatgaaccg | ggcggagaac | ggagggcggc | 240 |
| ctccccacca | ccccttttgag | accaaagacg | tgtccgagta | cagctgccgc | gagctgcact | 300 |
| tcaccgcta | cgtgaccgat | gggccgtgcc | gcagcgccaa | gccggtcacc | gagctggtgt | 360 |
| gctccggcca | gtgcggcccg | gcgcgcctgc | tgcccaacgc | catcggccgc | ggcaagtggt | 420 |
| ggcgacctag | tgggcccgac | ttccgctgca | tccccgaccg | ctaccgcgcg | cagcgcgtgc | 480 |
| agctgctgtg | tccggtggt | gaggcgccg | gcgcgcgcaa | ggtgcgcctg | gtggcctcgt | 540 |
| gcaagtgcaa | gcgcctcacc | cgcttccaca | accagtcgga | gctcaaggac | ttcgggaccg | 600 |
| aggccgctcg | gccgcagaag | ggccggaagc | cgcggccccg | cgcccggagc | gccaaagcca | 660 |
| accaggccga | gctggagaac | gcctactaga | gcccgcccgc | gcccctcccc | accggcgggc | 720 |
| gccccggccc | tgaacccgcg | ccccacattt | ctgtcctctg | cgcgtggttt | gattgtttat | 780 |

```
atttcattgt aaatgcctgc aacccagggc aggggggctga gaccttccag gccctgagga      840
atcccgggcg ccggcaaggc ccccctcagc ccgccagctg aggggtccca cggggcaggg      900
gagggaattg agagtcacag acactgagcc acgcagcccc gcctctgggg ccgcctacct      960
ttgctggtcc cacttcagag gaggcagaaa tggaagcatt tcaccgccc tggggttta      1020
agggagcggt gtgggagtgg gaaagtccag ggactggtta agaaagttgg ataagattcc     1080
cccttgcacc tcgctgccca tcagaaagcc tgaggcgtgc ccagagcaca agactggggg     1140
caactgtaga tgtggtttct agtcctggct ctgccactaa cttgctgtgt aaccttgaac     1200
tacacaattc tccttcggga cctcaatttc cactttgtaa aatgagggtg gaggtgggaa     1260
taggatctcg aggagactat tggcatatga ttccaaggac tccagtgcct tttgaatggg     1320
cagaggtgag agagagagag agaaagagag agaatgaatg cagttgcatt gattcagtgc     1380
caaggtcact tccagaattc agagttgtga tgctctcttc tgacagccaa agatgaaaaa     1440
caaacagaaa aaaaaagta aagagtctat ttatggctga catatttacg gctgacaaac     1500
tcctggaaga agctatgctg cttcccagcc tggcttcccc ggatgtttgg ctacctccac     1560
ccctccatct caaagaaata acatcatcca ttggggtaga aaggagagg gtccgagggt     1620
ggtgggaggg atagaaatca catccgcccc aacttcccaa agagcagcat ccctcccccg     1680
acccatagcc atgttttaaa gtcaccttcc gaagagaagt gaaaggttca aggacactgg     1740
ccttgcaggc ccgagggagc agccatcaca aactcacaga ccagcacatc ccttttgaga     1800
caccgccttc tgcccaccac tcacggacac atttctgcct agaaacagc ttcttactgc      1860
tcttacatgt gatggcatat cttacactaa aagaatatta ttggggggaaa aactacaagt    1920
gctgtacata tgctgagaaa ctgcagagca taatagctgc cacccaaaaa tcttttttgaa   1980
aatcatttcc agacaacctc ttactttctg tgtagttttt aattgttaaa aaaaaaaagt    2040
tttaaacaga agcacatgac atatgaaagc ctgcaggact ggtcgttttt ttggcaattc    2100
ttccacgtgg gacttgtcca caagaatgaa agtagtggtt tttaaagagt taagttacat    2160
atttattttc tcacttaagt tatttatgca aaagtttttc ttgtagagaa tgacaatgtt    2220
aatattgctt tatgaattaa cagtctgttc ttccagagtc cagagacatt gttaataaag    2280
acaatgaatc atgaccgaaa g                                              2301
```

<210> SEQ ID NO 8
<211> LENGTH: 213
<212> TYPE: PRT
<213> ORGANISM: Homo sapien

<400> SEQUENCE: 8

```
Met Gln Leu Pro Leu Ala Leu Cys Leu Val Cys Leu Leu Val His Thr
 1               5                  10                  15

Ala Phe Arg Val Val Glu Gly Gln Gly Trp Gln Ala Phe Lys Asn Asp
                20                  25                  30

Ala Thr Glu Ile Ile Arg Glu Leu Gly Glu Tyr Pro Glu Pro Pro
         35                  40                  45

Glu Leu Glu Asn Asn Lys Thr Met Asn Arg Ala Glu Asn Gly Gly Arg
     50                  55                  60

Pro Pro His His Pro Phe Glu Thr Lys Asp Val Ser Glu Tyr Ser Cys
 65                  70                  75                  80

Arg Glu Leu His Phe Thr Arg Tyr Val Thr Asp Gly Pro Cys Arg Ser
                 85                  90                  95
```

```
Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
        130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
            195                 200                 205

Leu Glu Asn Ala Tyr
        210

<210> SEQ ID NO 9
<211> LENGTH: 642
<212> TYPE: DNA
<213> ORGANISM: Cercopithecus pygerythrus

<400> SEQUENCE: 9
atgcagctcc cactggccct gtgtcttgtc tgcctgctgg tacacgcagc cttccgtgta      60
gtggagggcc aggggtggca ggccttcaag aatgatgcca cggaaatcat ccccgagctc     120
ggagagtacc ccgagcctcc accggagctg gagaacaaca agaccatgaa ccgggcggag     180
aatggagggc ggcctcccca ccacccctt gagaccaaaa acgtgtccga gtacagctgc     240
cgagagctgc acttcacccg ctacgtgacc gatgggccgt gccgcagcgc caagccagtc     300
accgagttgg tgtgctccgg ccagtgcggc cggcacgcc tgctgcccaa cgccatcggc     360
cgcggcaagt ggtggcgccc gagtgggccc gacttccgct gcatccccga ccgctaccgc     420
gcgcagcgtg tgcagctgct gtgtcccggt ggtgccgcgc cgcgcgcgcg caaggtgcgc     480
ctggtggcct cgtgcaagtg caagcgcctc acccgcttcc acaaccagtc ggagctcaag     540
gacttcggtc ccgaggccgc tcggccgcag aagggccgga gccgcggcc ccgcgcccgg     600
ggggccaaag ccaatcaggc cgagctggag aacgcctact ag                        642

<210> SEQ ID NO 10
<211> LENGTH: 213
<212> TYPE: PRT
<213> ORGANISM: Cercopithecus pygerythrus

<400> SEQUENCE: 10

Met Gln Leu Pro Leu Ala Leu Cys Leu Val Cys Leu Leu Val His Ala
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95
```

```
Ala Lys Pro Val Thr Glu Leu Val Cys Ser Gly Gln Cys Gly Pro Ala
            100                 105                 110
Arg Leu Leu Pro Asn Ala Ile Gly Arg Gly Lys Trp Trp Arg Pro Ser
        115                 120                 125
Gly Pro Asp Phe Arg Cys Ile Pro Asp Arg Tyr Arg Ala Gln Arg Val
    130                 135                 140
Gln Leu Leu Cys Pro Gly Gly Ala Ala Pro Arg Ala Arg Lys Val Arg
145                 150                 155                 160
Leu Val Ala Ser Cys Lys Cys Lys Arg Leu Thr Arg Phe His Asn Gln
                165                 170                 175
Ser Glu Leu Lys Asp Phe Gly Pro Glu Ala Ala Arg Pro Gln Lys Gly
            180                 185                 190
Arg Lys Pro Arg Pro Arg Ala Arg Gly Ala Lys Ala Asn Gln Ala Glu
        195                 200                 205
Leu Glu Asn Ala Tyr
    210
```

<210> SEQ ID NO 11
<211> LENGTH: 638
<212> TYPE: DNA
<213> ORGANISM: Mus musculus

<400> SEQUENCE: 11

```
atgcagccct cactagcccc gtgcctcatc tgcctacttg tgcacgctgc cttctgtgct      60
gtggagggcc aggggtggca agccttcagg aatgatgcca cagaggtcat cccagggctt     120
ggagagtacc ccgagcctcc tcctgagaac aaccagacca tgaaccgggc ggagaatgga     180
ggcagacctc cccaccatcc ctatgacgcc aaaggtgtgt ccgagtacag ctgccgcgag     240
ctgcactaca cccgcttcct gacagacggc ccatgccgca cgccaagcc ggtcaccgag      300
ttggtgtgct ccggccagtg cggccccgcg cggctgctgc ccaacgccat cgggcgcgtg     360
aagtggtggc gcccgaacgg accggatttc cgctgcatcc cggatcgcta ccgcgcgcag     420
cgggtgcagc tgctgtgccc cggggggcgcg gcgccgcgct cgcgcaaggt gcgtctggtg     480
gcctcgtgca gtgcaagcg cctcacccgc ttccacaacc agtcggagct caaggacttc     540
gggccggaga ccgcgcggcc gcagaagggt cgcaagccgc ggcccggcgc ccggggagcc     600
aaagccaacc aggcggagct ggagaacgcc tactagag                            638
```

<210> SEQ ID NO 12
<211> LENGTH: 211
<212> TYPE: PRT
<213> ORGANISM: Mus musculus

<400> SEQUENCE: 12

```
Met Gln Pro Ser Leu Ala Pro Cys Leu Ile Cys Leu Leu Val His Ala
  1               5                  10                  15
Ala Phe Cys Ala Val Glu Gly Gln Gly Trp Gln Ala Phe Arg Asn Asp
             20                  25                  30
Ala Thr Glu Val Ile Pro Gly Leu Gly Glu Tyr Pro Glu Pro Pro Pro
         35                  40                  45
Glu Asn Asn Gln Thr Met Asn Arg Ala Glu Asn Gly Gly Arg Pro Pro
     50                  55                  60
His His Pro Tyr Asp Ala Lys Asp Val Ser Glu Tyr Ser Cys Arg Glu
 65                  70                  75                  80
Leu His Tyr Thr Arg Phe Leu Thr Asp Gly Pro Cys Arg Ser Ala Lys
```

```
                85                  90                  95
Pro Val Thr Glu Leu Val Cys Ser Gly Gln Cys Gly Pro Ala Arg Leu
                100                 105                 110

Leu Pro Asn Ala Ile Gly Arg Val Lys Trp Trp Arg Pro Asn Gly Pro
        115                 120                 125

Asp Phe Arg Cys Ile Pro Asp Arg Tyr Arg Ala Gln Arg Val Gln Leu
    130                 135                 140

Leu Cys Pro Gly Gly Ala Ala Pro Arg Ser Arg Lys Val Arg Leu Val
145                 150                 155                 160

Ala Ser Cys Lys Cys Lys Arg Leu Thr Arg Phe His Asn Gln Ser Glu
                165                 170                 175

Leu Lys Asp Phe Gly Pro Glu Thr Ala Arg Pro Gln Lys Gly Arg Lys
            180                 185                 190

Pro Arg Pro Gly Ala Arg Gly Ala Lys Ala Asn Gln Ala Glu Leu Glu
        195                 200                 205

Asn Ala Tyr
    210

<210> SEQ ID NO 13
<211> LENGTH: 674
<212> TYPE: DNA
<213> ORGANISM: Rattus norvegicus

<400> SEQUENCE: 13
gaggaccgag tgcccttcct ccttctggca ccatgcagct ctcactagcc ccttgccttg      60
cctgcctgct tgtacatgca gccttcgttg ctgtggagag ccagggggtgg caagccttca    120 agaatgatgc cacagaaatc atcccgggac tcagagagta cccagagcct cctcaggaac    180
tagagaacaa ccagaccatg aaccgggccg agaacggagg cagacccccc caccatcctt    240
atgacaccaa agacgtgtcc gagtacagct gccgcgagct gcactacacc cgcttcgtga    300
ccgacggccc gtgccgcagt gccaagccgg tcaccgagtt ggtgtgctcg ggccagtgcg    360
gccccgcgcg gctgctgccc aacgccatcg gcgcgtgaa gtggtggcgc ccgaacggac     420
ccgacttccg ctgcatcccg gatcgctacc gcgcgcagcg ggtgcagctg ctgtgccccg    480
gcggcgcggc gccgcgctcg cgcaaggtgc gtctggtggc ctcgtgcaag tgcaagcgcc    540
tcacccgctt ccacaaccag tcggagctca aggacttcgg acctgagacc gcgcggccgc    600
agaagggtcg caagccgcgg ccccgcgccc ggggagccaa agccaaccag gcggagctgg    660
agaacgccta ctag                                                     674

<210> SEQ ID NO 14
<211> LENGTH: 213
<212> TYPE: PRT
<213> ORGANISM: Rattus norvegicus

<400> SEQUENCE: 14

Met Gln Leu Ser Leu Ala Pro Cys Leu Ala Cys Leu Leu Val His Ala
1               5                   10                  15

Ala Phe Val Ala Val Glu Ser Gln Gly Trp Gln Ala Phe Lys Asn Asp
            20                  25                  30

Ala Thr Glu Ile Ile Pro Gly Leu Arg Glu Tyr Pro Glu Pro Pro Gln
        35                  40                  45

Glu Leu Glu Asn Asn Gln Thr Met Asn Arg Ala Glu Asn Gly Gly Arg
    50                  55                  60

Pro Pro His His Pro Tyr Asp Thr Lys Asp Val Ser Glu Tyr Ser Cys
```

-continued

```
          65                  70                  75                  80
Arg Glu Leu His Tyr Thr Arg Phe Val Thr Asp Gly Pro Cys Arg Ser
                85                  90                  95
Ala Lys Pro Val Thr Glu Leu Val Cys Ser Gly Gln Cys Gly Pro Ala
            100                 105                 110
Arg Leu Leu Pro Asn Ala Ile Gly Arg Val Lys Trp Trp Arg Pro Asn
        115                 120                 125
Gly Pro Asp Phe Arg Cys Ile Pro Asp Arg Tyr Arg Ala Gln Arg Val
    130                 135                 140
Gln Leu Leu Cys Pro Gly Ala Ala Pro Arg Ser Arg Lys Val Arg
145                 150                 155                 160
Leu Val Ala Ser Cys Lys Cys Lys Arg Leu Thr Arg Phe His Asn Gln
                165                 170                 175
Ser Glu Leu Lys Asp Phe Gly Pro Glu Thr Ala Arg Pro Gln Lys Gly
            180                 185                 190
Arg Lys Pro Arg Pro Arg Ala Arg Gly Ala Lys Ala Asn Gln Ala Glu
        195                 200                 205
Leu Glu Asn Ala Tyr
    210

<210> SEQ ID NO 15
<211> LENGTH: 532
<212> TYPE: DNA
<213> ORGANISM: Bos torus

<400> SEQUENCE: 15
agaatgatgc cacagaaatc atccccgagc tgggcgagta ccccgagcct ctgccagagc      60
tgaacaacaa gaccatgaac cgggcggaga acggagggag acctccccac caccccttg     120
agaccaaaga cgcctccgag tacagctgcc gggagctgca cttcacccgc tacgtgaccg     180
atgggccgtg ccgcagcgcc aagccggtca ccgagctggt gtgctcgggc cagtgcggcc     240
cggcgcgcct gctgcccaac gccatcggcc gcggcaagtg gtggcgccca gcgggcccg     300
acttccgctg catccccgac cgctaccgcg cgcagcgggt gcagctgttg tgtcctggcg     360
gcgcggcgcc gcgcgcgcgc aaggtgcgcc tggtggcctc gtgcaagtgc aagcgcctca     420
ctcgcttcca caaccagtcc gagctcaagg acttcggccc cgaggccgcg cggccgcaaa     480
cgggccggaa gctgcggccc cgcgcccggg gcaccaaagc cagccgggcc ga             532

<210> SEQ ID NO 16
<211> LENGTH: 176
<212> TYPE: PRT
<213> ORGANISM: Bos torus

<400> SEQUENCE: 16

Asn Asp Ala Thr Glu Ile Ile Pro Glu Leu Gly Glu Tyr Pro Glu Pro
  1               5                  10                  15
Leu Pro Glu Leu Asn Asn Lys Thr Met Asn Arg Ala Glu Asn Gly Gly
             20                  25                  30
Arg Pro Pro His His Pro Phe Glu Thr Lys Asp Ala Ser Glu Tyr Ser
         35                  40                  45
Cys Arg Glu Leu His Phe Thr Arg Tyr Val Thr Asp Gly Pro Cys Arg
     50                  55                  60
Ser Ala Lys Pro Val Thr Glu Leu Val Cys Ser Gly Gln Cys Gly Pro
 65                  70                  75                  80
Ala Arg Leu Leu Pro Asn Ala Ile Gly Arg Gly Lys Trp Trp Arg Pro
```

|  |  |  |  |  |  |  |  |  |  |  |  |
|---|---|---|---|---|---|---|---|---|---|---|---|
|  |  | 85 |  |  |  | 90 |  |  |  | 95 |  |
| Ser | Gly | Pro | Asp | Phe | Arg | Cys | Ile | Pro | Asp | Arg | Tyr | Arg | Ala | Gln | Arg |
|  |  |  | 100 |  |  |  | 105 |  |  |  | 110 |
| Val | Gln | Leu | Leu | Cys | Pro | Gly | Gly | Ala | Ala | Pro | Arg | Ala | Arg | Lys | Val |
|  |  | 115 |  |  |  | 120 |  |  |  | 125 |  |
| Arg | Leu | Val | Ala | Ser | Cys | Lys | Cys | Lys | Arg | Leu | Thr | Arg | Phe | His | Asn |
|  | 130 |  |  |  | 135 |  |  |  | 140 |
| Gln | Ser | Glu | Leu | Lys | Asp | Phe | Gly | Pro | Glu | Ala | Ala | Arg | Pro | Gln | Thr |
| 145 |  |  |  | 150 |  |  |  | 155 |  |  |  | 160 |
| Gly | Arg | Lys | Leu | Arg | Pro | Arg | Ala | Arg | Gly | Thr | Lys | Ala | Ser | Arg | Ala |
|  |  |  | 165 |  |  |  | 170 |  |  |  | 175 |

<210> SEQ ID NO 17
<211> LENGTH: 35828
<212> TYPE: DNA
<213> ORGANISM: Mus musculus
<220> FEATURE:
<221> NAME/KEY: misc_feature
<222> LOCATION: (1)..(35828)
<223> OTHER INFORMATION: n = A,T,C or G

<400> SEQUENCE: 17

```
cgcgttttgg tgagcagcaa tattgcgctt cgatgagcct tggcgttgag attgatacct      60
ctgctgcaca aaggcaatc gaccgagctg gaccagcgca ttcgtgacac cgtctccttc      120
gaacttattc gcaatggagt gtcattcatc aaggacngcc tgatcgcaaa tggtgctatc      180
cacgcagcgg caatcgaaaa ccctcagccg gtgaccaata tctacaacat cagccttggt      240
atcctgcgtg atgagccagc gcagaacaag gtaaccgtca gtgccgataa gttcaaagtt      300
aaacctggtg ttgataccaa cattgaaacg ttgatcgaaa acgcgctgaa aaacgctgct      360
gaatgtgcgg cgctggatgt cacaaagcaa atggcagcag acaagaaagc gatggatgaa      420
ctggcttcct atgtccgcac ggccatcatg atggaatgtt ccccggtgg tgttatctgg      480
cagcagtgcc gtcgatagta tgcaattgat aattattatc atttgcgggt cctttccggc      540
gatccgcctt gttacggggc ggcgacctcg cgggttttcg ctatttatga aaattttccg      600
gtttaaggcg tttccgttct tcttcgtcat aacttaatgt ttttatttaa aatacctct      660
gaaagaaag gaaacgacag gtgctgaaag cgagcttttt ggcctctgtc gtttcctttc      720
tctgttttg tccgtggaat gaacaatgga agtcaacaaa agcagagct tatcgatgat      780
aagcggtcaa acatgagaat tcgcggccgc ataatacgac tcactatagg gatcgacgcc      840
tactccccgc gcatgaagcg gaggagctgg actccgcatg cccagagacg ccccccaacc      900
cccaaagtgc ctgacctcag cctctaccag ctctggcttg gcttgggcg gggtcaaggc      960
taccacgttc tcttaacagg tggctgggct gtctcttggc cgcgcgtcat gtgacagctg     1020
cctagttctg cagtgaggtc accgtggaat gtctgccttc gttgccatgg caacgggatg     1080
acgttacaat ctgggtgtgg agcttttcct gtccgtgtca ggaaatccaa atacctaaa     1140
ataccctaga agaggaagta gctgagccaa ggctttcctg gcttctccag ataaagtttg     1200
acttagatgg aaaaaaacaa aatgataaag acccgagcca tctgaaaatt cctcctaatt     1260
gcaccactag gaaatgtgta tattattgag ctcgtatgtg ttcttattt aaaaagaaaa     1320
ctttagtcat gttattaata agaatttctc agcagtggga gagaaccaat attaacacca     1380
agataaaagt tggcatgatc cacattgcag gaagatccac gttgggtttt catgaatgtg     1440
aagaccccat ttattaaagt cctaagctct gtttttgcac actaggaagc gatggccggg     1500
```

-continued

```
atggctgagg ggctgtaagg atctttcaat gtcttacatg tgtgtttcct gtcctgcacc      1560
taggacctgc tgcctagcct gcagcagagc cagagggtt tcacatgatt agtctcagac       1620
acttgggggc aggttgcatg tactgcatcg cttatttcca tacggagcac ctactatgtg     1680
tcaaacacca tatggtgttc actcttcaga acggtggtgg tcatcatggt gcatttgctg    1740
acggttggat tggtggtaga gagctgagat atatggacgc actcttcagc attctgtcaa    1800
cgtggctgtg cattcttgct cctgagcaag tggctaaaca gactcacagg gtcagcctcc    1860
agctcagtcg ctgcatagtc ttagggaacc tctcccagtc ctccctacct caactatcca    1920
agaagccagg gggcttggcg gtctcaggag cctgcttgct gggggacagg ttgttgagtt    1980
ttatctgcag taggttgcct aggcatagtg tcaggactga tggctgcctt ggagaacaca    2040
tcctttgccc tctatgcaaa tctgaccttg acatggggc gctgctcagc tgggaggatc     2100
aactgcatac ctaaagccaa gcctaaagct tcttcgtcca cctgaaactc ctggaccaag    2160
gggcttccgg cacatcctct caggccagtg agggagtctg tgtgagctgc actttccaat    2220
ctcagggcgt gagaggcaga gggaggtggg ggcagagcct tgcagctctt tcctcccatc    2280
tggacagcgc tctggctcag cagcccatat gagcacaggc acatcccacc cccaccccca    2340
cctttcctgt cctgcagaat ttaggctctg ttcacggggg ggggggggg ggggcagtcc     2400 tatcctctct taggtagaca ggactctgca ggagacactg ctttgtaaga tactgcagtt    2460
taaatttgga tgttgtgagg ggaaagcgaa gggcctcttt gaccattcag tcaaggtacc    2520
ttctaactcc catcgtattg gggggctact ctagtgctag acattgcaga gagcctcaga    2580
actgtagtta ccagtgtggt aggattgatc cttcagggag cctgacatgt gacagttcca    2640
ttcttcaccc agtcaccgaa catttattca gtacctaccc cgtaacaggc accgtagcag    2700
gtactgaggg acggaccact caaagaactg acagaccgaa gccttggaat ataaacacca    2760
aagcatcagg ctctgccaac agaacactct ttaacactca ggccctttaa cactcaggac    2820
ccccaccccc accccaagca gttggcactg ctatccacat tttacagaga ggaaaaacta    2880
ggcacaggac gatataagtg gcttgcttaa gcttgtctgc atggtaaatg gcagggctgg    2940
attgagaccc agacattcca actctagggt ctattttct tttttctcgt tgttcgaatc      3000
tgggtcttac tgggtaaact caggctagcc tcacactcat atccttctcc catggcttac    3060
gagtgctagg attccaggtg tgtgctacca tgtctgactc cctgtagctt gtctatacca    3120
tcctcacaac ataggaattg tgatagcagc acacacaccg aaggagctg gggaaatccc      3180 acagagggct ccgcaggatg acaggcgaat gcctacacag aaggtgggga agggaagcag    3240
agggaacagc atgggcgtgg gaccacaagt ctatttgggg aagctgccgg taaccgtata    3300 tggctgggt gaggggagag gtcatgagat gaggcaggaa gagccacagc aggcagcggg     3360
tacgggctcc ttattgccaa gaggctcgga tcttcctcct cttcctcctt ccggggctgc    3420
ctgttcattt tccaccactg cctcccatcc aggtctgtgg ctcaggacat cacccagctg    3480
cagaaactgg gcatcaccca cgtcctgaat gctgccgagg gcaggtcctt catgcacgtc    3540
aacaccagtg ctagcttcta cgaggattct ggcatcacct acttgggcat caaggccaat    3600
gatacgcagg agttcaacct cagtgcttac tttgaaaggg ccacagattt cattgaccag    3660
gcgctggccc ataaaaatgg taaggaacgt acattccggc acccatggag cgtaagccct    3720
ctgggacctg cttcctccaa agaggccccc acttgaaaaa ggttccagaa agatcccaaa    3780
atatgccacc aactagggat taagtgtcct acatgtgagc cgatggggc cactgcatat     3840 agtctgtgcc atagacatga caatggataa taatatttca gacagagagc aggagttagg    3900
```

-continued

```
tagctgtgct cctttccctt taattgagtg tgcccatttt tttattcatg tatgtgtata   3960
catgtgtgtg cacacatgcc ataggttgat actgaacacc gtcttcaatc gttccccacc   4020
ccaccttatt ttttgaggca gggtctcttc cctgatcctg gggctcattg gtttatctag   4080
gctgctggcc agtgagctct ggagttctgc ttttctctac ctccctagcc ctgggactgc   4140
aggggcatgt gctgggccag gcttttatgt cgcgttgggg atctgaactt aggtccctag   4200
gcctgagcac cgtaaagact ctgccacatc cccagcctgt ttgagcaagt gaaccattcc   4260
ccagaattcc cccagtgggg ctttcctacc cttttattgg ctaggcattc atgagtggtc   4320
acctcgccag aggaatgagt ggccacgact ggctcagggt cagcagccta gagatactgg   4380
gttaagtctt cctgccgctc gctccctgca gccgcagaca gaaagtagga ctgaatgaga   4440
gctggctagt ggtcagacag gacagaaggc tgagagggtc acagggcaga tgtcagcaga   4500
gcagacaggt tctccctctg tgggggaggg gtggcccact gcaggtgtaa ttggccttct   4560
ttgtgctcca tagaggcttc ctgggtacac agcagcttcc ctgtcctggt gattcccaaa   4620
gagaactccc taccactgga cttacagaag ttctattgac tggtgtaacg gttcaacagc   4680
tttggctctt ggtggacggt gcatactgct gtatcagctc aagagctcat tcacgaatga   4740
acacacacac acacacacac acacacacac acacaagcta attttgatat gccttaacta   4800
gctcagtgac tgggcatttc tgaacatccc tgaagttagc acacatttcc ctctggtgtt   4860
cctggcttaa caccttctaa atctatattt tatctttgct gccctgttac cttctgagaa   4920
gcccctaggg ccacttccct tcgcacctac attgctggat ggtttctctc ctgcagctct   4980
taaatctgat ccctctgcct ctgagccatg ggaacagccc aataactgag ttagacataa   5040
aaacgtctct agccaaaact tcagctaaat ttagacaata aatcttactg gttgtggaat   5100
ccttaagatt cttcatgacc tccttcacat ggcacgagta tgaagcttta ttacaattgt   5160
ttattgatca aactaactca taaaaagcca gttgtctttc acctgctcaa ggaaggaaca   5220
aaattcatcc ttaactgatc tgtgcacctt gcacaatcca tacgaatatc ttaagagtac   5280
taagattttg gttgtgagag tcacatgtta cagaatgtac agctttgaca aggtgcatcc   5340
ttgggatgcc gaagtgacct gctgttccag cccctacct tctgaggctg ttttggaagc   5400
aatgctctgg aagcaacttt aggaggtagg atgctggaac agcgggtcac ttcagcatcc   5460
cgatgacgaa tcccgtcaaa gctgtacatt ctgtaacaga ctgggaaagc tgcagacttt   5520
aaggccaggg ccctatggtc cctcttaatc cctgtcacac ccaacccgag cccttctcct   5580
ccagccgttc tgtgcttctc actctggata gatggagaac acggccttgc tagttaaagg   5640
agtgaggctt caccttctc acatggcagt ggttggtcat cctcattcag ggaactctgg   5700
ggcattctgc ctttacttcc tcttttggga ctacagggaa tatatgctga cttgttttga   5760
ccttgtgtat ggggagactg gatctttggt ctggaatgtt tcctgctagt ttttccccat   5820
cctttggcaa accctatcta tatcttacca ctaggcatag tggccctcgt tctggagcct   5880
gccttcaggc tggttctcgg ggaccatgtc cctggtttct ccccagcata tggtgttcac   5940
agtgttcact gcgggtggtt gctgaacaaa gcggggattg catcccagag ctccggtgcc   6000
ttgtgggtac actgctaaga taaatggat actggcctct ctctgaccac ttgcagagct   6060
ctggtgcctt gtgggtacac tgctaagata aaatggatac tggcctctct ctatccactt   6120
gcaggactct agggaacagg aatccattac tgagaaaacc aggggctagg agcagggagg   6180
tagctgggca gctgaagtgc ttggcgacta accaatgaat accagagttt ggatctctag   6240
```

-continued

| | |
|---|---|
| aatactctta aaatctgggt gggcagagtg gcctgcctgt aatcccagaa ctcgggaggc | 6300 |
| ggagacaggg aatcatcaga gcaaactggc taaccagaat agcaaaacac tgagctctgg | 6360 |
| gctctgtgag agatcctgcc ttaacatata agagagagaa taaaacattg aagaagacag | 6420 |
| tagatgccaa ttttaagccc ccacatgcac atggacaagt gtgcgtttga acacacatat | 6480 |
| gcactcatgt gaaccaggca tgcacactcg ggcttatcac acacataatt tgaaagagag | 6540 |
| agtgagagag gagagtgcac attagagttc acaggaaagt gtgagtgagc acccatgc | 6600 |
| acacagacat gtgtgccagg gagtaggaaa ggagcctggg tttgtgtata agagggagcc | 6660 |
| atcatgtgtt tctaaggagg gcgtgtgaag gaggcgttgt gtgggctggg actggagcat | 6720 |
| ggttgtaact gagcatgctc cctgtgggaa acaggagggg ggccaccctg cagagggtcc | 6780 |
| cactgtccag cgggatcagt aaaagcccct gctgagaact ttaggtaata gccagagaga | 6840 |
| gaaaggtagg aaagtggggg gactcccatc tctgatgtag gaggatctgg gcaagtagag | 6900 |
| gtgcgtttga ggtagaaaga ggggtgcaga ggagatgctc ttaattctgg gtcagcagtt | 6960 |
| tctttccaaa taatgcctgt gaggaggtgt aggtggtggc cattcactca ctcagcagag | 7020 |
| ggatgatgat gcccggtgga tgctggaaat ggccgagcat caaccctggc tctggaagaa | 7080 |
| ctccatcttt cagaaggaga gtggatctgt gtatggccag cggggtcaca ggtgcttggg | 7140 |
| gccctggggg gactcctagc actgggtgat gtttatcgag tgctcttgtg tgccaggcac | 7200 |
| tggcctgggg ctttgtttct gtctctgttt tgtttcgttt tttgagacag actcttgcta | 7260 |
| tgtatccgtg tcaatcttgg aatctcactg catagcccag gctgcggaga gaggggaggg | 7320 |
| caataggcct tgtaagcaag ccacacttca gagactagac tccaccctgc gaatgatgac | 7380 |
| aggtcagagc tgagttccgg aagatttttt ttccagctgc caggtggagt gtggagtggc | 7440 |
| agctagcggc aagggtagag ggcgagctcc ctgtgcagga gaaatgcaag caagagatgg | 7500 |
| caagccagtg agttaagcat tctgtgtggg gagcaggtgg atgaagagag aggctgggct | 7560 |
| ttcgcctctg gggggggggt gagggtggg gatgaggtga gaggagggca gctccctgca | 7620 |
| gtgtgatgag atttttcctg acagtgacct ttggcctctc cctcccccac ttcccttctt | 7680 |
| tcctttcttc ccaccattgc tttccttgtc cttgagaaat tctgagtttc cacttcactg | 7740 |
| gtgatgcaga cggaaacaga agccgtgtgt gtgtgtgtgt gtgtgtgtgt gtgtgtgtgt | 7800 |
| gtgtgtgtgt ttgtgtgtat gtgtgtgtgt gtgtttgtgt gtatgtgtgt cagtgggaat | 7860 |
| ggctcatagt ctgcaggaag gtgggcagga aggaataagc tgtaggctga ggcagtgtgg | 7920 |
| gatgcaggga gagaggagag gagggatacc agagaaggaa attaagggag ctacaagagg | 7980 |
| gcattgttgg ggtgtgtgtg tgtgtgtgtt gtttatattt gtattggaaa tacattcttt | 8040 |
| taaaaaatac ttatccattt atttattttt atgtgcacgt gtgtgtgcct gcatgagttc | 8100 |
| atgtgtgcca cgtgtgtgcg ggaacccttg gaggccacaa gggggcatct gatcccctgg | 8160 |
| aactggagtt ggaggaggtt gtgagtcccc tgacatgttt gctgggaact gaaccccggt | 8220 |
| cctatgcaag agcaggaagt gcagttatct gctgagccat ctctccagtc ctgaaatcca | 8280 |
| ttctcttaaa atacacgtgg cagagacatg atgggattta cgtatggatt taatgtggcg | 8340 |
| gtcattaagt tccggcacag gcaagcacct gtaaagccat caccacaacc gcaacagtga | 8400 |
| atgtgaccat caccccatg ttcttcatgt cccctgtccc ctccatcctc cattctcaag | 8460 |
| cacctcttgc tctgcctctg tcgctggaga acagtgtgca tctgcacact cttatgtcag | 8520 |
| tgaagtcaca cagcctgcac cccttcctgg tctgagtatt tgggttctga ctctgctatc | 8580 |
| acacactact gtactgcatt ctctcgctct cttttttaa acatatttt atttgtttgt | 8640 |

```
gtgtatgcac atgtgccaca tgtgtacaga tactatggag gccagaagag gccatggccg   8700
tccctggagc tggagttaca ggcagcgtgt gagctgcctg gtgtgggtgc tgggaaccaa   8760
acttgaatct aaagcaagca cttttaactg ctgaggcagc tctcagtacc cttcttcatt   8820
tctccgcctg ggttccattg tatggacaca tgtagctaga atatcttgct tatctaatta   8880
tgtacattgt tttgtgctaa gagagagtaa tgctctatag cctgagctgg cctcaacctt   8940
gccatcctcc tgcctcagcc tcctcctcct gagtgctagg atgacaggcg agtggtaact   9000
tacatggttt catgttttgt tcaagactga aggataacat tcatacagag aaggtctggg   9060
tcacaaagtg tgcagttcac tgaatggcac aacccgtgat caagaaacaa aactcagggg   9120
ctggagagat ggcactgact gctcttccag aggtccggag ttcaattccc agcaaccaca   9180
tggtggctca cagccatcta taacgagatc tgacgccctc ttctggtgtg tctgaagaca   9240
gctacagtgt actcacataa aataaataaa tctttaaaac acacacacac acacaattac   9300
caccccagaa agcccactcc atgttccctc ccacgtctct gcctacagta ctcccaggtt   9360
accactgttc aggcttctaa caacctggtt tacttgggcc tcttttctgc tctgtggagc   9420
cacacatttg tgtgcctcat acacgttctt tctagtaagt tgcatattac tctgcgtttt   9480
tacatgtatt tatttattgt agttgtgtgt gcgtgtgggc ccatgcatgg cacagtgtgt   9540
ggggatgtca gagtattgtg aacaggggac agttcttttc ttcaatcatg tgggttccag   9600
aggttgaact caggtcatca tgtgtggcag caaatgcctt tacccactga gacatctcca   9660
tattcttttt ttttcccctg aggtgggggc ttgttccata gcccaaactg gctttgcact   9720
tgcagttcaa agtgactccc tgtctccacc tcttagagta ttggaattac gatgtgtact   9780
accacacctg actggatcat taattctttg atgggggcgg ggaagcgcac atgctgcagg   9840
tgaagggatg actggactgg acatgagcgt ggaagccaga gaacagcttc agtctaatgc   9900
tctcccaact gagctatttc ggtttgccag agaacaactt acagaaagtt ctcagtgcca   9960
tgtggattcg gggttggagt tcaactcatc agcttgacat tggctcctct acccactgag  10020
ccttctcact actctctacc tagatcatta attcttttt aaaaagactt attagggggc  10080
tggagagatg gctcagccgt taagagcacc gaatgcccct tccagaggtcc tgagttcaat  10140 tcccagcatg ccattgctgg gcagtagggg gcgcaggtgt tcaacgtgag tagctgttgc  10200
cagttttccg cggtggagaa cctcttgaca ccctgctgtc cctggtcatt ctgggtgggt  10260
gcatggtgat atgcttgttg tatggaagac tttgactgtt acagtgaagt tgggcttcca  10320
cagttaccac gtctcccctg tttcttgcag gccgggtgct tgtccattgc cgcgagggct  10380
acagccgctc cccaacgcta gttatcgcct acctcatgat gcggcagaag atggacgtca  10440
agtctgctct gagtactgtg aggcagaatc gtgagatcgg ccccaacgat ggcttcctgg  10500
cccaactctg ccagctcaat gacagactag ccaaggaggg caaggtgaaa ctctagggtg  10560
cccacagcct cttttgcaga ggtctgactg ggagggccct ggcagccatg tttaggaaac  10620
acagtatacc cactccctgc accaccagac acgtgcccac atctgtccca ctctggtcct  10680
cgggggccac tccacccctta gggagcacat gaagaagctc cctaagaagt tctgctcctt  10740
agccatcctt tcctgtaatt tatgtctctc cctgaggtga ggttcaggtt tatgtccctg  10800
tctgtggcat agatacatct cagtgaccca gggtgggagg gctatcaggg tgcatggccc  10860
gggacacggg cactcttcat gacccctccc ccacctgggt tcttcctgtg tggtccagaa  10920
ccacgagcct ggtaaaggaa ctatgcaaac acaggccctg acctccccat gtctgttcct  10980
```

-continued

```
ggtcctcaca gcccgacacg ccctgctgag gcagacgaat gacattaagt tctgaagcag    11040
agtggagata gattagtgac tagatttcca aaagaagga aaaaaaggc tgcattttaa      11100 aattatttcc ttagaattaa agatactaca taggggccct tgggtaagca aatccatttt    11160
tcccagaggc tatcttgatt ctttggaatg tttaaagtgt gccttgccag agagcttacg    11220
atctatatct gctgcttcag agccttccct gaggatggct ctgttccttt gcttgttaga    11280
agagcgatgc cttgggcagg gtttccccct tttcagaata cagggtgtaa agtccagcct    11340
attacaaaca aacaaacaaa caaacaaaca aaggacctcc atttggagaa ttgcaaggat    11400
tttatcctga attatagtgt tggtgagttc aagtcatcac gccaagtgct tgccatcctg    11460
gttgctattc taagaataat taggaggagg aacctagcca attgcagctc atgtccgtgg    11520
gtgtgtgcac gggtgcatat gttggaaggg gtgcctgtcc ccttggggac agaaggaaaa    11580
tgaaaggccc ctctgctcac cctggccatt tacgggaggc tctgctggtt ccacggtgtc    11640
tgtgcaggat cctgaaactg actcgctgga cagaaacgag acttggcggc accatgagaa    11700
tggagagaga gagagcaaag aaagaaacag cctttaaaag aactttctaa gggtggtttt    11760
tgaacctcgc tggaccttgt atgtgtgcac atttgccaga gattgaacat aatcctcttg    11820
ggacttcacg ttctcattat ttgtatgtct ccggggtcac gcagagccgt cagccaccac    11880
cccagcaccc ggcacatagg cgtctcataa agcccatttt tatgagaacc agagctgttt    11940
gagtaccccg tgtatagaga gagttgttgt cgtggggcac ccggatccca gcagcctggt    12000
tgcctgcctg taggatgtct tacaggagtt tgcagagaaa ccttccttgg agggaaagaa    12060
atatcaggga ttttgttga atatttcaaa ttcagcttta agtgtaagac tcagcagtgt     12120
tcatggttaa ggtaaggaac atgccttttc cagagctgct gcaagaggca ggagaagcag    12180
acctgtctta ggatgtcact cccagggtaa agacctctga tcacagcagg agcagagctg    12240
tgcagcctgg atggtcattg tccctattc tgtgtgacca cagcaaccct ggtcacatag      12300
ggctggtcat cctttttttt tttttttttt ttttttttg cccagaatg aagtgaccat      12360 agccaagttg tgtacctcag tctttagttt ccaagcggct ctcttgctca atacaatgtg    12420
catttcaaaa taacactgta gagttgacag aactggttca tgtgttatga gagaggaaaa    12480
gagaggaaag aacaaaacaa aacaaaacac cacaaaccaa aaacatctgg gctagccagg    12540
catgattgca atgtctacag gcccagttca tgagaggcag agacaggaag accgccgaaa    12600
ggtcaaggat agcatggtct acgtatcgag actccagcca gggctacggt cccaagatcc    12660
taggttttgg attttgggct ttggtttttg agacagggtt tctctgtgta gccctggctg    12720
tcctggaact cgctctgtag accaggctgg cctcaaactt agagatctgc ctgactctgc    12780 cttttgagggc tgggacgaat gccaccactg cccaactaag attccattaa aaaaaaaaa   12840 agttcaagat aattaagagt tgccagctcg ttaaagctaa gtagaagcag tctcaggcct    12900
gctgcttgag gctgttcttg gcttggacct gaaatctgcc cccaacagtg tccaagtgca    12960
catgactttg agccatctcc agagaaggaa gtgaaaattg tggctcccca gtcgattggg    13020
acacagtctc tctttgtcta ggtaacacat ggtgacacat agcattgaac tctccactct    13080
gagggtgggt ttccctcccc ctgcctcttc tgggttggtc accccatagg acagccacag    13140
gacagtcact agcacctact ggaaacctct tgtgggaac atgaagaaag agcctttggg     13200
agattcctgg ctttccatta gggctgaaag tacaacggtt cttggttggc tttgcctcgt    13260
gtttataaaa ctagctacta ttcttcaggt aaaataccga tgttgtggaa aagccaaccc    13320
cgtggctgcc cgtgagtagg gggtggggtt gggaatcctg gatagtgttc tatccatgga    13380
```

-continued

```
aagtggtgga ataggaatta agggtgttcc cccccccccc aacctcttcc tcagacccag  13440
ccactttcta tgacttataa acatccaggt aaaaattaca aacataaaaa tggtttctct  13500
tctcaatctt ctaaagtctg cctgcctttt ccaggggtag gtctgtttct ttgctgttct  13560

attgtcttga gagcacagac taacacttac caaatgaggg aactcttggc ccatactaag  13620
gctcttctgg gctccagcac tcttaagtta ttttaagaat tctcacttgg cctttagcac  13680
acccgccacc cccaagtggg tgtggataat gccatggcca gcagggggca ctgttgaggc  13740
gggtgccttt ccaccttaag ttgcttatag tatttaagat gctaaatgtt ttaatcaaga  13800
gaagcactga tcttataata cgaggataag agattttctc acaggaaatt gtctttttca  13860
taattctttt acaggctttg tcctgatcgt agcatagaga gaatagctgg atatttaact  13920
tgtattccat tttcctctgc cagcgttagg ttaactccgt aaaaagtgat tcagtggacc  13980
gaagaggctc agagggcagg ggatggtggg gtgaggcaga gcactgtcac ctgccaggca  14040
tgggaggtcc tgccatccgg gaggaaaagg aaagtttagc ctctagtcta ccaccagtgt  14100
taacgcactc taaagttgta accaaaataa atgtcttaca ttacaaagac gtctgttttg  14160
tgtttccttt tgtgtgtttg ggctttttat gtgtgcttta taactgctgt ggtggtgctg  14220
ttgttagttt tgaggtagga tctcaggctg gccttgaact tctgatcgcc tgcccctgcc  14280
cctgcccctg cccctgtccc tgcctccaag tgctaggact aaaagcacat gccaccacac  14340
cagtacagca tttttctaac atttaaaaat aatcacctag gggctggaga gagggttcca  14400
gctaagagtg cacactgctc ttgggtagga cctgagttta gttcccagaa cctatactgg  14460
gtggctccag gtccagagga tccaggacct ctggcctcca tgggcatctg ctcttagcac  14520
atacccacat acagatacac acataaaaat aaaatgaagc ctttaaaaac ctcctaaaac  14580
ctagcccttg gaggtacgac tctggaaagc tggcatactg tgtaagtcca tctcatggtg  14640
ttctggctaa cgtaagactt acagagacag aaaagaactc agggtgtgct ggggggttggg  14700
atggaggaag agggatgagt agggggagca cggggaactt gggcagtgaa aattctttgc  14760
aggacactag aggaggataa ataccagtca ttgcacccac tactggacaa ctccagggaa  14820
ttatgctggg tgaaaagaga aggccccagg tattggctgc attggctgca tttgcgtaac  14880
atttttttaa attgaaaaga aaaagatgta aatcaaggtt agatgagtgg ttgctgtgag  14940
ctgagagctg ggtgagtga gacatgtgga caactccatc aaaaagcgac agaaagaacg  15000
ggctgtggtg acagctacct ctaatctcca cctccgggag gtgatcaagg ttagccctca  15060
gctagcctgt ggtgcatgag accctgtttc aaaaacttta ataaagaaat aatgaaaaaa  15120
gacatcaggg cagatccttg gggccaaagg cggacaggcg agtctcgtgg taaggtcgtg  15180
tagaagcgga tgcatgagca cgtgccgcag gcatcatgag agagccctag gtaagtaagg  15240
atggatgtga gtgtgtcggc gtcggcgcac tgcacgtcct ggctgtggtg ctggactggc  15300
atctttggtg agctgtggag gggaaatggg tagggagatc ataaaatccc tccgaattat  15360
ttcaagaact gtctattaca attatctcaa aatattaaaa aaaaagaaga attaaaaaac  15420
aaaaaaccta tccaggtgtg gtggtgtgca cctatagcca cgggcacttg gaaagctgga  15480
gcaagaggat ggcgagtttg aaggtatctg gggctgtaca gcaagaccgt cgtccccaaa  15540
ccaaaccaaa cagcaaaccc attatgtcac acaagagtgt ttatagtgag cggcctcgct  15600
gagagcatgg ggtgggggtg ggggtggggg acagaaatat ctaaactgca gtcaataggg  15660
atccactgag accctggggc ttgactgcag cttaaccttg ggaaatgata agggttttgt  15720
```

```
gttgagtaaa agcatcgatt actgacttaa cctcaaatga agaaaaagaa aaaaagaaaa    15780
caacaaaagc caaaccaagg ggctggtgag atggctcagt gggtaagagc acccgactgc    15840
tcttccgaag gtccagagtt caaatcccag caaccacatg gtggctcaca accatctgta    15900
acgagatatg atgccctctt ctggtgtgtc tgaagacagc tacagtgtac ttacatataa    15960
taaataaatc ttaaaaaaaa aaaaaaaaaa aaaagccaaa ccgagcaaac caggccccca    16020
aacagaaggc aggcacgacg gcaggcacca cgagccatcc tgtgaaaagg cagggctacc    16080
catgggccga ggagggtcca gagagatagg ctggtaagct cagtttctct gtataccctt    16140
tttcttgttg acactacttc aattacagat aaaataacaa ataaacaaaa tctagagcct    16200
ggccactctc tgctcgcttg attttttcctg ttacgtccag caggtggcgg aagtgttcca    16260
aggacagatc gcatcattaa ggtggccagc ataatctccc atcagcaggt ggtgctgtga    16320
gaaccattat ggtgctcaca gaatcccggg cccaggagct gccctctccc aagtctggag    16380
caataggaaa gctttctggc ccagacaggg ttaacagtcc acattccaga gcagggaaa    16440 aggagactgg aggtcacaga caaaagggcc agcttctaac aacttcacag ctctggtagg    16500
agagatagat cacccccaac aatggccaca gctggttttg tctgccccga aggaaactga    16560
cttaggaagc aggtatcaga gtcccttcc tgagggact tctgtctgcc ttgtaaagct    16620
gtcagagcag ctgcattgat gtgtgggtga cagaagatga aaaggaggac ccaggcagat    16680
cgccacagat ggaccggcca cttacaagtc gaggcaggtg gcagagcctt gcagaagctc    16740
tgcaggtgga cgacactgat tcattaccca gttagcatac cacagcgggc taggcggacc    16800
acagcctcct tcccagtctt cctccagggc tggggagtcc tccaaccttc tgtctcagtg    16860
cagcttccgc cagcccctcc tcctttttgca cctcaggtgt gaaccctccc tcctctcctt    16920
ctccctgtgg catggccctc ctgctactgc aggctgagca ttggatttct ttgtgcttag    16980
atagacctga gatggctttc tgatttatat atatatatcc atcccttgga tcttacatct    17040
aggacccaga gctgtttgtg ataccataag aggctgggga gatgatatgg taagagtgct    17100
tgctgtacaa gcatgaagac atgagttcga atccccagca accatgtgga aaataacct    17160 tctaacctca gagttgaggg gaaaggcagg tggattctgg gggcttactg ccagctagc    17220 cagcctaacc taaatgtctc agtcagagat cctgtctcag ggataacctt gggagaatga    17280
ctgagaaaga cacctcctca ggtctcccat gcacccacac agacacacgg ggggggggta    17340
atgtaataag ctaagaaata atgagggaaa tgattttttg ctaagaaatg aaattctgtg    17400
ttggccgcaa gaagcctggc cagggaagga actgcctttg gcacaccagc ctataagtca    17460
ccatgagttc cctggctaag aatcacatgt aatggagccc aggtccctct tgcctggtgg    17520
ttgcctctcc cactggtttt gaagagaaat tcaagagaga tctccttggt cagaattgta    17580
ggtgctgagc aatgtggagc tggggtcaat gggattcctt taaaggcatc cttcccaggg    17640
ctgggtcata cttcaatagt agggtgcttg cacagcaagc gtgagaccct aggttagagt    17700
ccccagaatc tgccccccaac ccccaaaaa ggcatccttc tgcctctggg tgggtggggg    17760
gagcaaacac ctttaactaa gaccattagc tggcagggt aacaaatgac cttggctaga    17820
ggaatttggt caagctggat ccgccttct gtagaagccc cacttgtttc ctttgttaag    17880
ctggcccaca gtttgttttg agaatgcctg aggggcccag ggagccagac aattaaaagc    17940
caagctcatt ttgatatctg aaaccacag cctgactgcc ctgccgtgg gaggtactgg    18000 gagagctggc tgtgtccctg cctcaccaac gccccccccc ccaacacaca ctcctcgggt    18060
cacctgggag gtgccagcag caatttggaa gtttactgag cttgagaagt cttgggaggg    18120
```

-continued

```
ctgacgctaa gcacacccct tctccacccc cccccacccc accccgtga ggaggagggt   18180 gaggaaacat gggaccagcc ctgctccagc ccgtccttat tggctggcat gaggcagagg   18240
gggctttaaa aaggcaaccg tatctaggct ggacactgga gcctgtgcta ccgagtgccc   18300
tcctccacct ggcagcatgc agccctcact agccccgtgc ctcatctgcc tacttgtgca   18360
cgctgccttc tgtgctgtgg agggccaggg gtggcaagcc ttcaggaatg atgccacaga   18420
ggtcatccca gggcttggag agtaccccga gcctcctcct gagaacaacc agaccatgaa   18480
ccgggcggag aatggaggca gacctcccca ccatccctat gacgccaaag gtacgggatg   18540
aagaagcaca ttagtggggg gggggtcct gggaggtgac tggggtggtt ttagcatctt   18600
cttcagaggt ttgtgtgggt ggctagcctc tgctacatca gggcagggac acatttgcct   18660
ggaagaatac tagcacagca ttagaacctg agggcagca ttggggggct ggtagagagc    18720
acccaaggca gggtggaggc tgaggtcagc cgaagctggc attaacacgg gcatgggctt   18780
gtatgatggt ccagagaatc tcctcctaag gatgaggaca caggtcagat ctagctgctg   18840
accagtgggg aagtgatatg gtgaggctgg atgccagatg ccatccatgg ctgtactata   18900
tcccacatga ccaccacatg aggtaaagaa ggccccagct tgaagatgga gaaaccgaga   18960
ggctcctgag ataaagtcac ctgggagtaa gaagagctga gactggaagc tggtttgatc   19020
cagatgcaag gcaaccctag attgggtttg ggtgggaacc tgaagccagg aggaatccct   19080
ttagttcccc cttgcccagg gtctgctcaa tgagcccaga gggttagcat taaaagaaca   19140
gggtttgtag gtggcatgtg acatgagggg cagctgagtg aaatgtcccc tgtatgagca   19200
caggtggcac cacttgccct gagcttgcac cctgacccca gctttgcctc attcctgagg   19260
acagcagaaa ctgtggaggc agagccagca cagagagatg cctggggtgg gggtgggggt   19320
atcacgcacg gaactagcag caatgaatgg ggtggggtgg cagctggagg gacactccag   19380
agaaatgacc ttgctggtca ccatttgtgt gggaggagag ctcatttttcc agcttgccac   19440 cacatgctgt ccctcctgtc tcctagccag taagggatgt ggaggaaagg gccaccccaa   19500
aggagcatgc aatgcagtca cgttttttgca gaggaagtgc ttgacctaag ggcactattc   19560
ttggaaagcc ccaaaactag tccttccctg ggcaaacagg cctcccccac ataccacctc   19620 tgcagggtg agtaaattaa gccagccaca gaagggtggc aaggcctaca cctccccct    19680 gttgtgcccc cccccccccc gtgaaggtgc atcctggcct ctgcccctct ggctttggta   19740
ctgggatttt ttttttcctt ttatgtcata ttgatcctga caccatggaa cttttggagg   19800
tagacaggac ccacacatgg attagttaaa agcctcccat ccatctaagc tcatggtagg   19860
agatagagca tgtccaagag aggagggcag gcatcagacc tagaagatat ggctgggcat   19920
ccaacccaat ctccttcccc ggagaacaga ctctaagtca gatccagcca cccttgagta   19980
accagctcaa ggtacacaga acaagagagt ctggtataca gcaggtgcta aacaaatgct   20040
tgtggtagca aaagctatag gttttgggtc agaactccga cccaagtcgc gagtgaagag   20100
cgaaaggccc tctactcgcc accgcccgc ccccacctgg ggtcctataa cagatcactt     20160
tcacccttgc gggagccaga gagccctggc atcctaggta gccccccccg ccccccccc    20220 gcaagcagcc cagccctgcc tttggggcaa gttctttttct cagcctggac ctgtgataat   20280 gaggggggttg gacgcgccgc ctttggtcgc tttcaagtct aatgaattct tatccctacc   20340
acctgccctt ctacccccgct cctccacagc agctgtcctg atttattacc ttcaattaac    20400
ctccactcct ttctccatct cctgggatac cgcccctgtc ccagtggctg gtaaaggagc   20460
```

```
ttaggaagga ccagagccag gtgtggctag aggctaccag gcagggctgg ggatgaggag   20520
ctaaactgga agagtgtttg gttagtaggc acaaagcctt gggtgggatc cctagtaccg   20580
gagaagtgga gatgggcgct gagaagttca agaccatcca tccttaacta cacagccagt   20640
ttgaggccag cctgggctac ataaaaaccc aatctcaaaa gctgccaatt ctgattctgt   20700
gccacgtagt gcccgatgta atagtggatg aagtcgttga atcctgggcc aacctatttt   20760
acagatgtgg ggaaaagcaa ctttaagtac cctgcccaca gatcacaaag aaagtaagtg   20820
acagagctcc agtgtttcat ccctgggttc caaggacagg gagagagaag ccagggtggg   20880
atctcactgc tccccggtgc ctccttccta taatccatac agattcgaaa gcgcagggca   20940
ggtttggaaa aagagagaag ggtggaagga gcagaccagt ctggcctagg ctgcagcccc   21000
tcacgcatcc ctctctccgc agatgtgtcc gagtacagct gccgcgagct gcactacacc   21060
cgcttcctga cagacggccc atgccgcagc gccaagccgg tcaccgagtt ggtgtgctcc   21120
ggccagtgcg gccccgcgcg gctgctgccc aacgccatcg ggcgcgtgaa gtggtggcgc   21180
ccgaacggac cggatttccg ctgcatcccc gatcgctacc gcgcgcagcg ggtgcagctg   21240
ctgtgccccg ggggcgcggc gccgcgctcg cgcaaggtgc gtctggtggc ctcgtgcaag   21300
tgcaagcgcc tcacccgctt ccacaaccag tcggagctca aggacttcgg gccggagacc   21360
gcgcggccgc agaagggtcg caagccgcgg cccggcgccc ggggagccaa agccaaccag   21420
gcggagctgg agaacgccta ctagagcgag cccgcgccta tgcagccccc gcgcgatccg   21480
attcgttttc agtgtaaagc ctgcagccca ggccaggggt gccaaacttt ccagaccgtg   21540
tggagttccc agcccagtag agaccgcagg tccttctgcc cgctgcgggg gatggggagg   21600
gggtggggtt cccgcgggcc aggagaggaa gcttgagtcc cagactctgc ctagccccgg   21660
gtgggatggg ggtctttcta ccctcgccgg acctatacag gacaaggcag tgtttccacc   21720 ttaagggaa gggagtgtgg aacgaaagac ctgggactgg ttatgacgt acagtaagat   21780 ctactccttc cacccaaatg taaagcctgc gtgggctaga tagggtttct gaccctgacc   21840
tggccactga gtgtgatgtt gggctacgtg gttctctttt ggtacggtct tctttgtaaa   21900
atagggaccg gaactctgct gagattccaa ggattggggt accccgtgta gactggtgag   21960
agagaggaga acaggggagg ggttagggga gagattgtgg tgggcaaccg cctagaagaa   22020
gctgtttgtt ggctcccagc ctcgccgcct cagaggtttg gcttccccca ctccttcctc   22080
tcaaatctgc cttcaaatcc atatctggga tagggaaggc cagggtccga gagatggtgg   22140
aagggccaga aatcacactc ctggcccccc gaagagcagt gtcccgcccc caactgcctt   22200
gtcatattgt aaagggattt tctacacaac agtttaaggt cgttggagga aactgggctt   22260
gccagtcacc tcccatcctt gtcccttgcc aggacaccac ctcctgcctg ccacccacgg   22320
acacatttct gtctagaaac agagcgtcgt cgtgctgtcc tctgagacag catatcttac   22380
attaaaaaga ataatacggg gggggggggc ggagggcgca agtgttatac atatgctgag   22440
aagctgtcag gcgccacagc accacccaca atctttttgt aaatcatttc cagacacctc   22500
ttactttctg tgtagatttt aattgttaaa agggaggag agagagcgtt tgtaacagaa   22560
gcacatggag ggggggggtag ggggttggg gctggtgagt ttggcgaact ttccatgtga   22620
gactcatcca caaagactga aagccgcgtt ttttttttta agagttcagt gacatattta   22680
ttttctcatt taagttattt atgccaacat tttttcttg tagagaaagg cagtgttaat   22740
atcgctttgt gaagcacaag tgtgtgtggt ttttgttttt ttgtttttc cccgaccaga   22800 ggcattgtta ataaagacaa tgaatctcga gcaggaggct gtggtcttgt tttgtcaacc   22860
```

```
acacacaatg tctcgccact gtcatctcac tcccttccct tggtcacaag acccaaacct    22920
tgacaacacc tccgactgct ctctggtagc ccttgtggca atacgtgttt cctttgaaaa    22980
gtcacattca tcctttcctt tgcaaacctg gctctcattc cccagctggg tcatcgtcat    23040
accctcaccc cagcctccct ttagctgacc actctccaca ctgtcttcca aaagtgcacg    23100
tttcaccgag ccagttccct ggtccaggtc atcccattgc tcctccttgc tccagaccct    23160
tctcccacaa agatgttcat ctcccactcc atcaagcccc agtggccctg cggctatccc    23220
tgtctcttca gttagctgaa tctacttgct gacaccacat gaattccttc ccctgtctta    23280
aggttcatgg aactcttgcc tgcccctgaa ccttccagga ctgtcccagc gtctgatgtg    23340
tcctctctct tgtaaagccc caccccacta tttgattccc aattctagat cttcccttgt    23400
tcattccttc acgggatagt gtctcatctg gccaagtcct gcttgatatt gggataaatg    23460
caaagccaag tacaattgag gaccagttca tcattgggcc aagcttttc aaaatgtgaa    23520 ttttacacct atagaagtgt aaaagccttc caaagcagag gcaatgcctg gctcttcctt    23580
caacatcagg gctcctgctt tatgggtctg gtggggtagt acattcataa acccaacact    23640
aggggtgtga aagcaagatg attgggagtt cgaggccaat cttggctatg aggccctgtc    23700
tcaacctctc ctccctccct ccaggggtttt gttttgtttt gttttttttga tttgaaactg    23760 caacactta aatccagtca agtgcatctt tgcgtgaggg gaactctatc cctaatataa    23820
gcttccatct tgattttgtgt atgtgcacac tgggggttga acctgggcct ttgtacctgc    23880
cgggcaagct ctctactgct ctaaacccag ccctcactgg ctttctgttt caactcccaa    23940
tgaattcccc taaatgaatt atcaatatca tgtctttgaa aaataccatt gagtgctgct    24000
ggtgtccctg tggttccaga ttccaggaag gactttcag ggaatccagg catcctgaag    24060
aatgtcttag agcaggaggc catggagacc ttggccagcc ccacaaggca gtgtggtgca    24120
gagggtgagg atggaggcag gcttgcaatt gaagctgaga cagggtactc aggattaaaa    24180
agcttccccc aaaacaattc caagatcagt tcctggtact tgcacctgtt cagctatgca    24240
gagcccagtg ggcataggtg aagacaccgg ttgtactgtc atgtactaac tgtgcttcag    24300
agccggcaga gacaaataat gttatggtga ccccagggga cagtgattcc agaaggaaca    24360
cagaagagag tgctgctaga ggctgcctga aggagaaggg gtcccagact ctctaagcaa    24420
agactccact cacataaaga cacaggctga gcagagctgg ccgtggatgc agggagccca    24480
tccaccatcc tttagcatgc ccttgtattc ccatcacatg ccaggatgga ggggcatcag    24540
agagtccaag tgatgcccaa acccaaacac acctaggact tgctttctgg gacagacaga    24600
tgcaggagag actaggttgg gctgtgatcc cattaccaca aagagggaaa aaacaaaaaa    24660
caaacaaaca aacaaaaaaa aacaaaacaa aacaaaaaaa aacccaaggt ccaaattgta    24720
ggtcaggtta gagtttattt atggaaagtt atattctacc tccatggggt ctacaaggct    24780
ggcgcccatc agaaagaaca aacaacaggc tgatctggga ggggtggtac tctatggcag    24840
ggagcacgtg tgcttggggt acagccgac acggggcttg tattaatcac agggcttgta    24900
ttaataggct gagagtcaag cagacagaga gacagaagga aacacacaca cacacacaca    24960
cacacacaca cacacacaca catgcacaca ccactcactt ctcactcgaa gagccccctac    25020 ttacattcta agaacaaacc attcctcctc ataaaggaga caaagttgca gaaacccaaa    25080
agagccacag gtcccccact ctctttgaaa tgacttggac ttgttgcagg gaagacagag    25140
gggtctgcag aggcttcctg ggtgacccag agccacagac actgaaatct ggtgctgaga    25200
```

-continued

```
cctgtataaa ccctcttcca caggttccct gaaaggagcc cacattcccc aaccctgtct   25260
cctgaccact gaggatgaga gcacttgggc cttccccatt cttggagtgc accctggttt   25320
ccccatctga gggcacatga ggtctcaggt cttgggaaag ttccacaagt attgaaagtg   25380
ttcttgtttt gtttgtgatt taatttaggt gtatgagtgc ttttgcttga atatatgcct   25440
gtgtagcatt tacaagcctg gtgcctgagg agatcagaag atggcatcag ataccctgga   25500
actggacttg cagacagtta tgagccactg tgtgggtgct aggaacagaa cctggatcct   25560
ccggaagagc agacagccag cgctcttagc cactaagcca tcactgaggt tctttctgtg   25620
gctaaagaga caggagacaa aggagagttt cttttagtca ataggaccat gaatgttcct   25680
cgtaacgtga gactagggca gggtgatccc ccagtgacac cgatggccct gtgtagttat   25740
tagcagctct agtcttattc cttaataagt cccagtttgg ggcaggagat atgtattccc   25800
tgctttgaag tggctgaggt ccagttatct acttccaagt acttgtttct ctttctggag   25860
ttggggaagc tccctgcctg cctgtaaatg tgtccattct tcaaccttag acaagatcac   25920
tttccctgag cagtcaggcc agtccaaagc ccttcaattt agctttcata aggaacaccc   25980
cttttgttgg gtggaggtag cacttgcctt gaatcccagc attaagaagg cagagacagt   26040
cggatctctg tgagttcaca gccagcctgg tctacggagt gagttccaag acagccaggc   26100
ctacacagag aaaccctgtc tcgaaaaaaa caaaaacaaa agaaataaag aaaaagaaaa   26160
caaaaacgaa caaacagaaa aacaagccag agtgtttgtc cccgtatttt attaatcata   26220
tttttgtccc tttgccattt tagactaaaa gactcgggaa agcaggtctc tctctgtttc   26280
tcatccggac acaccagaa ccagatgtat ggaagatggc taatgtgctg cagttgcaca   26340
tctggggctg ggtggattgg ttagatggca tgggctgggt gtggttacga tgactgcagg   26400
agcaaggagt atgtggtgca tagcaaacga ggaagtttgc acagaacaac actgtgtgta   26460
ctgatgtgca ggtatgggca catgcaagca gaagccaagg acagccttaa gggtagtgtt   26520
tccacagacc cctcccccct tttaacatgg gcatctctca ttggcctgga gcttgccaac   26580
tgggctgggc tggctagctt gtaggtccca gggatctgca tatctctgcc tccctagtgc   26640
tgggattaca gtcatatatg agcacacctg gcttttttat gtgggttctg ggctttgaac   26700
ccagatctga gtgcttgcaa ggcaatcggt tgaatgactg cttcatctcc ccagaccctg   26760
ggattctact ttctattaaa gtatttctat taaatcaatg agccctgcc cctgcactca   26820 gcagttctta ggcctgctga gagtcaagtg gggagtgaga gcaagcctcg agaccccatc   26880
agcgaagcag aggacaaaga aatgaaaact tgggattcga ggctcgggat atggagatac   26940
agaaagggtc agggaaggaa atgaaccaga tgaatagagg caggaagggt agggccctgc   27000
atacatggaa cctggtgtac atgttatctg catgggtttt gcattgcaat ggctcttcag   27060
caggttcacc acactgggaa acagaagcca aaagaagag taggtggtgt tggagtcaga   27120
tactgtcagt catgcctgaa gaaatggaag caattaacga tgcgccgcaa ttaggatatt   27180
agctccctga agaaaggcaa gaagctgggc tgtgggcact gaagggagct ttgaatgatg   27240
tcacattctc tgtatgccta gcagggcagt attggagact gagacttgac ttgtgtgtcc   27300
atatgattcc tccttttcct acagtcatct ggggctcctg agcttcgtcc ttgtccaaga   27360
acctggagct ggcagtgggc agctgcagtg atagatgtct gcaagaaaga tctgaaaaga   27420
gggaggaaga tgaaggaccc agaggaccac cgacctctgc tgcctgacaa agctgcagga   27480
ccagtctctc ctacagatgg gagacagagg cgagagatga atggtcaggg gaggagtcag   27540
agaaaggaga gggtgaggca gagaccaaag gagggaaaca cttgtgctct acagctactg   27600
```

```
actgagtacc agctgcgtgg cagacagcca atgccaaggc tcggctgatc atggcacctc    27660
gtgggactcc tagcccagtg ctggcagagg ggagtgctga atggtgcatg gtttggatat    27720
gatctgaatg tggtccagcc ctagtttcct tccagttgct gggataaagc accctgacca    27780
aagctacttt tttgtttgtt tgttttggtt tggttttgtt tggttttcg aggcagggtt     27840 tctctgtatc accctagctg tcctggaact cactctgtag accaggctgg cctcgaactc    27900
agaaatcccc ctgcctctgc ctcctaagtg ctggaattaa aggcctgcgc caccactgcc    27960
ggcccaaagc tactttaaga gagagagagg aatgtataag tattataatt ccaggttata    28020
gttcattgct gtagaattgg agtcttcata ttccaggtaa tctcccacag acatgccaca    28080
aaacaacctg ttctacgaaa tctctcatgg actcccttcc ccagtaattc taaactgtgt    28140
caaatctaca agaaatagtg acagtcacag tctctaacgt tttgggcatg agtctgaagt    28200
ctcattgcta agtactggga agatgaaaac tttacctagt gtcagcattt ggagcagagc    28260
ctttgggatt tgagatggtc ttttgcagag ctcctaatgg ctacatggag agaggggcc     28320 tgggagagac ccatacacct tttgctgcct tatgtcacct gacctgctcc ttgggaagct    28380
ctagcaagaa ggccttccct ggatcaccca ccaccttgca cctccagaac tcagagccaa    28440
attaaacttt cttgttactg tcgtcaaagc acagtcggtc tgggttgtat cactgtcaat    28500
gggaaacaga cttgcctgga tggataactt gtacattgca taatgtctag aaatgaaaag    28560
tcctatagag aaaaagaaaa ttagctggca cacagataga ggcctggag gaggctggct     28620 ttgtcctccc cgaggaggtg gcgagtaagg tgtaaatgtt catggatgta aatgggccca    28680
tatatgaggg tctggggtaa caagaaggcc tgtgaatata aagcactgaa ggtatgtcta    28740
gtctggagaa ggtcactaca gagagttctc caactcagtg cccatacaca cacacacaca    28800
cacacacaca cacacacaca cacacacaca ccacaaagaa aaaaaggaag aaaaatctga    28860
gagcaagtac agtacttaaa attgtgtgat tgtgtgtgtg actctgatgt cacatgctca    28920
tcttgcccta tgagttgaaa accaaatggc ccctgagagg cataacaacc acactgttgg    28980
ctgtgtgctc acgtttttct taaagcgtct gtctggtttg ctgctagcat caggcagact    29040
tgcagcagac tacatatgct cagccctgaa gtccttctag ggtgcatgtc tcttcagaat    29100
ttcagaaagt catctgtggc tccaggaccg cctgcactct ccctctgccg cgaggctgca    29160
gactctaggc tggggtggaa gcaacgctta ccctctggga caagtataaca tgttggcttt    29220 tctttccctc tgtggctcca acctggacat aaaatagatg caagctgtgt aataaatatt    29280
tcctcccgtc cacttagttc tcaacaataa ctactctgag agcacttatt aataggtggc    29340
ttagacataa gctttggctc attcccccac tagctcttac ttctttaact ctttcaaacc    29400
attctgtgtc ttccacatgg ttagttacct ctccttccat cctggttcgc ttcttccttc    29460
gagtcgccct cagtgtctct aggtgatgct tgtaagatat tctttctaca aagctgagag    29520
tggtggcact ctgggagttc aaagccagcc tgatctacac agcaagctcc aggatatcca    29580
gggcaatgtt gggaaaacct ttctcaaaca aaaagagggg ttcagttgtc aggaggagac    29640
ccatgggtta agaagtctag acgagccatg gtgatgcata cctttcatcc aagcacttag    29700
gaggcaaaga aaggtgaaac tctttgactt tgaggccagc taggttacat agtgataccc    29760
tgcttagtgt gtgtgtgtgt gtgtgtgt gtgtgtgt gtgtgtaatt taaaagtcta        29820
aaaatgcatt ctttttaaaaa tatgtataag tatttgcctg cacatatgta tgtatgtatg    29880
tataccatgt gtgtgtctgg tgctgaagga ctaggcatag actccctaga actagagtca    29940
```

-continued

```
tagacagttg tgacactccc caaccccca ccatgtgggt gcttgaagct aaactcctgt    30000
cctttgtaaa gcagcaggtg tctatgaacc ctgaaccatc tctccagtct ccagatgtgc    30060
attctcaaag aggagtcctt catatttccc taaactgaac atccttatca gtgagcatcc    30120
tcgagtcacc aaagctactg caaaccctct tagggaacat tcactattca cttctacttg    30180
gctcatgaaa cttaagtaca cacacacaaa cacacacaca cacagagt catgcactca    30240
caaaagcatg catgtacacc attcttatta gactatgctt tgctaaaaga ctttcctaga    30300
tactttaaaa catcacttct gccttttggt gggcaggttc caagattggt actggcgtac    30360
tggaaactga acaaggtaga gatctagaaa tcacagcagg tcagaagggc cagcctgtac    30420
aagagagagt tccacacctt ccaggaacac tgagcagggg gctgggacct tgcctctcag    30480
cccaagaaac tagtgcgttt cctgtatgca tgcctctcag agattccata agatctgcct    30540
tctgccataa gatcctctgc atccagacaa gcctagggga agttgagagg ctgcctgagt    30600
ctctcccaca ggccccttct tgcctggcag tatttttta tctggaggag aggaatcagg    30660
gtgggaatga tcaaatacaa ttatcaagga aaagtaaaa aacatatata tatatatatt    30720
aactgatcta gggagctggc tcagcagtta agagttctgg ctgcccttgc ttcagatctt    30780
gctttgattc ccagcaccca catgatggct ttcaactgta tctctgcttc caggggatcc    30840
aacagcctct tctgacctcc atagacaaga cctagtcctc tgcaagagca ccaaatgctc    30900
ttatctgttg atccatctct ctagcctcat gccagatcat ttaaaactac tggacactgt    30960
cccatttttac gaagatgtca ctgcccagtc atttgccatg agtggatatt tcgattcttt    31020
ctatgttctc acccttgcaa tttataagaa agatatctgc atttgtctcc tgagagaaca    31080
aagggtggag ggctactgag atggctctag gggtaaaggt gcttgccaca aaatctgaca    31140
acttaagttt ggtcttggaa tccacatggt ggagagagag aagagattcc cgtaagttgt    31200
cctcaaactt cccacacatg tgctgtggct tatgtgtaac cccaataagt aaagatagtt    31260
ttaaacacta cataaggtag ggtttcttca tgaccccaag gaatgatgcc cctgatagag    31320
cttatgctga aaccccatct ccattgtgcc atctggaaag agacaattgc atcccggaaa    31380
cagaatcttc atgaatggat taatgagcta ttaagaaagt ggcttggtta ttgcacatgc    31440
tggcggcgta atgacctcca ccatgatgtt atccagcatg aaggtcctca ccagaagtca    31500
tacaaatctt cttaggcttc cagagtcgtg agcaaaaaaa gcacacctct aaataaatta    31560
actagcctca ggtagttaac caccgaaaat gaaccaaggc agttctaata caaaccact    31620
tcccttccct gttcaaacca cagtgcccta ttatctaaaa gataaacttc aagccaagct    31680
tttaggttgc cagtatttat gtaacaacaa ggcccgttga cacacatctg taactcctag    31740
tactgggcct caggggcaga gacaggtgga gccctggagt ttgaattcca ggttctgtga    31800
gaaactctgt ctgaaaagac aatatggtga gtgacccggg aggatatctg atattgactt    31860
ctggccaaca cacagccatc tctgcacatc tgtagttgca agccttttgc actaagtttg    31920
gccagagtca gagtttgcaa gtgtttgtgg actgaatgca cgtgttgctg gtgatctaca    31980
aagtcaccct ccttctcaag ctagcagcac tggcttcggc cagctgctca ttcaagcctc    32040
tttgcagagt catcacgggg atgggggagc agggccctc cctagaacac caagcctgtg    32100
gttgtttatt caggacatta ttgagggcca agatgacaga taactctatc acttggccaa    32160
cagtcgggtg ttgcggtgtt aggttatttc tgtgtctgca gaaaacagtg caacctggac    32220
aaagaaaata aatgatatca ttttcattc aggcaactag attccgtggt acaaaaggct    32280
ccctggggaa cgaggccggg acagcgcggc tcctgagtcg ctatttccgt ctgtcaactt    32340
```

```
ctctaatctc ttgatttcct ccctctgtct gtttccttcc tcttgctggg gcccagtgga   32400
gtctgtgtac tcacagggag gagggtggca aagccctggt cctctacggg ctgggggaag   32460
gggggaagct gtcggcccag tgacttttc  ccctttctct ttttcttaga aaccagtctc   32520
aatttaagat aatgagtctc ctcattcacg tgtgctcact attcataggg acttatccac   32580
ccccgccctg tcaatctggc taagtaagac aagtcaaatt taaaagggaa cgttttcta    32640 aaaatgtggc tggaccgtgt gccggcacga aaccagggat ggcggtctaa gttacatgct   32700
ctctgccagc cccggtgcct tttccttcg  gaaaggagac ccggaggtaa aacgaagttg   32760
ccaacttttg atgatggtgt gcgccgggtg actctttaaa atgtcatcca tacctgggat   32820
agggaaggct cttcagggag tcatctagcc ctcccttcag gaaaagattc cacttccggt   32880
ttagttagct tccacctggt cccttatccg ctgtctctgc ccactagtcc tcatccatcc   32940
ggtttccgcc ctcatccacc ttgccctttt agttcctaga aagcagcacc gtagtcttgg   33000
caggtgggcc attggtcact ccgctaccac tgttaccatg gccaccaagg tgtcatttaa   33060
atatgagctc actgagtcct gcgggatggc ttggttggta atatgcttgc tgcaaaatcg   33120
tgagaactgg agttcaattc ccagcacatg gatgtatttc cagcacctgg aaggcaggga   33180
gcagagatct taaagctcct ggccagacag cccagcctaa ttagtaatca gtgagagacc   33240
ctgtctcaag aaacaagatg gaacatcaaa ggtcaacctc ttgtctccac acacacaaat   33300
acacacatgc acatacatcc acacacaggc aaacacatgc acacacctga acaccctcca   33360
caaatacata cataaaaaaa taaatacata cacacataca tacatacacc aacattccct   33420
ctccttagtc tcctggctac gctcttgtca ccccactaa  ggcttcaact tcttctattt   33480
cttcatcttg actcctctgt actttgcatg ccttttccag caaaggcttt tctttaaatc   33540
tccgtcattc ataaactccc tctaaatttc ttccctgcc  cttttctttc tctctaggga   33600
gataaagaca cacactacaa agtcaccgtg ggaccagttt attcacccac ccacccctgc   33660
ttctgttcat ccggccagct aagtagtcca acctctctgg tgctgtaccc tggaccctgg   33720
cttcaccaca gctcctccat gctacccagc cctgcaaacc ttcagcctag cctctggttc   33780
tccaaccagc acaggcccag tctggcttct atgtcctaga aatctccttc attctctcca   33840
tttccctcct gaatctacca ccttctttct cccttctcct gacctctaat gtcttggtca   33900
aacgattaca aggaagccaa tgaaattagc agtttggggt acctcagagt cagcagggga   33960
gctgggatga attcacattt ccaggccttt gctttgctcc ccggattctg acaggcagtt   34020
ccgaagctga gtccaggaag ctgaatttaa aatcacactc cagctgggtt ctgaggcagc   34080
cctaccacat cagctggccc tgactgagct gtgtctgggg ggcagtggtg ctggtggtgc   34140
tggtggtgct ggtggtggtg gtggtggtgg tggtggtggt ggtggtggtg tgtgtgtgtg   34200
ttttctgctt ttacaaaact tttctaattc ttatacaaag acaaatctg  cctcatatag   34260 gcagaaagat gacttatgcc tatataagat ataagatga  ctttatgcca cttattagca   34320
atagttactg tcaaaagtaa ttctatttat acacccttat acatggtatt gcttttgttg   34380
gagactctaa aatccagatt atgtatttaa aaaaaaattc cccagtcctt aaaaggtgaa   34440
gaatggaccc agatagaagg tcacggcaca agtatggagt cggagtgtgg agtcctgcca   34500
atggtctgga cagaagcatc cagagagggt ccaagacaaa tgcctcgcct cctaaggaac   34560
actggcagcc ctgatgaggt accagagatt gctaagtgga ggaatacagg atcagaccca   34620 tggagggggct taaagcgtga ctgtagcagc cctccgctga ggggctccag gtgggcgccc   34680
```

-continued

```
aaggtgctgc agtgggagcc acatgagagg tgatgtcttg gagtcacctc gggtaccatt      34740
gtttagggag gtgggatttt gtggtgtgga gacaggcagc ctcaaggatg cttttcaaca      34800
atggttgatg agttggaact aaaacagggg ccatcacact ggctcccata gctctgggct      34860
tgccagcttc cacatctgcc ccccacccc  tgtctggcac cagctcaagc tctgtgattc      34920
tacacatcca aaagaggaag agtagcctac tgggcatgcc acctcttctg gaccatcagg      34980
tgagagtgtg gcaagcccta ggctcctgtc caggatgcag ggctgccaga taggatgctc      35040
agctatctcc tgagctggaa ctattttagg aataaggatt atgcccgccc ggggttggcc      35100
agcaccccag cagcctgtgc ttgcgtaaaa gcaagtgctg ttgatttatc taaaaacaga      35160
gccgtggacc cacccacagg acaagtatgt atgcatctgt ttcatgtatc tgaaaagcga      35220
cacaaccatt tttcacatca tggcatcttc ctaaccccca ttcttttttg ttttgttttt      35280
ttgagacagg gtttctctgt gtagtcctgg ctgtcctgga actcactttg tagaccaggc      35340
tggcctcgaa ctcagaaatc ctgggattaa aggtgtgtgc caccacgccc ggccctaacc      35400
cccattctta atggtgatcc agtggttgaa atttcgggcc acacacatgt ccattaggga      35460
ttagctgctg tcttctgagc tacctggtac aatctttatc ccctgggcc  tgggctcctg      35520 atccctgact cgggcccgat caagtccagt tcctgggccc gatcaagtcc agttcctggg      35580
cccgaacaag tccagtccct agctcgatta gctcatcctg gctccctggc ctgttcttac      35640
ttacactctt ccccttgctc tggacttgtt gctttcttta ctcaagttgt ctgccacagt      35700
ccctaagcca cctctgtaag acaactaaga taatacttcc ctcaagcacg gaaagtcctg      35760
agtcaccaca ccctctggag gtgtgtggac acatgttcat gcgtgtggtt gcgcttacgt      35820
acgtgtgc                                                               35828
```

<210> SEQ ID NO 18
<211> LENGTH: 9301
<212> TYPE: DNA
<213> ORGANISM: Homo sapien

<400> SEQUENCE: 18

```
tagaggagaa gtctttgggg agggtttgct ctgagcacac cccttccct  ccctccgggg        60 ctgagggaaa catgggacca gccctgcccc agcctgtcct cattggctgg catgaagcag       120
agagggcttt aaaaaaggcg accgtgtctc ggctggagac cagagcctgt gctactggaa       180
ggtggcgtgc cctcctctgg ctggtaccat gcagctccca ctggccctgt gtctcgtctg       240
cctgctggta cacacagcct tccgtgtagt ggagggccag gggtggcagg cgttcaagaa       300
tgatgccacg gaaatcatcc ccgagctcgg agagtacccc gagcctccac cggagctgga       360
gaacaacaag accatgaacc gggcggagaa cggagggcgg cctccccacc accccttga        420 gaccaaaggt atggggtgga ggagagaatt cttagtaaaa gatcctgggg aggttttaga       480
aacttctctt tgggaggctt ggaagactgg ggtagaccca gtgaagattg ctggcctctg       540
ccagcactgg tcgaggaaca gtcttgcctg gaggtggggg aagaatggct cgctggtgca       600
gccttcaaat tcaggtgcag aggcatgagg caacagacgc tggtgagagc ccagggcagg       660
gaggacgctg gggtggtgag ggtatggcat cagggcatca aacaggctc  aggggctcag       720 aaaagaaaag gtttcaaaga atctcctcct gggaatatag gagccacgtc cagctgctgg       780
taccactggg aagggaacaa ggtaaggggag cctcccatcc acagaacagc acctgtgggg       840
caccggacac tctatgctgg tggtggctgt ccccaccaca cagacccaca tcatggaatc       900
cccaggaggt gaaccccag  ctcgaagggg aagaaacagg ttccaggcac tcagtaactt       960
```

-continued

```
ggtagtgaga agagctgagg tgtgaacctg gtttgatcca actgcaagat agccctggtg   1020 tgtgggggg tgtggggac agatctccac aaagcagtgg ggaggaaggc cagagaggca    1080
cccctgcagt gtgcattgcc catggcctgc ccagggagct ggcacttgaa ggaatgggag   1140
ttttcggcac agttttagcc cctgacatgg gtgcagctga gtccaggccc tggaggggag   1200
agcagcatcc tctgtgcagg agtagggaca tctgtcctca gcagccaccc cagtcccaac   1260
cttgcctcat tccaggggag ggagaaggaa gaggaaccct gggttcctgg tcaggcctgc   1320
acagagaagc ccaggtgaca gtgtgcatct ggctctataa ttggcaggaa tcctgaggcc   1380 atggggcgt ctgaaatgac acttcagact aagagcttcc ctgtcctctg gccattatcc    1440
aggtggcaga aagtccact gcccaggctc ctggacccca gccctcccg cctcacaacc     1500 tgttgggact atgggtgct aaaaagggca actgcatggg aggccagcca ggaccctccg    1560
tcttcaaaat ggaggacaag ggcgcctccc cccacagctc cccttctagg caaggtcagc   1620
tgggctccag cgactgcctg aagggctgta aggaacccaa acacaaaatg tccaccttgc   1680
tggactccca cgagaggcca cagccccctga ggaagccaca tgctcaaaac aaagtcatga  1740
tctgcagagg aagtgcctgg cctaggggcg ctattctcga aaagccgcaa aatgcccct    1800 tccctgggca aatgcccccc tgaccacaca cacattccag ccctgcagag gtgaggatgc   1860
aaaccagccc acagaccaga aagcagcccc agacgatggc agtggccaca tctcccctgc   1920
tgtgcttgct cttcagagtg ggggtggggg gtggccttct ctgtccctc tctggttttgg    1980 tcttaagact atttttcatt ctttcttgtc acattggaac tatccccatg aaacctttgg   2040
gggtggactg gtactcacac gacgaccagc tatttaaaaa gctcccaccc atctaagtcc   2100
accataggag acatggtcaa ggtgtgtgca ggggatcagg ccaggcctcg gagcccaatc   2160
tctgcctgcc cagggagtat caccatgagg cgcccattca gataacacag aacaagaaat   2220
gtgcccagca gagagccagg tcaatgtttg tggcagctga acctgtaggt tttgggtcag   2280
agctcagggc ccctatggta ggaaagtaac gacagtaaaa agcagccctc agctccatcc   2340
cccagcccag cctcccatgg atgctcgaac gcagagcctc cactcttgcc ggagccaaaa   2400
ggtgctggga ccccagggaa gtggagtccg gagatgcagc ccagccttttt gggcaagttc   2460 ttttctctgg ctgggcctca gtattctcat tgataatgag ggggttggac acactgcctt   2520
tgattccttt caagtctaat gaattcctgt cctgatcacc tcccccttcag tccctcgcct   2580 ccacagcagc tgccctgatt tattaccttc aattaaacctc tactccttc tccatcccct     2640 gtccaccct cccaagtggc tggaaaagga atttgggaga agccagagcc aggcagaagg   2700
tgtgctgagt acttaccctg cccaggccag ggaccctgcg gcacaagtgt ggcttaaatc   2760
ataagaagac cccagaagag aaatgataat aataatacat aacagccgac gctttcagct   2820
atatgtgcca aatggtattt tctgcattgc gtgtgtaatg gattaactcg caatgcttgg   2880
ggcggcccat tttgcagaca ggaagaagag agaggttaag gaacttgccc aagatgacac   2940
ctgcagtgag cgatggagcc ctggtgtttg aaccccagca gtcatttggc tccgagggga   3000
cagggtgcgc aggagagctt tccaccagct ctagagcatc tgggaccttc ctgcaataga   3060
tgttcagggg caaaagcctc tggagacagg cttggcaaaa gcaggctgg ggtggagaga    3120 gacgggccgg tccagggcag gggtggccag gcgggcggcc accctcacgc gcgcctctct   3180
ccacagacgt gtccgagtac agctgccgcg agctgcactt caccccgctac gtgaccgatg   3240 ggccgtgccg cagcgccaag ccggtcaccg agctggtgtg ctccggccag tgcggcccgg   3300
```

```
cgcgcctgct gcccaacgcc atcggccgcg gcaagtggtg cgacctagt gggcccgact    3360 tccgctgcat ccccgaccgc taccgcgcgc agcgcgtgca gctgctgtgt cccggtggtg    3420
aggcgccgcg cgcgcgcaag gtgcgcctgg tggcctcgtg caagtgcaag cgcctcaccc    3480
gcttccacaa ccagtcggag ctcaaggact cgggaccga ggccgctcgg ccgcagaagg     3540
gccggaagcc gcgcccccgc gcccggagcg ccaaagccaa ccaggccgag ctggagaacg    3600
cctactagag cccgcccgcg cccctcccca ccggcgggcg ccccggccct gaacccgcgc    3660
cccacatttc tgtcctctgc gcgtggtttg attgtttata tttcattgta aatgcctgca    3720
acccagggca gggggctgag accttccagg ccctgaggaa tcccgggcgc cggcaaggcc    3780
cccctcagcc cgccagctga ggggtcccac ggggcagggg agggaattga gagtcacaga    3840
cactgagcca cgcagccccg cctctggggc cgcctacctt tgctggtccc acttcagagg    3900
aggcagaaat ggaagcattt tcaccgccct ggggttttaa gggagcggtg tgggagtggg    3960
aaagtccagg gactggttaa gaaagttgga taagattccc ccttgcacct cgctgcccat    4020
cagaaagcct gaggcgtgcc cagagcacaa gactgggggc aactgtagat gtggtttcta    4080
gtcctggctc tgccactaac ttgctgtgta accttgaact acacaattct ccttcgggac    4140
ctcaatttcc actttgtaaa atgagggtgg aggtgggaat aggatctcga ggagactatt    4200
ggcatatgat tccaaggact ccagtgcctt ttgaatgggc agaggtgaga gagagagaga    4260
gaaagagaga gaatgaatgc agttgcattg attcagtgcc aaggtcactt ccagaattca    4320
gagttgtgat gctctcttct gacagccaaa gatgaaaaac aaacagaaaa aaaaaagtaa    4380
agagtctatt tatggctgac atatttacgg ctgacaaact cctggaagaa gctatgctgc    4440
ttcccagcct ggcttccccg gatgtttggc tacctccacc cctccatctc aaagaaataa    4500
catcatccat tggggtagaa aaggagaggg tccgagggtg gtgggaggga tagaaatcac    4560
atccgcccca acttcccaaa gagcagcatc cctcccccga cccatagcca tgttttaaag    4620
tcaccttccg aagagaagtg aaaggttcaa ggacactggc cttgcaggcc cgagggagca    4680
gccatcacaa actcacagac cagcacatcc cttttgagac accgccttct gcccaccact    4740
cacggacaca tttctgccta gaaacagct tcttactgct cttacatgtg atggcatatc     4800
ttacactaaa agaatattat tggggggaaaa actacaagtg ctgtacatat gctgagaaac    4860
tgcagagcat aatagctgcc acccaaaaat cttttgaaa atcatttcca gacaacctct    4920
tactttctgt gtagttttta attgttaaaa aaaaaaagtt ttaaacagaa gcacatgaca    4980
tatgaaagcc tgcaggactg gtcgtttttt tggcaattct tccacgtggg acttgtccac    5040
aagaatgaaa gtagtggttt ttaaagagtt aagttacata tttattttct cacttaagtt    5100
atttatgcaa aagttttttct tgtagagaat gacaatgtta atattgcttt atgaattaac    5160
agtctgttct tccagagtcc agagacattg ttaataaaga caatgaatca tgaccgaaag    5220
gatgtggtct cattttgtca accacacatg acgtcatttc tgtcaaagtt gacacccttc    5280
tcttggtcac tagagctcca accttggaca caccttttgac tgctctctgg tggcccttgt    5340
ggcaattatg tcttcctttg aaaagtcatg tttatccctt cctttccaaa cccagaccgc    5400
atttcttcac ccagggcatg gtaataacct cagccttgta tccttttagc agcctcccct    5460
ccatgctggc ttccaaaatg ctgttctcat tgtatcactc ccctgctcaa aagccttcca    5520
tagctccccc ttgcccagga tcaagtgcag tttccctatc tgacatggga ggccttctct    5580
gcttgactcc cacctcccac tccaccaagc ttcctactga ctccaaatgg tcatgcagat    5640
ccctgcttcc ttagtttgcc atccacactt agcaccccca ataactaatc ctctttcttt    5700
```

```
aggattcaca ttacttgtca tctcttcccc taaccttcca gagatgttcc aatctcccat  5760
gatccctctc tcctctgagg ttccagcccc ttttgtctac accactactt tggttcctaa  5820
ttctgttttc catttgacag tcattcatgg aggaccagcc tggccaagtc ctgcttagta  5880
ctggcataga caacacaaag ccaagtacaa ttcaggacca gctcacagga aacttcatct  5940
tcttcgaagt gtggatttga tgcctcctgg gtagaaatgt aggatcttca aaagtgggcc  6000
agcctcctgc acttctctca aagtctcgcc tccccaaggt gtcttaatag tgctggatgc  6060
tagctgagtt agcatcttca gatgaagagt aaccctaaag ttactcttca gttgccctaa  6120
ggtgggatgg tcaactggaa agctttaaat taagtccagc ctaccttggg ggaacccacc  6180
cccacaaaga aagctgaggt ccctcctgat gacttgtcag tttaactacc aataacccac  6240
ttgaattaat catcatcatc aagtctttga taggtgtgag tgggtatcag tggccggtcc  6300
cttcctgggg ctccagcccc cgaggaggcc tcagtgagcc cctgcagaaa atccatgcat  6360
catgagtgtc tcagggccca gaatatgaga gcaggtagga aacagagaca tcttccatcc  6420
ctgagaggca gtgcggtcca gtgggtgggg acacgggctc tgggtcaggt ttgtgttgtt  6480
tgtttgtttg ttttgagaca gagtctcgct ctattgccca ggctggagtg cagtgtcaca  6540
atctcggctt actgcaactt ctgccttccc ggattcaagt gattctcctg cctcagcctc  6600
cagagtagct gggattacag gtgcgtgcca ccacgcctgg ctaattttg tattttgat  6660 agagacgggg tttcaccatg ttggccaggc tagtctcgaa ctcttgacct caagtgatct  6720
gcctgcctcg gcctcccaaa gtgctgggat tacaggcgtg agccaccaca cccagcccca  6780
ggttggtgtt tgaatctgag gagactgaag caccaagggg ttaaatgttt tgcccacagc  6840
catacttggg ctcagttcct tgccctaccc ctcacttgag ctgcttagaa cctggtgggc  6900
acatgggcaa taaccaggtc acactgtttt gtaccaagtg ttatgggaat ccaagatagg  6960
agtaatttgc tctgtggagg ggatgaggga tagtggttag ggaaagcttc acaaagtggg  7020
tgttgcttag agattttcca ggtggagaag ggggcttcta ggcagaaggc atagcccaag  7080
caaagactgc aagtgcatgg ctgctcatgg gtagaagaga atccaccatt cctcaacatg  7140
taccgagtcc ttgccatgtg caaggcaaca tgggggtacc aggaattcca agcaatgtcc  7200
aaacctaggg tctgctttct gggacctgaa gatacaggat ggatcagccc aggctgcaat  7260
cccattacca cgaggggaa aaaaacctga aggctaaatt gtaggtcggg ttagaggtta  7320
tttatggaaa gttatattct acctacatgg ggtctataag cctggcgcca atcagaaaag  7380
gaacaaacaa cagacctagc tgggaggggc agcattttgt tgtaggggc ggggcacatg  7440 ttctggggggt acagccagac tcaggcttg tattaatagt ctgagagtaa gacagacaga  7500
gggatagaag gaaataggtc cctttctctc tctctctctc tctctctctc actctctctc  7560
tctctcacac acacacacag acacacacac acgctctgta ggggtctact tatgctccaa  7620
gtacaaatca ggccacattt acacaaggag gtaaaggaaa agaacgttgg aggagccaca  7680
ggaccccaaa attccctgtt ttccttgaat caggcaggac ttacgcagct gggagggtgg  7740
agagcctgca gaagccacct gcgagtaagc caagttcaga gtcacagaca ccaaaagctg  7800
gtgccatgtc ccacacccgc ccactcccca cctgctcctt gacacagccc tgtgctccac  7860
aacccggctc ccagatcatt gattatagct ctggggcctg caccgtcctt cctgccacat  7920
ccccacccca ttcttggaac ctgccctctg tcttctccct tgtccaaggg caggcaaggg  7980
ctcagctatt gggcagcttt gaccaacagc tgaggctcct tttgtggctg gagatgcagg  8040
```

-continued

| | |
|---|---|
| aggcaggga atattcctct tagtcaatgc gaccatgtgc ctggtttgcc cagggtggtc | 8100 |
| tcgtttacac ctgtaggcca agcgtaatta ttaacagctc ccacttctac tctaaaaaat | 8160 |
| gacccaatct gggcagtaaa ttatatggtg cccatgctat aagagctgc aacttgctgg | 8220 |
| gcgtggtggc tcacacctgt aatcccagta cttgggacg tcaaggcggg tggatcacct | 8280 |
| gaggtcacga gttagagact ggcctggcca gcatggcaaa accccatctt tactaaaaat | 8340 |
| acaaaaatta gcaaggcatg gtggcatgca cctgtaatcc caggtactcg ggaggctgag | 8400 |
| acaggagaat ggcttgaacc caggaggcag aggttgcagt gagccaagat tgtgccactg | 8460 |
| ccctccagcc ctggcaacag agcaagactt catctcaaaa gaaaaggat actgtcaatc | 8520 |
| actgcaggaa gaacccaggt aatgaatgag gagaagagag gggctgagtc accatagtgg | 8580 |
| cagcaccgac tcctgcagga aaggcgagac actgggtcat gggtactgaa gggtgccctg | 8640 |
| aatgacgttc tgctttagag accgaacctg agccctgaaa gtgcatgcct gttcatgggt | 8700 |
| gagagactaa attcatcatt ccttggcagg tactgaatcc tttcttacgg ctgccctcca | 8760 |
| atgcccaatt tccctacaat tgtctggggt gcctaagctt ctgccacca agagggccag | 8820 |
| agctggcagc gagcagctgc aggtaggaga gataggtacc cataagggag gtgggaaaga | 8880 |
| gagatggaag gagagggtg cagagcacac acctcccctg cctgacaact tcctgagggc | 8940 |
| tggtcatgcc agcagattta aggcggaggc aggggagatg gggcgggaga ggaagtgaaa | 9000 |
| aaggagaggg tgggatgga gaggaagaga gggtgatcat tcattcattc cattgctact | 9060 |
| gactggatgc cagctgtgag ccaggcacca ccctagctct gggcatgtgg ttgtaatctt | 9120 |
| ggagcctcat ggagctcaca gggagtgctg gcaaggagat ggataatgga cggataacaa | 9180 |
| ataaacattt agtacaatgt ccgggaatgg aaagttctcg aaagaaaaat aaagctggtg | 9240 |
| agcatataga cagccctgaa ggcggccagg ccaggcattt ctgaggaggt ggcatttgag | 9300 |
| c | 9301 |

<210> SEQ ID NO 19
<211> LENGTH: 21
<212> TYPE: DNA
<213> ORGANISM: Artificial Sequence
<220> FEATURE:
<223> OTHER INFORMATION: Primer for PCR

<400> SEQUENCE: 19
ccggagctgg agaacaacaa g                                        21

<210> SEQ ID NO 20
<211> LENGTH: 19
<212> TYPE: DNA
<213> ORGANISM: Artificial Sequence
<220> FEATURE:
<223> OTHER INFORMATION: PRimer for PCR

<400> SEQUENCE: 20
gcactggccg gagcacacc                                           19

<210> SEQ ID NO 21
<211> LENGTH: 23
<212> TYPE: DNA
<213> ORGANISM: Artificial Sequence
<220> FEATURE:
<223> OTHER INFORMATION: Primer for PCR

<400> SEQUENCE: 21
aggccaaccg cgagaagatg acc                                      23

<210> SEQ ID NO 22
<211> LENGTH: 21
<212> TYPE: DNA
<213> ORGANISM: Artificial Sequence
<220> FEATURE:
<223> OTHER INFORMATION: Primer for PCR

<400> SEQUENCE: 22
gaagtccagg gcgacgtagc a                                             21

<210> SEQ ID NO 23
<211> LENGTH: 25
<212> TYPE: DNA
<213> ORGANISM: Artificial Sequence
<220> FEATURE:
<223> OTHER INFORMATION: Primer for PCR

<400> SEQUENCE: 23
aagcttggta ccatgcagct cccac                                         25

<210> SEQ ID NO 24
<211> LENGTH: 50
<212> TYPE: DNA
<213> ORGANISM: Artificial Sequence
<220> FEATURE:
<223> OTHER INFORMATION: Primer for PCR

<400> SEQUENCE: 24
aagcttctac ttgtcatcgt cgtccttgta gtcgtaggcg ttctccagct               50

<210> SEQ ID NO 25
<211> LENGTH: 19
<212> TYPE: DNA
<213> ORGANISM: Artificial Sequence
<220> FEATURE:
<223> OTHER INFORMATION: Primer for PCR

<400> SEQUENCE: 25
gcactggccg gagcacacc                                                19

<210> SEQ ID NO 26
<211> LENGTH: 39
<212> TYPE: DNA
<213> ORGANISM: Artificial Sequence
<220> FEATURE:
<223> OTHER INFORMATION: Primer for PCR

<400> SEQUENCE: 26
gtcgtcggat ccatggggtg gcaggcgttc aagaatgat                          39

<210> SEQ ID NO 27
<211> LENGTH: 57
<212> TYPE: DNA
<213> ORGANISM: Artificial Sequence
<220> FEATURE:
<223> OTHER INFORMATION: Primer for PCR

<400> SEQUENCE: 27
gtcgtcaagc ttctacttgt catcgtcctt gtagtcgtag gcgttctcca gctcggc      57

<210> SEQ ID NO 28
<211> LENGTH: 29
<212> TYPE: DNA
<213> ORGANISM: Artificial Sequence
<220> FEATURE:

<223> OTHER INFORMATION: Primer for PCR

<400> SEQUENCE: 28
gacttggatc ccagggtgg caggcgttc                               29

<210> SEQ ID NO 29
<211> LENGTH: 29
<212> TYPE: DNA
<213> ORGANISM: Artificial Sequence
<220> FEATURE:
<223> OTHER INFORMATION: Primer for PCR

<400> SEQUENCE: 29
agcataagct tctagtaggc gttctccag                              29

<210> SEQ ID NO 30
<211> LENGTH: 29
<212> TYPE: DNA
<213> ORGANISM: Artificial Sequence
<220> FEATURE:
<223> OTHER INFORMATION: Primer for PCR

<400> SEQUENCE: 30
gacttggatc cgaagggaaa aagaaaggg                              29

<210> SEQ ID NO 31
<211> LENGTH: 29
<212> TYPE: DNA
<213> ORGANISM: Artificial Sequence
<220> FEATURE:
<223> OTHER INFORMATION: Primer for PCR

<400> SEQUENCE: 31
agcataagct tttaatccaa atcgatgga                              29

<210> SEQ ID NO 32
<211> LENGTH: 33
<212> TYPE: DNA
<213> ORGANISM: Artificial Sequence
<220> FEATURE:
<223> OTHER INFORMATION: Primer for PCR

<400> SEQUENCE: 32
actacgagct cggccccacc acccatcaac aag                         33

<210> SEQ ID NO 33
<211> LENGTH: 34
<212> TYPE: DNA
<213> ORGANISM: Artificial Sequence
<220> FEATURE:
<223> OTHER INFORMATION: Primer for PCR

<400> SEQUENCE: 33
acttagaagc tttcagtcct cagcccctc ttcc                         34

<210> SEQ ID NO 34
<211> LENGTH: 66
<212> TYPE: DNA
<213> ORGANISM: Artificial Sequence
<220> FEATURE:
<223> OTHER INFORMATION: Primer for PCR

<400> SEQUENCE: 34
aatctggatc cataacttcg tatagcatac attatacgaa gttatctgca ggattcgagg    60
gcccct                                                              66

<210> SEQ ID NO 35
<211> LENGTH: 82
<212> TYPE: DNA
<213> ORGANISM: Artificial Sequence
<220> FEATURE:
<223> OTHER INFORMATION: Primer for PCR

<400> SEQUENCE: 35
aatctgaatt ccaccggtgt taattaaata acttcgtata atgtatgcta tacgaagtta    60
tagatctaga gtcagcttct ga                                              82

<210> SEQ ID NO 36
<211> LENGTH: 62
<212> TYPE: DNA
<213> ORGANISM: Artificial Sequence
<220> FEATURE:
<223> OTHER INFORMATION: Primer for PCR

<400> SEQUENCE: 36
atttaggtga cactatagaa ctcgagcagc tgaagcttaa ccacatggtg gctcacaacc    60
at                                                                    62

<210> SEQ ID NO 37
<211> LENGTH: 54
<212> TYPE: DNA
<213> ORGANISM: Artificial Sequence
<220> FEATURE:
<223> OTHER INFORMATION: Primer for PCR

<400> SEQUENCE: 37
aacgacggcc agtgaatccg taatcatggt catgctgcca ggtggaggag ggca          54

<210> SEQ ID NO 38
<211> LENGTH: 31
<212> TYPE: DNA
<213> ORGANISM: Artificial Sequence
<220> FEATURE:
<223> OTHER INFORMATION: Primer for PCR

<400> SEQUENCE: 38
attaccaccg gtgacacccg cttcctgaca g                                    31

<210> SEQ ID NO 39
<211> LENGTH: 61
<212> TYPE: DNA
<213> ORGANISM: Artificial Sequence
<220> FEATURE:
<223> OTHER INFORMATION: Primer for PCR

<400> SEQUENCE: 39
attacttaat taaacatggc gcgccatatg gccggcccct aattgcggcg catcgttaat    60
t                                                                     61

<210> SEQ ID NO 40
<211> LENGTH: 34
<212> TYPE: DNA
<213> ORGANISM: Artificial Sequence
<220> FEATURE:
<223> OTHER INFORMATION: Primer for PCR

<400> SEQUENCE: 40
attacggccg gccgcaaagg aattcaagat ctga                                 34

-continued

<210> SEQ ID NO 41
<211> LENGTH: 34
<212> TYPE: DNA
<213> ORGANISM: Artificial Sequence
<220> FEATURE:
<223> OTHER INFORMATION: Primer for PCR

<400> SEQUENCE: 41
attacggcgc gcccctcaca ggccgcaccc agct                    34

<210> SEQ ID NO 42
<211> LENGTH: 184
<212> TYPE: PRT
<213> ORGANISM: Homo sapiens

<400> SEQUENCE: 42

Met Ser Arg Thr Ala Tyr Thr Val Gly Ala Leu Leu Leu Leu Leu Gly
 1               5                  10                  15

Thr Leu Leu Pro Ala Ala Glu Gly Lys Lys Gly Ser Gln Gly Ala
             20                  25                  30

Ile Pro Pro Pro Asp Lys Ala Gln His Asn Asp Ser Glu Gln Thr Gln
             35                  40                  45

Ser Pro Gln Gln Pro Gly Ser Arg Asn Arg Gly Arg Gly Gln Gly Arg
         50                  55                  60

Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                 85                  90                  95

Gln Pro Leu Lys Gln Thr Ile His Glu Glu Gly Cys Asn Ser Arg Thr
            100                 105                 110

Ile Ile Asn Arg Phe Cys Tyr Gly Gln Cys Asn Ser Phe Tyr Ile Pro
            115                 120                 125

Arg His Ile Arg Lys Glu Glu Gly Ser Phe Gln Ser Cys Ser Phe Cys
        130                 135                 140

Lys Pro Lys Lys Phe Thr Thr Met Met Val Thr Leu Asn Cys Pro Glu
145                 150                 155                 160

Leu Gln Pro Pro Thr Lys Lys Lys Arg Val Thr Arg Val Lys Gln Cys
                165                 170                 175

Arg Cys Ile Ser Ile Asp Leu Asp
            180

<210> SEQ ID NO 43
<211> LENGTH: 267
<212> TYPE: PRT
<213> ORGANISM: Homo sapiens

<400> SEQUENCE: 43

Met His Leu Leu Leu Phe Gln Leu Leu Val Leu Leu Pro Leu Gly Lys
 1               5                  10                  15

Thr Thr Arg His Gln Asp Gly Arg Gln Asn Gln Ser Ser Leu Ser Pro
             20                  25                  30

Val Leu Leu Pro Arg Asn Gln Arg Glu Leu Pro Thr Gly Asn His Glu
         35                  40                  45

Glu Ala Glu Glu Lys Pro Asp Leu Phe Val Ala Val Pro His Leu Val
     50                  55                  60

Ala Thr Ser Pro Ala Gly Glu Gly Gln Arg Gln Arg Glu Lys Met Leu
65                  70                  75                  80

```
Ser Arg Phe Gly Arg Phe Trp Lys Lys Pro Glu Arg Glu Met His Pro
                85                  90                  95

Ser Arg Asp Ser Asp Ser Glu Pro Phe Pro Pro Gly Thr Gln Ser Leu
            100                 105                 110

Ile Gln Pro Ile Asp Gly Met Lys Met Glu Lys Ser Pro Leu Arg Glu
            115                 120                 125

Glu Ala Lys Lys Phe Trp His His Phe Met Phe Arg Lys Thr Pro Ala
        130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys
            165                 170                 175

Glu Lys Val Val Val Gln Asn Asn Leu Cys Phe Gly Lys Cys Gly Ser
            180                 185                 190

Val His Phe Pro Gly Ala Ala Gln His Ser His Thr Ser Cys Ser His
        195                 200                 205

Cys Leu Pro Ala Lys Phe Thr Thr Met His Leu Pro Leu Asn Cys Thr
        210                 215                 220

Glu Leu Ser Ser Val Ile Lys Val Val Met Leu Val Glu Glu Cys Gln
225                 230                 235                 240

Cys Lys Val Lys Thr Glu His Glu Asp Gly His Ile Leu His Ala Gly
            245                 250                 255

Ser Gln Asp Ser Phe Ile Pro Gly Val Ser Ala
            260                 265

<210> SEQ ID NO 44
<211> LENGTH: 180
<212> TYPE: PRT
<213> ORGANISM: Homo sapiens

<400> SEQUENCE: 44

Met Leu Arg Val Leu Val Gly Ala Val Leu Pro Ala Met Leu Leu Ala
 1               5                  10                  15

Ala Pro Pro Pro Ile Asn Lys Leu Ala Leu Phe Pro Asp Lys Ser Ala
                20                  25                  30

Trp Cys Glu Ala Lys Asn Ile Thr Gln Ile Val Gly His Ser Gly Cys
            35                  40                  45

Glu Ala Lys Ser Ile Gln Asn Arg Ala Cys Leu Gly Gln Cys Phe Ser
        50                  55                  60

Tyr Ser Val Pro Asn Thr Phe Pro Gln Ser Thr Glu Ser Leu Val His
65                  70                  75                  80

Cys Asp Ser Cys Met Pro Ala Gln Ser Met Trp Glu Ile Val Thr Leu
                85                  90                  95

Glu Cys Pro Gly His Glu Glu Val Pro Arg Val Asp Lys Leu Val Glu
            100                 105                 110

Lys Ile Leu His Cys Ser Cys Gln Ala Cys Gly Lys Glu Pro Ser His
        115                 120                 125

Glu Gly Leu Ser Val Tyr Val Gln Gly Glu Asp Gly Pro Gly Ser Gln
        130                 135                 140

Pro Gly Thr His Pro His Pro His Pro His Pro Gly Gly Gln
145                 150                 155                 160

Thr Pro Glu Pro Glu Asp Pro Pro Gly Ala Pro His Thr Glu Glu
                165                 170                 175

Gly Ala Glu Asp
            180
```

```
<210> SEQ ID NO 45
<211> LENGTH: 642
<212> TYPE: DNA
<213> ORGANISM: Homo sapiens
<220> FEATURE:
<221> NAME/KEY: CDS
<222> LOCATION: (1)..(639)

<400> SEQUENCE: 45 atg cag ctc cca ctg gcc ctg tgt ctc gtc tgc ctg ctg gta cac aca      48
Met Gln Leu Pro Leu Ala Leu Cys Leu Val Cys Leu Leu Val His Thr
 1               5                  10                  15 gcc ttc cgt gta gtg gag ggc cag ggg tgg cag gcg ttc aag aat gat      96
Ala Phe Arg Val Val Glu Gly Gln Gly Trp Gln Ala Phe Lys Asn Asp
                 20                  25                  30 gcc acg gaa atc atc ccc gag ctc gga gag tac ccc gag cct cca ccg     144
Ala Thr Glu Ile Ile Pro Glu Leu Gly Glu Tyr Pro Glu Pro Pro Pro
             35                  40                  45 gag ctg gag aac aac aag acc atg aac cgg gcg gag aac gga ggg cgg     192
Glu Leu Glu Asn Asn Lys Thr Met Asn Arg Ala Glu Asn Gly Gly Arg
         50                  55                  60 cct ccc cac cac ccc ttt gag acc aaa gac gtg tcc gag tac agc tgc     240
Pro Pro His His Pro Phe Glu Thr Lys Asp Val Ser Glu Tyr Ser Cys
 65                  70                  75                  80 cgc gag ctg cac ttc acc cgc tac gtg acc gat ggg ccg tgc cgc agc     288
Arg Glu Leu His Phe Thr Arg Tyr Val Thr Asp Gly Pro Cys Arg Ser
                 85                  90                  95 gcc aag ccg gtc acc gag ctg gtg tgc tcc ggc cag tgc ggc ccg gcg     336
Ala Lys Pro Val Thr Glu Leu Val Cys Ser Gly Gln Cys Gly Pro Ala
                100                 105                 110 cgc ctg ctg ccc aac gcc atc ggc cgc ggc aag tgg tgg cga cct agt     384
Arg Leu Leu Pro Asn Ala Ile Gly Arg Gly Lys Trp Trp Arg Pro Ser
            115                 120                 125 ggg ccc gac ttc cgc tgc atc ccc gac cgc tac cgc gcg cag cgc gtg     432
Gly Pro Asp Phe Arg Cys Ile Pro Asp Arg Tyr Arg Ala Gln Arg Val
        130                 135                 140 cag ctg ctg tgt ccc ggt ggt gag gcg ccg cgc gcg cgc aag gtg cgc     480
Gln Leu Leu Cys Pro Gly Gly Glu Ala Pro Arg Ala Arg Lys Val Arg
145                 150                 155                 160 ctg gtg gcc tcg tgc aag tgc aag cgc ctc acc cgc ttc cac aac cag     528
Leu Val Ala Ser Cys Lys Cys Lys Arg Leu Thr Arg Phe His Asn Gln
                165                 170                 175 tcg gag ctc aag gac ttc ggg acc gag gcc gct cgg ccg cag aag ggc     576
Ser Glu Leu Lys Asp Phe Gly Thr Glu Ala Ala Arg Pro Gln Lys Gly
            180                 185                 190 cgg aag ccg cgg ccc cgc gcc cgg agc gcc aaa gcc aac cag gcc gag     624
Arg Lys Pro Arg Pro Arg Ala Arg Ser Ala Lys Ala Asn Gln Ala Glu
        195                 200                 205 ctg gag aac gcc tac tag                                             642
Leu Glu Asn Ala Tyr
    210
```

SEQUENCES

Sequence ID No. 1: Human BEER cDNA (complete coding region plus 5'and UTRs)

```
AGAGCCTGTGCTACTGGAAGGTGGCGTGCCCTCCTCTGGCTGGTACCATGCAGCTCCCACTGGCCCTGTGTCTCGTCTGC
CTGCTGGTACACACAGCCTTCCGTGTAGTGGAGGGCCAGGGGTGGCAGGCGTTCAAGAATGATGCCACGGAAATCATCCC
CGAGCTCGGAGAGTACCCCGAGCCTCCACCGGAGCTGGAGAACAACAAGACCATGAACCGGGCGGAGAACGGAGGGCGGC
CTCCCCACCACCCCTTTGAGACCAAAGACGTGTCCGAGTACAGCTGCCGCGAGCTGCACTTCACCCGCTACGTGACCGAT
GGGCCGTGCCGCAGCGCCAAGCCGGTCACCGAGCTGGTGTGCTCCGGCCAGTGCGGCCCGGCGCGCCTGCTGCCCAACGC
CATCGGCCGCGGCAAGTGGTGGCGACCTAGTGGGCCCGACTTCCGCTGCATCCCCGACCGCTACCGCGCGCAGCGCGTGC
AGCTGCTGTGTCCCGGTGGTGAGGCGCCGCGCGCGCGCAAGGTGCGCCTGGTGGCCTCGTGCAAGTGCAAGCGCCTCACC
CGCTTCCACAACCAGTCGGAGCTCAAGGACTTCGGGACCGAGGCCGCTCGGCCGCAGAAGGGCCGGAAGCCGCGGCCCCG
CGCCCGGAGCGCCAAAGCCAACCAGGCCGAGCTGGAGAACGCCTACTAGAGCCCGCCCGCGCCCCTCCCCACCGGCGGGC
GCCCCGGCCCTGAACCCGCGCCCCACATTTCTGTCCTCTGCGCGTGGTTTGATTGTTTATATTTCATTGTAAATGCCTGC
AACCCAGGGCAGGGGGCTGAGACCTTCCAGGCCCTGAGGAATCCCGGGCGCCGGCAAGGCCCCCCTCAGCCCGCCAGCTG
AGGGGTCCCACGGGGCAGGGGAGGGAATTGAGAGTCACAGACACTGAGCCACGCAGCCCCGCCTCTGGGGCCGCCTACCT
TTGCTGGTCCCACTTCAGAGGAGGCAGAAATGGAAGCATTTTCACCGCCCTGGGGTTTTAAGGGAGCGGTGTGGGAGTGG
GAAAGTCCAGGGACTGGTTAAGAAAGTTGGATAAGATTCCCCCTTGCACCTCGCTGCCCATCAGAAAGCCTGAGGCGTGC
CCAGAGCACAAGACTGGGGCAACTGTAGATGTGGTTTCTAGTCCTGGCTCTGCCACTAACTTGCTGTGTAACCTTGAAC
TACACAATTCTCCTTCGGGACCTCAATTTCCACTTTGTAAAATGAGGGTGGAGGTGGGAATAGGATCTCGAGGAGACTAT
TGGCATATGATTCCAAGGACTCCAGTGCCTTTTGAATGGGCAGAGGTGAGAGAGAGAGAGAGAAAGAGAGAGAATGAATG
CAGTTGCATTGATTCAGTGCCAAGGTCACTTCCAGAATTCAGAGTTGTGATGCTCTCTTCTGACAGCCAAAGATGAAAAA
CAAACAGAAAAAAAAAAGTAAAGAGTCTATTTATGGCTGACATATTTACGGCTGACAAACTCCTGGAAGAAGCTATGCTG
CTTCCCAGCCTGGCTTCCCCGGATGTTTGGCTACCTCCACCCCTCCATCTCAAAGAAATAACATCATCCATTGGGGTAGA
AAAGGAGAGGGTCCGAGGGTGGTGGGAGGGATAGAAATCACATCCGCCCCAACTTCCCAAAGAGCAGCATCCCTCCCCCG
ACCCATAGCCATGTTTTAAAGTCACCTTCCGAAGAGAAGTGAAAGGTTCAAGGACACTGGCCTTGCAGGCCCGAGGGAGC
AGCCATCACAAACTCACAGACCAGCACATCCCTTTTGAGACACCGCCTTCTGCCCACCACTCACGGACACATTTCTGCCT
AGAAAACAGCTTCTTACTGCTCTTACATGTGATGGCATATCTTACACTAAAAGAATATTATTGGGGGAAAAACTACAAGT
GCTGTACATATGCTGAGAAACTGCAGAGCATAATAGCTGCCACCCAAAAATCTTTTTGAAAATCATTTCCAGACAACCTC
TTACTTTCTGTGTAGTTTTTAATTGTTAAAAAAAAAAAGTTTTAAACAGAAGCACATGACATATGAAAGCCTGCAGGACT
GGTCGTTTTTTTGGCAATTCTTCCACGTGGGACTTGTCCACAAGAATGAAAGTAGTGGTTTTTAAAGAGTTAAGTTACAT
ATTTATTTTCTCACTTAAGTTATTTATGCAAAGTTTTTCTTGTAGAGAATGACAATGTTAATATTGCTTTATGAATTAA
CAGTCTGTTCTTCCAGAGTCCAGAGACATTGTTAATAAAGACAATGAATCATGACCGAAAG
```

Sequence ID No. 2: Human BEER protein (complete sequence)

```
MQLPLALCLVCLLVHTAFRVVEGQGWQAFKNDATEIIPELGEYPEPPPELENNKTMNRAENGGRPPHHPFETKDVSEYSC
RELHFTRYVTDGPCRSAKPVTELVCSGQCGPARLLPNAIGRGKWWRPSGPDFRCIPDRYRAQRVQLLCPGGEAPRARKVR
LVASCKCKRLTRFHNQSELKDFGTEAARPQKGRKPRPRARSAKANQAELENAY
```

Sequence ID No. 3: Human Beer cDNA containing Sclerosteosis nonsense mutation

```
AGAGCCTGTGCTACTGGAAGGTGGCGTGCCCTCCTCTGGCTGGTACCATGCAGCTCCCACTGGCCCTGTGTCTCGTCTGC
CTGCTGGTACACACAGCCTTCCGTGTAGTGGAGGGCTAGGGGTGGCAGGCGTTCAAGAATGATGCCACGGAAATCATCCc
CGAGCTCGGAGAGTACCCCGAGCCTCCACCGGAGCTGGAGAACAACAAGACCATGAACCGGGCGGAGAACGGAGGGCGGC
CTCCCCACCACCCCTTTGAGACCAAAGACGTGTCCGAGTACAGCTGCCGCGAGCTGCACTTCACCCGCTACGTGACCGAT
GGGCCGTGCCGCAGCGCCAAGCCGGTCACCGAGCTGGTGTGCTCCGGCCAGTGCGGCCCGGCGCGCCTGCTGCCCAACGC
CATCGGCCGCGGCAAGTGGTGGCGACCTAGTGGGCCCGACTTCCGCTGCATCCCCGACCGCTACCGCGCGCAGCGCGTGC
AGCTGCTGTGTCCCGGTGGTGAGGCGCCGCGCGCGCGCAAGGTGCGCCTGGTGGCCTCGTGCAAGTGCAAGCGCCTCACC
CGCTTCCACAACCAGTCGGAGCTCAAGGACTTCGGGACCGAGGCCGCTCGGCCGCAGAAGGGCCGGAAGCCGCGGCCCCG
CGCCCGGAGCGCCAAAGCCAACCAGGCCGAGCTGGAGAACGCCTACTAGAGCCCGCCCGCGCCCCTCCCCACCGGCGGGC
GCCCCGGCCCTGAACCCGCGCCCCACATTTCTGTCCTCTGCGCGTGGTTTGATTGTTTATATTTCATTGTAAATGCCTGC
AACCCAGGGCAGGGGGCTGAGACCTTCCAGGCCCTGAGGAATCCCGGGCGCCGGCAAGGCCCCCCTCAGCCCGCCAGCTG
AGGGGTCCCACGGGGCAGGGGAGGGAATTGAGAGTCACAGACACTGAGCCACGCAGCCCCGCCTCTGGGGCCGCCTACCT
TTGCTGGTCCCACTTCAGAGGAGGCAGAAATGGAAGCATTTTCACCGCCCTGGGGTTTTAAGGGAGCGGTGTGGGAGTGG
GAAAGTCCAGGGACTGGTTAAGAAAGTTGGATAAGATTCCCCCTTGCACCTCGCTGCCCATCAGAAAGCCTGAGGCGTGC
CCAGAGCACAAGACTGGGGCAACTGTAGATGTGGTTTCTAGTCCTGGCTCTGCCACTAACTTGCTGTGTAACCTTGAAC
TACACAATTCTCCTTCGGGACCTCAATTTCCACTTTGTAAAATGAGGGTGGAGGTGGGAATAGGATCTCGAGGAGACTAT
TGGCATATGATTCCAAGGACTCCAGTGCCTTTTGAATGGGCAGAGGTGAGAGAGAGAGAGAGAAAGAGAGAGAATGAATG
CAGTTGCATTGATTCAGTGCCAAGGTCACTTCCAGAATTCAGAGTTGTGATGCTCTCTTCTGACAGCCAAAGATGAAAAA
```

```
CAAACAGAAAAAAAAAAGTAAAGAGTCTATTTATGGCTGACATATTTACGGCTGACAAACTCCTGGAAGAAGCTATGCTG
CTTCCCAGCCTGGCTTCCCCGGATGTTTGGCTACCTCCACCCCTCCATCTCAAAGAAATAACATCATCCATTGGGGTAGA
AAAGGAGAGGGTCCGAGGGTGGTGGGAGGGATAGAAATCACATCCGCCCCAACTTCCCAAAGAGCAGCATCCCTCCCCCG
ACCCATAGCCATGTTTTAAAGTCACCTTCCGAAGAGAAGTGAAAGGTTCAAGGACACTGGCCTTGCAGGCCCGAGGGAGC
AGCCATCACAAACTCACAGACCAGCACATCCCTTTTGAGACACCGCCTTCTGCCCACCACTCACGGACACATTTCTGCCT
AGAAAACAGCTTCTTACTGCTCTTACATGTGATGGCATATCTTACACTAAAAGAATATTATTGGGGGAAAAACTACAAGT
GCTGTACATATGCTGAGAAACTGCAGAGCATAATAGCTGCCACCCAAAAATCTTTTTGAAAATCATTTCCAGACAACCTC
TTACTTTCTGTGTAGTTTTTAATTGTTAAAAAAAAAAAGTTTTAAACAGAAGCACATGACATATGAAAGCCTGCAGGACT
GGTCGTTTTTTGGCAATTCTTCCACGTGGGACTTGTCCACAAGAATGAAAGTAGTGGTTTTTAAAGAGTTAAGTTACAT
ATTTATTTTCTCACTTAAGTTATTTATGCAAAAGTTTTTCTTGTAGAGAATGACAATGTTAATATTGCTTTATGAATTAA
CAGTCTGTTCTTCCAGAGTCCAGAGACATTGTTAATAAAGACAATGAATCATGACCGAAAG
```

Sequence ID No. 4:   Truncated Human Beer protein from Sclerosteosis

MQLPLALCLVCLLVHTAFRVVEG*

Sequence ID No. 5:   Human BEER cDNA encoding protein variant   (V10I)

```
AGAGCCTGTGCTACTGGAAGGTGGCGTGCCCTCCTCTGGCTGGTACCATGCAGCTCCCACTGGCCCTGTGTCTCATCTGC
CTGCTGGTACACACAGCCTTCCGTGTAGTGGAGGGCCAGGGGTGGCAGGCGTTCAAGAATGATGCCACGGAAATCATCCG
CGAGCTCGGAGAGTACCCCGAGCCTCCACCGGAGCTGGAGAACAACAAGACCATGAACCGGGCGGAGAACGGAGGGCGGC
CTCCCCACCACCCCTTTGAGACCAAAGACGTGTCCGAGTACAGCTGCCGCGAGCTGCACTTCACCCGCTACGTGACCGAT
GGGCCGTGCCGCAGCGCCAAGCCGGTCACCGAGCTGGTGTGCTCCGGCCAGTGCGGCCCGGCGCGCCTGCTGCCCAACGC
CATCGGCCGCGGCAAGTGGTGGCGACCTAGTGGGCCCGACTTCCGCTGCATCCCCGACCGCTACCGCGCGCAGCGCGTGC
AGCTGCTGTGTCCCGGTGGTGAGGCGCCGCGCGCGCAAGGTGCGCCTGGTGGCCTCGTGCAAGTGCAAGCGCCTCACC
CGCTTCCACAACCAGTCGGAGCTCAAGGACTTCGGGACCGAGGCCGCTCGGCCGCAGAAGGGCCGGAAGCCGCGCCCCG
CGCCCGGAGCGCAAAGCCAACCAGGCCGAGCTGGAGAACGCCTACTAGAGCCCGCCCGCGCCCCTCCCCACCGGCGGGC
GCCCGGCCCTGAACCCGCCGCCCCACATTTCTGTCCTCTGCGCGTGGTTTGATTGTTTATATTTCATTGTAAATGCCTGC
AACCCAGGGCAGGGGGCTGAGACCTTCCAGGCCCTGAGGAATCCCGGGCGCCGGCAAGGCCCCCCTCAGCCCGCCAGCTG
AGGGGTCCCACGGGGCAGGGGAGGGAATTGAGAGTCACAGACACTGAGCCACGCAGCCCCGCCTCTGGGGCCGCCTACCT
TTGCTGGTCCCACTTCAGAGGAGGCAGAAATGGAAGCATTTTCACCGCCCTGGGGTTTAAGGGAGCGGTGTGGGAGTGG
GAAAGTCCAGGGACTGGTTAAGAAAGTTGGATAAGATTCCCCCTTGCACCTCGCTGCCCATCAGAAAGCCTGAGGCGTGC
CCAGAGCACAAGACTGGGGGCAACTGTAGATGTGGTTTCTAGTCCTGGCTCTGCCACTAACTTGCTGTGTAACCTTGAAC
TACACAATTCTCCTTCGGGACCTCAATTTCCACTTTGTAAAATGAGGGTGGAGGTGGGAATAGGATCTCGAGGAGACTAT
TGGCATATGATTCCAAGGACTCCAGTGCCTTTTGAATGGGCAGAGGTGAGAGAGAGAGAGAGAAAGAGAGAGAATGAATG
CAGTTGCATTGATTCAGTGCCAAGGTCACTTCCAGAATTCAGAGTTGTGATGCTCTCTTCTGACAGCCAAAGATGAAAAA
CAAACAGAAAAAAAAAGTAAAGAGTCTATTTATGGCTGACATATTTACGGCTGACAAACTCCTGGAAGAAGCTATGCTG
CTTCCCAGCCTGGCTTCCCCGGATGTTTGGCTACCTCCACCCCTCCATCTCAAAGAAATAACATCATCCATTGGGGTAGA
AAAGGAGAGGGTCCGAGGGTGGTGGGAGGGATAGAAATCACATCCGCCCCAACTTCCCAAAGAGCAGCATCCCTCCCCCG
ACCCATAGCCATGTTTTAAAGTCACCTTCCGAAGAGAAGTGAAAGGTTCAAGGACACTGGCCTTGCAGGCCCGAGGGAGC
AGCCATCACAAACTCACAGACCAGCACATCCCTTTTGAGACACCGCCTTCTGCCCACCACTCACGGACACATTTCTGCCT
AGAAAACAGCTTCTTACTGCTCTTACATGTGATGGCATATCTTACACTAAAAGAATATTATTGGGGGAAAAACTACAAGT
GCTGTACATATGCTGAGAAACTGCAGAGCATAATAGCTGCCACCCAAAAATCTTTTTGAAAATCATTTCCAGACAACCTC
TTACTTTCTGTGTAGTTTTTAATTGTTAAAAAAAAAAAGTTTTAAACAGAAGCACATGACATATGAAAGCCTGCAGGACT
GGTCGTTTTTTGGCAATTCTTCCACGTGGGACTTGTCCACAAGAATGAAAGTAGTGGTTTTTAAAGAGTTAAGTTACAT
ATTTATTTTCTCACTTAAGTTATTTATGCAAAAGTTTTTCTTGTAGAGAATGACAATGTTAATATTGCTTTATGAATTAA
CAGTCTGTTCTTCCAGAGTCCAGAGACATTGTTAATAAAGACAATGAATCATGACCGAAAG
```

Sequence ID No. 6:   Human BEER protein variant   (V10I)

MQLPLALCLICLLVHTAFRVVEGQGWQAFKNDATEIIRELGEYPEPPPELENNKTMNRAENGGRPPHHPFETKDVSEYSC
RELHFTRYVTDGPCRSAKPVTELVCSGQCGPARLLPNAIGRGKWWRPSGPDFRCIPDRYRAQRVQLLCPGGEAPRARKVR
LVASCKCKRLTRFHNQSELKDFGTEAARPQKGRKPRPRARSAKANQAELENAY

Sequence ID No. 7:   Human Beer cDNA encoding protein variant   (P38R)

```
AGAGCCTGTGCTACTGGAAGGTGGCGTGCCCTCCTCTGGCTGGTACCATGCAGCTCCCACTGGCCCTGTGTCTCGTCTGC
CTGCTGGTACACACAGCCTTCCGTGTAGTGGAGGGCCAGGGGTGGCAGGCGTTCAAGAATGATGCCACGGAAATCATCCG
CGAGCTCGGAGAGTACCCCGAGCCTCCACCGGAGCTGGAGAACAACAAGACCATGAACCGGGCGGAGAACGGAGGGCGGC
```

83

```
CATCGGCCGCGGCAAGTGGTGGCGACCTAGTGGGCCCGACTTCCGCTGCATCCCCGACCGCTACCGCGCGCAGCGCGTGC
AGCTGCTGTGTCCCGGTGGTGAGGCGCCGCGCGCGCAAGGTGCGCCTGGTGGCCTCGTGCAAGTGCAAGCGCCTCACC
CGCTTCCACAACCAGTCGGAGCTCAAGGACTTCGGGACCGAGGCCGCTCGGCCGCAGAAGGGCCGGAAGCCGCGGCCCCG
CGCCCGGAGCGCCAAAGCCAACCAGGCCGAGCTGGAGAACGCCTACTAGAGCCCGCCCGCGCCCCTCCCCACCGGCGGGC
GCCCCGGCCCTGAACCCGCGCCCCACATTTCTGTCCTCTGCGCGTGGTTTGATTGTTTATATTTCATTGTAAATGCCTGC
AACCCAGGGCAGGGGGCTGAGACCTTCCAGGCCCTGAGGAATCCCGGGCGCCGGCAAGGCCCCCCTCAGCCCGCCAGCTG
AGGGGTCCCACGGGGCAGGGGAGGGAATTGAGAGTCACAGACACTGAGCCACGCAGCCCCGCTCTGGGGCCGCCTACCT
TTGCTGGTCCCACTTCAGAGGAGGCAGAAATGAAGCATTTTCACCGCCCTGGGGTTTTAAGGGAGCGGTGTGGGAGTGG
GAAAGTCCAGGGACTGGTTAAGAAAGTTGGATAAGATTCCCCCTTGCACCTCGCTGCCCATCAGAAAGCCTGAGGCGTGC
CCAGAGCACAAGACTGGGGGCAACTGTAGATGTGGTTTCTAGTCCTGGCTCTGCCACTAACTTGCTGTGTAACCTTGAAC
TACACAATTCTCCTTCGGGACCTCAATTTCCACTTTGTAAAATGAGGGTGGAGGTGGGAATAGGATCTCGAGGAGACTAT
TGGCATATGATTCCAAGGACTCCAGTGCCTTTTGAATGGGCAGAGGTGAGAGAGAGAGAGAAAGAGAGAGAATGAATG
CAGTTGCATTGATTCAGTGCCAAGGTCACTTCCAGAATTCAGAGTTGTGATGCTCTCTTCTGACAGCCAAAGATGAAAAA
CAAACAGAAAAAAAAAAGTAAAGAGTCTATTTATGGCTGACATATTTACGGCTGACAAACTCCTGGAAGAAGCTATGCTG
CTTCCCAGCCTGGCTTCCCCGGATGTTTGGCTACCTCCACCCCTCCATCTCAAAGAAATAACATCATCCATTGGGGTAGA
AAAGGAGAGGGTCCGAGGGTGGTGGGAGGGATAGAAATCACATCCGCCCCAACTTCCCAAAGAGCAGCATCCCTCCCCCG
ACCCATAGCCATGTTTTAAAGTCACCTTCCGAAGAGAAGTGAAAGGTTCAAGGACACTGGCCTTGCAGGCCCGAGGGAGC
AGCCATCACAAACTCACAGACCAGCACATCCCTTTTGAGACACCGCCTTCTGCCCACCACTCACGGACACATTTCTGCCT
AGAAAACAGCTTCTTACTGCTCTTACATGTGATGGCATATCTTACACTAAAAGAATATTATTGGGGGAAAAACTACAAGT
GCTGTACATATGCTGAGAAACTGCAGAGCATAATAGCTGCCACCCAAAAATCTTTTTGAAAATCATTTCCAGACAACCTC
TTACTTTCTGTGTAGTTTTTAATTGTTAAAAAAAAAAAGTTTTAAACAGAAGCACATGACATATGAAAGCCTGCAGGACT
GGTCGTTTTTTTGGCAATTCTTCCACGTGGGACTTGTCCACAAGAATGAAAGTAGTGGTTTTTAAAGAGTTAAGTTACAT
ATTTATTTTCTCACTTAAGTTATTTATGCAAAAGTTTTTCTTGTAGAGAATGACAATGTTAATATTGCTTTATGAATTAA
CAGTCTGTTCTTCCAGAGTCCAGAGACATTGTTAATAAAGACAATGAATCATGACCGAAAG
```

Sequence ID No. 8: Human Beer protein variant (P38R)

MQLPLALCLVCLLVHTAFRVVEGQGWQAFKNDATEIIRELGEYPEPPPELENNKTMNRAENGGRPPHHPFETKDVSEYSC
RELHFTRYVTDGPCRSAKPVTELVCSGQCGPARLLPNAIGRGKWWRPSGPDFRCIPDRYRAQRVQLLCPGGEAPRARKVR
LVASCKCKRLTRFHNQSELKDFGTEAARPQKGRKPRPRARSAKANQAELENAY

Sequence ID No. 9: Vervet BEER cDNA (complete coding region)

```
ATGCAGCTCCCACTGGCCCTGTGTCTTGTCTGCCTGCTGGTACACGCAGCCTTCCGTGTAGTGGAGGGCCAGGGGTGGCA
GGCCTTCAAGAATGATGCCACGGAAATCATCCCCGAGCTCGGAGAGTACCCCGAGCCTCCACCGGAGCTGGAGAACAACA
AGACCATGAACCGGGCGGAGAATGGAGGGCGGCCTCCCCACCACCCCTTTGAGACCAAAGACGTGTCCGAGTACAGCTGC
CGAGAGCTGCACTTCACCCGCTACGTGACCGATGGGCCGTGCCGCAGCGCCAAGCCAGTCACCGAGTTGGTGTGCTCCGG
CCAGTGCGGCCCGGCACGCCTGCTGCCCAACGCCATCGGCCGCGGCAAGTGGTGGCGCCCGAGTGGGCCCGACTTCCGCT
GCATCCCCGACCGCTACCGCGCGCAGCGTGTGCAGCTGCTGTGTCCCGGTGGTGCCGCGCCGCGCGCGCAAGGTGCGC
CTGGTGGCCTCGTGCAAGTGCAAGCGCCTCACCCGCTTCCACAACCAGTCGGAGCTCAAGGACTTCGGTCCCGAGGCCGC
TCGGCCGCAGAAGGGCCGGAAGCCGCGGCCCCGCGCCCGGGGGGCCAAAGCCAATCAGGCCGAGCTGGAGAACGCCTACT
AG
```

Sequence ID No. 10: Vervet BEER protein (complete sequence)

MQLPLALCLVCLLVHAAFRVVEGQGWQAFKNDATEIIPELGEYPEPPPELENNKTMNRAENGGRPPHHPFETKDVSEYSC
RELHFTRYVTDGPCRSAKPVTELVCSGQCGPARLLPNAIGRGKWWRPSGPDFRCIPDRYRAQRVQLLCPGGAAPRARKVR
LVASCKCKRLTRFHNQSELKDFGPEAARPQKGRKPRPRARGAKANQAELENAY

Sequence ID No. 11: Mouse BEER cDNA (coding region only)

```
ATGCAGCCCTCACTAGCCCCGTGCCTCATCTGCCTACTTGTGCACGCTGCCTTCTGTGCTGTGGAGGGCCAGGGGTGGCA
AGCCTTCAGGAATGATGCCACAGAGGTCATCCCAGGGCTTGGAGAGTACCCCGAGCCTCCTCCTGAGAACAACCAGACCA
TGAACCGGGCGGAGAATGGAGGCAGACCTCCCCACCATCCCTATGACGCCAAAGGTGTGTCCGAGTACAGCTGCCGCGAG
CTGCACTACACCCGCTTCCTGACAGACGGCCCATGCCGCAGCGCCAAGCCGGTCACCGAGTTGGTGTGCTCCGGCCAGTG
CGGCCCCGCGCGGCTGCTGCCCAACGCCATCGGGCGCGTGAAGTGGTGGCGCCCGAACGGACCGGATTTCCGCTGCATCC
CGGATCGCTACCGCGCGCAGCGGGTGCAGCTGCTGTGCCCGGGGGCGCGGCGCCGCGCTCGCGCAAGGTGCGTCTGGTG
GCCTCGTGCAAGTGCAAGCGCCTCACCCGCTTCCACAACCAGTCGGAGCTCAAGGACTTCGGGCCGGAGACCGCGCGGCC
GCAGAAGGGTCGCAAGCCGCGGCCCCGGCGCCCGGGGAGCCAAAGCCAACCAGGCGGAGCTGGAGAACGCCTACTAGAG
```

Sequence ID No. 12:   Mouse BEER protein   (complete sequence)

MQPSLAPCLICLLVHAAFCAVEGQGWQAFRNDATEVIPGLGEYPEPPPENNQTMNRAENGGRPPHHPYDAKDVSEYSCRE
LHYTRFLTDGPCRSAKPVTELVCSGQCGPARLLPNAIGRVKWWRPNGPDFRCIPDRYRAQRVQLLCPGGAAPRSRKVRLV
ASCKCKRLTRFHNQSELKDFGPETARPQKGRKPRPGARGAKANQAELENAY

Sequence ID No. 13:   Rat BEER cDNA   (complete coding region plus 5' UTR)

GAGGACCGAGTGCCCTTCCTCCTTCTGGCACCATGCAGCTCTCACTAGCCCCTTGCCTTGCCTGCCTGCTTGTACATGCA
GCCTTCGTTGCTGTGGAGAGCCAGGGGTGGCAAGCCTTCAAGAATGATGCCACAGAAATCATCCCGGGACTCAGAGAGTA
CCCAGAGCCTCCTCAGGAACTAGAGAACAACCAGACCATGAACCGGGCCGAGAACGGAGGCAGACCCCCCCACCATCCTT
ATGACACCAAAGACGTGTCCGAGTACAGCTGCCGCGAGCTGCACTACACCCGCTTCGTGACCGACGGCCCGTGCCGCAGT
GCCAAGCCGGTCACCGAGTTGGTGTGCTCGGGCCAGTGCGGCCCCGCGGCTGCTGCCCAACGCCATCGGGCGCGTGAA
GTGGTGGCGCCCGAACGGACCCGACTTCCGCTGCATCCCGGATCGCTACCGCGCGCAGCGGGTGCAGCTGCTGTGCCCCG
GCGGCGCGGCGCCCGCGTCGCGCAAGGTGCGTCTGGTGGCCTCGTGCAAGTGCAAGCGCTCACCCGCTTCCACAACCAG
TCGGAGCTCAAGGACTTCGGACCTGAGACCGCGCGGCCGCAGAAGGGTCGCAAGCCGCGGCCCCGCGCCCGGGGAGCCAA
AGCCAACCAGGCGGAGCTGGAGAACGCCTACTAG

Sequence ID No. 14:   Rat BEER protein   (complete sequence)

MQLSLAPCLACLLVHAAFVAVESQGWQAFKNDATEIIPGLREYPEPPQELENNQTMNRAENGGRPPHHPYDTKDVSEYSC
RELHYTRFVTDGPCRSAKPVTELVCSGQCGPARLLPNAIGRVKWWRPNGPDFRCIPDRYRAQRVQLLCPGGAAPRSRKVR
LVASCKCKRLTRFHNQSELKDFGPETARPQKGRKPRPRARGAKANQAELENAY

Sequence ID No. 15:   Bovine BEER cDNA   (partial coding sequence)

AGAATGATGCCACAGAAATCATCCCCGAGCTGGGCGAGTACCCCGAGCCTCTGCCAGAGCTGAACAACAAGACCATGAAC
CGGGCGGAGAACGGAGGGAGACCTCCCCACCACCCCTTTGAGACCAAAGACGCCTCCGAGTACAGCTGCCGGGAGCTGCA
CTTCACCCGCTACGTGACCGATGGGCCGTGCCGCAGCGCCAAGCCGGTCACCGAGCTGGTGTGCTCGGGCCAGTGCGGCC
CGGCGCGCCTGCTGCCCAACGCCATCGGCCGCGGCAAGTGGTGGCGCCCAAGCGGGCCCGACTTCCGCTGCATCCCCGAC
CGCTACCGCGCGCAGCGGGTGCAGCTGCTGTGTGTCCTGGCGGCGCGGCGCCGCGCGCGCGCAAGGTGCGCCTGGTGGCCTC
GTGCAAGTGCAAGCGCCTCACTCGCTTCCACAACCAGTCCGAGCTCAAGGACTTCGGGCCCGAGGCCGCGCGGCCGCAAA
CGGGCCGGAAGCTGCGGCCCCGCGCCCGGGGCACCAAAGCCAGCCGGGCCGA

Sequence ID No. 16:   Bovine BEER protein   (partial sequence -- missing signal
sequence and last 6 residues)

NDATEIIPELGEYPEPLPELNNKTMNRAENGGRPPHHPPETKDASEYSCRELHFTRYVTDGPCRSAKPVTELVCSGQCGP
ARLLPNAIGRGKWWRPSGPDFRCIPDRYRAQRVQLLCPGGAAPRARKVRLVASCKCKRLTRFHNQSELKDFGPEAARPQT
GRKLRPRARGTKASRA

Sequence ID No. 17:   MluI - AviII restriction fragment used to make mouse Beer
transgene CGCGTTTTGGTGAGCAGCAATATTGCGCTTCGATGAGCCTTGGCGTTGAGATTGATACCTCTGCTGCACAAAAGGCAATC
GACCGAGCTGGACCAGCGCATTCGTGACACCGTCTCCTTCGAACTTATTCGCAATGGAGTGTCATTCATCAAGGACNGCC
TGATCGCAAATGGTGCTATCCACGCAGCGGCAATCGAAAACCCTCAGCCGGTGACCAATATCTACAACATCAGCCTTGGT
ATCCTGCGTGATGAGCCAGCGCAGAACAAGGTAACCGTCAGTGCCGATAAGTTCAAAGTTAAACCTGGTGTTGATACCAA
CATTGAAACGTTGATCGAAAACGCGCTGAAAAACGCTGCTGAATGTGCGGCGCTGGATGTCACAAAGCAAATGGCAGCAG
ACAAGAAAGCGATGGATGAACTGGCTTCCTATGTCCGCACGGCCATCATGATGGAATGTTTCCCCGGTGGTGTTATCTGG
CAGCAGTGCCGTCGATAGTATGCAATTGATAATTATTATCATTTGCGGGTCCTTTCCGGCGATCCGCCTTGTTACGGGGC
GGCGACCTCGCGGGTTTTCGCTATTTATGAAAATTTTCCGGTTTAAGGCGTTTCCGTTCTTCTTCGTCATAACTTAATGT
TTTTATTTAAAATACCCTCTGAAAAGAAAGGAAACGACAGGTGCTGAAAGCGAGCTTTTTGGCCTCTGTCGTTTCCTTTC
TCTGTTTTTGTCCGTGGAATGAACAATGGAAGTCAACAAAAAGCAGAGCTTATCGATGATAAGCGGTCAAACATGAGAAT

85

```
TCGCGGCCGCATAATACGACTCACTATAGGGATCGACGCCTACTCCCCGCGCATGAAGCGGAGGAGCTGGACTCCGCATG
CCCAGAGACGCCCCCCAACCCCCAAAGTGCCTGACCTCAGCCTCTACCAGCTCTGGCTTGGGCTTGGGCGGGGTCAAGGC
TACCACGTTCTCTTAACAGGTGGCTGGGCTGTCTCTTGGCCGCGCGTCATGTGACAGCTGCCTAGTTCTGCAGTGAGGTC
ACCGTGGAATGTCTGCCTTCGTTGCCATGGCAACGGGATGACGTTACAATCTGGGTGTGGAGCTTTTCCTGTCCGTGTCA
GGAAATCCAAATACCCTAAAATACCCTAGAAGAGGAAGTAGCTGAGCCAAGGCTTTCCTGGCTTCTCCAGATAAAGTTTG
ACTTAGATGGAAAAAAACAAAATGATAAAGACCCGAGCCATCTGAAAATTCCTCCTAATTGCACCACTAGGAAATGTGTA
TATTATTGAGCTCGTATGTGTTCTTATTTTAAAAAGAAAACTTTAGTCATGTTATTAATAAGAATTTCTCAGCAGTGGGA
GAGAACCAATATTAACACCAAGATAAAAGTTGGCATGATCCACATTGCAGGAAGATCCACGTTGGGTTTTCATGAATGTG
AAGACCCCATTTATTAAAGTCCTAAGCTCTGTTTTTGCACACTAGGAAGCGATGGCCGGGATGGCTGAGGGGCTGTAAGG
ATCTTTCAATGTCTTACATGTGTGTTTCCTGTCCTGCACCTAGGACCTGCTGCCTAGCCTGCAGCAGAGCCAGAGGGGTT
TCACATGATTAGTCTCAGACACTTGGGGGCAGGTTGCATGTACTGCATCGCTTATTCCATACGGAGCACCTACTATGTG
TCAAACACCATATGGTGTTCACTCTTCAGAACGGTGGTGGTCATCATGGTGCATTTGCTGACGGTTGGATTGGTGGTAGA
GAGCTGAGATATATGGACGCACTCTTCAGCATTCTGTCAACGTGGCTGTGCATTCTTGCTCCTGAGCAAGTGGCTAAACA
GACTCACAGGGTCAGCCTCCAGCTCAGTCGCTGCATAGTCTTAGGGAACCTCTCCCAGTCCTCCCTACCTCAACTATCCA
AGAAGCCAGGGGGGCTTGGCGGTCTCAGGAGCCTGCTTGCTGGGGGACAGGTTGTTCAGTTTTATCTGCAGTAGGTTGCCT
AGGCATAGTGTCAGGACTGATGGCTGCCTTGGAGAACACATCCTTTGCCCTCTATGCAAATCTGACCTTGACATGGGGGC
GCTGCTCAGCTGGGAGGATCAACTGCATACCTAAAGCCAAGCCTAAAGCTTCTTCGTCCACCTGAAACTCCTGGACCAAG
GGGCTTCCGGCACATCCTCTCAGGCCAGTGAGGGAGTCTGTGTGAGCTGCACTTTCCAATCTCAGGGCGTGAGAGGCAGA
GGGAGGTGGGGCAGAGCCTTGCAGCTCTTTCCTCCCATCTGGACAGCGCTCTGGCTCAGCAGCCCATATGAGCACAGGC
ACATCCCCACCCCACCCCCACCTTTCCTGTCCTGCAGAATTTAGGCTCTGTTCACGGGGGGGGGGGGGGGGCAGTCC
TATCCTCTCTTAGGTAGACAGGACTCTGCAGGAGACACTGCTTTGTAAGATACTGCAGTTTAAATTTGGATGTTGTGAGG
GGAAAGCGAAGGGCCTCTTTGACCATTCAGTCAAGGTACCTTCTAACTCCCATCGTATTGGGGGGCTACTCTAGTGCTAG
ACATTGCAGAGAGCCTCAGAACTGTAGTTACCAGTGTGGTAGGATTGATCCTTCAGGGAGCCTGACATGTGACAGTTCCA
TTCTTCACCCAGTCACCGAACATTTATTCAGTACCTACCCCGTAACAGGCACCGTAGCAGGTACTGAGGGACGGACCACT
CAAAGAACTGACAGACCGAAGCCTTGGAATATAAACACCAAAGCATCAGGCTCTGCCAACAGAACACTCTTTAACACTCA
GGCCCTTTAACACTCAGGACCCCCACCCCCACCCCAAGCAGTTGGCACTGCTATCCACATTTTACAGAGAGGAAAAACTA
GGCACAGGACGATATAAGTGGCTTGCTTAAGCTTGTCTGCATGGTAAATGGCAGGGCTGGATTGAGACCCAGACATTCCA
ACTCTAGGGTCTATTTTTCTTTTTTTCTCGTTGTTCGAATCTGGGTCTTACTGGGTAAACTCAGGCTAGCCTCACACTCAT
ATCCTTCTCCCATGCTTACGAGTGCTAGGATTCCAGGTGTGTGCTACCATGTCTGACTCCCTGTAGCTTGTCTATACCA
TCCTCACAACATAGGAATTGTGATAGCAGCACACACACCGGAAGGAGCTGGGGAAATCCCACAGAGGGCTCCGCAGGATG
ACAGGCGAATGCCTACACAGAAGGTGGGGAAGGGAAGCAGAGGGAACAGCATGGGCGTGGGACCACAAGTCTATTTGGGG
AAGCTGCCGGTAACCGTATATGGCTGGGGTGAGGGGAGAGGTCATGAGATGAGGCAGGAAGAGCCACAGCAGGCAGCGGG
TACGGGCTCCTTATTGCCAAGAGGCTCGGATCTTCCTCCTCTTCCTCCTTCCGGGGCTGCCTGTTCATTTTCCACCACTG
CCTCCCATCCAGGTCTGTGGCTCAGGACATCACCCAGCTGCAGAAACTGGGCATCACCCACGTCCTGAATGCTGCCGAGG
GCAGGTCCTTCATGCACGTCAACACCAGTGCTAGCTTCTACGAGGATTCTGGCATCACCTACTTGGGCATCAAGGCCAAT
GATACGCAGGAGTTCAACCTCAGTGCTTACTTTGAAAGGGCCACAGATTTCATTGACCAGGCGCTGGCCCATAAAAATGG
TAAGGAACGTACATTCCGGCACCCATGGAGCGTAAGCCCTCTGGGACTTGCTTCCTCCAAAGAGGCCCCCACTTGAAAAA
GGTTCCAGAAAGATCCCAAAATATGCCACCAACTAGGGATTAAGTGTCCTACATGTCAGCCGATGGGGGCCACTGCATAT
AGTCTGTGCCATAGACATGACAATGGATAATAATATTTCAGACAGAGAGCAGGAGTTAGGTAGCTGTGCTCCTTTCCCTT
TAATTGAGTGTGCCCATTTTTTATTCATGTATGTGTATACATGTGTGTGCACACATGCCATAGGTTGATACTGAACACC
GTCTTCAATCGTTCCCCACCCCACCTTATTTTTGAGGCAGGGTCTCTTCCCTGATCCTGGGGCTCATTGGTTTATCTAG
GCTGCTGGCCAGTGAGCTCTGGAGTTCTGCTTTTCTCTACCTCCCTAGCCTCTGGGACTGCAGGGGCATGTGCTGGGCCAG
GCTTTTATGTCGCGTTGGGGATCTGAACTTAGGTCCCTAGGCCTGAGCACCGTAAAGACTCTGCCACATCCCCAGCCTGT
TTGAGCAAGTGAACCATTCCCCAGAATTCCCCCAGTGGGGCTTTCCTACCCTTTTATTGGCTAGGCATTCATGAGTGGTC
ACCTCGCCAGAGGAATGAGTGGCCACAGACTGGCTCAGGGTCAGCAGCCTAGAGATACTGGGTTAAGTCTTCCTGCCGCTC
GCTCCCTGCAGCCGCAGACAGAAAGTAGGACTGAATGAGAGCTGGCTAGTGGTCAGACAGGACAGAAGGCTGAGAGGGTC
ACAGGGCAGATGTCAGCAGAGCAGACAGGTTCTCCCTCTGTGGGGAGGGGTGGCCCACTGCAGGTGTAATTGGCCTTCT
TTGTGCTCCATAGAGGCTTCCTGGGTACACAGCAGCTTCCCTGTCCTGGTGATTCCCAAAGAGAACTCCCTACCACTGGA
CTTACAGAAGTTCTATTGACTGGTGTAACGGTTCAACAGCTTTGGCTCTTGGTGGACGGTGCATACTGCTGTATCAGCTC
AAGAGCTCATTCACGAATGAACACACACACACACACACACACACACACACAAGCTAATTTTGATATGCCTTAACTA
GCTCAGTGACTGGGCATTTCTGAACATCCCTGAAGTTAGCACACATTTCCCTCTGGTGTTCCTGGCTTAACACCTTCTAA
ATCTATATTTTATCTTTGCTGCCCTGTTACCTTCTGAGAAGCCCCTAGGGCCACTTCCCTTCGCACCTACATTGCTGGAT
GGTTTCTCTCCTGCAGCTCTTAAATCTGATCCCTCTGCCTCTGAGCCATGGGAACAGCCCAATAACTGAGTTAGACATAA
AAACGTCTCTAGCCAAAACTTCAGCTAAATTTAGACAATAAATCTTACTGGTTGTGGAATCCTTAAGATTCTTCATGACC
TCCTTCACATGGCACGAGTATGAAGCTTTATTACAATTGTTTATTGATCAAACTAACTCATAAAAAGCCAGTTGTCTTTC
ACCTGCTCAAGGAAGGAACAAAATTCATCCTTAACTGATCTGTGCACCTTGCACAATCCATACGAATATCTTAAGAGTAC
TAAGATTTTGGTTGTGAGAGTCACATGTTACAGAATGTACAGCTTTGACAAGGTGCATCCTTGGGATGCCGAAGTGACCT
GCTGTTCCAGCCCCTACCTTCTGAGGCGTGTTTTGGAAGCAATGCTCTGGAAGCAACTTTAGGAGGTAGGATGCTGGAAC
AGCGGGTCACTTCAGCATCCCGATGACGAATCCCGTCAAAGCTGTACATTCGTAACAGACTGGGAAAGCTGCAGACTTT
AAGGCCAGGGCCCTATGGTCCCTCTTAATCCCTGTCACACCCAACCCGAGCCCTTCTCCTCCAGCCGTTCTGTGCTTCTC
ACTCTGGATAGATGGAGAACACGGCCTTGCTAGTTAAAGGAGTGAGGCTTCACCCTTCTCACATGGCAGTGGTTGGTCAT
CCTCATTCAGGGAACTCTGGGGCATTCTGCCTTTACTTCCTCTTTTTGGACTACAGGGAATATATGCTGACTTGTTTTGA
CCTTGTGTATGGGGAGACTGGATCTTTGGTCTGGAATGTTTCCTGCTAGTTTTTCCCCATCCTTTGGCAAACCCTATCTA
TATCTTACCACTAGGCATAGTGGCCCTCGTTCTGGAGCCTGCCTTCAGGCTGGTTCTCGGGGACCATGTCCCTGGTTTCT
CCCCAGCATATGGTGTTCACAGTGTTCACTGCGGGTGGTTGCTGAACAAAGCGGGGATTGCATCCCAGAGCTCCGGTGCC
TTGTGGGTACACTGCTAAGATAAAATGGATACTGGCCTCTCTCTGACCACTTGCAGAGCTCTGGTGCCTTGTGGGTACAC
TGCTAAGATAAAATGGATACTGGCCTCTCTCTATCCACTTGCAGGACTCTAGGGAACAGGAATCCATTACTGAGAAAACC
AGGGGCTAGGAGCAGGGAGGTAGCTGGGCAGCTGAAGTGCTTGGCGACTAACCAATGAATACCAGAGTTTGGATCTCTAG
```

86

```
AATACTCTTAAAATCTGGGTGGGCAGAGTGGCCTGCCTGTAATCCCAGAACTCGGGAGGCGGAGACAGGGAATCATCAGA
GCAAACTGGCTAACCAGAATAGCAAAACACTGAGCTCTGGGCTCTGTGAGAGATCCTGCCTTAACATATAAGAGAGAGAA
TAAAACATTGAAGAAGACAGTAGATGCCAATTTTAAGCCCCCACATGCACATGGACAAGTGTGCGTTTGAACACACATAT
GCACTCATGTGAACCAGGCATGCACACTCGGGCTTATCACACACATAATTTGAAAGAGAGAGTGAGAGAGGAGAGTGCAC
ATTAGAGTTCACAGGAAAGTGTGAGTGAGCACACCCATGCACACAGACATGTGTGCCAGGGAGTAGGAAAGGAGCCTGGG
TTTGTGTATAAGAGGGAGCCATCATGTGTTTCTAAGGAGGGCGTGTGAAGGAGGCGTTGTGTGGGCTGGGACTGGAGCAT
GGTTGTAACTGAGCATGCTCCCTGTGGGAAACAGGAGGGTGGCCACCCTGCAGAGGGTCCCACTGTCCAGCGGGATCAGT
AAAAGCCCCTGCTGAGAACTTTAGGTAATAGCCAGAGAGAGAAAGGTAGGAAAGTGGGGGGACTCCCATCTCTGATGTAG
GAGGATCTGGGCAAGTAGAGGTGCGTTTGAGGTAGAAAGAGGGGTGCAGAGGAGATGCTCTTAATTCTGGGTCAGCAGTT
TCTTTCCAAATAATGCCTGTGAGGAGGTGTAGGTGGTGGCCATTCACTCACTCAGCAGAGGATGCTGATGATGCCCGGTGGA
TGCTGGAAATGGCCGAGCATCAACCCTGGCTCTGGAAGAACTCCATCTTTCAGAAGGAGAGTGGATCTGTGTATGGCCAG
CGGGGTCACAGGTGCTTGGGGCCCCTGGGGGACTCCTAGCACTGGGTGATGTTTATCGAGTGCTCTTGTGTGCCAGGCAC
TGGCCTGGGGCTTTGTTTCTGTCTCTGTTTTGTTTCGTTTTTTGAGACAGACTCTTGCTATGTATCCGTGTCAATCTTGG
AATCTCACTGCATAGCCCAGGCTGCGGAGAGAGGGGAGGGCAATAGGCCTTGTAAGCAAGCCACACTTCAGAGACTAGAC
TCCACCCTGCGAATGATGACAGGTCAGAGCTGAGTTCGGAAGATTTTTTTCCAGCTGCCAGGTGGAGTGTGGAGTGGC
AGCTAGCGGCAAGGGTAGAGGGCGAGCTCCCTGTGCAGGAGAAATGCAAGCAAGAGATGGCAAGCCAGTGAGTTAAGCAT
TCTGTGTGGGGAGCAGGTGGATGAAGAGAGAGGCTGGGCTTTCGCCTCTGGGGGGGGGTGAGGGGTGGGGATGAGGTGA
GAGGAGGGCAGCTCCCTGCAGTGTGATGAGATTTTCCTGACAGTGACCTTTGGCCTCTCCCTCCCCCACTTCCCTTCTT
TCCTTTCTTCCCACCATTGCTTTCCTTGTCCTTGAGAAATTCTGAGTTTCCACTTCACTGGTGATGCAGACGGAAACAGA
AGCCGTGTGTGTGTGTGTGTGTGTGTGTGTGTGTGTGTGTGTGTTTGTGTGTATGTGTGTGTGTGTTTGTGT
GTATGTGTGTCAGTGGGAATGGCTCATAGTCTGCAGGAAGGTGGGCAGGAAGGAATAAGCTGTAGGCTGAGGCAGTGTGG
GATGCAGGGAGAGAGGAGAGGAGGGATACCAGAGAAGGAAATTAAGGGAGCTACAAGAGGGCATTGTTGGGGTGTGTGTG
TGTGTGTGTTGTTTATATTTGTATTGGAAATACATTCTTTTAAAAAATACTTATCCATTTATTTATTTTTATGTGCACGT
GTGTGTGCCTGCATGAGTTCATGTGTGCCACGTGTGTGCGGGAACCCTTGGAGGCCACAAGGGGCATCTGATCCCCTGG
AACTGGAGTTGGAGGAGGTTTGTGAGTCCCCTGACATGTTTGCTGGGAACTGAACCCCGGTCCTATGCAAGAGCAGGAAGT
GCAGTTATCTGCTGAGCCATCTCTCCAGTCCTGAAATCCATTCTCTTAAAATACACGTGGCAGAGACATGATGGGATTTA
CGTATGGATTTAATGTGGCGGTCATTAAGTTCCGGCACAGGCAAGCACCTGTAAAGCCATCACCAACGCAACAGTGA
ATGTGACCATCACCCCCATGTTCTTCATGTCCCCTGTCCCCTCCATCCTCCATTCTCAAGCACCTCTTGCTCTGCCTCTG
TCGCTGGAGAACAGTGTGCATCTGCACACTCTTATGTACGTCAGTGAAGTCACACAGCCTGCACCCCTTCCTGGTCTGAGTATT
TGGGTTCTGACTCTGTATCACACACTACTGTACTGCATTCTCTCGCTCTCTTTTTTAAACATATTTTTATTTGTTTGT
GTGTATGCACATGTGCCACATGTGTACAGATACTATGGAGGCCAGAAGAGGCCATGGCCGTCCCTGGAGCTGGAGTTACA
GGCAGCGTGTGAGCTGCCTGGTGTGGGTGCTCGGAACCAAACTTGAATCTAAAGCAAGCACTTTTAACTGCTGAGGCAGC
TCTCAGTACCCTTCTTCATTTCTCCGCCTGGGTTCCATTGTATGGACACATGTAGCTAGCTAGAATATCTTGCTTATCTAATTA
TGTACATTGTTTTGTGCTAAGAGAGTAATGCTCTATAGCCTGAGCTGGCCTCAACCTTGCCATCCTCCTGCCTCAGCC
TCCTCCTCCTGAGTGCTAGGATGACAGGCGAGTGGTAACTTACATGGTTTCATGTTTTGTTCAAGACTGAAGGATAACAT
TCATACAGAGAAGGTCTGGGTCACAAAGTGTGCAGTTCACTGAATGGCACAACCCGTGATCAAGAAACAAAACTCAGGGG
CTGGAGAGATGGCACTGACTGCTCTTCCAGAGGTCCGGAGTTCAATTCCCAGCAACCACATGGTGGCTCACAGCCATCTA
TAACGAGATCTGACGCCCTCTTCTGGTGTGTCTGAAGACAGCTACAGTGTACTCACATAAAATAAATAAATCTTTAAAAC
ACACACACACACAATTACCACCCCAGAAAGCCCACTCCATGTTCCCTCCCACGTCTCTGCCTACAGTACTCCCAGGTT
ACCACTGTTCAGGCTTCTAACAACCTGGTTTACTTGGGCCTCTTTTCTGCTCTGTGGAGCCACACATTTGTGTGCCTCAT
ACACGTTCTTTCTAGTAAGTTGCATATTACTCTGCGTTTTTACATGTATTTATTGTAGTTGTGTGTGCGTGTGGGC
CCATGCATGGCACAGTGTGTGGGGATGTCAGAGTATTGTGAACAGGGGACAGTTCTTTTCTTCAATCATGTGGGTTCCAG
AGGTTGAACTCAGGTCATCATGTGTGGCAGCAAATGCCTTTACCCACTGAGACATCTCCATATTCTTTTTTTTTCCCCTG
AGGTGGGGCTTGTTCCATAGCCCAAACTGGCTTTGCACTTGCAGTTCAAAGTGACTCCCTGTCTCCACCTCTTAGAGTA
TTGGAATTACGATGTGTACTACCACACCTGACTGGATCATTAATTCTTTGATGGGGCGGGAAGCGCACATGCTGCAGG
TGAAGGGATGACTGGACTGGACATGAGCGTGGAAGCCAGAGAACAGCTTCAGTCTAATGCTCTCCCAACTGAGCTATTTC
GGTTTGCCAGAGAACAACTTACAGAAAGTTCTCAGTGCCATGTGGATTCGGGGTTGGAGTTCAACTCATCAGCTTGACAT
TGGCTCCTCTACCCACTGAGCCTTCTCACTACTCTCTACCTAGATCATTAATTCTTTTTTAAAAAGACTTATTAGGGGGC
TGGAGAGATGGCTCAGCCGTTAAGAGCACCGAATGCCCTTCCAGAGGTCCTGAGTTCAATTCCCAGCATGCCATTGCTGG
GCAGTAGGGGGCGCAGGTGTTCAACGTGAGTAGCTGTTGCCAGTTTTCCGCGGTGGAGAACCTCTTGACACCCTGCTGTC
CCTGGTCATTCTGGGTGGGTGCATGGTGATATGCTTGTTGTATGGAAGACTTTGACTGTTACAGTGAAGTTGGGCTTCCA
CAGTTACCACGTCTCCCCTGTTTCTTGCAGGCCGGGTGCTTGTCCATTGCCGCGAGGGCTACAGCCGCTCCCCAACGCTA
GTTATCGCCTACCTCATGATGCGGCAGAAGATGGACGTCAAGTCTGCTCTGAGTACTGTGAGGCAGAATCGTGAGATCGG
CCCCAACGATGGCTTCCTGGCCCAACTCTGCCAGCTCAATGACAGACTAGCCAAGGAGGGCAAGGTGAAACTCTAGGGTG
CCCACAGCCTCTTTTGCAGAGGTCTGACTGGGAGGGCCCTGGCAGCCATGTTTAGGAAACACAGTATACCCACTCCCTGC
ACCACCAGACACGTGCCCACATCTGTCCCACTCTGGTCCTCGGGGGCCACTCCACCCTTAGGGAGCACATGAAGAAGCTC
CCTAAGAAGTTCTGCTCCTTAGCCATCCTTTCCTGTAATTTATGTCTCTCCCTGAGGTGAGGTTCAGGTTTATGTCCCTG
TCTGTGGCATAGATACATCTCAGTGACCCAGGGTGGGAGGGCTATCAGGGTGCATGGCCCGGGACACGGGCACTCTTCAT
GACCCCTCCCCCACCTGGGTTCTTCCTGTGTGGTCCAGAACCACGAGCCTGGTAAAGGAACTATGCAAACACAGGCCCTG
ACCTCCCCATGTCTGTTCCTGGTCCTCACAGCCCGACACGCCCTGCTGAGGCAGACGAATGACATTAAGTTCTGAAGCAG
AGTGGAGATAGATTAGTGACTAGATTTCCAAAAAGAAGGAAAAAAAAAGGCTGCATTTTAAAATTATTTCCTTAGAATTAA
AGATACTACATAGGGGCCCTTGGGTAAGCAAATCCATTTTTCCCAGAGGCTATCTTGATTCTTTGGAATGTTTAAAGTGT
GCCTTGCCAGAGAGCTTACGATCTATATCTGCTGCTTCAGAGCCTTCCCTGAGGATGGCTCTGTTCCTTTGCTTGTTAGA
AGAGCGATGCCTTGGGCAGGGTTTCCCCCTTTTCAGAATACAGGGTGTAAAGTCCAGCCTATTACAAACAAACAAACAAA
CAAACAAACAAAGGACCTCCATTTGGAGAATTGCAAGGATTTTATCCTGAATTATAGTGTTGGTGAGTTCAAGTCATCAC
GCCAAGTGCTTGCCATCCTGGTTGCTATTCTAAGAATAATTAGGAGGAGGAACCTAGCCAATTGCAGCTCATGTCCGTGG
GTGTGTGCACGGGTGCATATGTTGGAAGGGGTGCCTGTCCCCTTGGGGACAGAAGGAAAATGAAAGCCCCTCTGCTCAC
CCTGGCCATTTACGGGAGGCTCTGCTGGTTCCACGGTGTCTGTGCAGGATCCTGAAACTGACTCGCTGGACAGAAACGAG
```

87

```
ACTTGGCGGCACCATGAGAATGGAGAGAGAGAGCAAAGAAAGAAACAGCCTTTAAAAGAACTTTCTAAGGGTGGTTTT
TGAACCTCGCTGGACCTTGTATGTGTGCACATTTGCCAGAGATTGAACATAATCCTCTTGGGACTTCACGTTCTCATTAT
TTGTATGTCTCCGGGGTCACGCAGAGCCGTCAGCCACCACCCCAGCACCCGGCACATAGGCGTCTCATAAAAGCCCATTT
TATGAGAACCAGAGCTGTTTGAGTACCCCGTGTATAGAGAGAGTTGTTGTCGTGGGGCACCCGGATCCCAGCAGCCTGGT
TGCCTGCCTGTAGGATGTCTTACAGGAGTTTGCAGAGAAACCTTCCTTGGAGGGAAAGAAATATCAGGGATTTTTGTTGA
ATATTTCAAATTCAGCTTTAAGTGTAAGACTCAGCAGTGTTCATGGTTAAGGTAAGGAACATGCCTTTTCCAGAGCTGCT
GCAAGAGGCAGGAGAAGCAGACCTGTCTTAGGATGTCACTCCCAGGGTAAAGACCTCTGATCACAGCAGGAGCAGAGCTG
TGCAGCCTGGATGGTCATTGTCCCCTATTCTGTGTGACCACAGCAACCCTGGTCACATAGGGCTGGTCATCCTTTTTTTT
TTTTTTTTTTTTTTTTTTGGCCCAGAATGAAGTGACCATAGCCAAGTTGTGTACCTCAGTCTTTAGTTTCCAAGCGGCT
CTCTTGCTCAATACAATGTGCATTTCAAAATAACACTGTAGAGTTGACAGAACTGGTTCATGTGTTATGAGAGAGGAAAA
GAGAGGAAAGAACAAAACAAAACAAAACACCACAAACCAAAAACATCTGGGCTAGCCAGGCATGATTGCAATGTCTACAG
GCCCAGTTCATGAGAGGCAGAGACAGGAAGACCGCCGAAAGGTCAAGGATAGCATGGTCTACGTATCGAGACTCCAGCCA
GGGCTACGGTCCCAAGATCCTAGGTTTTGGATTTTGGGCTTTGGTTTTTGAGACAGGGTTTCTCTGTGTAGCCCTGGCTG
TCCTGGAACTCGCTCTGTAGACCAGGCTGGCCTCAAACTTAGAGATCTGCCTGACTCTGCCTTTGAGGGCTGGGACGAAT
GCCACCACTGCCCAACTAAGATTCCATTAAAAAAAAAAAAAGTTCAAGATAATTAAGAGTTGCCAGCTCGTTAAAGCTAA
GTAGAAGCAGTCTCAGGCCTGCTGCTTGAGGCTGTTCTTGGCTTGGACCTGAAATCTGCCCCCAACAGTGTCCAAGTGCA
CATGACTTTGAGCCATCTCCAGAGAAGGAAGTGAAAATTGTGGCTCCCCAGTCGATTGGGACACAGTCTCTCTTTGTCTA
GGTAACACATGGTGACACATAGCATTGAACTCTCCACTCTGAGGGTGGGTTTCCCTCCCCCTGCCTCTTCTGGGTTGGTC
ACCCCATAGGACAGCCACAGGACAGTCACTAGCACCTACTGGAAACCTCTTTGTGGGAACATGAAGAAAGAGCCTTTGGG
AGATTCCTGGCTTTCCATTAGGGCTGAAAGTACAACGGTTCTTGGTTGGCTTTGCCTCGTGTTTATAAAACTAGCTACTA
TTCTTCAGGTAAAATACCGATGTTGTGGAAAAGCCAACCCCGTGGCTGCCCGTGAGTAGGGGGTGGGGTTGGGAATCCTG
GATAGTGTTCTATCCATGGAAAGTGGTGGAATAGGAATTAAGGGTGTTCCCCCCCCCCCCAACCTCTTCCTCAGACCCAG
CCACTTTCTATGACTTATAAACATCCAGGTAAAAATTACAAACATAAAATGGTTTCTCTTCTCAATCTTCTAAAGTCTG
CCTGCCTTTTCCAGGGGTAGGTCTGTTTCTTTGCTTCTATTGTCTTGAGAGCACAGACTAACACTTACCAAATGAGGG
AACTCTTGGCCCATACTAAGGCTCTTCTGGGCTCCAGCACTCTTAAGTTATTTTAAGAATTCTCACTTGGCCTTTAGCAC
ACCCGCCACCCCCAAGTGGGTGTGGATAATGCCATGGCCAGCAGGGGGCACTGTTGAGGCGGGTGCCTTTCCACCTTAAG
TTGCTTATAGTATTTAAGATGCTAAATGTTTTAATCAAGAGAAGCACTGATCTTATAATACGAGGATAAGAGATTTTCTC
ACAGGAAATTGTCTTTTTCATAATTCTTTTACAGGCTTTGTCCTGATCGTAGCATAGAGAGAATAGCTGGATATTTAACT
TGTATTCCATTTTCCTCTGCCAGCGTTAGGTTAACTCCGTAAAAAGTGATTCAGTCGACCGAAGAGGCTCAGAGGGCAGG
GGATGGTGGGGTGAGGCAGAGCACTGTCACCTGCCAGGCATGGGAGGTCCTGCCATCCGGGAGGAAAAGGAAAGTTTAGC
CTCTAGTCTACCACCAGTGTTAACGCACTCTAAAGTTGTAACCAAAATAAATGTCTTACATTACAAAGACGTCTGTTTTG
TGTTTCCTTTTGTGTGTTTGGGCTTTTTATGTGTGCTTTATAACTGCTGTGGTGGTGCTGTTGTTAGTTTTGAGGTAGGA
TCTCAGGCTGGCCTTGAACTTCTGATCGCCTGCCCCTGCCCCTGCCCCTGCCCCTGTCCCTGCCTCCAAGTGCTAGGACT
AAAAGCACATGCCACCACACCAGTACAGCATTTTTCTAACATTTAAAAATAATCACCTAGGGGCTGGAGAGAGGGTTCCA
GCTAAGAGTGCACACTGCTCTTGGGTAGGACCTGAGTTTAGTTCCCAGAACCTATACTGGGTGGCTCCAGGTCCAGAGGA
TCCAGGACCTCTGGCCTCCATGGGCATCTGCTCTTAGCACATACCCACATACAGATACACATAAAAATAAAATGAAGC
CTTTAAAAACCTCCTAAAACCTAGCCCTTGGAGGTACGACTCTGGAAAGCTGGCATACTGTGTAAGTCCATCTCATGGTG
TTCTGGCTAACGTAAGACTTACAGAGACAGAAAAGAACTCAGGGTGTGCTGGGGGTTGGGATGGAGGAAGAGGGATGAGT
AGGGGGAGCACGGGGAACTTGGGCAGTGAAAATTCTTTGCAGGACACTAGAGGAGGATAAATACCAGTCATTGCACCCAC
TACTGGACAACTCCAGGGAATTATGCTGGGTGAAAAGAGAAGGCCCCAGGTATTGGCTGCATTGGCTGCATTTGCGTAAC
ATTTTTTTAAATTGAAAAGAAAAAGATGTAAATCAAGGTTAGATGAGTGGTTGCTGTGAGCTGAGAGCTGGGGTGAGTGA
GACATGTGGACAACTCCATCAAAAAGCGACAGAAAGAACGGGCTGTGGTGACAGCTACCTCTAATCTCCACCTCCGGGAG
GTGATCAAGGTTAGCCCTCAGCTAGCCTGTGGTGCATGAGACCCTGTTTCAAAAACTTTAATAAAGAAATAATGAAAAAA
GACATCAGGGCAGATCCTTGGGGCCAAAGGCGGACAGGCGAGTCTCGTGGTAAGGTCGTGTAGAAGCGGATGCATGAGCA
CGTGCCGCAGGCATCATGAGAGAGCCCTAGGTAAGTAAGGATGGATGTGAGTGTGTCGGCGTCGGCGCACTGCACGTCCT
GGCTGTGGTGCTGGACTGGCATCTTTGGTGAGCTGTGGAGGGGAAATGGGTAGGGAGATCATAAAATCCCTCCGAATTAT
TTCAAGAACTGTCTATTACAATTATCTCAAAATATTAAAAAAAAGAAGAATTAAAAAACAAAAAACCTATCCAGGTGTG
GTGGTGTGCACCTATAGCCACGGGCACTTGGAAAGCTGGAGCAAGAGGATGGCGAGTTTGAAGGTATCTGGGCGTGTACA
GCAAGACCGTCGTCCCCAAACCAAACCAAACAGCAAACCCATTATGTCACACAAGAGTGTTTATAGTGAGCGGCCTCGCT
GAGAGCATGGGTGGGGTGGGGTGGGGACAGAAATATCTAAACTGCAGTCAATAGGGATCCACTGAGACCCTGGGGC
TTGACTGCAGCTTAACCTTGGGAAATGATAAGGGTTTTGTGTTGAGTAAAAGCATCGATTACTGACTTAACCTCAAATGA
AGAAAAAGAAAAAAAGAAAACAACAAAAGCCAAACCAAGGGGCTGGTGAGATGGCTCAGTGGGTAAGAGCACCCGACTGC
TCTTCCGAAGGTCCAGAGTTCAAATCCCAGCAACCACATGGTGGCTCACAACCATCTGTAACGAGATATGATGCCCTCTT
CTGGTGTGTCTGAAGCAGCTACAGTGTACTTACATATAATAAATAAATCTTAAAAAAAAAAAAAAAAAAAAAAGCCAAA
CCGAGCAAACCAGGCCCCCAAACAGAAGGCAGGCACGACGGCAGGCACCACGAGCCATCCTGTGAAAAGGCAGGGCTACC
CATGGGCCGAGGAGGGTCCAGAGAGATAGGCTGGTAAGCTCAGTTTCTCTGTATACCCTTTTTCTTGTTGACACTACTTC
AATTACAGATAAAATAACAAATAAACAAAATCTAGAGCCTGGCCACTCTCTGCTCGCTTGATTTTTCCTGTTACGTCCAG
CAGGTGGCGGAAGTGTTCCAAGGACAGATCGCATCATTAAGGTGGCCAGCATAATCTCCCATCAGCAGGTGGTGCTGTGA
GAACCATTATGGTGCTCACAGAATCCCGGGCCCAGGAGCTGCCCTCTCCCAAGTCTGGAGCAATAGGAAAGCTTTCTGGC
CCAGACAGGGTTAACAGTCCACATTCCAGAGCAGGGGAAAAGGAGACTGGAGGTCACAGACAAAAGGGCCAGCTTCTAAC
AACTTCACGACTCTGGTAGGAGAGATAGATCACCCCCAACAATGGCCACAGCTGGTTTTGTCTGCCCCGAAGGAAACTGA
CTTAGGAAGCAGGTATCAGAGTCCCCTTCCTGAGGGGACTTCTGTCTGCCTTGTAAAGCTGTCAGAGCAGCTGCATTGAT
GTGTGGGTGACAGAAGATGAAAAGGAGGACCCAGGCAGATCGCCACAGATGGACCGGCCACTTACAAGTCGAGGCAGGTG
GCAGAGCCTTGCAGAAGCTCTGCAGGTGGACGACACTGATTCATTACCCAGTTAGCATACCACAGCGGGCTAGGCGGACC
ACAGCCTCCTTCCCAGTCTTCCTCCAGGGGTCGGGAGTCCTCCAACCTTCTGTCTCAGTGCAGCTTCCGCCAGCCCCTCC
TCCTTTTGCACCTCAGGTGTGAACCCTCCCTCCTCTCCTTCTCCCTGTGGCATGGCCCTCCTGCTACTGCAGGCTGAGCA
TTGGATTTCTTTGTGCTTAGATAGACCTGAGATGGCTTTCTGATTTATATATATATATCCATCCCTTGGATCTTACATCT
AGGACCCAGAGCTGTTTGTGATACCATAAGGAGGCTGGGGAGATGATATGGTAAGAGTGCTTGCTGTACAAGCATGAAGAC
```

88

```
ATGAGTTCGAATCCCCAGCAACCATGTGGAAAAATAACCTTCTAACCTCAGAGTTGAGGGGAAAGGCAGGTGGATTCTGG
GGGCTTACTGGCCAGCTAGCCAGCCTAACCTAAATGTCTCAGTCAGAGATCCTGTCTCAGGGAATAACTTGGGAGAATGA
CTGAGAAAGACACCTCCTCAGGTCTCCCATGCACCCACACAGACACACGGGGGGGGGGTAATGTAATAAGCTAAGAAATA
ATGAGGGAAATGATTTTTTGCTAAGAAATGAAATTCTGTGTTGGCCGCAAGAAGCCTGGCCAGGGAAGGAACTGCCTTTG
GCACACCAGCCTATAAGTCACCATGAGTTCCCTGGCTAAGAATCACATGTAATGGAGCCCAGGTCCCTCTTGCCTGGTGG
TTGCCTCTCCCACTGGTTTTGAAGAGAAATTCAAGAGAGATCTCCTTGGTCAGAATTGTAGGTGCTGAGCAATGTGGAGC
TGGGGTCAATGGGATTCCTTTAAAGGCATCCTTCCCAGGGCTGGGTCATACTTCAATAGTAGGGTGCTTGCACAGCAAGC
GTGAGACCCTAGGTTAGAGTCCCCAGAATCTGCCCCCAACCCCCAAAAAGGCATCCTTCTGCCTCTGGGTGGGTGGGGG
GAGCAAACACCTTTAACTAAGACCATTAGCTGGCAGGGGTAACAAATGACCTTGGCTAGAGGAATTTGGTCAAGCTGGAT
TCCGCCTTCGTAGAAGCCCCACTTGTTTCCTTTGTTAAGCTGGCCCACAGTTTGTTTTGAGAATGCCTGAGGGGCCCAG
GGAGCCAGACAATTAAAAGCCAAGCTCATTTTGATATCTGAAAACCACAGCCTGACTGCCCTGCCCGTGGGAGGTACTGG
GAGAGCTGGCTGTGTCCCTGCCTCACCAACGCCCCCCCCCCCAACACACACTCCTCGGGTCACCTGGGAGGTGCCAGCAG
CAATTTGGAAGTTTACTGAGCTTGAGAAGTCTTGGGAGGGCTGACGCTAAGCACACCCCTTCTCCACCCCCCCCCACCCC
ACCCCCGTGAGGAGGAGGGTGAAGGAAACATGGGACCAGCCCTGCTCAGCCCGTCCTTATTGGCTGGCATGAGGCAGAGG
GGGCTTTAAAAAGGCAACCGTATCTAGGCTGGACACTGGAGCCTGTGCTACCGAGTGCCCTCCTCCACCTGGCAGCATGC
AGCCCTCACTAGCCCCGTGCCTCATCTGCCTACTTGTGCACGCTGCCTTCTGTGCTGTGGAGGGCCAGGGGTGGCAAGCC
TTCAGGAATGATGCCACAGAGGTCATCCCAGGGCTTGGAGAGTACCCCGAGCCTCCTCCTGAAGAACAACCAGACCATGAA
CCGGGCGGAGAATGGAGGCAGACCTCCCCACCATCCCTATGACGCCAAAGGTACGGGATGAAGAAGCACATTAGTGGGGG
GGGGGTCCTGGGAGGTGACTGGGGTGGTTTTAGCATCTTCTTCAGAGGTTTGTGTGGGTGGCTAGCCTCTGCTACATCA
GGGCAGGGACACATTTGCCTGGAAGAATACTAGCACAGCATTAGAACCTGGAGGGCAGCATTGGGGGGCTGGTAGAGAGC
ACCCAAGGCAGGGTGGAGGCTGAGGTCAGCCGAAGCTGGCATTAACACGGGCATGGTCCCCCATGGCTTGTATGATGGTCAGAGAATC
TCCTCCTAAGGATGAGGACACAGGTCAGATCTAGCTGCTGACCAGTGGGGAAGTGATATGGTGAGGCTGGATGCCAGATG
CCATCCATGGCTGTACTATATCCCACATGACCACCACATGAGGTAAAGAAGGCCCCAGCTTGAAGATGGAGAAACCGAGA
GGCTCCTGAGATAAAGTCACCTGGGAGTAAGAAGAGCTGAGACTGGAAGCTGGTTTGATCCAGATGCAAGGCAACCCTAG
ATTTGGGTTTGGGTGGGAACCTGAAGCCAGGAGGAATCCCTTTAGTTCCCCCTTGCCCAGGGTCTGCTCAATGAGCCCAGA
GGGTTAGCATTAAAAGAACAGGGTTTGTAGGTGGCATGTGACATGAGGGGCAGCTGAGTGAAATGTCCCCTGTATGAGCA
CAGGTGGCACCACTTGCCCTGAGCTTGCACCCTGACCCCAGCTTTGCCTCATTCCTGAGGACAGCAGAAACTGTGGAGGC
AGAGCCAGCACAGAGAGATGCCTGGGGTGGGGGTGGGGTATCACGCACGGAACTAGCAGCAATGAATGGGGTGGGGTGG
CAGCTGGAGGGACACTCCAGAGAAATGACCTTGCTGGTCACCATTTGTGTGGGAGGAGAGCTCATTTTCCAGCTTGCCAC
CACATGCTGTCCCTCCTGTCTCCTAGCCAGTAAGGGATGTGGAGGAAAGGGCCACCCCAAAGGAGCATGCAATGCAGTCA
CGTTTTTGCAGAGGAAGTGCTTGACCTAAGGGCACTATTCTTGGAAAAGCCCCAAAACTAGTCCTTCCCTGGGCAAACAGG
CCTCCCCCACATACCACCTCTGCAGGGGTGGAGTAAATTAAGCCAGCCACAGAAGGGTGGCAAGGCCTACACCTCCCCCCT
GTTGTGCCCCCCCCCCCCCCCGTGAAGGTGCATCCTGGCCTCTGCCCCTCTGGCTTTGGTACTGGGATTTTTTTTTTCCTT
TTATGTCATATTGATCCTGACACCATGGAACTTTTGGAGGTAGACAGGACCCACACATGGATTAGTTAAAAGCCTCCCAT
CCATCTAAGCTCATGGTAGGAGATAGAGCATGTCCAAGAGAGGAGGGCAGGCATCAGACCTAGAAGATATGGCTGGGCAT
CCAACCCAATCTCCTTCCCCGGAGAACAGACTCTAAGTCAGATCCAGCCACCCTTGAGTAACCAGCTCAAGGTACACAGA
ACAAGAGAGTCTGGTATACAGCAGGTGCTAAACAAATGCTTGTGGTAGCAAAAGCTATAGGTTTTGGGTCAGAACTCCGA
CCCAAGTCGCGAGTGAAGAGCGAAAGGCCCTCTACTCGCCACCGCCCCGCCCCCACCTGGGGTCCTATAACAGATCACTT
TCACCCTTGCGGGAGCCAGAGAGCCCTGGCATCCTAGGTAGCCCCCCCGCCCCCCCCCGCAAGCAGCCCAGCCCTGCC
TTTGGGGCAAGTTCTTTTCTCAGCCTGGACCTGTGATAATGAGGGGGTTGGACGCGCCGCCTTTGGTCGCTTTCAAGTCT
AATGAATTCTTATCCCTACCACCTGCCCTTCTACCCCGCTCCTCCACAGCAGCTGTCCTGATTTATTACCTTCAATTAAC
CTCCACTCCTTTCTCCATCTCCTGGGATACCGCCCCTGTCCCAGTGGCTGGTAAAGGAGCTTAGGAAGGACCAGAGCCAG
GTGTGGCTAGAGGCTACCAGGCAGGGCTGGGGATGAGGAGCTAAACTGGAAGAGTGTTTGGTTAGTAGGCACAAAGCCTT
GGGTGGGATCCCTAGTACCGGAGAAGTGGAGATGGGCGCTGAGAAGTTCAAGACCATCCATCCTTAACTACACAGCCAGT
TTGAGGCCAGCCTGGGCTACATAAAAAACCCAATCTCAAAAGCTGCCAATTCTGATTCTGTGCCACGTAGTGCCCGATGTA
ATAGTGGATGAAGTCGTTGAATCCTGGGGCAACCTATTTTACAGATGTGGGGAAAAGCAACTTTAAGTACCCTGCCCACA
GATCACAAAGAAAGTAAGTGACAGAGCTCCAGTGTTTCATCCCTGGGTTCCAAGGACAGGGAGAGAGAAGCCAGGGTGGG
ATCTCACTGCTCCCCGGTGCCTCCTTCCTATAATCCATACAGATTCGAAAGCGCAGGGCAGGTTTGGAAAAAGAGAGAAG
GGTGGAAGGAGCAGACCAGTCTGGCCTAGGCTGCAGCCCCTCACGCATCCCTCTCTCTCCGCAGATGTGTCCGAGTACAGCT
GCCGCGAGCTGCACTACACCCGCTTCCTGACAGACGGCCCATGCCGCAGCGCCAAGCCGGTCACCGAGTTGGTGTGCTCC
GGCCAGTGCGGCCCCGCGCGGCTGCTGCCCAACGCCATCGGGCGCGTGAAGTGGTGGCGCCCGAACGGACCGGATTTCCG
CTGCATCCCGGATCGCTACCGCGCGCAGCGGGTGCAGCTGCTGTGCCCCGGGGCGCGGCGCCGCGCTGCGCGCAAGGTGC
GTCTGGTGGCCTCGTGCAAGTGCAAGCGCCTCACCCGCTTCCACAACCAGTCGGAGCTCAAGGACTTCGGGCCGGAGACC
GCGCGGCCGCAGAAGGGTCGCAAGCGCGGCCCGGCGCCCGGGGAGCCAAAGCCAACCAGGCGGAGCTGGAACGCCTA
CTAGAGCGAGCCCGCGCCTATGCAGCCCCCGCGGATCCGATTCGTTTTCAGTGTAAAGCCTGCAGCCCAGGCCAGGGGT
GCCAAACTTTCCAGACCGTGTGGAGTTCCCAGCCCAGTAGAGACCGCAGGTCCTTCTGCCCGCTGCGGGGGATGGGGAGG
GGGTGGGGTTCCCGCGGGCCAGGAGAGGAAGCTTGAGTCCCAGACTCTGCCTAGCCCCGGGTGGGATGGGGGTCTTTCTA
CCCTCGCCGGACCTATACAGGACAAGGCAGTGTTTCCACCTTAAAGGGAAAGGGAGTGTGGAACGAAAGACCTGGGACTGG
TTATGGACGTACAGTAAGATCTACTCCTTCCACCCAAATGTAAAGCCTGCGTGGGCTAGATAGGGTTTCTGACCCTGACC
TGGCCACTGAGTGTGATGTTGGGCTACGTGGTTCTCTTTTGGTACGGTCTTCTTTGTAAAATAGGGACCGGAACTCTGCT
GAGATTCCAAGGATTGGGGTACCCCGTGTAGACTGGTGAGAGAGAGGAGAACAGGGGAGGGGTTAGGGGAGAGATTGTGG
TGGGCAACCGCCTAGAAGAAGCTGTTTGTTGGCTCCCAGCCTCGCCGCCTCAGAGGTTTGGCTTCCCCCACTCCTTCCTC
TCAAATCTGCCTTCAAATCCATATCTGGGATAGGGAAGGCCAGGGTCCGAGAGATGGTGGAAGGGCAGAAATCACACTC
CTGGCCCCCGAAGAGCAGTGTCCCGCCCCCAACTGCCTTGTCATATTGTAAAGGGATTTTCTACACAACAGTTTAAGGT
CGTTGGAGGAAACTGGGCTTGCCAGTCACCTCCCATCCTTGTCCCTTGCCAGGACACCACCTCCTGCCTGCCACCCACGG
ACACATTTCTGTCTAGAAACAGAGCGTCGTCGTCGTGTCCTCTGAGACAGCATATCTTACATTAAAAAGAATAATACGGG
GGGGGGGGGCGGAGGGCGCAAGTGTTATACATATGCTGAGAAGCTGTCAGGCGCCACAGCACCACCCACAATCTTTTTGT
AAATCATTTCCAGACACCTCTTACTTTCTGTGTAGATTTTAATTGTTAAAAGGGGAGGAGAGAGAGCGTTTGTAACAGAA
```

89

```
GCACATGGAGGGGGGGGTAGGGGGGTTGGGGCTGGTGAGTTTGGCGAACTTTCCATGTGAGACTCATCCACAAAGACTGA
AAGCCGCGTTTTTTTTTTAAGAGTTCAGTGACATATTTATTTTCTCATTTAAGTTATTTATGCCAACATTTTTTTCTTG
TAGAGAAAGGCAGTGTTAATATCGCTTTGTGAAGCACAAGTGTGTGTGGTTTTTTGTTTTTTGTTTTTTCCCCGACCAGA
GGCATTGTTAATAAAGACAATGAATCTCGAGCAGGAGGCTGTGTGGTCTTGTTTTGTCAACCACACACAATGTCTCGCCACT
GTCATCTCACTCCCTTCCCTTGGTCACAAGACCCAAACCTTGACAACACCTCCGACTGCTCTCTGGTAGCCCTTGTGGCA
ATACGTGTTTCCTTTGAAAAGTCACATTCATCCTTTCCTTTGCAAACCTGGCTCTCATTCCCCAGCTGGGTCATCGTCAT
ACCCTCACCCCAGCCTCCCTTTAGCTGACCACTCTCCACACTGTCTTCCAAAAGTGCACGTTTCACCGAGCCAGTTCCCT
GGTCCAGGTCATCCCATTGCTCCTCCTTGCTCCAGACCCTTCTCCCACAAAGATGTTCATCTCCCACTCCATCAAGCCCC
AGTGGCCCTGCGGCTATCCCTGTCTCTTCAGTTAGCTGAATCTACTTGCTGACACCACATGAATTCCTTCCCCTGTCTTA
AGGTTCATGGAACTCTTGCCTGCCCCTGAACCTTCCAGGACTGTCCCAGCGTCTGATGTGTCCTCTCTCTTGTAAAGCCC
CACCCCACTATTTGATTCCCAATTCTAGATCTTCCCTTGTTCATTCCTTCACGGGATAGTGTCTCATCTGGCCAAGTCCT
GCTTGATATTGGGATAAATGCAAAGCCAAGTACAATTGAGGACCAGTTCATCATTGGGCAAGCTTTTTCAAAATGTGAA
TTTTACACCCTATAGAAGTGTAAAAGCCTTCCAAAGCAGAGGCAATGCCTGGCTCTTCCTTCAACATCAGGGCTCCTGCTT
TATGGGTCTGGTGGGGTAGTACATTCATAAACCCAACACTAGGGGTGTGAAAGCAAGATGATTGGGAGTTCGAGGCCAAT
CTTGGCTATGAGGCCCTGTCTCAACCTCTCCTCCCCTCCCTCCAGGGGTTTGTTTTGTTTTTGTTTTTTTGATTTGAAACTG
CAACACTTTAAATCCAGTCAAGTGCATCTTTGCGTGAGGGGAACTCTATCCCTAATATAAGCTTCCATCTTGATTTGTGT
ATGTGCACACTGGGGGTTGAACCTGGGCCTTTGTACCTGCCGGGCAAGCTCTCTACTGCTCTAAACCCAGCCCTCACTGG
CTTTCTGTTTCAACTCCCAATGAATTCCCCTAAATGAATTATCAATATCATGTCTTTGAAAAATACCATTGAGTGCTGCT
GGTGTCCCTGTGGTTCCAGATTCCAGGAAGGACTTTTCAGGGAATCCAGGCATCCTGAAGAATGTCTTAGAGCAGGAGGC
CATGGAGACCTTGGCCAGCCCCACAAGGCAGTGTGGTGCAGAGGGTGAGGATGGAGGCAGGCTTGCAATTGAAGCTGAGA
CAGGGTACTCAGGATTAAAAAGCTTCCCCCAAAACAATTCCAAGATCAGTTCCTGGTACTTGCACCTGTTCAGCTATGCA
GAGCCCAGTGGGCATAGGTGAAGACACCGGTTGTACTGTCATGTACTAACTGTGCTTCAGAGCCGGCAGAGACAAATAAT
GTTATGGTGACCCCAGGGGACAGTGATTCCAGAAGGAACACAGAAGAGAGTGCTGCTAGAGGCTGCCTGAAGGAGAAGGG
GTCCCAGACTCTCTAAGCAAAGACTCCACTCACATAAAGACACAGGCTGAGCAGAGCTGGCCGTGGATGCAGGGAGCCCA
TCCACCATCCTTTAGCATGCCCTTGTATTCCCATCACATGCCAGGGATGAGGGGCATCAGAGAGTCCAAGTGATGCCCAA
ACCCAAACACACCTAGGACTTGCTTTCTGGGACAGACAGATGCAGGAGAGACTAGGTTGGGCTGTGATCCCATTACCACA
AAGAGGGAAAAAACAAAAAACAAACAAACAAACAAAAAAAAACAAAACAAACAAAAAAAACCCAAGGTCCAAATTGTA
GGTCAGGTTAGAGTTTATTTATGGAAAGTTTATATTCTACCTCCATGGGGTCTACAAGGCTGGCGCCCATCAGAAAGAACA
AACAACAGGCTGATCTGGGAGGGGTGGTACTCTATGGCAGGGAGCACGTGTGCTTGGGGTACAGCCAGACACGGGCTTG
TATTAATCACAGGGCTTGTATTAATAGGCTGAGAGTCAAGCAGACAGAGAGACAGAAGGAAACACACACACACACACACA
CACACACACACACACACACATGCACACACCACTCACTTCTCACTCGAAGAGCCCCTACTTACATTCTAAGAACAAACC
ATTCCTCCTCATAAAGGAGACAAAGTTGCAGAAACCCAAAAGAGCCACAGGGTCCCCACTCTCTTTGAAATGACTTGGAC
TTGTTGCAGGGAAGACAGAGGGGTCTGCAGAGGCTTCCTGGGTGACCCAGAGCCACAGACACTGAAATCTGGTGCTGAGA
CCTGTATAAACCCTCTTCCACAGGTTCCCTGAAAGGGAGCCCACATTCCCCAACCCTGTCTCCTGACCACTGAGGATGAGA
GCACTTGGGCCTTCCCCATTCTTGGAGTGCACCCTGGTTTCCCCATCTGAGGGCACATGAGGTCTCAGGTCTTGGGAAAG
TTCCACAAGTATTGAAAGTGTTCTTGTTTTGTTTGTGATTTAATTTAGGTGTATGAGTGCTTTTGCTTGAATATATGCCT
GTGTAGCATTTACAAGCCTGGTGCCTGAGGAGATCAGAAGATGGCATCAGATACCCTGGAACTGGACTTGCAGACAGTTA
TGAGCCACTGTGTGGGTGCTAGGAACAGAACCTGGATCCTCCGGAAGAGCAGACAGCCAGCGCTCTTAGCCACTAAGCCA
TCACTGAGGTTCTTTCTGTGGCTAAAGACACAGGAGACAAAGGAGAGTTTCTTTTAGTCAATAGGACCATGAATGTTCCT
CGTAACGTGAGACTAGGGCAGGGTGATCCCCCAGTGACACCGATGGCCCTGTGTAGTTATTAGCAGCTCTAGTCTTATTC
CTTAATAAGCTCCCAGTTTGGGGCAGGAGATATGTATTCCCTGCTTTGAAGTGGCTGAGGTCCAGTTATCTACTTCCAAGT
ACTTGTTTCTCTTTCTGGAGTTGGGGAAGCTCCCTGCCTGCCTGTAAATGTGTCCATTCTTCAACCTTAGACAAGATCAC
TTTCCCTGAGCAGTCAGGCCAGTCCAAAGCCCTTCAATTTAGCTTTCATAAGGAACACCCCTTTTGTTGGGTGGAGGTAG
CACTTGCCTTGAATCCCAGCATTAAGAAGGCAGAGACAGTCGGATCTCTGTGAGTTCACAGCCAGCCTGGTCTACGGAGT
GAGTTCCAAGACAGCCAGGCCTACACAGAGAAACCCTGTCTCGAAAAAAACAAAAACAAAAGAAATAAAGAAAAAGAAAA
CAAAAACGAACAAACAGAAAAAACAAGCCAGAGTGTTTGTCCCCGTATTTTATTAATCATATTTTTGTCCCTTTGCCATTT
TAGACTAAAAGACTCGGGAAAGCAGGTCTCTCTCTGTTTCTCATCCGGACACACCCAGAACCAGATGTATGGAAGATGGC
TAATGTGCTGCAGTTGCACATCTGGGGCTGGGTGGGTGATTGGTTAGATGGCATGGGCTGGGTGGGTGGTTACGATGACTGCAGG
AGCAAGGAGTATGTGGTGCATAGCAAACGAGGGAAGTTTGCACAGAACAACACTGTGTGTACTGATGTGCAGGTATGGGCA
CATGCAAGCAGAAGCCAAGGGACAGCCTTAGGGTAGTGTTTCCACAGACCCCTCCCCCCTTTTAACATGGGCATCTCTCA
TTGGCCTGGAGCTTGCCAACTGGGCTGGGCTGGCTAGCTTGTAGGTCCCAGGGATCTGCATATCTCTGCCTCCCCTAGTGC
TGGGATTACAGTCATATATGAGCACACCTGGCTTTTTTATGTGGGTTCTGGGCTTTGAACCCAGATCTGAGTGCTTGCAA
GGCAATCGGTTGAATGACTGCTTCATCTCCCCAGACCCTGGGATTCTACTTTCTATTAAAGTATTTCTATTAAATCAATG
AGCCCCTGCCCCTGCACTCAGCAGTTCTTAGGCCTGCTGAGAGTCAAGTGGGGAGTGAGAGCAAGCCTCGAGACCCCATC
AGCGAAGCAGAGGACAAAGAAATGAAAACTTGGGATTCGAGGCTCGGGATATGGAGATACAGAAAGGGTCAGGGAAGGAA
ATGAACCAGATGAATAGAGGCAGGAAGGGTAGGGCCCTGCATACATGGAACCTGGTGTACATGTTATCTGCATGGGGTTT
GCATTGCAATGGCTCTTCAGCAGGTTCACCACACTGGGAAACAGAAGCCAAAAAGAAGAGTAGGTGGTGTTGGAGTCAGA
TACTGTCAGTCATGCCTGAAGAAATGGAAGCAATTAACGATGCGCCGCAATTAGGATATTAGCTCCCTGAAGAAAGGCAA
GAAGCTGGGCTGTGGGCACTGAAGGGAGCTTTGAATGATGTCACATTCTCTGTATGCCTAGCAGGGCAGTATTGGAGACT
GAGACTTGACTTGTGTGTCCATATGATTCCTCCTTTTCCTACAGTCATCTGGGGCTCCTGAGCTTCGTCCTTGTCCAAGA
ACCTGGAGCTGGCAGTGGGCAGCTGCAGTGATAGATGTCTGCAAGAAAGATCTGAAAAGAGGGAGGAAGATGAAGGACCC
AGAGGACCACCGACCTCTGCTGCCTGACAAAGCTGCAGGACCAGTCTCTCCTACAGATGGGAGACAGAGGCGAGAGATGA
ATGGTCAGGGGAGGAGTCAGAGAAAGGAGAGGGTGAGGCAGAGACCAAAGGAGGGAAACACTTGTGCTCTACAGCTACTG
ACTGAGTACCAGCTGCGTGGCAGACAGCCAATGCCAAGGCTCGGCTGATCATGGCACCTCGTGGGACTCCTAGCCCAGTG
CTGGCAGAGGGGAGTGCTGAATGGTGCATGGTTTGGATATGATCTGAATGTGGTCCAGCCCTAGTTTCCTTCCAGTTGCT
GGGATAAAGCACCCTGACCAAAGCTACTTTTTTGTTTGTTTGGTTTGGTTTTTTGTTTGGTTTTTCGAGGCAGGGTT
TCTCTGTATCACCCTAGCTGTCCTGGAACTCACTCTGTAGACCAGGCTGGCCTCGAACTCAGAAATCCCCCTGCCTCTGC
CTCCTAAGTGCTGGAATTAAAGGCCTGCGCCACCACTGCCGGCCCAAAGCTACTTTAAGAGAGAGAGAGGAATGTATAAG
```

90

```
     TATTATAATTCCAGGTTATAGTTCATTGCTGTAGAATTGGAGTCTTCATATTCCAGGTAATCTCCCACAGACATGCCACA
     AAACAACCTGTTCTACGAAATCTCTCATGGACTCCCTTCCCCAGTAATTCTAAACTGTGTCAAATCTACAAGAAATAGTG
     ACAGTCACAGTCTCTAACGTTTTGGGCATGAGTCTGAAGTCTCATTGCTAAGTACTGGGAAGATGAAAACTTTACCTAGT
     GTCAGCATTTGGAGCAGAGCCTTTGGGATTTGAGATGGTCTTTTGCAGAGCTCCTAATGGCTACATGGAGAGGGGGCC
 5   TGGGAGAGACCCATACACCTTTTGCTGCCTTATGTCACCTGACCTGCTCCTTGGGAAGCTCTAGCAAGAAGGCCTTCCCT
     GGATCACCCACCCACCTTGCACCTCCAGAACTCAGAGCCAAATTAAACTTTCTTGTTACTGTCGTCAAAGCACAGTCGGTC
     TGGGTTGTATCACTGTCAATGGGAAACAGACTTGCCTGGATGGATAACTTGTACATTGCATAATGTCTAGAAATGAAAAG
     TCCTATAGAGAAAAAGAAAATTAGCTGGCACACAGATAGAGGCCCTGGAGGAGGCTGGCTTTGTCCTCCCCGAGGAGGTG
     GCGAGTAAGGTGTAAATGTTCATGGATGTAAATGGGCCCATATATGAGGGTCTGGGGTAACAAGAAGGCCTGTGAATATA
10   AAGCACTGAAGGTATGTCTAGTCTGGAGAAGGTCACTACAGAGAGTTCTCCAACTCAGTGCCCATACACACACACACACA
     CACACACACACACACACACACACACACACACCACAAAGAAAAAAAGGAAGAAAAATCTGAGAGCAAGTACAGTACTTAAA
     ATTGTGTGATTGTGTGTGACTCTGATGTCACATGCTCATCTTGCCCTATGAGTTGAAAACCAAATGGCCCCTGAGAGG
     CATAACAACCACACTGTTGGCTGTGTGCTCACGTTTTTCTTAAAGCGTCTGTCTGGTTTGCTGCTAGCATCAGGCAGACT
     TGCAGCAGACATACATATGCTCAGCCCTGAAGTCCTTCTAGGGTGCATGTCTCTTCAGAATTTCAGAAAGTCATCTGTGGC
15   TCCAGGACCGCCTGCACTCTCCCTCTGCCGCGAGGCTGCAGACTCTAGGCTGGGGTGGAAGCAACGCTTACCTCTGGGAC
     AAGTATAACATGTTGGCTTTTCTTTCCCTCTGTGGCTCCAACCTGGACATAAAATAGATGCAAGCTGTGTAATAAATATT
     TCCTCCCGTCCACTTAGTTCTCAACAATAACTACTCTGAGAGCACTTATTAATAGGTGGCTTAGACATAAGCATTCTTTTAAAAA
     ATTCCCCCACTAGCTCTTACTTCTTTAACTCTTTCAAACCATTCTGTGTCTTCCACATGGTTAGTTACCTCTCCTTCCAT
     CCTGGTTCGCTTCTTCCTTCGAGTCGCCCTCAGTGTCTCTAGGTGATGCTTGTAAGATATTCTTTCTACAAAGCTGAGAG
20   TGGTGGCACTCTGGGAGTTCAAAGCCAGCCTGATCTACACAGCAAGCTCCAGGATATCCAGGGCAATGTTGGGAAAACCT
     TTCTCAAACAAAAAGAGGGGTTCAGTTGTCAGGAGGAGACCCATGGGTTAAGAAGTCTAGACGAGCCATGGTGATGCATA
     CCTTTCATCCAAGCACTTAGGAGGCAAAGAAAGGTGAAACTCTTTGACTTTGAGGCCAGCTAGGTTACATAGTGATACCC
     TGCTTAGTGTGTGTGTGTGTGTGTGTGTGTGTGTGTGTAATTTAAAAGTCTAAAAATGCATTCTTTTAAAAA
     TATGTATAAGTATTTGCCTGCACATATGTATGTATGTATGTATACCATGTGTGTGTCTGGTGCTGAAGGACTAGGCATAG
25   ACTCCCTAGAACTAGAGTCATAGACAGTTGTGACACTCCCCAACCCCCCACCATGTGGGTGCTTGAAGCTAAACTCCTGT
     CCTTTGTAAAGCAGCAGGTGTCTATGAACCCTGAACCATCTCTCCAGTCTCCAGATGTGCATTCTCAAAGAGGAGTCCTT
     CATATTTCCCTAAACTGAACATCCTTATCAGTGAGCATCCTCGAGTCACCAAAGCTACTGCAAACCCTCTTAGGGAACAT
     TCACTATTCACTTCTACTTGGCTCATGAAACTTAAGTACACACACACAAACACACACACACACACACAGAGTCATGCACTCA
     CAAAAGCATGCATGTACACCATTCTTATTAGACTATGCTTTGCTAAAAGACTTTCCTAGATACTTTAAAACATCACTTCT
30   GCCTTTTGGTGGGCAGGTTCCAAGATTGGTACTGGCGTACTGGAAACTGAACAAGGTAGAGATCTAGAAATCACAGCAGG
     TCAGAAGGGCCAGCCTGTACAAGAGAGTTCCACACCTTCCAGGAACACTGAGCAGGGGGCTGGGACCTTGCCTCTCAG
     CCCAAGAAACTAGTGCGTTCCTGTATGCATGCCTCTCAGAGATTCCATAAGATCTGCCTTCTGCCATAAGATCTCCTGC
     ATCCAGACAAGCCTAGGGGAAGTTGAGAGGCTGCCTGAGTCTCTCCCACAGGCCCCTTCTTGCCTGGCAGTATTTTTTTA
     TCTGGAGGAGGAATCAGGGTGGGAATGATCAAATACAATTATCAAGGAAAAAGTAAAAAACATATATATATATATATT
35   AACTGATCTAGGGAGCTGGCTCAGCAGTTAAGAGTTCTGGCTGCCCTTGCTTCAGATCTTGCTTTGATTCCCAGCACCCA
     CATGATGGCTTTCAACTGTATCTCTGCTTCCAGGGGATCCAACAGCCTCTTCTGACCTTCCATAGACAAGACCTAGTCCTC
     TGCAAGAGCACCAAATGCTCTTATCTGTTGATCCATCTCTAGCCTCATGCCAGATCATTTAAAACTACTGGACACTGT
     CCCATTTTACGAAGATGTCACTGCCCAGTCATTTGCCATGAGTGGATATTTCGATTCTTTCTATGTTCTCACCCTTGCAA
     TTTTATAAGAAAGATATCTGCATTTGTCTCCTGAGAGAACAAAGGGTGGAGGGCTACTGAGATGGCTCTAGGGGTAAAGGT
40   GCTTGCCACAAAATCTGACAACTTAAGTTTGGTCTTGGAATCCACATGGTGGAGAGAGAGGAAGAGATTCCCGTAAGTTGT
     CCTCAAACTTCCCACACATGTGCTGTGGCTTATGTGTAACCCCAATAAGTAAAGATAGTTTTAAACACTACATAAGGTAG
     GGTTTCTTCATGACCCCAAGGAATGATGCCCCTGATAGAGCTTATGCTGAAACCCCATCTCCATTGTGCCATCTGGAAAG
     AGACAATTGCATCCCGGAAACAGAATCTTCATGAATGGATTAATGAGCTATTAAGAAAGTGGCTTGGTTATTGCACATGC
     TGGCGGCGTAATGACCTCCACCATGATGTTATCCAGCATGAAGGTCCTCACCAGAAGTCATACAAATCTTCTTAGGCTTC
45   CAGAGTCGTGAGCAAAAAAAGCACACCTCTAAATAAATTCTAGCCTCAGGTAGTTAACCACCGAAAATGAACCAAGGC
     AGTTCTAATACAAAACCACTTCCCTTCCCTGTTCAAACCACAGTGCCCTATTATCTAAAAGATAAACTTCAAGCCAAGCT
     TTTAGGTTGCCAGTATTTATGTAACAACAAGGCCCGTTGACACACATCTGTAACTCCTAGTACTGGGCCTCAGGGGCAGA
     GACAGGTGGAGCCCTGGAGTTTGAATTCCAGGTTCTGTGAGAAACTCTGTCTGAAAAGACAATATGGTGAGTGACCCGGG
     AGGATATCTGATATTGACTTCTGGCCAACACACAGCCATCTCTGCACATCTGTAGTTGCAAGCCTTTTGCACTAAGTTTG
50   GCCAGAGTCAGAGTTTGCAAGTGTTTGTGGACTGAATGCACGTGTTGCTGGTGATCTACAAAGTCACCCTCCTTCTCAAG
     CTAGCAGCACTGGCTTCGGCCAGCTGCTCATTCAAGCCTCTTTGCAGAGTCATCACGGGGATGGGGGAGCAGGGCCCCTC
     CCTAGAACACCAAGCCTGTGGTTGTTTATTCAGGACATTATTGAGGGCAAGATGACAGATAACTCTATCACTTGGCCAA
     CAGTCGGGTGTTGCGGTGTTAGGTTATTTCTGTGTCTGCAGAAAAACAGTGCAACCTGGACAAAAGAAATAAATGATATCA
     TTTTTCATTCAGGCAACTAGATTCCGTGGTACAAAAGGCTCCCTGGGGAACGAGGCCGGGACAGCGCGGCTCCTGAGTCG
55   CTATTTCCGTCTGTCAACTTCTCTAATCTCTTGATTTCCTCCCTCTGTCTGTTTCCTTCCTCTTGCTGGGGCCCAGTGGA
     GTCTGTGTACTCACAGGGAGGAGGGTGGCAAAGCCCTGGTCCTCTACGGGCTGGGGAAGGGGGGAAGCTGTCGGCCCAG
     TGACTTTTTCCCCTTTCTCTTTTTCTTAGAAACCAGTCTCAATTTAAGATAATGAGTCTCCTCATTCACGTGTGCTCACT
     ATTCATAGGGACTTATCCACCCCCGCCCTGTCAATCTGGCTAAGTAAGACAAGTCAAATTTAAAAGGGAACGTTTTCTA
     AAAATGTGGCTGGACCGTGTGCCGGCACGAAACCAGGGATGGCGGTCTAAGTTACATGCTCTGCCAGCCCCGGTGCCT
60   TTTCCTTTCGGAAAGGAGACCCGGAGGTAAAACGAAGTTGCCAACTTTTGATGATGGTGTGCGCCGGGTGACTCTTTAAA
     ATGTCATCCATACCTGGGATAGGGAAGGCTCTTCAGGGAGTCATCTAGCCCTCCCTTCAGGAAAAGATTCCACTTCCGGT
     TTAGTTAGCTTCCACCTGGTCCCTTATCCGCTGTCTCTGCCCACTAGTCCTCATCCATCCGGTTTCCGCCCTCATCCACC
     TTGCCCTTTTAGTTCCTAGAAAGCAGCACCGTAGTCTTGGCAGGTGGGCCATTGGTCACTCCGCTACCACTGTTACCATG
     GCCACCAAGGTGTCATTTAAATATGAGCTCACTGAGTCCTGCGGGATGGCTTGGTTGGTAATATGCTTGCTGCAAAATCG
65   TGAGAACTGGAGTTCAATTCCCAGCACATGGATGTATTTCCAGCACCTGGAAGGCAGGGAGCAGAGATCTTAAAGCTCCT
     GGCCAGACAGCCCAGCCTAATTAGTAATCAGTGAGAGACCCTGTCTCAAGAAACAAGATGGAACATCAAAGGTCAACCTC
     TTGTCTCCACACACACAAATACACACATGCACATACATCCACACACAGGCAAACACATGCACACACCTGAACACCCTCCA
     CAAATACATACATAAAAAAATAAATACATACACACATACATACATACACCAACATTCCCTCTCCTTAGTCTCCTGGCTAC
```

91

```
GCTCTTGTCACCCCCACTAAGGCTTCAACTTCTTCTATTTCTTCATCTTGACTCCTCTGTACTTTGCATGCCTTTTCCAG
CAAAGGCTTTTCTTTAAATCTCCGTCATTCATAAACTCCCTCTAAATTTCTTCCCCTGCCCTTTTCTTTCTCTCTAGGGA
GATAAAGACACACACTACAAAGTCACCGTGGGACCAGTTTATTCACCCACCCACCCCTGCTTCTGTTCATCCGGCCAGCT
AAGTAGTCCAACCTCTCTGGTGCTGTACCCTGGACCCTGGCTTCACCACAGCTCCTCCATGCTACCCAGCCCTGCAAACC
TTCAGCCTAGCCTCTGGTTCTCCAACCAGCACAGGCCCAGTCTGGCTTCTATGTCCTAGAAATCTCCTTCATTCTCTCCA
TTTCCCTCCTGAATCTACCACCTTCTTTCTCCCTTCTCCTGACCTCTAATGTCTTGGTCAAACGATTACAAGGAAGCCAA
TGAAATTAGCAGTTTGGGGTACCTCAGAGTCAGCAGGGGAGCTGGGATGAATTCACATTTCCAGGCCTTTGCTTTGCTCC
CCGGATTCTGACAGGCAGTTCCGAAGCTGAGTCCAGGAAGCTGAATTTAAAATCACACTCCAGCTGGGTTCTGAGGCAGC
CCTACCACATCAGCTGGCCCTGACTGAGCTGTGTCTGGGTGGCAGTGGTGCTGGTGGTGCTGGTGGTGCTGGTGGTGGTG
GTGGTGGTGGTGGTGGTGGTGGTGTGTGTGTGTTTTCTGCTTTTACAAAACTTTTCTAATTCTTATACAAAG
GACAAATCTGCCTCATATAGGCAGAAAGATGACTTATGCCTATATAAGATATAAAGATGACTTTATGCCACTTATTAGCA
ATAGTTACTGTCAAAAGTAATTCTATTTATACACCCTTATACATGGTATTGCTTTTGTTGGAGACTCTAAAATCCAGATT
ATGTATTTAAAAAAAAATTCCCCAGTCCTTAAAAGGTGAAGAATGGACCCAGATAGAAGGTCACGGCACAAGTATGGAGT
CGGAGTGTGGAGTCCTGCCAATGGTCTGGACAGAAGCATCCAGAGAGGGTCCAAGACAAATGCCTCGCCTCCTAAGGAAC
ACTGGCAGCCCTGATGAGGTACCAGAGATTGCTAAGTGGAGGAATACAGGATCAGACCCATGGAGGGGCTTAAAGCGTGA
CTGTAGCAGCCCTCCGCTGAGGGGCTCCAGGTGGGCGCCCAAGGTGCTGCAGTGGGAGCCACATGAGAGGTGATGTCTTG
GAGTCACCTCGGGTACCATTGTTTAGGGAGGTGGGGATTTGTGGTGTGGAGACAGGCAGCCTCAAGGATGCTTTTCAACA
ATGGTTGATGAGTTGGAACTAAAACAGGGGCCATCACACTGGCTCCCATAGCTCTGGGCTTGCCAGCTTCCACATCTGCC
CCCCACCCCCTGTCTGGCACCAGCTCAAGCTCTGTGATTCTACACATCCAAAAGAGGAAGAGTAGCCTACTGGGCATGCC
ACCTCTTCTGGACCATCAGGTGAGAGTGTGGCAAGCCCTAGGCTCCTGTCCAGGATGCAGGGCTGCCAGATAGGATGCTC
AGCTATCTCCTGAGCTGGAACTATTTTAGGAATAAGGATTATGCCCGCCCGGGGTTGGCCAGCACCCCAGCAGCCTGTGC
TTGCGTAAAAGCAAGTGCTGTTGATTTATCTAAAAACAGAGCCGTGGACCCACCCACAGGACAAGTATGTATGCATCTGT
TTCATGTATCTGAAAAGCGACACAACCATTTTTCACATCATGGCATCTTCCTAACCCCCATTCTTTTTTGTTTTGTTTTT
TTGAGACAGGGTTTCTCTGTGTAGTCCTGGCTGTCCTGGAACTCACTTTGTAGACCAGGCTGGCCTCGAACTCAGAAATC
CTGGGATTAAAGGTGTGTGCCACCACGCCCGGCCCTAACCCCCATTCTTAATGGTGATCCAGTGGTTGAAATTTCGGGCC
ACACACATGTCCATTAGGGATTAGCTGCTGTCTTCTGAGCTACCTGGTACAATCTTTATCCCCTGGGGCCTGGGCTCCTG
ATCCCTGACTCGGGCCCGATCAAGTCCAGTTCCTGGGCCCGATCAAGTCCAGTTCCTGGGCCCGAACAAGTCCAGTCCCT
AGCTCGATTAGCTCATCCTGGCTCCCTGGCCTGTTCTTACTTACACTCTTCCCCTTGCTCTGGACTTGTTGCTTTCTTTA
CTCAAGTTGTCTGCCACAGTCCCTAAGCCACCTCTGTAAGACAACTAAGATAATACTTCCCTCAAGCACGGAAAGTCCTG
AGTCACCACACCCTCTGGAGGTGTGTGGACACATGTTCATGCGTGTGGTTGCGCTTACGTACGTGTGC
```

Sequence ID No. 18: Human Beer Genomic Sequence (This gene has two exons, at positions 161-427 abd 3186-5219).

```
tagaggagaa gtctttgggg agggtttgct ctgagcacac ccctttcccT cCCTCCGGGG 60
ctgagggaaa catgggacca gccctgcccc agcctgtcct cattggctgg catgaagcag 120
agaggggctt taaaaaggcg accgtgtctc ggctggagac cagagcctgt gctactggaa 180
ggtggcgtgc cctcctctgg ctggtaccat gcagctccca ctggccctgt gtctcgtctg 240
cctgctggta cacacagcct tccgtgtagt ggagggccag gggtggcagg cgttcaagaa 300
tgatgccacg gaaatcatcc ccgagctcgg agagtacccc gagcctccac cggagctgga 360
gaacaacaag accatgaacc gggcggagaa cggagggcgg cctccccacc accccttga 420 gaccaaaggt atggggtgga ggagagaatt cttagtaaaa gatcctgggg aggttttaga 480
aacttctctt tgggaggctt ggaagactgg ggtagaccca gtgaagattg ctggcctctg 540
ccagcactgg tcgaggaaca gtcttgcctg gaggtggggg aagaatggct cgctggtgca 600
gccttcaaat tcaggtgcag aggcatgagg caacagacgc tggtgagagc ccagggcagg 660
gaggacgctg gggtggtgag ggtatggcat cagggcatca gaacaggctc aggggctcag 720
aaaagaaaag gtttcaaaga atctcctcct gggaatatag gagccacgtc cagctgctgg 780
```

92

```
taccactggg aagggaacaa ggtaagggag cctcccatcc acagaacagc acctgtgggg   840
caccggacac tctatgctgg tggtggctgt ccccaccaca cagacccaca tcatggaatc   900
cccaggaggt gaaccccag ctcgaagggg aagaaacagg ttccaggcac tcagtaactt   960
ggtagtgaga agagctgagg tgtgaacctg gtttgatcca actgcaagat agccctggtg  1020
tgtgggggg tgtgggggac agatctccac aaagcagtgg ggaggaaggc cagagaggca  1080
ccctgcagt gtgcattgcc catggcctgc ccagggagct ggcacttgaa ggaatgggag  1140
ttttcggcac agttttagcc cctgacatgg gtgcagctga gtccaggccc tggaggggag  1200
agcagcatcc tctgtgcagg agtagggaca tctgtcctca gcagccaccc cagtcccaac  1260
cttgcctcat tccaggggag ggagaaggaa gaggaacccc gggttcctgg tcaggcctgc  1320
acagagaagc ccaggtgaca gtgtgcatct ggctctataa ttggcaggaa tcctgaggcc  1380
atggggcgt ctgaaatgac acttcagact aagagcttcc ctgtcctctg gccattatcc  1440
aggtggcaga gaagtccact gcccaggctc ctggacccca gccctccccg cctcacaacc  1500
tgttgggact atgggtgct aaaaagggca actgcatggg aggccagcca ggaccctccg  1560
tcttcaaaat ggaggacaag ggcgcctccc cccacagctc cccttctagg caaggtcagc  1620
tgggctccag cgactgcctg aagggctgta aggaacccaa acacaaaatg tccaccttgc  1680
tggactccca cgagaggcca cagccctga ggaagccaca tgctcaaaac aaagtcatga  1740
tctgcagagg aagtgcctgg cctaggggcg ctattctcga aaagccgcaa aatgcccct  1800
tccctgggca aatgccccc tgaccacaca cacattccag ccctgcagag gtgaggatgc  1860
aaaccagccc acagaccaga aagcagcccc agacgatggc agtggccaca tctcccctgc  1920
tgtgcttgct cttcagagtg ggggtggggg gtggccttct ctgtcccctc tctggtttgg  1980
tcttaagact atttttcatt ctttcttgtc acattggaac tatcccatg aaaccttttgg  2040
gggtggactg gtactcacac gacgaccagc tatttaaaaa gctcccaccc atctaagtcc  2100
accataggag acatggtcaa ggtgtgtgca ggggatcagg ccaggcctcg gagcccaatc  2160
tctgcctgcc cagggagtat caccatgagg cgcccattca gataacacag aacaagaaat  2220
gtgcccagca gagagccagg tcaatgtttg tggcagctga acctgtaggt tttgggtcag  2280
agctcagggc ccctatggta ggaaagtaac gacagtaaaa agcagccctc agctccatcc  2340
cccagcccag cctcccatgg atgctcgaac gcagagcctc cactcttgcc ggagccaaaa  2400
```

```
ggtgctggga ccccagggaa gtggagtccg gagatgcagc ccagcctttt gggcaagttc 2460
tttctctgg ctgggcctca gtattctcat tgataatgag ggggttggac acactgcctt 2520
tgattccttt caagtctaat gaattcctgt cctgatcacc tcccttcag tccctcgcct 2580
ccacagcagc tgccctgatt tattaccttc aattaacctc tactcctttc tccatcccct 2640
gtccacccct cccaagtggc tggaaaagga atttgggaga agccagagcc aggcagaagg 2700
tgtgctgagt acttaccctg cccaggccag ggaccctgcg gcacaagtgt ggcttaaatc 2760
ataagaagac cccagaagag aaatgataat aataatacat aacagccgac gctttcagct 2820
atatgtgcca aatggtattt tctgcattgc gtgtgtaatg gattaactcg caatgcttgg 2880
ggcggcccat tttgcagaca ggaagaagag agaggttaag gaacttgccc aagatgacac 2940
ctgcagtgag cgatggagcc ctggtgtttg aaccccagca gtcatttggc tccgagggga 3000
cagggtgcgc aggagagctt tccaccagct ctagagcatc tgggaccttc ctgcaataga 3060
tgttcagggg caaaagcctc tggagacagg cttggcaaaa gcagggctgg ggtggagaga 3120
gacgggccgg tccaggcag gggtggccag gcgggcggcc accctcacgc gcgcctctct 3180
ccacagacgt gtccgagtac agctgccgcg agctgcactt cacccgctac gtgaccgatg 3240
ggccgtgccg cagcgccaag ccggtcaccg agctggtgtg ctccggccag tgcggcccgg 3300
cgcgcctgct gcccaacgcc atcggccgcg gcaagtggtg gcgacctagt gggcccgact 3360
tccgctgcat ccccgaccgc taccgcgcgc agcgcgtgca gctgctgtgt cccggtggtg 3420
aggcgccgcg cgcgcgcaag gtgcgcctgg tggcctcgtg caagtgcaag cgcctcaccc 3480
gcttccacaa ccagtcggag ctcaaggact tcggaccga ggccgctcgg ccgcagaagg 3540
gccggaagcc gcggccccgc gcccggagcg ccaaagccaa ccaggccgag ctggagaacg 3600
cctactagag cccgccgcg cccctcccca ccggcgggcg ccccggccct gaacccgcgc 3660
cccacatttc tgtcctctgc gcgtggtttg attgtttata tttcattgta aatgcctgca 3720
acccagggca gggggctgag accttccagg ccctgaggaa tcccgggcgc cggcaaggcc 3780
cccctcagcc cgccagctga ggggtcccac ggggcagggg agggaattga gagtcacaga 3840
cactgagcca cgcagccccg cctctggggc cgcctacctt tgctggtccc acttcagagg 3900
aggcagaaat ggaagcattt tcaccgccct ggggttttaa gggagcggtg tgggagtggg 3960
aaagtccagg gactggttaa gaaagttgga taagattccc ccttgcacct cgctgccat 4020
cagaaagcct gaggcgtgcc cagagcacaa gactgggggc aactgtagat gtggtttcta 4080
```

94

```
gtcctggctc tgccactaac ttgctgtgta accttgaact acacaattct ccttcgggac 4140
ctcaatttcc actttgtaaa atgagggtgg aggtgggaat aggatctcga ggagactatt 4200
ggcatatgat tccaaggact ccagtgcctt ttgaatgggc agaggtgaga gagagagaga 4260
gaaagagaga gaatgaatgc agttgcattg attcagtgcc aaggtcactt ccagaattca 4320
gagttgtgat gctctcttct gacagccaaa gatgaaaaac aaacagaaaa aaaaaagtaa 4380
agagtctatt tatggctgac atatttacgg ctgacaaact cctggaagaa gctatgctgc 4440
ttcccagcct ggcttccccg gatgtttggc tacctccacc cctccatctc aaagaaataa 4500
catcatccat tggggtagaa aaggagaggg tccgagggtg gtgggaggga tagaaatcac 4560
atccgcccca acttcccaaa gagcagcatc cctcccccga cccatagcca tgttttaaag 4620
tcaccttccg aagagaagtg aaaggttcaa ggacactggc cttgcaggcc cgagggagca 4680
gccatcacaa actcacagac cagcacatcc cttttgagac accgccttct gcccaccact 4740
cacggacaca tttctgccta gaaaacagct tcttactgct cttacatgtg atggcatatc 4800
ttacactaaa agaatattat tgggggaaaa actacaagtg ctgtacatat gctgagaaac 4860
tgcagagcat aatagctgcc acccaaaaat cttttttgaaa atcatttcca gacaacctct 4920
tactttctgt gtagttttta attgttaaaa aaaaaaagtt ttaaacagaa gcacatgaca 4980
tatgaaagcc tgcaggactg gtcgttttttt tggcaattct tccacgtggg acttgtccac 5040
aagaatgaaa gtagtggttt ttaaagagtt aagttacata tttatttct cacttaagtt 5100
atttatgcaa aagtttttct tgtagagaat gacaatgtta atattgcttt atgaattaac 5160
agtctgttct tccagagtcc agagacattg ttaataaaga caatgaatca tgaccgaaag 5220
gatgtggtct cattttgtca accacacatg acgtcatttc tgtcaaagtt gacacccttc 5280
tcttggtcac tagagctcca accttggaca cacctttgac tgctctctgg tggcccttgt 5340
ggcaattatg tcttcctttg aaaagtcatg tttatccctt cctttccaaa cccagaccgc 5400
atttcttcac ccagggcatg gtaataacct cagccttgta tccttttagc agcctcccct 5460
ccatgctggc ttccaaaatg ctgttctcat tgtatcactc ccctgctcaa aagccttcca 5520
tagctccccc ttgcccagga tcaagtgcag tttccctatc tgacatggga ggccttctct 5580
gcttgactcc cacctcccac tccaccaagc ttcctactga ctccaaatgg tcatgcagat 5640
ccctgcttcc ttagtttgcc atccacactt agcaccccca ataactaatc ctctttcttt 5700
```

95

```
aggattcaca ttacttgtca tctcttcccc taaccttcca gagatgttcc aatctcccat 5760
gatccctctc tcctctgagg ttccagcccc ttttgtctac accactactt tggttcctaa 5820
ttctgttttc catttgacag tcattcatgg aggaccagcc tggccaagtc ctgcttagta 5880
ctggcataga caacacaaag ccaagtacaa ttcaggacca gctcacagga aacttcatct 5940
tcttcgaagt gtggatttga tgcctcctgg gtagaaatgt aggatcttca aaagtgggcc 6000
agcctcctgc acttctctca aagtctcgcc tccccaaggt gtcttaatag tgctggatgc 6060
tagctgagtt agcatcttca gatgaagagt aaccctaaag ttactcttca gttgccctaa 6120
ggtgggatgg tcaactggaa agctttaaat taagtccagc ctaccttggg ggaacccacc 6180
cccacaaaga aagctgaggt ccctcctgat gacttgtcag tttaactacc aataacccac 6240
ttgaattaat catcatcatc aagtctttga taggtgtgag tgggtatcag tggccggtcc 6300
cttcctgggg ctccagcccc cgaggaggcc tcagtgagcc cctgcagaaa atccatgcat 6360
catgagtgtc tcagggccca gaatatgaga gcaggtagga aacagagaca tcttccatcc 6420
ctgagaggca gtgcggtcca gtgggtgggg acacgggctc tgggtcaggt ttgtgttgtt 6480
tgtttgtttg ttttgagaca gagtctcgct ctattgccca ggctggagtg cagtgtcaca 6540
atctcggctt actgcaactt ctgccttccc ggattcaagt gattctcctg cctcagcctc 6600
cagagtagct gggattacag gtgcgtgcca ccacgcctgg ctaattttg tatttttgat 6660
agagacgggg tttcaccatg ttggccaggc tagtctcgaa ctcttgacct caagtgatct 6720
gcctgcctcg gcctcccaaa gtgctgggat tacaggcgtg agccaccaca cccagcccca 6780
ggttggtgtt tgaatctgag gagactgaag caccaagggg ttaaatgttt tgcccacagc 6840
catactgggg ctcagttcct tgccctaccc ctcacttgag ctgcttagaa cctggtgggc 6900
acatgggcaa taaccaggtc acactgtttt gtaccaagtg ttatgggaat ccaagatagg 6960
agtaatttgc tctgtggagg ggatgaggga tagtggttag ggaaagcttc acaaagtggg 7020
tgttgcttag agattttcca ggtggagaag ggggcttcta ggcagaaggc atagcccaag 7080
caaagactgc aagtgcatgg ctgctcatgg gtagaagaga atccaccatt cctcaacatg 7140
taccgagtcc ttgccatgtg caaggcaaca tgggggtacc aggaattcca agcaatgtcc 7200
aaacctaggg tctgctttct gggacctgaa gatacaggat ggatcagccc aggctgcaat 7260
cccattacca cgaggggaa aaaaacctga aggctaaatt gtaggtcggg ttagaggtta 7320
tttatggaaa gttatattct acctacatgg ggtctataag cctggcgcca atcagaaaag 7380
```

```
gaacaaacaa cagacctagc tgggaggggc agcattttgt tgtaggggc ggggcacatg 7440
ttctgggggt acagccagac tcagggcttg tattaatagt ctgagagtaa gacagacaga 7500
gggatagaag gaaataggtc cctttctctc tctctctctc tctctctctc actctctctc 7560
tctctcacac acacacacag acacacacac acgctctgta ggggtctact tatgctccaa 7620
gtacaaatca ggccacattt acacaaggag gtaaaggaaa agaacgttgg aggagccaca 7680
ggaccccaaa attccctgtt ttccttgaat caggcaggac ttacgcagct gggagggtgg 7740
agagcctgca gaagccacct gcgagtaagc caagttcaga gtcacagaca ccaaaagctg 7800
gtgccatgtc ccacacccgc ccacctccca cctgctcctt gacacagccc tgtgctccac 7860
aacccggctc ccagatcatt gattatagct ctggggcctg caccgtcctt cctgccacat 7920
ccccacccca ttcttggaac ctgccctctg tcttctccct tgtccaaggg caggcaaggg 7980
ctcagctatt gggcagcttt gaccaacagc tgaggctcct tttgtggctg gagatgcagg 8040
aggcagggga atattcctct tagtcaatgc gaccatgtgc ctggtttgcc cagggtggtc 8100
tcgtttacac ctgtaggcca agcgtaatta ttaacagctc ccacttctac tctaaaaaat 8160
gacccaatct gggcagtaaa ttatatggtg cccatgctat taagagctgc aacttgctgg 8220
gcgtggtggc tcacacctgt aatcccagta ctttgggacg tcaaggcggg tggatcacct 8280
gaggtcacga gttagagact ggcctggcca gcatggcaaa accccatctt tactaaaaat 8340
acaaaaatta gcaaggcatg gtggcatgca cctgtaatcc caggtactcg ggaggctgag 8400
acaggagaat ggcttgaacc caggaggcag aggttgcagt gagccaagat tgtgccactg 8460
ccctccagcc ctggcaacag agcaagactt catctcaaaa gaaaaggat actgtcaatc 8520
actgcaggaa gaacccaggt aatgaatgag gagaagagag gggctgagtc accatagtgg 8580
cagcaccgac tcctgcagga aaggcgagac actgggtcat gggtactgaa gggtgccctg 8640
aatgacgttc tgctttagag accgaacctg agccctgaaa gtgcatgcct gttcatgggt 8700
gagagactaa attcatcatt ccttggcagg tactgaatcc tttcttacgg ctgccctcca 8760
atgcccaatt tccctacaat tgtctggggt gcctaagctt ctgcccacca agagggccag 8820
agctggcagc gagcagctgc aggtaggaga gataggtacc cataagggag gtgggaaaga 8880
gagatggaag gagagggtg cagagcacac acctcccctg cctgacaact tcctgagggc 8940
tggtcatgcc agcagattta aggcggaggc agggagatg gggcgggaga ggaagtgaaa 9000
```

97

```
     aaggagaggg tggggatgga gaggaagaga gggtgatcat tcattcattc cattgctact 9060
     gactggatgc cagctgtgag ccaggcacca ccctagctct gggcatgtgg ttgtaatctt 9120
  5  ggagcctcat ggagctcaca gggagtgctg gcaaggagat ggataatgga cggataacaa 9180
     ataaacattt agtacaatgt ccgggaatgg aaagttctcg aaagaaaaat aaagctggtg 9240
     agcatataga cagccctgaa ggcggccagg ccaggcattt ctgaggaggt ggcatttgag 9300
 10  c                                                                9301
```

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A transgenic mouse whose genome comprises a transgene comprising a nucleic acid molecule encoding a TGF-beta binding-protein wherein said nucleic acid molecule is operably linked to a promoter effective for the expression of said gene, and wherein said nucleic acid molecule is selected from the group consisting of an isolated nucleic acid molecule comprising SEQ ID Nos. 1, 5, 9, 11, 13 and 15, wherein said mouse exhibits decreased bone mineral density.

2. A transgenic mouse the germ and somatic cells of which comprise a transgene encoding an amino acid sequence of a BEER TGF-beta binding-protein wherein said mouse exhibits decreased bone mineral density.

* * * * *

UNITED STATES PATENT AND TRADEMARK OFFICE
CERTIFICATE OF CORRECTION

PATENT NO. : 6,495,736 B1
DATED : December 17, 2002
INVENTOR(S) : Mary E. Brunkow et al.

It is certified that error appears in the above-identified patent and that said Letters Patent is hereby corrected as shown below:

<u>Title page,</u>
Item [75], the second listed inventor's data should read as -- David J. Galas, Claremont, CA (US); --.

Signed and Sealed this

Eighth Day of July, 2003

JAMES E. ROGAN
*Director of the United States Patent and Trademark Office*